United States Patent
Duffy et al.

(10) Patent No.: US 10,214,509 B2
(45) Date of Patent: Feb. 26, 2019

(54) AMINO-SUBSTITUTED HETEROCYCLIC DERIVATIVES AS SODIUM CHANNEL INHIBITORS

(71) Applicant: ALMIRALL, S.A., Barcelona (ES)

(72) Inventors: James Duffy, Saffron Walden Essex (GB); Mark Stuart Chambers, Saffron Walden Essex (GB); Alastair Rae, Saffron Walden Essex (GB); James Osborne, Saffron Walden Essex (GB); Isabelle Anne Lemasson, Saffron Walden Essex (GB); Michael Daniel Goldsmith, Saffron Walden Essex (GB); Andrew Sharpe, Saffron Walden Essex (GB); Silvia Fonquerna Pou, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 15/567,668

(22) PCT Filed: Apr. 20, 2016

(86) PCT No.: PCT/EP2016/058802
§ 371 (c)(1),
(2) Date: Oct. 19, 2017

(87) PCT Pub. No.: WO2016/170009
PCT Pub. Date: Oct. 27, 2016

(65) Prior Publication Data
US 2018/0105509 A1 Apr. 19, 2018

(30) Foreign Application Priority Data
Apr. 21, 2015 (EP) .................................. 15382198

(51) Int. Cl.
| | | |
|---|---|---|
| *C07D 401/04* | (2006.01) | |
| *C07D 401/12* | (2006.01) | |
| *C07D 401/14* | (2006.01) | |
| *C07D 405/12* | (2006.01) | |
| *C07D 405/14* | (2006.01) | |
| *C07D 413/14* | (2006.01) | |
| *C07D 403/06* | (2006.01) | |
| *C07D 403/10* | (2006.01) | |
| *C07D 403/12* | (2006.01) | |
| *C07D 249/14* | (2006.01) | |
| *C07D 249/06* | (2006.01) | |
| *C07D 231/38* | (2006.01) | |
| *A61K 31/4439* | (2006.01) | |
| *A61K 31/415* | (2006.01) | |
| *A61P 25/02* | (2006.01) | |

(52) U.S. Cl.
CPC .......... *C07D 401/12* (2013.01); *A61P 25/02* (2018.01); *C07D 231/38* (2013.01); *C07D 249/06* (2013.01); *C07D 249/14* (2013.01); *C07D 401/04* (2013.01); *C07D 401/14* (2013.01); *C07D 403/06* (2013.01); *C07D 403/10* (2013.01); *C07D 403/12* (2013.01); *C07D 405/12* (2013.01); *C07D 405/14* (2013.01); *C07D 413/14* (2013.01)

(58) Field of Classification Search
None
See application file for complete search history.

(56) References Cited

FOREIGN PATENT DOCUMENTS

| WO | WO 2006/011050 A2 | 2/2006 |
|---|---|---|
| WO | WO 2014/120994 A1 | 8/2014 |

OTHER PUBLICATIONS

Nazariy, Pokhodylo et al., "Synthesis and anticancer activity evaluation of new 1,2,3-triazole-4-carboxamine derivatives," Medicinal Chemistry Research, vol. 23, No. 5, pp. 2426-2438 (2014).
Database PubChem Compound, XP002741235, Database Accession No. CID3411823 (2005).
Database Pubhem Compound, XP002741236, Database Accession No. CID27261825 (2009).
Database PubChem Compound, XP002741237, Database Accession No. CID3411824 (2005).
Database PubChem Compound, XP002741238, Database Accession No. CID6498349 (2006).
Database PubChem Compound, XP002741239, Database Accession No. CID1614863 (2007).
Database PubChem Compound, XP002741240, Database Accession No. CID16425761 (2007).
Database PubChem Compound, XP002741241, Database Accession No. CID17014894 (2007).

(Continued)

*Primary Examiner* — Samantha L Shterengarts
(74) *Attorney, Agent, or Firm* — Finnegan, Henderson, Farabow, Garrett & Dunner, LLP

(57) ABSTRACT

The present invention relates to novel aminoindazolyl derivative compounds of Formula (I), the use of said compounds in treating diseases mediated by modulation of voltage-gated sodium channels in particular Nav1.7 AND to compositions containing said derivatives.

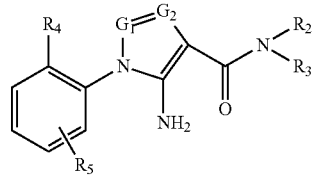

Formula (I)

20 Claims, No Drawings

(56) References Cited

OTHER PUBLICATIONS

Database PubChem Compound, XP002741242, Database Accession No. CID17015728 (2007).
Database PubChem Compound, XP002741243, Database Accession No. CID17015768 (2007).
Database PubChem Compound, XP002741244, Database Accession No. CID17590729 (2007).
Database PubChem Compound, XP002741245, Database Accession No. CID27260561 (2009).
Database PubChem Compound, XP002741246, Database Accession No. CID27260736 (2009).
Database PubChem Compound, XP002741247, Database Accession No. CID49814349 (2010).
Database PubChem Compound, XP002741248, Database Accession No. CID27261523 (2009).
International Search Report for International Application No. PCT/EP2016/058802, dated May 24, 2016.
Written Opinion of the International Searching Authority for International Application No. PCT/EP2016/058802.

AMINO-SUBSTITUTED HETEROCYCLIC DERIVATIVES AS SODIUM CHANNEL INHIBITORS

This application is a national stage filing under 35 U.S.C. § 371 of International Application No. PCT/EP2016/058802, filed on Apr. 20, 2016, which claims priority of European Patent Application No. 15382198.8, filed Apr. 21, 2015. The contents of these applications are each incorporated herein by reference.

FIELD OF THE INVENTION

The present invention relates to novel amino-substituted heterocyclic derivative compounds, the use of said compounds in treating diseases mediated by modulation of voltage-gated sodium channels in particular Nav1.7, to compositions containing said derivatives and processes for their preparation.

BACKGROUND OF THE INVENTION

Voltage-gated sodium channels have a relevant role in the initiation and propagation of electrical signalling in excitable cells. Genetic studies have proven that inherited disorders like cardiac arrhythmias, epilepsy and loss or gain of pain sensation could be linked to mutations of genes that encode Nav subtypes. (Nardi A. et al, *Chem Med Chem*, 2012, 7, 1-30).

There are nine subtypes of voltage-gated sodium channels in humans. Although they are very similar in sequence, different sodium channel subtypes have important and diverse physiological roles. Nav1.1, Nav1.2, and Nav1.3 are highly expressed in the central nervous system. Nav1.4 is primarily found in skeletal muscle and Nav1.5 is expressed mainly in the cardiac muscle. Nav1.6 is a widely expressed sodium channel and it can be found throughout the central and the peripheral nervous system. Nav1.7, Nav1.8 and Nav1.9 are found predominantly in peripheral sympathetic and sensory neurons.

Most of the small Nav1.7 inhibitors are known to bind a region of the channel in the inner vestibule of the pore on transmembrane S6 domain IV which is highly conserved between subtypes. However, it is possible to find selective Nav1.7 inhibitors.

A selective Nav1.7 would be highly desirable to avoid undesired adverse effects observed with existing non-selective Nav inhibitors such as Lidocaine which have a limited therapeutic window.

Particularly, finding selectivity of Nav1.7 with respect to Nav1.5 would be desirable to avoid any cardiovascular side effects.

State dependent inhibitors are thought to stabilise an inactivated conformation of the channel which is adopted rapidly after the channel opens. This inactivated state provides a refractory period before the channel returns to its resting state ready to be reactivated. State dependent inhibition is proposed to reflect an allosteric mechanism by which the drug receptor site is in the low-affinity conformation when the channel is at rest and converts into a high-affinity conformation when the channel is open or inactivated. This ability for sodium channels to adopt different conformations depending on the voltage would increase therapeutic index by enhancing functional selectivity as in healthy tissues sodium channels mostly reside in the resting state whereas inactivated state has a greater relevance in diseased tissue. (Priest B. T. et al, *Curr. Top. Med. Chem.* 2008, 3, 121-143, Ragsdale D. S., *Brain Res. Brain Res. Rev.* 1998, 26, 16-28, Yanagidate F., *Exp. Pharmacol.* 2007, 95-127)

Several studies relate gain-of-function mutations of the gene that encodes Nav1.7 to pain whereas loss-of-function mutations in this gene lead to an indifference to pain (Dib-Hajj, S. D et al, *Annu. Rev. Neurosci.* 2010, 33, 325-347). Additional studies have linked Nav1.7 to cough reflex (Muroi, Y. et al, *J. Physiol.* 2011, 589, 5663-5676).

Nav1.7 inhibitors are potentially useful in the treatment of a wide range of disorders, such as pain, including but not limited to acute pain, chronic pain, inflammatory pain, visceral pain, nociceptive pain, neuropathic pain, postherpethic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, schizophrenia and bipolar disorder. They can also be potentially used as analgesic and anaesthetic drugs.

We have now discovered novel amino-substituted heterocyclic derivative compounds as potent state dependent and selective Nav1.7 inhibitors.

SCOPE OF THE INVENTION

Accordingly, the present invention provides a compound of Formula (I), or a pharmaceutically acceptable salt, or N-oxide, or isotopically-labeled derivate thereof:

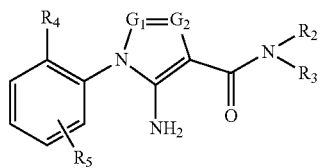

Formula (I)

Wherein
G$_1$ represents —N— or —CH—;
G$_2$ represents —N— or —CR$_1$, wherein R$_1$ is selected from the group consisting of a hydrogen atom and a lineal or branched C$_{1-4}$ alkyl group, with the proviso that at least one of G$_1$ and G$_2$ should be a —N—;
R$_2$ represents a hydrogen atom and R$_3$ represent a group of Formula (i):

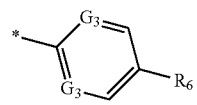

Formula (i)

wherein each G$_3$ independently represents —N— or —CR$_7$, wherein R$_7$ is selected from the group consisting of a hydrogen atom, a halogen atom, a hydroxyl group, a cyano group, a phenyl group, a lineal or branched C$_{1-4}$ alkyl group, a lineal or branched (C$_{1-4}$ alkoxy)-(C$_{1-4}$ alkyl) group, —O—(CH$_2$)$_{1-2}$—NR$^a$R$^b$, —NR$^a$R$^b$, —CO—NR$^a$R$^b$, —OR$^c$ and —CH$_2$—R$^d$;
R$_6$ is selected from the group consisting of a halogen atom, a cyano group, a lineal or branched C$_{1-4}$ alkyl group, a lineal or branched C$_{1-4}$ haloalkyl group, a lineal or branched $C_{1-4}$ haloalkoxy group, —$SO_2$—$CF_3$ group, a —O-phenyl group, a benzyl group and a —O-benzyl group;

or $R_2$ and $R_3$ together with the nitrogen atom to which they are attached form the group of Formula (ii):

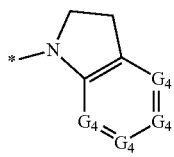

Formula (ii)

wherein each $G_4$ independently represents —$CR^8$— or —N—, wherein $R^8$ is selected from the group consisting of a hydrogen atom and a halogen atom, $R_4$ is selected from the group consisting of a halogen atom; a hydroxyl group; a lineal or branched $C_{1-4}$ alkyl group; a lineal or branched $C_{1-4}$ haloalkyl group; a lineal or branched ($C_{1-4}$ alkyl)-($C_{1-4}$ alkoxy) group; a lineal or branched ($C_{1-4}$ alkoxy)-($C_{1-4}$ alkyl) group; a lineal or branched ($C_{1-4}$ alkoxy)-($C_{1-4}$ alkoxy) group; —$O_{(0-1)}$—$(CH_2)_{(0-2)}$—$NR^aR^b$ group; —O—$(CH_2)_{(0-2)}R^c$ group; —O—$(CHR^f)_1$—CO—$NR^aR^b$ group; —$SO_2$—$NR^aR^b$ group; a $C_{6-8}$ aryl group; a monocyclic 5- to 8-membered heteroaryl group containing at least one heteroatom selected from N, O and S, wherein said heteroaryl ring is optionally substituted with one or more substituents selected from a halogen atom, a $C_{1-2}$ alkyl group, a $C_{1-2}$ alkoxy group and amino group optionally substituted with one or two $C_{1-2}$ alkyl group; and a 4- to 6-membered saturated or non-saturated heterocyclyl group containing at least one heteroatom selected from N, O and S, wherein said heterocyclyl ring is optionally substituted with one or more substituents selected from a $C_{1-2}$ alkyl group, a $C_{1-2}$ alkoxy group and —C(O)O—$R^e$ group, wherein $R^e$ represents a lineal or branched $C_{1-4}$ alkyl group, and wherein $R^f$ represents a hydrogen atom, a halogen atom or a lineal or branched $C_{1-4}$ alkyl group;

$R_5$ is selected from the group consisting of a hydrogen atom, a halogen atom, a lineal or branched $C_{1-4}$ alkyl group and a lineal or branched $C_{1-4}$ haloalkyl group;

$R^a$ and $R^b$ independently are selected from the group consisting of a hydrogen atom, a lineal or branched $C_{1-4}$ alkyl group, a lineal or branched ($C_{1-4}$ alkyl)-($C_{1-4}$ alkoxy) group, a lineal or branched ($C_{1-4}$ alkoxy)-($C_{1-4}$ alkyl) group and a 5- to 8-membered monocyclic heteroaryl group containing at least one heteroatom selected from N, S and O, or $R^a$ and $R^b$ together with nitrogen atom to which they are attached form a 3- to 6-membered heterocyclyl group optionally containing further heteroatom selected from N, S and O, wherein said heterocyclyl group is optionally substituted with one or more substituents selected from a $C_{1-2}$ alkyl group;

$R^c$ is selected from the group consisting of a lineal or branched $C_{1-4}$ alkyl group, a lineal or branched $C_{1-4}$ hydroxyalkyl group, a lineal or branched $C_{1-4}$ haloalkyl group, a lineal or branched ($C_{1-4}$ alkoxy)-($C_{1-4}$ alkyl) group, a lineal or branched ($C_{1-4}$ alkyl)-($C_{1-4}$ alkoxy) group, a $C_{6-8}$ aryl group, a monocyclic 5- to 8-membered heteroaryl group containing at least one heteroatom selected from N, O and S, and a 4- to 6-membered heterocyclyl group containing at least one heteroatom selected from N, O and S, wherein said heterocyclyl ring is optionally substituted with one or more substituents selected from a $C_{1-2}$ alkyl group and a $C_{1-2}$ alkoxy group;

$R^d$ is selected from the group consisting of a —$NR^aR^b$ group and a 4- to 6-membered heterocyclyl group containing at least one heteroatom selected from N, O and S, wherein said heterocyclyl group is optionally substituted with one or more substituents selected from a halogen atom;

With the proviso that the compound is not any one of the following:

5-amino-N-(4-ethylphenyl)-1-(2-methylphenyl)-1H-1,2,3-triazole-4-carboxamide, 5-amino-N-(2,4-dimethylphenyl)-1-(2-methylphenyl)-1H-1,2,3-triazole-4-carboxamide, 5-amino-1-(2,5-dimethylphenyl)-N-(4-fluorophenyl)-1H-1,2,3-triazole-4-carboxamide, 5-amino-N-(2,4-dichlorophenyl)-1-(2-methylphenyl)-1H-1,2,3-triazole-4-carboxamide, 5-amino-1-(2-methylphenyl)-N-(4-methylphenyl)-1H-1,2,3-triazole-4-carboxamide, 5-amino-N-(4-chlorophenyl)-1-(2-methylphenyl)-1H-1,2,3-triazole-4-carboxamide, 5-amino-N-(4-fluorophenyl)-1-(2-methylphenyl)-1H-1,2,3-triazole-4-carboxamide, 5-amino-N-(4-bromophenyl)-1-(2-methoxyphenyl)-1H-1,2,3-triazole-4-carboxamide, 5-amino-N-(2,4-difluorophenyl)-1-(2-methoxyphenyl)-1H-1,2,3-triazole-4-carboxamide, 5-amino-1-(2-methoxyphenyl)-N-(4-methylphenyl)-1H-1,2,3-triazole-4-carboxamide, 5-amino-N-(4-fluorophenyl)-1-(2-methoxyphenyl)-1H-1,2,3-triazole-4-carboxamide.

In another embodiment, the present invention provides a compound of Formula (I), or a pharmaceutically acceptable salt, or N-oxide, or isotopically-labeled derivate thereof:

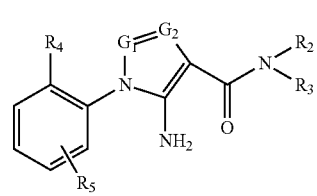

Formula (I)

Wherein $G_1$ represents —N— or —CH—;

$G_2$ represents —N— or —$CR_1$, wherein $R_1$ is selected from the group consisting of a hydrogen atom and a lineal or branched $C_{1-4}$ alkyl group, with the proviso that at least one of $G_1$ and $G_2$ should be —N—;

$R_2$ represents a hydrogen atom and $R_3$ represent a group of Formula (i):

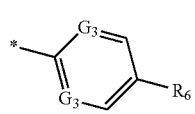

Formula (i)

wherein each $G_3$ independently represents —N— or —$CR_7$, wherein $R_7$ is selected from the group consisting of a hydrogen atom, a halogen atom, a hydroxyl group, a cyano group, a phenyl group, a lineal or branched $C_{1-4}$ alkyl group, a lineal or branched ($C_{1-4}$ alkoxy)-($C_{1-4}$ alkyl) group, —O—$(CH_2)_{1-2}$—$NR^aR^b$, —$NR^aR^b$, —CO—$NR^aR^b$, —$OR^c$ and —$CH_2$—$R^d$;

$R_6$ is selected from the group consisting of a halogen atom, a cyano group, a lineal or branched $C_{1-4}$ alkyl group, a lineal or branched $C_{1-4}$ haloalkyl group, a lineal or branched $C_{1-4}$ haloalkoxy group, —$SO_2$—$CF_3$ group, a benzyl group and a —O-benzyl group;

or $R_2$ and $R_3$ together with the nitrogen atom to which they are attached form the group of Formula (ii):

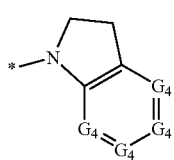

Formula (ii)

wherein each $G_4$ independently represents —$CR^8$— or —N—, wherein $R^8$ is selected from the group consisting of a hydrogen atom and a halogen atom, $R_4$ is selected from the group consisting of a halogen atom; a hydroxyl group; a lineal or branched $C_{1-4}$ alkyl group; a lineal or branched $C_{1-4}$ haloalkyl group; a lineal or branched ($C_{1-4}$ alkyl)-($C_{1-4}$ alkoxy) group; a lineal or branched ($C_{1-4}$ alkoxy)-($C_{1-4}$ alkyl) group; a lineal or branched ($C_{1-4}$ alkoxy)-($C_{1-4}$ alkoxy) group; —$O_{(0-1)}$—$(CH_2)_{(0-2)}$—$NR^aR^b$ group; —O—$(CH_2)_{(0-2)}R^c$ group; —O—$(CHR^f)_1$—CO—$NR^aR^b$ group; —$SO_2$—$NR^aR^b$ group; a $C_{6-8}$ aryl group; a monocyclic 5- to 8-membered heteroaryl group containing at least one heteroatom selected from N, O and S, wherein said heteroaryl ring is optionally substituted with one or more substituents selected from a halogen atom, a $C_{1-2}$ alkyl group, a $C_{1-2}$ alkoxy group and amino group optionally substituted with one or two $C_{1-2}$ alkyl group; and a 4- to 6-membered saturated or non-saturated heterocyclyl group containing at least one heteroatom selected from N, O and S, wherein said heterocyclyl ring is optionally substituted with one or more substituents selected from a $C_{1-2}$ alkyl group, a $C_{1-2}$ alkoxy group and —C(O)O—$R^e$ group, wherein $R^e$ represents a lineal or branched $C_{1-4}$ alkyl group, and wherein $R^f$ represents a lineal or branched $C_{1-4}$ alkyl group;

$R_5$ is selected from the group consisting of a hydrogen atom, a halogen atom, a lineal or branched $C_{1-4}$ alkyl group and a lineal or branched $C_{1-4}$ haloalkyl group;

$R^a$ and $R^b$ independently are selected from the group consisting of a hydrogen atom, a lineal or branched $C_{1-4}$ alkyl group, a lineal or branched ($C_{1-4}$ alkyl)-($C_{1-4}$ alkoxy) group and a 5- to 8-membered monocyclic heteroaryl group containing at least one heteroatom selected from N, S and O, or $R^a$ and $R^b$ together with nitrogen atom to which they are attached form a 3- to 6-membered heterocyclyl group optionally containing further heteroatom selected from N, S and O, wherein said heterocyclyl group is optionally substituted with one or more substituents selected from a $C_{1-2}$ alkyl group;

$R^c$ is selected from the group consisting of a lineal or branched $C_{1-4}$ alkyl group, a lineal or branched $C_{1-4}$ hydroxyalkyl group, a lineal or branched $C_{1-4}$ haloalkyl group, a lineal or branched ($C_{1-4}$ alkoxy)-($C_{1-4}$ alkyl) group, a lineal or branched ($C_{1-4}$ alkyl)-($C_{1-4}$ alkoxy) group, a $C_{6-8}$ aryl group, a monocyclic 5- to 8-membered heteroaryl group containing at least one heteroatom selected from N, O and S, and a 4- to 6-membered heterocyclyl group containing at least one heteroatom selected from N, O and S, wherein said heterocyclyl ring is optionally substituted with one or more substituents selected from a $C_{1-2}$ alkyl group and a $C_{1-2}$ alkoxy group;

$R^d$ is selected from the group consisting of a —$NR^aR^b$ group and a 4- to 6-membered heterocyclyl group containing at least one heteroatom selected from N, O and S, wherein said heterocyclyl group is optionally substituted with one or more substituents selected from a halogen atom;

With the proviso that the compound is not any one of the following:

5-amino-N-(4-ethylphenyl)-1-(2-methylphenyl)-1H-1,2,3-triazole-4-carboxamide, 5-amino-N-(2,4-dimethylphenyl)-1-(2-methylphenyl)-1H-1,2,3-triazole-4-carboxamide, 5-amino-1-(2,5-dimethylphenyl)-N-(4-fluorophenyl)-1H-1,2,3-triazole-4-carboxamide, 5-amino-N-(2,4-dichlorophenyl)-1-(2-methylphenyl)-1H-1,2,3-triazole-4-carboxamide, 5-amino-1-(2-methylphenyl)-N-(4-methylphenyl)-1H-1,2,3-triazole-4-carboxamide, 5-amino-N-(4-chlorophenyl)-1-(2-methylphenyl)-1H-1,2,3-triazole-4-carboxamide, 5-amino-N-(4-fluorophenyl)-1-(2-methylphenyl)-1H-1,2,3-triazole-4-carboxamide, 5-amino-N-(4-bromophenyl)-1-(2-methoxyphenyl)-1H-1,2,3-triazole-4-carboxamide, 5-amino-N-(2,4-difluorophenyl)-1-(2-methoxyphenyl)-1H-1,2,3-triazole-4-carboxamide, 5-amino-1-(2-methoxyphenyl)-N-(4-methylphenyl)-1H-1,2,3-triazole-4-carboxamide, 5-amino-N-(4-fluorophenyl)-1-(2-methoxyphenyl)-1H-1,2,3-triazole-4-carboxamide.

The invention further provides synthetic processes and intermediates described herein, which are useful for preparing said compounds.

The invention also provides a pharmaceutical composition comprising at least a compound of the invention and a pharmaceutically acceptable diluent or carrier.

The invention also provides a compound of the invention for use in the treatment of the human or animal body by therapy.

The invention is also directed to the compounds of the invention as described herein, for use in the treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, schizophrenia and bipolar disorder. They can also be potentially used as analgesic and anaesthetic drugs.

The invention also provides the use of the compounds of the invention as described herein, for the manufacture of a medicament for the treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, schizophrenia and bipolar disorder.

The invention is also directed to a method of treatment of a pathological condition or disease mediated by modulation of voltage-gated sodium channels in particular Nav1.7, which condition or disease is selected from pain, including but not limited to acute pain, chronic pain, inflammatory pain, visceral pain, nociceptive pain, neurophatic pain, postherpetic pain, trigeminal neuralgia, diabetic neuropathy, chronic back pain, chronic pelvic pain, pain resulting from cancer and chemotherapy, migraine, idiopathic cough, chronic cough or cough related to respiratory diseases, respiratory diseases, itch, dermatological diseases, epilepsy, schizophrenia and bipolar disorder, comprising administering a therapeutically effective amount of the compounds of the invention or a pharmaceutical composition of the invention to a subject in need of such treatment.

The invention also provides a combination product comprising (i) at least a compound of the invention as described herein; and (ii) one or more active ingredients selected from:
(a) Opioid receptor agonists such as but not restricted to morphine, phentanyl, hydromorphone or hydrocodone,
(b) Opioid receptor partial agonists such as but not restricted to meptazinol,
(c) NSAIDS such as but not restricted to acetyl salicilic acid, ibuprofen, naproxen, aceclofenac or diclofenac,
(d) COX-2 inhibitors such as but not restricted to rofecoxib or celecoxib,
(e) Ion channel modulators such as but not restricted to ziconotide or gabapentine,
(f) Centrally acting agents such as but not restricted to flupirtine or neofam,
(g) Agents for neuropathic pain such as but not restricted to carbamazepine, gabapentine, duloxetine or pregabaline,
(h) Agents for cancer pain such as but not restricted to calcitonine, lexidronam or oxycodone for pain patients,
(i) Anti-fibrotics such as but not restricted to pirfenidone, nintenadib for patients with idiopathic pulmonary fibrosis,
(j) Prostacyclin analogues such as but not restricted to epoprostenol, beraprost, treprostinil or iloprost,
(k) Endothelin antagonists such as but not restricted to bosentac, sitaxentan, ambrisentan or macitentan,
(l) Phosphodiesterase V inhibitors such as but not restricted to sildenafil or taldenafil,
(m) Guanylate cyclase stimulators such as but not restricted to riociguat for patients with pulmonary hypertension,
(n) Oral and inhaled corticosteroids such as but not restricted to fluticasone,
(o) Phosphodiesterase IV inhibitors like roflumilast,
(p) Beta2-adrenoceptor agonists such as but not restricted to salbutamol, salmeterol, indacaterol or olodaterol,
(q) Muscarinic antagonists such as but not restricted to ipratropium, tiotropium, aclidinium, glycopyrronium or umeclidinium,
(r) Xantines such as but not restricted to teophyline,
(s) Mast cell stabilizers such as but not restricted to tranilast and tazonilast,
(t) Leukotriene modifiers such as but not restricted to montelukast, zafirlukast and zileuton,
(u) Th2 cytokine inhibitors such as but not restricted to suplatast,
(v) Thromboxane antagonists/thromboxane synthase inhibitors such as but not restricted to ozagrel and seratrodast,
(w) Anti-IgE therapy compounds such as but not restricted to xolair for patients with asthma,
(x) Histamine antagonists such as but not restricted to ebastine, cetiricine and loratadine,
(y) Antiinflammatory agents such as NSAIDs, corticosteroids, calcineurin inhibitors, anti-TNF, anti-IL17, anti-IL12/IL13, anti-IL5, anti IL4/IL-13, anti-IL31 or anti-IgE antibodies,
(z) JAK inhibitors such as but not restricted to ruxolitinib or tofacitinib,
(aa) Syk inhibitors,
(ab) Immunosupressants;
(ac) Antipruritic agents such as kappa opioid agonists, mu opioid agonists, neurokinin receptor 1 antagonists such as but not restricted to aprepitant, 5-HT3 antagonists and cannabinoids,
(ad) Anti-tussive agents, Decongestants, Mucolytics, Expectorants or Proton Pump Inhibitors, for simultaneous, separate or sequential use in the treatment of the human or animal body.

DETAILED DESCRIPTION OF THE INVENTION

When describing the compounds, compositions and methods of the invention, the following terms have the following meanings, unless otherwise indicated.

As used herein the term $C_{1-4}$ alkyl embraces linear or branched radicals having 1 to 4 carbon atoms. Examples include methyl, ethyl, n-propyl, i-propyl, n-butyl, sec-butyl and t-butyl radicals.

As used herein, the term $C_{1-4}$ haloalkyl group is a $C_{1-4}$ linear or branched alkyl group, which is substituted by one or more halogen atoms. Examples of said haloakyl group include, among others, $—CF_3$, $—CHF_2$, $—CHFCF_3$, $—CF_2—CF_3$, $—CH_2CF_3$, $—CH_2CF_2CF_3$, $—CH_2CHF_2$ and $—CH_2CF_2CF_2CF_3$.

As used herein, the term $C_{1-2}$ alkoxy (or alkyloxy) embraces optionally substituted, oxy-containing radicals each having alkyl portions of 1 to 2 carbon atoms. Examples include methoxy and ethoxy.

As used herein, the term $C_{1-4}$ alkoxy (or alkyloxy) embraces optionally substituted, oxy-containing radicals each having alkyl portions of 1 to 4 carbon atoms. Examples include methoxy, ethoxy, n-propoxy, i-propoxy, n-butoxy, sec-butoxy and t-butoxy.

As used herein, the term $C_{1-4}$ haloalkoxy group is a $C_{1-4}$ linear or branched alkoxy group, which is substituted by one or more halogen atoms. Examples of said haloakyl group include, among others, $—OCF_3$, $—OCHF_2$, $—OCHFCF_3$, $—OCF_2—CF_3$, $—OCH_2CF_3$, $—OCH_2CF_2CF_3$, $—OCH_2CHF_2$ and $—OCH_2CF_2CF_2CF_3$.

As used herein, the term $C_{1-4}$ hydroxyalkyl embraces linear or branched alkyl radicals having 1 to 4 carbon atoms, any one of which may be substituted with one or more hydroxyl radicals. Examples of such radicals include hydroxymethyl, hydroxyethyl, hydroxypropyl, and hydroxybutyl.

As used herein, the term $C_{6-8}$ aryl radical embraces typically a $C_{6-8}$, monocyclic aryl radical such as phenyl.

As used herein, the term 6- to 8-membered heteroaryl radical embraces typically a monocyclic 6- to 8-membered ring system comprising one heteroaromatic ring and containing at least one heteroatom selected from O, S and N. Examples include pyridyl, pyrazinyl, pyrimidinyl, pyridazinyl, azepinyl, diazepinyl, azocinyl, diazocinyl and triazocinyl.

As used herein, the term 5- to 8-membered heteroaryl radical embraces typically a monocyclic 5- to 8-membered ring system comprising one heteroaromatic ring and containing at least one heteroatom selected from O, S and N. Examples include pyridyl, pyrazinyl, pyrimidinyl, pyridazinyl, furyl, oxadiazolyl, oxazolyl, isoxazolyl, imidazolyl, pyrazolyl, thiazolyl, thiadiazolyl, thienyl, pyrrolyl, azepinyl, diazepinyl, azocinyl, diazocinyl and triazocinyl.

As used herein, the term monocyclic 4 to 7-membered heterocyclyl radical embraces typically a single ring non-aromatic, saturated or unsaturated $C_{4-7}$ carbocyclic ring system in which one or more of the carbon atoms are replaced by a heteroatom selected from N, O and S. Examples of 4 to 7-membered heterocyclic radicals include piperidyl, pyrrolidyl, pyrrolinyl, piperazinyl, morpholinyl, thiomorpholinyl, pyrrolyl, pyrazolinyl and pirazolidinyl.

As used herein, the term monocyclic 3 to 7-membered heterocyclyl radical embraces typically a single ring non-aromatic, saturated or unsaturated $C_{3-7}$ carbocyclic ring system in which one or more of the carbon atoms are replaced by a heteroatom selected from N, O and S. Examples of 3 to 7-membered heterocyclic radicals include oxiranyl, thiaranyl, aziridinyl, oxetanyl, thiatanyl, azetidinyl, piperidyl, pyrrolidyl, pyrrolinyl, tetrahydrofuranyl, tetrahydropyranyl, piperazinyl, morpholinyl, thiomorpholinyl, pyrrolyl, pyrazolinyl and pirazolidinyl.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

As used herein, the term halogen atom embraces chlorine, fluorine, bromine and iodine atoms. Examples of halogen atoms include a fluorine, chlorine or bromine atom. The term halo when used as a prefix has the same meaning.

Also included within the scope of the invention are the isomers, polymorphs, pharmaceutically acceptable salts, N-oxides, isotopes, solvates and prodrugs of the compounds of Formula (I). Any reference to a compound of Formula (I) throughout the present specification includes a reference to any isomer, polymorph, pharmaceutically acceptable salt, N-oxide, isotope, solvate or prodrug of such compound of Formula (I).

Compounds containing one or more chiral centre may be used in enantiomerically or diastereoisomerically pure form, in the form of racemic mixtures and in the form of mixtures enriched in one or more stereoisomer. The compounds of Formula (I) as described and claimed encompass the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereoisomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of the invention as described and claimed encompasses the racemic forms of the compounds as well as the individual atropisomers (an atropisomer "substantially free" of tis corresponding enantionmer) and stereoisomer-enriched mixtures, i.e. mixtures of atropisomers.

Separation of atropisomers is possibly by chiral resolution methods such as selective crystallization. In an atropoenantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

As used herein, an N-oxide is formed from the tertiary basic amines or imines present in the molecule, using a convenient oxidising agent.

The invention also includes isotopically-labeled derivatives of the compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled derivatives of the compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled derivatives include deuterated derivatives of the compounds of the invention. As used herein, the term deuterated derivative embraces compounds of the invention where in a particular position at least one hydrogen atom is replaced by deuterium. Deuterium (D or $^2$H) is a stable isotope of hydrogen which is present at a natural abundance of 0.015 molar %.

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'pro-moieties' as described, for example, in Design of Prodrugs by H. Bundgaard (Elsevier, 1985).

In one embodiment, the invention provides a compound of Formula (I), or a pharmaceutically acceptable salt, or N-oxide, or isotopically-labeled derivate thereof:

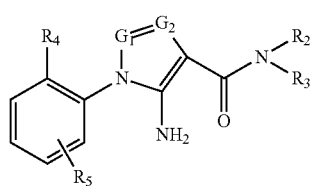

Formula (I)

Wherein
$G_1$ represents —N— or —CH—;
$G_2$ represents —N— or —CR$_1$, wherein $R_1$ is selected from the group consisting of a hydrogen atom and a lineal or branched $C_{1-4}$ alkyl group, with the proviso that at least one of $G_1$ and $G_2$ should be a —N—;

$R_2$ represents a hydrogen atom and $R_3$ represent a group of Formula (i):

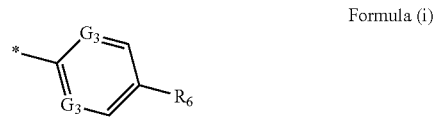

Formula (i)

wherein each $G_3$ independently represents —N— or —CR$_7$, wherein R$_7$ is selected from the group consisting of a hydrogen atom, a halogen atom, a hydroxyl group, a cyano group, a phenyl group, a lineal or branched $C_{1-4}$ alkyl group, a lineal or branched ($C_{1-4}$ alkoxy)-($C_{1-4}$ alkyl) group, —O—(CH$_2$)$_{1-2}$—NR$^a$R$^b$, —NR$^a$R$^b$, —CO—NR$^a$R$^b$, —OR$^c$ and —CH$_2$—R$^d$;

$R_6$ is selected from the group consisting of a halogen atom, a cyano group, a lineal or branched $C_{1-4}$ alkyl group, a lineal or branched $C_{1-4}$ haloalkyl group, a lineal or branched $C_{1-4}$ haloalkoxy group, —SO$_2$—CF$_3$ group, a benzyl group and —O-benzyl group;

or $R_2$ and $R_3$ together with the nitrogen atom to which they are attached form the group of Formula (ii):

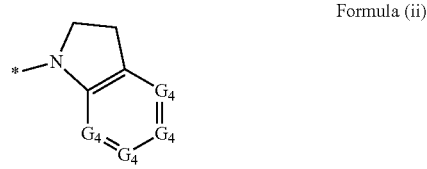

Formula (ii)

wherein each $G_4$ independently represents —CR$^8$— or —N—, wherein R$^8$ is selected from the group consisting of a hydrogen atom and a halogen atom;

$R_4$ is selected from the group consisting of a halogen atom; a hydroxyl group; a lineal or branched $C_{1-4}$ alkyl group: a lineal or branched $C_{1-4}$ haloalkyl group; a lineal or branched ($C_{1-4}$ alkyl)-($C_{1-4}$ alkoxy) group; a lineal or branched ($C_{1-4}$ alkoxy)-($C_{1-4}$ alkyl) group; a lineal or branched ($C_{1-4}$ alkoxy)-($C_{1-4}$ alkoxy) group; —O$_{(0-1)}$—(CH$_2$)$_{(0-2)}$—NR$^a$R$^b$ group; —O—(CH$_2$)$_{(0-2)}$R$^c$ group; —O—(CHR$^f$)$_1$—CO—NR$^a$R$^b$ group; —SO$_2$—NR$^a$R$^b$ group; a $C_{6-8}$ aryl group; a monocyclic 5- to 8-membered heteroaryl group containing at least one heteroatom selected from N, O and S, wherein said heteroaryl ring is optionally substituted with one or more substituents selected from a halogen atom, a $C_{1-2}$ alkyl group, a $C_{1-2}$ alkoxy group and amino group optionally substituted with one or two $C_{1-2}$ alkyl group; and a 4- to 6-membered saturated or non-saturated heterocyclyl group containing at least one heteroatom selected from N, O and S, wherein said heterocyclyl ring is optionally substituted with one or more substituents selected from a $C_{1-2}$ alkyl group, a $C_{1-2}$ alkoxy group and —C(O)O—R$^e$ group, wherein R$^e$ represents a lineal or branched $C_{1-4}$ alkyl group, and wherein R$^f$ represents a a lineal or branched $C_{1-4}$ alkyl group;

$R_5$ is selected from the group consisting of a hydrogen atom, a halogen atom, a lineal or branched $C_{1-4}$ alkyl group and a lineal or branched $C_{1-4}$ haloalkyl group;

R$^a$ and R$^b$ independently are selected from the group consisting of a hydrogen atom, a lineal or branched $C_{1-4}$ alkyl group, a lineal or branched ($C_{1-4}$ alkoxy)-($C_{1-4}$ alkyl) group and a 5- to 8-membered monocyclic heteroaryl group containing at least one heteroatom selected from N, S and O, or $R^a$ and $R^b$ together with nitrogen atom to which they are attached form a 3- to 6-membered heterocyclyl group optionally containing further heteroatom selected from N, S and O, wherein said heterocyclyl group is optionally substituted with one or more substituents selected from a $C_{1-2}$ alkyl group;

$R^c$ is selected from the group consisting of a lineal or branched $C_{1-4}$ alkyl group; a lineal or branched $C_{1-4}$ hydroxyalkyl group; a lineal or branched $C_{1-4}$ haloalkyl group; a lineal or branched ($C_{1-4}$ alkoxy)-($C_{1-4}$ alkyl) group; a lineal or branched ($C_{1-4}$ alkyl)-($C_{1-4}$ alkoxy) group; a $C_{6-8}$ aryl group; a monocyclic 5- to 8-membered heteroaryl group containing at least one heteroatom selected from N, O and S, and a 4- to 6-membered heterocyclyl group containing at least one heteroatom selected from N, O and S, wherein said heterocyclyl ring is optionally substituted with one or more substituents selected from a $C_{1-2}$ alkyl group and a $C_{1-2}$ alkoxy group;

$R^d$ is selected from the group consisting of —$NR^aR^b$ group, a 4- to 6-membered heterocyclyl group containing at least one heteroatom selected from N, O and S, wherein said heterocyclyl group is optionally substituted with one or more substituents selected from a halogen atom;

With the proviso that the compound is not any one of the following:
5-amino-N-(4-ethylphenyl)-1-(2-methylphenyl)-1H-1,2,3-triazole-4-carboxamide,
5-amino-N-(2,4-dimethylphenyl)-1-(2-methylphenyl)-1H-1,2,3-triazole-4-carboxamide,
5-amino-1-(2,5-dimethylphenyl)-N-(4-fluorophenyl)-1H-1,2,3-triazole-4-carboxamide,
5-amino-N-(2,4-dichlorophenyl)-1-(2-methylphenyl)-1H-1,2,3-triazole-4-carboxamide,
5-amino-1-(2-methylphenyl)-N-(4-methylphenyl)-1H-1,2,3-triazole-4-carboxamide,
5-amino-N-(4-chlorophenyl)-1-(2-methylphenyl)-1H-1,2,3-triazole-4-carboxamide,
5-amino-N-(4-fluorophenyl)-1-(2-methylphenyl)-1H-1,2,3-triazole-4-carboxamide,
5-amino-N-(4-bromophenyl)-1-(2-methoxyphenyl)-1H-1,2,3-triazole-4-carboxamide,
5-amino-N-(2,4-difluorophenyl)-1-(2-methoxyphenyl)-1H-1,2,3-triazole-4-carboxamide,
5-amino-1-(2-methoxyphenyl)-N-(4-methylphenyl)-1H-1,2,3-triazole-4-carboxamide,
5-amino-N-(4-fluorophenyl)-1-(2-methoxyphenyl)-1H-1,2,3-triazole-4-carboxamide.

Typically, in Formula (ii), $G_4$ represents —$CR^8$—, wherein $R^8$ is selected from the group consisting of a hydrogen atom and a halogen atom.

Typically, $R_2$ represents a hydrogen atom and $R_3$ represents a group of Formula (i), wherein each $G_3$ independently represents —N— or —$CR_7$, wherein $R_7$ is selected from the group consisting of a hydrogen atom, a cyano group, a lineal or branched $C_{1-4}$ alkyl group, a ($C_{1-2}$ alkoxy)-($C_{1-2}$ alkyl) group, and —$OR^c$, wherein $R^c$ is selected from the group consisting of a $C_{1-2}$ alkyl group and a $C_{1-2}$ haloalkyl group, preferably, $R_7$ is selected from the group consisting of a hydrogen atom, a cyano group, a lineal or branched $C_{1-4}$ alkyl group and —$OR^c$, wherein $R^c$ is a $C_{1-2}$ alkyl group. More preferably, $R_2$ represents a hydrogen atom and $R_3$ represents a group of Formula (i), wherein $G_3$ represents —N— group, preferably $R_3$ represents a pyridyn-2-yl group substituted with $R_6$. In another more preferred embodiment, $R_2$ represents a hydrogen atom and $R_3$ represents a group of Formula (i), wherein one $G_3$ represents a —N— group and the other $G_3$ represents a —$CR_7$ group, preferably $R_3$ represents a pyridyn-2-yl group substituted with $R_6$.

Typically, $R_6$ is selected from the group consisting of a halogen atom, a cyano group, a lineal or branched $C_{1-4}$ alkyl group, a lineal or branched $C_{1-4}$ haloalkyl group and a lineal or branched $C_{1-4}$ haloalkoxy group, preferably, $R_6$ is selected from the group consisting of a halogen atom, a lineal or branched $C_{1-4}$ alkyl group and a $C_{1-2}$ haloalkyl group. More preferably, $R_6$ is selected from the group consisting of a chlorine, a bromine atom, a methyl group, an ethyl group and a —$CF_3$ group, being most preferred, a chlorine atom, a methyl group and a —$CF_3$ group.

In a preferred embodiment, both $G_1$ and $G_2$ represent a —N— group.

On still another preferred embodiment, $G_1$ represents a —N— group while $G_2$ represents —$CR_1$— group, wherein $R_1$ is selected from the group consisting of a hydrogen atom, a methyl group and an ethyl group.

Typically, $R_4$ is selected from the group consisting of a halogen atom, a lineal or branched $C_{1-4}$ alkyl group, a lineal or branched $C_{1-4}$ haloalkyl group, a $C_{6-8}$ aryl group, —$O_{(0-1)}$—$(CH_2)_{(0-2)}$—$NR^aR^b$ group, —$O$—$(CH_2)_{(0-2)}R^c$ group, —$O$—$(CH_2)_1$—$CO$—$NR^aR^b$ group, wherein $R^a$ and $R^b$ independently are selected from the group consisting of a hydrogen atom, a lineal or branched $C_{1-4}$ alkyl group, and wherein $R^c$ is selected from the group consisting of a lineal or branched $C_{1-4}$ alkyl group, a lineal or branched $C_{1-4}$ hydroxyalkyl group, a lineal or branched $C_{1-4}$ haloalkyl group, preferably $R_4$ is selected from the group consisting of a halogen atom, a $C_{1-2}$ alkyl group, —$O$—$R^c$ group and —$O$—$(CH_2)_1$—$CO$—$NR^aR^b$ group, wherein $R^a$ and $R^b$ independently are selected from the group consisting of a hydrogen atom and a $C_{1-2}$ alkyl group, and wherein $R^c$ is selected from the group consisting of a $C_{1-2}$ alkyl group and a $C_{1-2}$ hydroxyalkyl group. More preferably, $R_4$ is selected from the group consisting of a fluorine atom, a methyl group, —$O$—$R^c$ group and —$O$—$(CH_2)_1$—$CO$—$NR^aR^b$ group, wherein both $R^a$ and $R^b$ represents a hydrogen atom and wherein $R^c$ is selected from the group consisting of a methyl group and a hydroxyethyl group.

Typically, $R_4$ is selected from the group consisting of a halogen atom, a hydroxyl group, a lineal or branched $C_{1-4}$ alkyl group, a lineal or branched $C_{1-4}$ haloalkyl group, a $C_{6-8}$ aryl group, —$O_{(0-1)}$—$(CH_2)_{(0-2)}$—$NR^aR^b$ group, —$O$—$(CH_2)_{(0-2)}R^c$ group, —$O$—$(CH_2)_1$—$CO$—$NR^aR^b$ group, wherein $R^a$ and $R^b$ independently are selected from the group consisting of a hydrogen atom, a lineal or branched $C_{1-4}$ alkyl group, and wherein $R^c$ is selected from the group consisting of a lineal or branched $C_{1-4}$ alkyl group, a lineal or branched ($C_{1-4}$ alkoxy)-($C_{1-4}$ alkyl) group, a lineal or branched $C_{1-4}$ haloalkyl group, preferably $R_4$ is selected from the group consisting of a halogen atom, a hydroxyl group, a $C_{1-2}$ alkyl group, —$O$—$R^c$ group and —$O$—$(CH_2)_1$—$CO$—$NR^aR^b$ group, wherein $R^a$ and $R^b$ independently are selected from the group consisting of a hydrogen atom and a $C_{1-2}$ alkyl group, and wherein $R^c$ is selected from the group consisting of a $C_{1-2}$ alkyl group and a ($C_{1-2}$ alkoxy)-($C_{1-2}$ alkyl) group. More preferably, $R_4$ is selected from the group consisting of a fluorine atom, a hydroxyl group, a methyl group, —$O$—$R^c$ group and —$O$—$(CH_2)_1$—$CO$—$NR^aR^b$ group, wherein both $R^a$ and $R^b$ represents a hydrogen atom and wherein $R^c$ is selected from the group consisting of a methyl group and a methoxyethyl group.

Typically, $R_5$ is selected from the group consisting of a hydrogen atom and a halogen atom, preferably a hydrogen atom and a fluorine atom.

In a still preferred embodiment, compounds of the present invention having the following Formula (II)

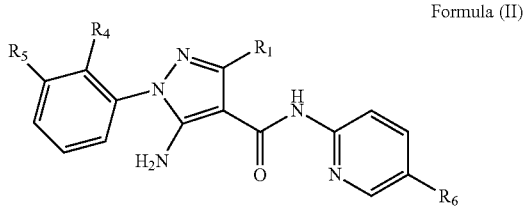

Formula (II)

wherein:
- $R_1$ is selected from the group consisting of a hydrogen atom, a methyl group and an ethyl group,
- $R_4$ is selected from the group consisting of a fluorine atom, a methyl group, —O—$R^c$ group and —O—$(CH_2)_1$—CO—$NR^aR^b$ group, wherein both $R^a$ and $R^b$ represents a hydrogen atom and wherein $R^c$ is selected from the group consisting of a methyl group and a hydroxyethyl group,
- $R_5$ is selected from the group consisting of a hydrogen atom and a fluorine atom,
- $R_6$ is selected from the group consisting of a chlorine atom, a methyl group and a —$CF_3$ group.

In a still preferred embodiment compounds of the present invention having the following Formula (II)

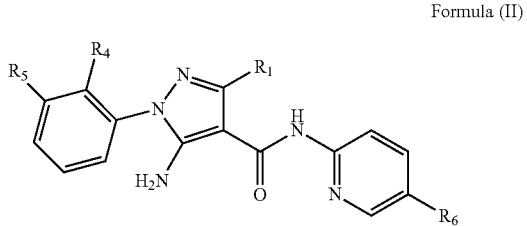

Formula (II)

wherein:
- $R_1$ is selected from the group consisting of a hydrogen atom, a methyl group and an ethyl group;
- $R_4$ is selected from the group consisting of a fluorine atom, a hydroxyl group, a methyl group, a —O—$R^c$ group and a —O—$(CH_2)_1$—CO—$NR^aR^b$ group, wherein both $R^a$ and $R^b$ represents a hydrogen atom and wherein $R^c$ is selected from the group consisting of a methyl group and a methoxyethyl group;
- $R_5$ is selected from the group consisting of a hydrogen atom and a fluorine atom;
- $R_6$ is selected from the group consisting of a chlorine atom, a methyl group and a —$CF_3$ group;

Particular individual compounds of the invention include:
5-Amino-N-(4-chlorophenyl)-1-(2-methoxyphenyl)-1H-pyrazole-4-carboxamide
5-Amino-N-(4-bromophenyl)-1-(2-methoxyphenyl)-1H-pyrazole-4-carboxamide
5-Amino-1-(2-methoxyphenyl)-N-(p-tolyl)-1H-pyrazole-4-carboxamide
5-Amino-N-(5-chloropyridin-2-yl)-1-(o-tolyl)-1H-pyrazole-4-carboxamide
5-Amino-1-(o-tolyl)-N-(5-(trifluoromethyl)pyridin-2-yl)-1H-pyrazole-4-carboxamide
5-Amino-N-(4-chloro-2-methyl-phenyl)-1-(o-tolyl)-1H-pyrazole-4-carboxamide
5-Amino-N-(4-chloro-2-fluoro-phenyl)-1-(o-tolyl)-1H-pyrazole-4-carboxamide
5-Amino-N-(4-chloro-2-cyano-phenyl)-1-(o-tolyl)-1H-pyrazole-4-carboxamide
5-Amino-N-(4-chloro-2-methoxy-phenyl)-1-(o-tolyl)-1H-pyrazole-4-carboxamide
5-Amino-N-(5-chloro-3-methyl-2-pyridyl)-1-(o-tolyl)-1H-pyrazole-4-carboxamide
5-Amino-N-[3-fluoro-5-(trifluoromethyl)-2-pyridyl]-1-(o-tolyl)-1H-pyrazole-4-carboxamide
5-Amino-N-(5-chloro-3-methoxy-2-pyridyl)-1-(o-tolyl)-1H-pyrazole-4-carboxamide
5-Amino-N-(4-chloro-2-(methylamino)phenyl)-1-(o-tolyl)-1H-pyrazole-4-carboxamide
5-Amino-N-(2-carbamoyl-4-chlorophenyl)-1-(o-tolyl)-1H-pyrazole-4-carboxamide
5-Amino-N-(2-cyano-4-(trifluoromethyl)phenyl)-1-(o-tolyl)-1H-pyrazole-4-carboxamide
5-Amino-N-(2-methoxy-4-(trifluoromethyl)phenyl)-1-(o-tolyl)-1H-pyrazole-4-carboxamide
5-Amino-N-(4-chloro-2-hydroxyphenyl)-1-(o-tolyl)-1H-pyrazole-4-carboxamide
5-Amino-N-(4-chloro-2-((dimethylamino)methyl)phenyl)-1-(o-tolyl)-1H-pyrazole-4-carboxamide
5-Amino-N-(4-chloro-2-(methoxymethyl)phenyl)-1-(o-tolyl)-1H-pyrazole-4-carboxamide
5-Amino-N-(4-bromo-2-methoxy-phenyl)-1-(o-tolyl)-1H-pyrazole-4-carboxamide
5-Amino-N-(4-chloro-2-fluoro-phenyl)-1-[2-(2-methoxyethoxy)phenyl]-1H-pyrazole-4-carboxamide
5-Amino-N-(4-chloro-2-methoxy-phenyl)-1-[2-(2-methoxyethoxy)phenyl]-1H-pyrazole-4-carboxamide
5-Amino-N-(5-chloro-2-pyridyl)-1-[2-(2-methoxyethoxy)phenyl]-1H-pyrazole-4-carboxamide
5-Amino-N-[4-chloro-2-[[isopropyl(methyl)amino]methyl]phenyl]-1-(o-tolyl)-1H-pyrazole-4-carboxamide
5-Amino-N-[4-chloro-2-(pyrrolidin-1-ylmethyl)phenyl]-1-(o-tolyl)-1H-pyrazole-4-carboxamide
5-Amino-N-[4-chloro-2-(morpholinomethyl)phenyl]-1-(o-tolyl)-1H-pyrazole-4-carboxamide
5-Amino-N-(4-cyanophenyl)-1-(o-tolyl)-1H-pyrazole-4-carboxamide
5-Amino-N-(4-tert-butylphenyl)-1-(o-tolyl)-1H-pyrazole-4-carboxamide
5-Amino-N-[4-chloro-2-[[(3R)-3-fluoropyrrolidin-1-yl]methyl]phenyl]-1-(o-tolyl)-1H-pyrazole-4-carboxamide
5-Amino-N-(4-chloro-2-phenyl-phenyl)-1-(o-tolyl)-1H-pyrazole-4-carboxamide
5-Amino-1-[2-(2-methoxyethoxy)phenyl]-N-[4-(trifluoromethyl)phenyl]-1H-pyrazole-4-carboxamide
5-Amino-N-[2-fluoro-4-(trifluoromethyl)phenyl]-1-[2-(2-methoxyethoxy)phenyl]-1H-pyrazole-4-carboxamide
5-Amino-N-(2-bromo-4-chloro-phenyl)-1-(o-tolyl)-1H-pyrazole-4-carboxamide
5-Amino-1-[2-(2-methoxyethoxy)phenyl]-N-[2-methyl-4-(trifluoromethyl)phenyl]-1H-pyrazole-4-carboxamide
5-Amino-N-(4-chloro-2-methoxy-phenyl)-3-methyl-1-(o-tolyl)-1H-pyrazole-4-carboxamide
5-Amino-N-(4-chloro-2-methoxy-phenyl)-1-[2-(2-methoxyethoxy)phenyl]-3-methyl-1H-pyrazole-4-carboxamide 5-Amino-1-[2-(2-methoxyethoxy)phenyl]-N-[2-methoxy-4-(trifluoromethyl)phenyl]-3-methyl-1H-pyrazole-4-carboxamide
5-Amino-N-(2-fluoro-4-(trifluoromethyl)phenyl)-1-(2-(2-methoxyethoxy)phenyl)-3-methyl-1H-pyrazole-4-carboxamide
5-Amino-N-[2-cyano-4-(trifluoromethyl)phenyl]-1-(2-ethylphenyl)-3-methyl-1H-pyrazole-4-carboxamide
5-Amino-N-(4-bromo-2-methoxy-phenyl)-1-(2-ethylphenyl)-3-methyl-1H-pyrazole-4-carboxamide
5-Amino-N-(4-chloro-2-methoxy-phenyl)-1-(2-ethylphenyl)-3-methyl-1H-pyrazole-4-carboxamide
5-Amino-N-(5-chloro-2-pyridyl)-1-(2-ethylphenyl)-3-methyl-1H-pyrazole-4-carboxamide
5-Amino-N-(4-chloro-2-fluoro-phenyl)-1-[2-(2-methoxyethoxy)phenyl]-3-methyl-1H-pyrazole-4-carboxamide
5-Amino-N-[2-fluoro-4-(trifluoromethyl)phenyl]-3-methyl-1-(o-tolyl)-1H-pyrazole-4-carboxamide
5-Amino-1-(2-ethylphenyl)-3-methyl-N-[5-(trifluoromethyl)-2-pyridyl]-1H-pyrazole-4-carboxamide
5-Amino-N-(5-chloro-2-pyridyl)-1-[2-(2-methoxyethoxy)phenyl]-3-methyl-1H-pyrazole-4-carboxamide
5-Amino-1-(o-tolyl)-N-[4-(trifluoromethylsulfonyl)phenyl]-1H-pyrazole-4-carboxamide
5-Amino-N-[4-bromo-2-(difluoromethoxy)phenyl]-1-(o-tolyl)-1H-pyrazole-4-carboxamide
5-Amino-N-(4-chloro-2-fluoro-phenyl)-3-methyl-1-(o-tolyl)-1H-pyrazole-4-carboxamide
5-Amino-N-(5-methylpyridin-2-yl)-1-(o-tolyl)-1H-pyrazole-4-carboxamide
5-Amino-N-(5-cyanopyridin-2-yl)-1-(o-tolyl)-1H-pyrazole-4-carboxamide
5-Amino-N-(5-bromopyridin-2-yl)-1-(o-tolyl)-1H-pyrazole-4-carboxamide
5-Amino-1-(o-tolyl)-N-(5-(trifluoromethoxy)pyridin-2-yl)-1H-pyrazole-4-carboxamide
5-Amino-1-(2-methoxyphenyl)-N-[5-(2,2,2-trifluoroethoxy)-2-pyridyl]pyrazole-4-carboxamide
5-Amino-1-(3-fluoro-2-methylphenyl)-N-(5-(trifluoromethoxy)pyridin-2-yl)-1H-pyrazole-4-carboxamide
5-Amino-N-(5-bromopyridin-2-yl)-1-(2-fluorophenyl)-1H-pyrazole-4-carboxamide
(5-Amino-1-(3-fluoro-2-methylphenyl)-1H-pyrazol-4-yl)(5-chloroindolin-1-yl)methanone
5-Amino-1-(3-fluoro-2-methylphenyl)-N-(4-(trifluoromethyl)phenyl)-1H-pyrazole-4-carboxamide
(5-Amino-1-(o-tolyl)-1H-pyrazol-4-yl)(5-chloroindolin-1-yl)methanone
[5-Amino-1-(2-fluorophenyl)pyrazol-4-yl]-(5-chloroindolin-1-yl)methanone
(5-Amino-1-(2-methoxyphenyl)-1H-pyrazol-4-yl)(5-chloroindolin-1-yl)methanone
5-Amino-N-(4-bromophenyl)-1-(o-tolyl)-1H-1,2,3-triazole-4-carboxamide
5-Amino-1-(2-methoxyphenyl)-N-(5-(trifluoromethyl)pyridin-2-yl)-1H-1,2,3-triazole-4-carboxamide
5-Amino-1-(2-methoxyphenyl)-N-(p-tolyl)-1H-1,2,3-triazole-4-carboxamide
5-Amino-1-(2-methoxyphenyl)-N-(4-(trifluoromethyl)phenyl)-1H-1,2,3-triazole-4-carboxamide
5-Amino-1-(2-methoxyphenyl)-N-(4-(trifluoromethoxy)phenyl)-1H-1,2,3-triazole-4-carboxamide
5-Amino-N-(4-isopropylphenyl)-1-(2-methoxyphenyl)-1H-1,2,3-triazole-4-carboxamide
5-Amino-N-(5-chloropyridin-2-yl)-1-(2-methoxyphenyl)-1H-1,2,3-triazole-4-carboxamide
5-Amino-1-(2-methoxyphenyl)-N-(4-phenoxyphenyl)-1H-1,2,3-triazole-4-carboxamide
5-Amino-1-(2-methoxyphenyl)-N-(4-(1,1,2,2-tetrafluoroethoxy)phenyl)-1H-1,2,3-triazole-4-carboxamide
5-Amino-N-(4-(benzyloxy)phenyl)-1-(2-methoxyphenyl)-1H-1,2,3-triazole-4-carboxamide
5-Amino-N-(4-benzylphenyl)-1-(2-methoxyphenyl)-1H-1,2,3-triazole-4-carboxamide
5-Amino-N-(5-chloropyridin-2-yl)-1-(o-tolyl)-1H-1,2,3-triazole-4-carboxamide
5-Amino-1-(o-tolyl)-N-(5-(trifluoromethyl)pyridin-2-yl)-1H-1,2,3-triazole-4-carboxamide
5-Amino-N-(5-chloropyridin-2-yl)-1-(3-fluoro-2-methylphenyl)-1H-1,2,3-triazole-4-carboxamide
5-Amino-1-(3-fluoro-2-methylphenyl)-N-(5-(trifluoromethyl)pyridin-2-yl)-1H-1,2,3-triazole-4-carboxamide
5-Amino-N-(4-chlorophenyl)-1-(2,6-dimethylphenyl)-1H-pyrazole-4-carboxamide
5-Amino-1-(2-chlorophenyl)-N-(4-chlorophenyl)pyrazole-4-carboxamide
5-Amino-N-(4-chlorophenyl)-1-(o-tolyl)pyrazole-4-carboxamide
5-Amino-N-(4-chlorophenyl)-1-[2-(trifluoromethyl)phenyl]pyrazole-4-carboxamide
5-Amino-N-(4-chlorophenyl)-1-(2,3-dichlorophenyl)-1H-pyrazole-4-carboxamide
5-Amino-N-(4-chlorophenyl)-1-(2-fluorophenyl)pyrazole-4-carboxamide
5-Amino-N-(4-chlorophenyl)-1-[3-(trifluoromethyl)phenyl]pyrazole-4-carboxamide
5-Amino-1-(2-ethylphenyl)-N-[5-trifluoromethyl-2-pyridyl]pyrazole-4-carboxamide
5-Amino-1-(2-chlorophenyl)-N-[5-trifluoromethyl-2-pyridyl]pyrazole-4-carboxamide
5-Amino-1-(2-isopropylphenyl)-N-[5-trifluoromethyl-2-pyridyl]pyrazole-4-carboxamide
5-Amino-1-[2-(trifluoromethoxy)phenyl]-N-[5-trifluoromethyl-2-pyridyl]pyrazole-4-carboxamide
5-Amino-1-[2-(2-methoxyethoxy)phenyl]-N-[5-trifluoromethyl-2-pyridyl]pyrazole-4-carboxamide
5-Amino-N-(5-chloropyridin-2-yl)-1-(2-ethylphenyl)-1H-pyrazole-4-carboxamide
5-Amino-1-(2-(methoxymethyl)phenyl)-N-(5-(trifluoromethyl)pyridin-2-yl)-1H-pyrazole-4-carboxamide
5-Amino-N-(5-chloropyridin-2-yl)-1-(2-methoxyphenyl)-1H-pyrazole-4-carboxamide
5-Amino-1-(2-chlorophenyl)-N-(5-chloropyridin-2-yl)-1H-pyrazole-4-carboxamide
5-Amino-N-(4-chloro-2-methoxyphenyl)-1-(2-methoxyphenyl)-1H-pyrazole-4-carboxamide
5-Amino-N-(4-chloro-2-methoxyphenyl)-1-(2-ethylphenyl)-1H-pyrazole-4-carboxamide
1-(2-(1H-Pyrazol-1-yl)phenyl)-5-amino-N-(5-(trifluoromethyl)pyridin-2-yl)-1H-pyrazole-4-carboxamide
5-Amino-1-(2-bromophenyl)-N-(5-chloropyridin-2-yl)-1H-pyrazole-4-carboxamide
5-Amino-N-(4-chloro-2-methoxyphenyl)-1-(5-fluoro-2-methylphenyl)-1H-pyrazole-4-carboxamide
5-Amino-N-(4-chloro-2-methoxyphenyl)-1-(4-fluoro-2-methylphenyl)-1H-pyrazole-4-carboxamide
5-Amino-N-(4-chloro-2-methoxyphenyl)-1-(3-fluoro-2-methylphenyl)-1H-pyrazole-4-carboxamide
5-Amino-N-(4-chloro-2-methoxyphenyl)-1-(2,3-dimethylphenyl)-1H-pyrazole-4-carboxamide
5-Amino-N-(4-chloro-2-methoxyphenyl)-1-(2,5-dimethylphenyl)-1H-pyrazole-4-carboxamide 5-Amino-1-(2-bromophenyl)-N-(5-(trifluoromethyl)pyridin-2-yl)-1H-pyrazole-4-carboxamide
5-Amino-N-(4-chloro-2-methoxyphenyl)-1-(2-chlorophenyl)-1H-pyrazole-4-carboxamide
5-Amino-1-(2-methyl-5-(trifluoromethyl)phenyl)-N-(5-(trifluoromethyl)pyridin-2-yl)-1H-pyrazole-4-carboxamide
5-Amino-1-[2-(5-methyl-1,2,4-oxadiazol-3-yl)phenyl]-N-[5-trifluoromethyl-2-pyridyl]pyrazole-4-carboxamide
5-Amino-1-(2-fluoro-6-methylphenyl)-N-[5-trifluoromethyl-2-pyridyl]pyrazole-4-carboxamide
5-Amino-1-(2-(oxazol-5-yl)phenyl)-N-(5-(trifluoromethyl)pyridin-2-yl)-1H-pyrazole-4-carboxamide
5-Amino-1-[2-(dimethylaminomethyl)phenyl]-N-[5-trifluoromethyl-2-pyridyl]pyrazole-4-carboxamide
5-Amino-N-(4-chloro-2-methoxyphenyl)-1-[3-fluoro-2-(2-methoxyethoxy)phenyl]pyrazole-4-carboxamide
5-Amino-N-(5-chloro-2-pyridyl)-1-[3-fluoro-2-(2-methoxyethoxy)phenyl]-pyrazole-4-carboxamide
5-Amino-N-(5-chloro-2-pyridyl)-1-[2-(dimethylaminomethyl)-phenyl]-pyrazole-4-carboxamide
5-Amino-1-[3-fluoro-2-(2-methoxyethoxy)phenyl]-N-[5-trifluoromethyl-2-pyridyl]pyrazole-4-carboxamide
5-Amino-1-[3-fluoro-2-(2-methoxyethoxy)phenyl]-3-methyl-N-[5-(trifluoromethyl)-2-pyridyl]pyrazole-4-carboxamide
5-Amino-3-ethyl-1-(2-methoxyphenyl)-N-(5-(trifluoromethyl)pyridin-2-yl)-1H-pyrazole-4-carboxamide
5-Amino-1-(2-(2-methoxyethoxy)phenyl)-3-methyl-N-(2-methyl-4-(trifluoromethyl)phenyl)-1H-pyrazole-4-carboxamide
5-Amino-1-(2-bromo-3-fluorophenyl)-3-methyl-N-[5-trifluoromethyl-2-pyridyl]pyrazole-4-carboxamide
5-Amino-1-(2-bromo-6-fluorophenyl)-3-methyl-N-[5-trifluoromethyl-2-pyridyl]pyrazole-4-carboxamide
5-Amino-1-(2-chloro-6-fluorophenyl)-3-methyl-N-[5-trifluoromethyl-2-pyridyl]pyrazole-4-carboxamide
5-Amino-1-(2-bromo-3-fluorophenyl)-N-(5-chloro-2-pyridyl)-3-methyl-pyrazole-4-carboxamide
5-Amino-1-(2-chloro-6-fluorophenyl)-N-(5-chloro-2-pyridyl)-3-methyl-pyrazole-4-carboxamide
5-Amino-1-(2-bromophenyl)-N-(5-chloro-2-pyridyl)-3-methyl-pyrazole-4-carboxamide
5-Amino-1-(3-fluoro-2-methylphenyl)-3-methyl-N-[5-trifluoromethyl-2-pyridyl]pyrazole-4-carboxamide
5-Amino-1-(2-methoxyphenyl)-3-methyl-N-[5-trifluoromethyl-2-pyridyl]pyrazole-4-carboxamide
5-Amino-N-(5-chloro-2-pyridyl)-1-(2-methoxyphenyl)-3-methyl-pyrazole-4-carboxamide
5-Amino-1-(2-bromo-6-fluorophenyl)-N-[5-trifluoromethyl-2-pyridyl]pyrazole-4-carboxamide
5-Amino-1-(2-chloro-6-fluorophenyl)-N-[5-trifluoromethyl-2-pyridyl]pyrazole-4-carboxamide
5-Amino-N-(5-chloropyridin-2-yl)-1-(3-fluoro-2-methylphenyl)-1H-pyrazole-4-carboxamide
5-Amino-1-(2-bromo-6-fluorophenyl)-N-(5-chloro-2-pyridyl)pyrazole-4-carboxamide
5-Amino-1-(2-fluoro-6-methoxyphenyl)-3-methyl-N-[5-trifluoromethyl-2-pyridyl]pyrazole-4-carboxamide
5-Amino-1-(2-chloro-3-fluorophenyl)-3-methyl-N-[5-trifluoromethyl-2-pyridyl]pyrazole-4-carboxamide
5-Amino-N-(5-chloro-2-pyridyl)-1-(2-fluoro-6-methoxyphenyl)-3-methyl-pyrazole-4-carboxamide
5-Amino-1-(2-chloro-3-fluorophenyl)-N-(5-chloro-2-pyridyl)-3-methyl-pyrazole-4-carboxamide
5-Amino-N-(5-chloro-2-pyridyl)-1-(2-fluoro-6-methylphenyl)-3-methyl-pyrazole-4-carboxamide
5-Amino-3-ethyl-1-(o-tolyl)-N-[5-trifluoromethyl-2-pyridyl]pyrazole-4-carboxamide
5-Amino-3-ethyl-1-(2-(2-methoxyethoxy)phenyl)-N-(5-(trifluoromethyl)pyridin-2-yl)-1H-pyrazole-4-carboxamide
5-Amino-1-(2-chloro-6-fluorophenyl)-N-(5-chloro-2-pyridyl)pyrazole-4-carboxamide
5-Amino-N-(5-chloro-2-pyridyl)-1-(3-fluoro-2-methylphenyl)-3-methyl-pyrazole-4-carboxamide
5-Amino-1-(2-ethylphenyl)-N-(3-fluoro-5-(trifluoromethyl)pyridin-2-yl)-1H-pyrazole-4-carboxamide
5-Amino-1-(o-tolyl)-N-(5-(2,2,2-trifluoroethoxy)pyridin-2-yl)-1H-pyrazole-4-carboxamide
5-Amino-1-(2-ethylphenyl)-N-(5-(2,2,2-trifluoroethoxy)pyridin-2-yl)-1H-pyrazole-4-carboxamide
5-Amino-1-(2-(2-methoxyethoxy)phenyl)-N-(5-(2,2,2-trifluoroethoxy)pyridin-2-yl)-1H-pyrazole-4-carboxamide
5-Amino-1-(3-fluoro-2-methylphenyl)-N-(5-(2,2,2-trifluoroethoxy)pyridin-2-yl)-1H-pyrazole-4-carboxamide
5-Amino-3-ethyl-1-(3-fluoro-2-methylphenyl)-N-[5-trifluoromethyl-2-pyridyl]pyrazole-4-carboxamide
5-Amino-N-(5-chloro-2-pyridyl)-3-ethyl-1-(3-fluoro-2-methylphenyl)pyrazole-4-carboxamide
5-Amino-1-(3-fluoro-2-methylphenyl)-N-[5-trifluoromethyl-2-pyridyl]pyrazole-4-carboxamide
5-Amino-N-(4-chloro-2-fluorophenyl)-1-(2-methoxyphenyl)-1H-pyrazole-4-carboxamide
5-Amino-1-(3-fluoro-2-methylphenyl)-N-(5-iodopyridin-2-yl)-1H-pyrazole-4-carboxamide
5-Amino-N-(5-chloropyridin-2-yl)-1-(2-fluorophenyl)-1H-pyrazole-4-carboxamide
5-amino-1-(2-fluorophenyl)-N-(5-(trifluoromethyl)pyridin-2-yl)-1H-pyrazole-4-carboxamide
5-Amino-3-methyl-1-(2-(oxazol-5-yl)phenyl)-N-(5-(trifluoromethyl)pyridin-2-yl)-1H-pyrazole-4-carboxamide
5-Amino-3-ethyl-1-(2-fluorophenyl)-N-(5-(trifluoromethyl)pyridin-2-yl)-1H-pyrazole-4-carboxamide
5-Amino-N-(5-chloropyridin-2-yl)-3-ethyl-1-(2-fluorophenyl)-1H-pyrazole-4-carboxamide
5-Amino-1-(2-fluorophenyl)-3-methyl-N-(5-(trifluoromethyl)pyridin-2-yl)-1H-pyrazole-4-carboxamide
5-Amino-N-(5-chloropyridin-2-yl)-1-(2-fluorophenyl)-3-methyl-1H-pyrazole-4-carboxamide
5-Amino-N-(5-chloropyridin-2-yl)-1-(2-fluoro-3-methylphenyl)-1H-pyrazole-4-carboxamide
5-Amino-1-(2-fluoro-3-methylphenyl)-N-(5-(trifluoromethyl)pyridin-2-yl)-1H-pyrazole-4-carboxamide
5-Amino-N-(5-chloropyridin-2-yl)-1-(2-iodophenyl)-1H-pyrazole-4-carboxamide
5-Amino-N-(5-chloropyridin-2-yl)-1-(3-fluoro-2-(oxazol-5-yl)phenyl)-3-methyl-1H-pyrazole-4-carboxamide
5-Amino-1-(3-fluoro-2-(oxazol-5-yl)phenyl)-3-methyl-N-(5-(trifluoromethyl)pyridin-2-yl)-1H-pyrazole-4-carboxamide
5-Amino-N-(5-chloropyridin-2-yl)-1-(3-fluoro-2-(oxazol-5-yl)phenyl)-1H-pyrazole-4-carboxamide
5-Amino-1-(3-fluoro-2-(oxazol-5-yl)phenyl)-N-(5-(trifluoromethyl)pyridin-2-yl)-1H-pyrazole-4-carboxamide
5-Amino-3-ethyl-1-(3-fluoro-2-(oxazol-5-yl)phenyl)-N-(5-(trifluoromethyl)pyridin-2-yl)-1H-pyrazole-4-carboxamide
5-Amino-3-ethyl-1-(2-(oxazol-5-yl)phenyl)-N-(5-(trifluoromethyl)pyridin-2-yl)-1H-pyrazole-4-carboxamide
5-Amino-1-(2-iodophenyl)-N-(5-(trifluoromethyl)pyridin-2-yl)-1H-pyrazole-4-carboxamide
5-Amino-1-(2-iodophenyl)-3-methyl-N-(5-(trifluoromethyl)pyridin-2-yl)-1H-pyrazole-4-carboxamide 5-Amino-N-(5-chloropyridin-2-yl)-1-(2-(oxazol-5-yl)phenyl)-1H-pyrazole-4-carboxamide
5-Amino-1-(2-chloro-3-fluorophenyl)-N-(5-chloropyridin-2-yl)-1H-pyrazole-4-carboxamide
5-Amino-1-(2-chloro-3-fluorophenyl)-N-(5-(trifluoromethyl)pyridin-2-yl)-1H-pyrazole-4-carboxamide
5-Amino-1-(2-(5-chlorothiopheN-2-yl)phenyl)-N-(5-(trifluoromethyl)pyridin-2-yl)-1H-pyrazole-4-carboxamide
5-Amino-N-(5-chloropyridin-2-yl)-1-(2-(pyrrolidin-1-ylsulfonyl)phenyl)-1H-pyrazole-4-carboxamide
5-Amino-N-(5-chloropyridin-2-yl)-1-(2-(N-methyl-N-(pyridin-3-yl)sulfamoyl)phenyl)-1H-pyrazole-4-carboxamide
5-Amino-1-(2-bromophenyl)-3-methyl-N-[5-trifluoromethyl-2-pyridyl]pyrazole-4-carboxamide
5-Amino-N-(5-chloro-2-pyridyl)-1-(2-fluoro-6-methylphenyl)pyrazole-4-carboxamide
5-Amino-N-(5-chloro-2-pyridyl)-1-(2-fluoro-6-methoxyphenyl)pyrazole-4-carboxamide
5-Amino-1-(2-chlorophenyl)-N-(5-chloro-2-pyridyl)-3-methyl-pyrazole-4-carboxamide
5-Amino-1-(2-chlorophenyl)-3-methyl-N-[5-trifluoromethyl-2-pyridyl]pyrazole-4-carboxamide
5-Amino-3-methyl-1-(2-morpholinophenyl)-N-[5-trifluoromethyl-2-pyridyl]pyrazole-4-carboxamide
5-Amino-1-(2-bromo-6-fluorophenyl)-N-(5-chloro-2-pyridyl)-3-methyl-pyrazole-4-carboxamide
5-Amino-3-isopropyl-1-(o-tolyl)-N-[5-(trifluoromethyl)-2-pyridyl]pyrazole-4-carboxamide
5-Amino-1-(2-fluoro-6-methylphenyl)-3-methyl-N-[5-trifluoromethyl-2-pyridyl]pyrazole-4-carboxamide
5-Amino-1-(2-fluoro-6-methoxyphenyl)-N-[5-trifluoromethyl-2-pyridyl]pyrazole-4-carboxamide
5-Amino-1-[2-(2-methoxyethoxy)phenyl]-3-methyl-N-[5-trifluoromethyl-2-pyridyl]pyrazole-4-carboxamide
5-Amino-1-(3-fluoro-2-methoxyphenyl)-N-[5-trifluoromethyl-2-pyridyl]pyrazole-4-carboxamide
5-Amino-N-(5-chloro-2-pyridyl)-1-(3-fluoro-2-methoxyphenyl)pyrazole-4-carboxamide
5-Amino-1-(2,6-difluorophenyl)-N-[5-trifluoromethyl-2-pyridyl]pyrazole-4-carboxamide
5-Amino-1-(2,6-dimethyl phenyl)-N-[5-trifluoromethyl-2-pyridyl]pyrazole-4-carboxamide
5-Amino-1-(2,6-difluorophenyl)-3-methyl-N-[5-trifluoromethyl-2-pyridyl]pyrazole-4-carboxamide
5-Amino-1-(2,6-dimethyl phenyl)-3-methyl-N-[5-trifluoromethyl-2-pyridyl]pyrazole-4-carboxamide
5-Amino-1-(2-chloro-6-methylphenyl)-3-methyl-N-[5-trifluoromethyl-2-pyridyl]pyrazole-4-carboxamide
5-Amino-1-(2,6-dichlorophenyl)-N-[5-trifluoromethyl-2-pyridyl]pyrazole-4-carboxamide
5-Amino-1-(2-chloro-6-methylphenyl)-N-[5-trifluoromethyl-2-pyridyl]pyrazole-4-carboxamide
5-Amino-1-(2,6-dichlorophenyl)-3-methyl-N-[5-trifluoromethyl-2-pyridyl]pyrazole-4-carboxamide
5-Amino-1-(2-bromo-3-methylphenyl)-N-(5-chloropyridin-2-yl)-1H-pyrazole-4-carboxamide
1-([1,1'-Biphenyl]-2-yl)-5-amino-N-(5-chloropyridin-2-yl)-1H-pyrazole-4-carboxamide
5-Amino-1-(2-(2-methoxypyridin-4-yl)phenyl)-N-(5-(trifluoromethyl)pyridin-2-yl)-1H-pyrazole-4-carboxamide
5-Amino-N-(5-chloropyridin-2-yl)-1-(2-(pyridin-3-yl)phenyl)-1H-pyrazole-4-carboxamide
5-Amino-N-(5-chloropyridin-2-yl)-1-(2-(2-methoxypyridin-4-yl)phenyl)-1H-pyrazole-4-carboxamide
5-Amino-N-(5-chloropyridin-2-yl)-1-(2-(1-methyl-1H-pyrazol-4-yl)phenyl)-1H-pyrazole-4-carboxamide
5-Amino-3-methyl-1-(2-(pyridin-3-yl)phenyl)-N-(5-(trifluoromethyl)pyridin-2-yl)-1H-pyrazole-4-carboxamide
5-Amino-1-(2-(2-methoxypyridin-4-yl)phenyl)-3-methyl-N-(5-(trifluoromethyl)pyridin-2-yl)-1H-pyrazole-4-carboxamide
5-Amino-1-(2-(pyridin-3-yl)phenyl)-N-(5-(trifluoromethyl)pyridin-2-yl)-1H-pyrazole-4-carboxamide
5-Amino-1-(2-(pyridin-4-yl)phenyl)-N-(5-(trifluoromethyl)pyridin-2-yl)-1H-pyrazole-4-carboxamide
5-Amino-1-(2-(5-fluoropyridin-3-yl)phenyl)-N-(5-(trifluoromethyl)pyridin-2-yl)-1H-pyrazole-4-carboxamide
5-Amino-N-(5-chloropyridin-2-yl)-1-(2-(6-methoxypyridin-3-yl)phenyl)-1H-pyrazole-4-carboxamide
1-(2-(1H-Pyrazol-4-yl)phenyl)-5-amino-N-(5-chloropyridin-2-yl)-1H-pyrazole-4-carboxamide
5-Amino-N-(5-chloropyridin-2-yl)-1-(3-fluoro-2-(2-methoxypyridin-4-yl)phenyl)-1H-pyrazole-4-carboxamide
5-Amino-N-(5-chloropyridin-2-yl)-1-(2-hydroxyphenyl)-1H-pyrazole-4-carboxamide
5-Amino-1-(2-hydroxyphenyl)-N-(5-(trifluoromethyl)pyridin-2-yl)-1H-pyrazole-4-carboxamide
5-Amino-N-(5-chloropyridin-2-yl)-1-(2-ethoxyphenyl)-1H-pyrazole-4-carboxamide
5-Amino-N-(5-chloropyridin-2-yl)-1-(2-(2-(dimethylamino)ethoxy)phenyl)-1H-pyrazole-4-carboxamide
(R)-5-Amino-N-(5-chloropyridin-2-yl)-1-(2-((tetrahydrofuraN-3-yl)oxy)phenyl)-1H-pyrazole-4-carboxamide
5-Amino-N-(5-chloropyridin-2-yl)-1-(2-((1-methylpiperidiN-4-yl)oxy)phenyl)-1H-pyrazole-4-carboxamide
5-Amino-1-(2-(benzyloxy)phenyl)-N-(5-chloropyridin-2-yl)-1H-pyrazole-4-carboxamide
5-Amino-1-(2-isopropoxyphenyl)-N-(5-(trifluoromethyl)pyridin-2-yl)-1H-pyrazole-4-carboxamide
5-Amino-N-(4-chloro-2-(2-(dimethylamino)ethoxy)phenyl)-1-(o-tolyl)-1H-pyrazole-4-carboxamide
(R)-5-Amino-N-(4-chloro-2-((tetrahydrofuraN-3-yl)oxy)phenyl)-1-(o-tolyl)-1H-pyrazole-4-carboxamide
5-Amino-N-(4-chloro-2-ethoxyphenyl)-1-(o-tolyl)-1H-pyrazole-4-carboxamide
5-Amino-N-(4-chloro-2-(2-methoxyethoxy)phenyl)-1-(o-tolyl)-1H-pyrazole-4-carboxamide
5-Amino-N-(4-chloro-2-((1-methylpiperidiN-4-yl)oxy)phenyl)-1-(o-tolyl)-1H-pyrazole-4-carboxamide
5-Amino-1-(2-((2-methoxyethyl)amino)phenyl)-N-(5-(trifluoromethyl)pyridin-2-yl)-1H-pyrazole-4-carboxamide
5-Amino-1-(2-((2-methoxyethyl)(methyl)amino)phenyl)-N-(5-(trifluoromethyl)pyridin-2-yl)-1H-pyrazole-4-carboxamide
5-Amino-1-(2-(3-methoxypyrrolidin-1-yl)phenyl)-N-(5-(trifluoromethyl)pyridin-2-yl)-1H-pyrazole-4-carboxamide
5-Amino-1-(2-(4-methoxypiperidiN-1-yl)phenyl)-N-(5-(trifluoromethyl)pyridin-2-yl)-1H-pyrazole-4-carboxamide
5-Amino-1-(2-((3-methyloxetan-3-yl)methoxy)phenyl)-N-(5-(trifluoromethyl)pyridin-2-yl)-1H-pyrazole-4-carboxamide
1-(2-(2-(1H-Imidazol-1-yl)ethoxy)phenyl)-5-amino-N-(5-(trifluoromethyl)pyridin-2-yl)-1H-pyrazole-4-carboxamide
5-Amino-1-(2-((tetrahydro-2H-pyraN-4-yl)oxy)phenyl)-N-(5-(trifluoromethyl)pyridin-2-yl)-1H-pyrazole-4-carboxamide
5-Amino-1-(2-((tetrahydrofuraN-3-yl)oxy)phenyl)-N-(5-(trifluoromethyl)pyridin-2-yl)-1H-pyrazole-4-carboxamide 5-Amino-1-(2-((4-methylmorpholiN-2-yl)methoxy)phenyl)-N-(5-(trifluoromethyl)pyridin-2-yl)-1H-pyrazole-4-carboxamide
1-(2-(2-(1H-Pyrazol-1-yl)ethoxy)phenyl)-5-amino-N-(5-(trifluoromethyl)pyridin-2-yl)-1H-pyrazole-4-carboxamide
5-Amino-1-(2-((1-methylpiperidiN-3-yl)methoxy)phenyl)-N-(5-(trifluoromethyl)pyridin-2-yl)-1H-pyrazole-4-carboxamide
5-Amino-1-(2-(2-amino-2-oxoethoxy)phenyl)-N-(5-(trifluoromethyl)pyridin-2-yl)-1H-pyrazole-4-carboxamide
5-Amino-1-(2-(2-amino-2-oxoethoxy)phenyl)-3-ethyl-N-(5-(trifluoromethyl)pyridin-2-yl)-1H-pyrazole-4-carboxamide
5-Amino-1-(2-(2-amino-2-oxoethoxy)phenyl)-N-(5-(trifluoromethoxy)pyridin-2-yl)-1H-pyrazole-4-carboxamide
5-Amino-1-(2-(2-amino-2-oxoethoxy)-3-fluorophenyl)-N-(5-(trifluoromethyl)pyridin-2-yl)-1H-pyrazole-4-carboxamide
5-Amino-1-(2-(2-amino-2-oxoethoxy)phenyl)-N-(5-chloropyridin-2-yl)-3-ethyl-1H-pyrazole-4-carboxamide
5-Amino-1-(2-(2-(methylamino)-2-oxoethoxy)phenyl)-N-(5-(trifluoromethyl)pyridin-2-yl)-1H-pyrazole-4-carboxamide
5-Amino-1-(2-((2,2-dimethyl-1,3-dioxolaN-4-yl)methoxy)phenyl)-N-(5-(trifluoromethyl)pyridin-2-yl)-1H-pyrazole-4-carboxamide
5-Amino-1-(2-(2-amino-1-fluoro-2-oxoethoxy)phenyl)-N-(5-(trifluoromethyl)pyridin-2-yl)-1H-pyrazole-4-carboxamide
5-Amino-1-(2-(2-amino-2-oxoethoxy)phenyl)-3-methyl-N-(5-(trifluoromethyl)pyridin-2-yl)-1H-pyrazole-4-carboxamide
5-Amino-1-(2-(2,2,3,3,3-pentafluoropropoxy)phenyl)-N-(5-(trifluoromethyl)pyridin-2-yl)-1H-pyrazole-4-carboxamide
5-Amino-1-(2-(2,2,2-trifluoroethoxy)phenyl)-N-(5-(trifluoromethyl)pyridin-2-yl)-1H-pyrazole-4-carboxamide
5-Amino-1-[2-(oxetaN-3-yloxy)phenyl]-N-[5-(trifluoromethyl)pyridin-2-yl]-1H-pyrazole-4-carboxamide
5-Amino-1-[2-[(5-methylisoxazol-3-yl)methoxy]phenyl]-N-[5-(trifluoromethyl)pyridin-2-yl]-1H-pyrazole-4-carboxamide
5-Amino-1-[2-(3-methoxypropoxy)phenyl]-N-[5-(trifluoromethyl)pyridin-2-yl]-1H-pyrazole-4-carboxamide
5-Amino-1-(2-(2-hydroxyethoxy)phenyl)-N-(5-(trifluoromethyl)pyridin-2-yl)-1H-pyrazole-4-carboxamide
5-Amino-1-(2-(2-hydroxyethoxy)phenyl)-3-methyl-N-(5-(trifluoromethyl)pyridin-2-yl)-1H-pyrazole-4-carboxamide
5-Amino-N-(5-chloropyridin-2-yl)-3-ethyl-1-(2-(2-hydroxyethoxy)phenyl)-1H-pyrazole-4-carboxamide
5-Amino-N-(5-chloropyridin-2-yl)-1-(2-(2-hydroxyethoxy)phenyl)-1H-pyrazole-4-carboxamide
5-Amino-3-ethyl-1-(2-(2-hydroxyethoxy)phenyl)-N-(5-(trifluoromethyl)pyridin-2-yl)-1H-pyrazole-4-carboxamide
5-Amino-1-(2-(difluoromethoxy)phenyl)-N-(5-(trifluoromethyl)pyridin-2-yl)-1H-pyrazole-4-carboxamide
5-Amino-1-(3-fluoro-2-methylphenyl)-N-(5-(trifluoromethyl)pyridin-2-yl)-1H-imidazole-4-carboxamide
5-Amino-N-(5-chloropyridin-2-yl)-1-(3-fluoro-2-methylphenyl)-1H-imidazole-4-carboxamide
5-Amino-N-(4-bromophenyl)-1-(2-methoxyphenyl)-1H-imidazole-4-carboxamide
5-Amino-N-(4-chlorophenyl)-1-(2-methoxyphenyl)-1H-imidazole-4-carboxamide
5-Amino-1-(2-methoxyphenyl)-N-(4-(trifluoromethyl)phenyl)-1H-imidazole-4-carboxamide
5-Amino-1-(2-(6-aminopyridin-3-yl)phenyl)-N-(5-chloropyridin-2-yl)-1H-pyrazole-4-carboxamide
5-Amino-1-(2-(6-aminopyridin-3-yl)phenyl)-N-(5-(trifluoromethyl)pyridin-2-yl)-1H-pyrazole-4-carboxamide
5-Amino-N-(5-chloropyridin-2-yl)-1-(2-(6-(dimethylamino)pyridin-3-yl)phenyl)-1H-pyrazole-4-carboxamide
5-Amino-N-(5-chloropyridin-2-yl)-1-(2-(5-methoxypyridin-3-yl)phenyl)-1H-pyrazole-4-carboxamide
5-Amino-1-(2-(2-(4-methylpiperaziN-1-yl)-2-oxoethoxy)phenyl)-N-(5-(trifluoromethyl)pyridin-2-yl)-1H-pyrazole-4-carboxamide
tert-Butyl 3-(2-(5-amino-4-((5-chloropyridin-2-yl)carbamoyl)-1H-pyrazol-1-yl)phenyl)-5,6-dihydropyridine-1(2H)-carboxylate
tert-Butyl 5-(2-(5-amino-4-((5-chloropyridin-2-yl)carbamoyl)-1H-pyrazol-1-yl)phenyl)-3,4-dihydropyridine-1(2H)-carboxylate
tert-Butyl 4-(2-(5-amino-4-((5-chloropyridin-2-yl)carbamoyl)-1H-pyrazol-1-yl)phenyl)-5,6-dihydropyridine-1(2H)-carboxylate
5-Amino-1-(2-(2-oxo-2-(pyrrolidin-1-yl)ethoxy)phenyl)-N-(5-(trifluoromethyl)pyridin-2-yl)-1H-pyrazole-4-carboxamide
5-amino-1-(2-(N-methyl-N-(pyridin-3-yl)sulfamoyl)phenyl)-N-(5-(trifluoromethyl)pyridin-2-yl)-1H-pyrazole-4-carboxamide
or a pharmaceutically acceptable salt, or N-oxide, or isotopically-labeled derivate thereof.

Of outstanding interest are:
5-Amino-1-(o-tolyl)-N-(5-(trifluoromethyl)pyridin-2-yl)-1H-pyrazole-4-carboxamide
5-Amino-N-(4-chloro-2-fluoro-phenyl)-1-(o-tolyl)-1H-pyrazole-4-carboxamide
5-Amino-N-(4-chloro-2-methoxy-phenyl)-1-(o-tolyl)-1H-pyrazole-4-carboxamide
5-Amino-N-(4-bromo-2-methoxy-phenyl)-1-(o-tolyl)-1H-pyrazole-4-carboxamide
5-Amino-N-[2-cyano-4-(trifluoromethyl)phenyl]-1-(2-ethylphenyl)-3-methyl-1H-pyrazole-4-carboxamide
5-Amino-N-[2-fluoro-4-(trifluoromethyl)phenyl]-3-methyl-1-(o-tolyl)-1H-pyrazole-4-carboxamide
5-Amino-1-(2-ethylphenyl)-3-methyl-N-[5-(trifluoromethyl)-2-pyridyl]-1H-pyrazole-4-carboxamide
5-Amino-N-(5-chloro-2-pyridyl)-1-[2-(2-methoxyethoxy)phenyl]-3-methyl-1H-pyrazole-4-carboxamide
5-Amino-N-[4-bromo-2-(difluoromethoxy)phenyl]-1-(o-tolyl)-1H-pyrazole-4-carboxamide
5-Amino-N-(4-chloro-2-fluoro-phenyl)-3-methyl-1-(o-tolyl)-1H-pyrazole-4-carboxamide
5-Amino-1-(o-tolyl)-N-(5-(trifluoromethoxy)pyridin-2-yl)-1H-pyrazole-4-carboxamide
5-Amino-1-(3-fluoro-2-methylphenyl)-N-(5-(trifluoromethoxy)pyridin-2-yl)-1H-pyrazole-4-carboxamide
(5-Amino-1-(o-tolyl)-1H-pyrazol-4-yl)(5-chloroindolin-1-yl)methanone
5-Amino-1-(2-methoxyphenyl)-N-(5-(trifluoromethyl)pyridin-2-yl)-1H-1,2,3-triazole-4-carboxamide
5-Amino-1-(2-methoxyphenyl)-N-(4-(trifluoromethyl)phenyl)-1H-1,2,3-triazole-4-carboxamide
5-Amino-1-(o-tolyl)-N-(5-(trifluoromethyl)pyridin-2-yl)-1H-1,2,3-triazole-4-carboxamide
5-Amino-1-(3-fluoro-2-methylphenyl)-N-(5-(trifluoromethyl)pyridin-2-yl)-1H-1,2,3-triazole-4-carboxamide
5-Amino-N-(4-chlorophenyl)-1-(o-tolyl)pyrazole-4-carboxamide 5-Amino-1-(2-ethylphenyl)-N-[5-trifluoromethyl-2-pyridyl]pyrazole-4-carboxamide
5-Amino-1-(2-chlorophenyl)-N-[5-trifluoromethyl-2-pyridyl]pyrazole-4-carboxamide
5-Amino-1-[2-(trifluoromethoxy)phenyl]-N-[5-trifluoromethyl-2-pyridyl]pyrazole-4-carboxamide
5-Amino-1-[2-(2-methoxyethoxy)phenyl]-N-[5-trifluoromethyl-2-pyridyl]pyrazole-4-carboxamide
5-Amino-N-(5-chloropyridin-2-yl)-1-(2-methoxyphenyl)-1H-pyrazole-4-carboxamide
5-Amino-1-(2-chlorophenyl)-N-(5-chloropyridin-2-yl)-1H-pyrazole-4-carboxamide
5-Amino-1-(2-fluoro-6-methylphenyl)-N-[5-trifluoromethyl-2-pyridyl]pyrazole-4-carboxamide
5-Amino-1-[3-fluoro-2-(2-methoxyethoxy)phenyl]-3-methyl-N-[5-(trifluoromethyl)-2-pyridyl]pyrazole-4-carboxamide
5-Amino-3-ethyl-1-(2-methoxyphenyl)-N-(5-(trifluoromethyl)pyridin-2-yl)-1H-pyrazole-4-carboxamide
5-Amino-1-(2-chloro-6-fluorophenyl)-3-methyl-N-[5-trifluoromethyl-2-pyridyl]pyrazole-4-carboxamide
5-Amino-1-(3-fluoro-2-methylphenyl)-3-methyl-N-[5-trifluoromethyl-2-pyridyl]pyrazole-4-carboxamide
5-Amino-1-(2-methoxyphenyl)-3-methyl-N-[5-trifluoromethyl-2-pyridyl]pyrazole-4-carboxamide
5-Amino-N-(5-chloropyridin-2-yl)-1-(3-fluoro-2-methylphenyl)-1H-pyrazole-4-carboxamide
5-Amino-1-(2-fluoro-6-methoxyphenyl)-3-methyl-N-[5-trifluoromethyl-2-pyridyl]pyrazole-4-carboxamide
5-Amino-3-ethyl-1-(o-tolyl)-N-[5-trifluoromethyl-2-pyridyl]pyrazole-4-carboxamide
5-Amino-3-ethyl-1-(2-(2-methoxyethoxy)phenyl)-N-(5-(trifluoromethyl)pyridin-2-yl)-1H-pyrazole-4-carboxamide
5-Amino-3-ethyl-1-(3-fluoro-2-methylphenyl)-N-[5-trifluoromethyl-2-pyridyl]pyrazole-4-carboxamide
5-Amino-1-(3-fluoro-2-methylphenyl)-N-[5-trifluoromethyl-2-pyridyl]pyrazole-4-carboxamide
5-Amino-1-(2-fluorophenyl)-N-(5-(trifluoromethyl)pyridin-2-yl)-1H-pyrazole-4-carboxamide
5-Amino-3-methyl-1-(2-(oxazol-5-yl)phenyl)-N-(5-(trifluoromethyl)pyridin-2-yl)-1H-pyrazole-4-carboxamide
5-Amino-3-ethyl-1-(2-fluorophenyl)-N-(5-(trifluoromethyl)pyridin-2-yl)-1H-pyrazole-4-carboxamide
5-Amino-1-(2-fluorophenyl)-3-methyl-N-(5-(trifluoromethyl)pyridin-2-yl)-1H-pyrazole-4-carboxamide
5-Amino-1-(2-hydroxyphenyl)-N-(5-(trifluoromethyl)pyridin-2-yl)-1H-pyrazole-4-carboxamide
5-Amino-1-(3-fluoro-2-methylphenyl)-N-(5-(trifluoromethyl)pyridin-2-yl)-1H-imidazole-4-carboxamide or a pharmaceutically acceptable salt, or N-oxide, or isotopically-labeled derivate thereof.

The invention is also directed to a compound of the invention as described herein for use in the treatment of the human or animal body by therapy.

The invention also provides pharmaceutical compositions comprising at least a compound of Formula (I), as hereinabove described, in association with a pharmaceutically acceptable diluent or carrier.

The invention is also directed to the compounds of the invention as described herein, for use in the treatment of a pathological condition or disease mediated by modulation of voltage-gated sodium channels in particular Nav1.7, which condition or disease is preferably selected from pain, including but not limiting to, acute pain, chronic pain, inflammatory pain, visceral pain, nociceptive pain, neuropathic pain, postherpetic pain, trigeminal neuralgia, diabetic neuropathy, chronic back pain, chronic pelvic pain, migraine and pain resulting from cancer and chemotherapy, idiopathic cough, chronic cough or cough related to respiratory diseases, respiratory diseases, itch, dermatological diseases, epilepsy, schizophrenia and bipolar disorder.

The invention also provides the use of the compounds of the invention as described herein, for the manufacture of a medicament for the treatment of a pathological condition or disease as described above. The invention is also directed to a method of treatment of said pathological condition or disease described above, comprising administering a therapeutically effective amount of the compounds of the invention or a pharmaceutical composition of the invention to a subject in need of such treatment.

In still another embodiment the present invention covers a combination product comprising (i) at least a compound of Formula (I), as herein above described, and (ii) one or more active ingredients as mentioned above, for simultaneous, separate or sequential use in the treatment of the human or animal body.

As used herein, the term therapeutically effective amount refers to an amount sufficient to effect treatment when administered to a patient in need of treatment.

As used herein, the term treatment refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

As used herein, the term disease or condition associated with modulation of voltage-gated sodium channels in particular Nav1.7 activity includes all disease states and/or conditions that are acknowledged now, or that are found in the future, to be associated with modulation of voltage-gated sodium channels in particular Nav1.7 activity. Such disease states include, but are not limited to pain, including but not limiting to, acute pain, chronic pain, inflammatory pain, visceral pain, nociceptive pain, neuropathic pain, postherpetic pain, trigeminal neuralgia, diabetic neuropathy, chronic back pain, chronic pelvic pain, migraine and pain resulting from cancer and chemotherapy, cough, respiratory diseases, itch, dermatological diseases, epilepsy, schizophrenia and bipolar disorder.

General Synthetic Procedures

The compounds of the invention can be prepared using the methods and procedures described herein, or using similar methods and procedures. It will be appreciated that typical or preferred process conditions (i.e., reaction temperatures, times, mole ratios of reactants, solvents, pressures, etc.) are given. Other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein. Processes for preparing compounds of the invention are provided as further embodiments of the invention and are illustrated by the procedures below.

One of the most convenient route for the preparation of compounds of Formula (Ia) is depicted in Scheme 1.

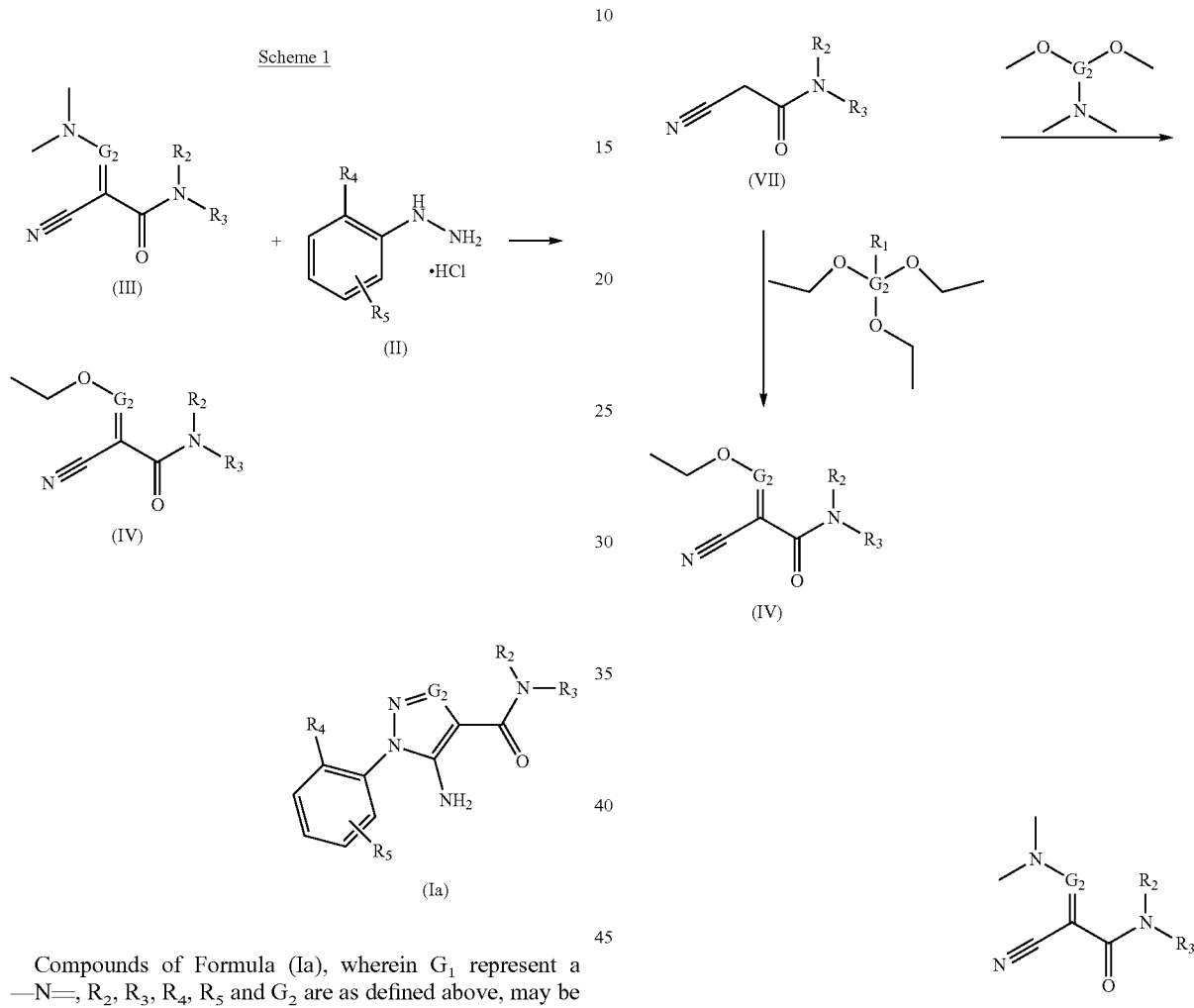

Compounds of Formula (Ia), wherein $G_1$ represent a —N═, $R_2$, $R_3$, $R_4$, $R_5$ and $G_2$ are as defined above, may be prepared by reacting intermediates of Formula (II) with compounds of Formula (III) and (IV). Intermediate of Formula (II) may be prepared by reacting intermediate (V) and (VI) with acid chloride 4M in dioxane at room temperature and alternatively by reacting with the corresponding commercially available aniline with sodium nitrite and $SnCl_2$ at low temperatures (Scheme 2b).

Scheme 2a

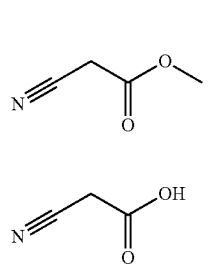

Intermediate of formula (IV) may be obtained by reacting triethylorthopropionate with intermediate of formula (VII) in acetic anhydride at a temperature between 50 and 100° C. for 0.2 to 5 hrs, and intermediate of formula (III) was also prepared by reacting intermediate of formula (VII) and N,N-dimethylformamide dimethyl acetal in xylene at reflux (Scheme 2a).

Intermediate of formula (VII) may be prepared by reacting the corresponding commercially available amine with cianoacetic acid or methyl cianoacetate using DMF, DCM, EDC, $Et_3N$ or $PCl_5$ at 100° C. or 65° C. for 16 hours to 72° C. (Scheme 2a).

Scheme 2b

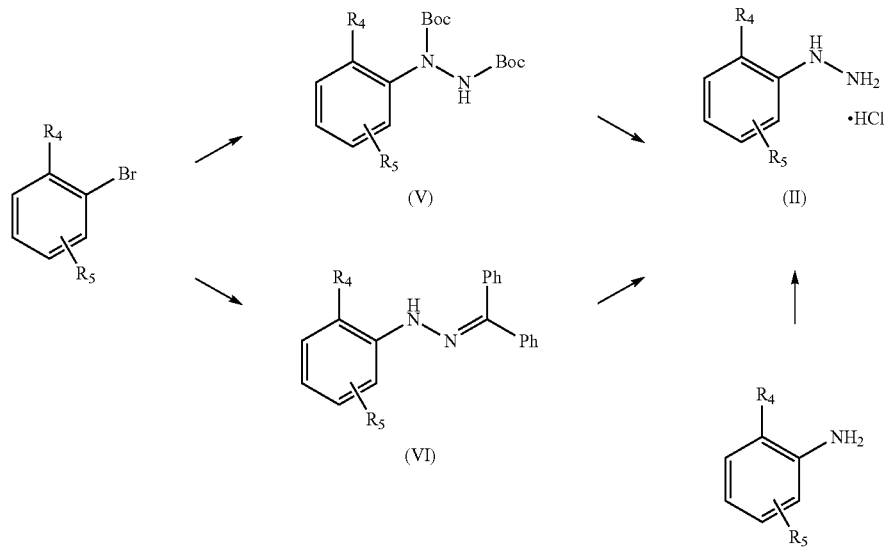

Intermediate of formula (VI) was obtained by reacting (diphenylmethylene)hydrazine and the corresponding commercially available bromphenyl derivate using Na$^t$OBu, Pd(OAc)$_2$, Xanthphos in Toluene at a temperature between 75 and 100° C. (Scheme 2b).

Intermediate of formula (V) was obtained by reacting i-PrMgBr.LiCl in THF at 00° C. or t-BuLi in ether at −78° C., and then adding diBoc hydrazine with the corresponding commercially available bromphenyl derivate (Scheme 2b).

Alternatively, compounds of formula (Ia) may be prepared through amide formation following Scheme 3.

Compounds of formula (Ia) may be prepared by reacting intermediate of formula (VIII) with the corresponding amine and using SOCl$_2$ in acetonitrile or PyBOP, Et$_3$N in DCM at room temperature.

Intermediate of formula (VIII) may be prepared trough intermediate of formula (IX) in sodium hydroxide 2M in THF/MeOH at a temperature between 50 and 75° C. for 3 to 6 hrs.

Scheme 3:

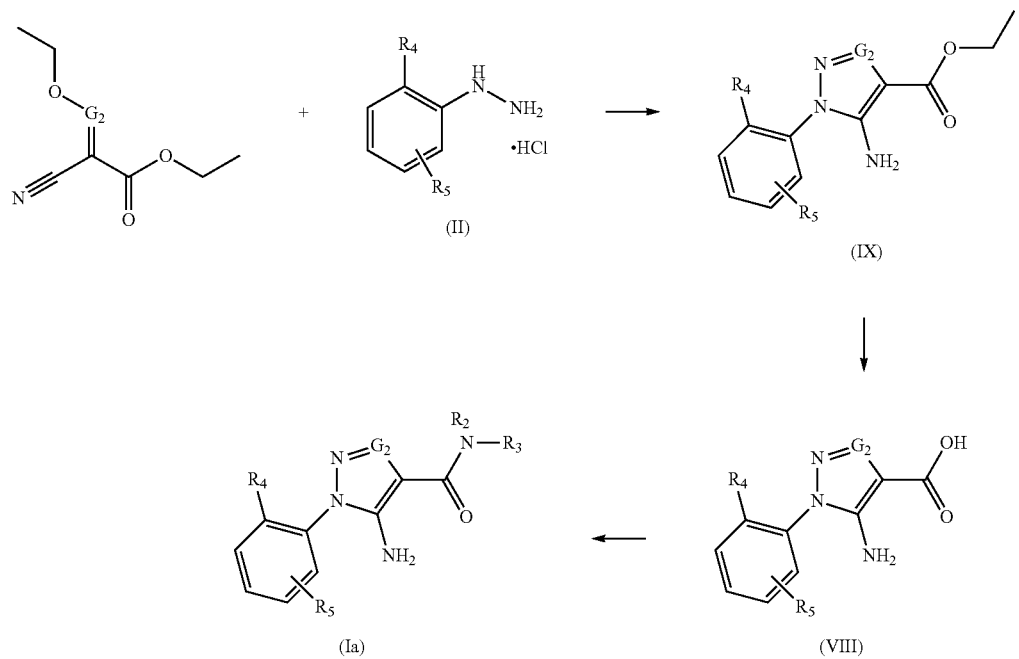

Finally, intermediate of formula (IX) may be prepared by reacting intermediate of formula (II) and ethyl 2-cyano-3-ethoxyacrylate and Et₃N in ethanol at a temperature between 70 and 90° C. for 1 to 6 hr.

Others ways to prepare compounds of Formula (Ia) are depicted in the following Schemes 4a-4e:

Scheme 4a:

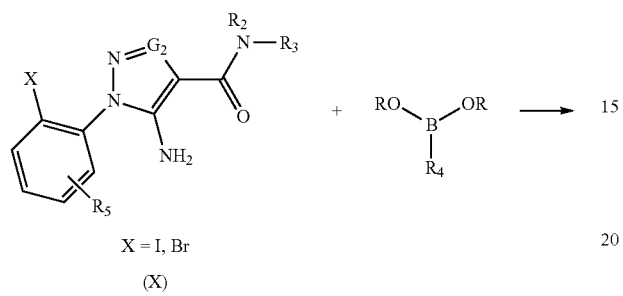

X = I, Br
(X)

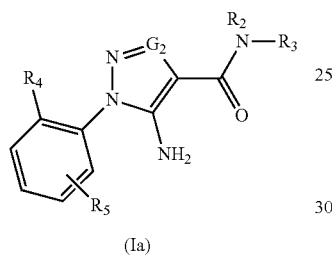

(Ia)

Compound of Formula (Ia) may be obtained by reacting intermediate of formula (X), which can be obtained following same conditions described in Scheme 1, and the corresponding boron derivative using potassium carbonate, DCM, Pd, Dioxane/Water at 90° C. for 18 hrs.

In the particular case, wherein $R_4$ represents $—OR^c$, compounds of Formula (Iaa) maybe prepared following Scheme 4b:

Scheme 4b:

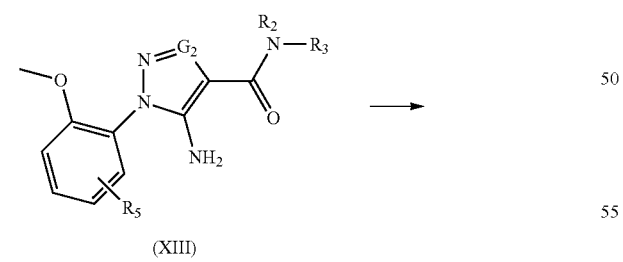

(XIII)

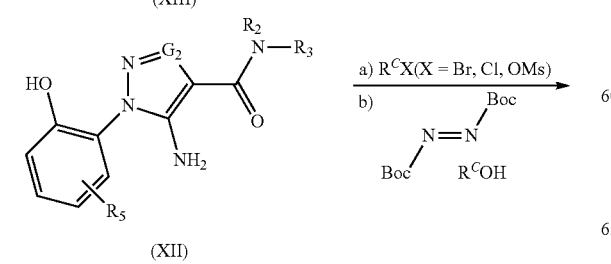

(XII)

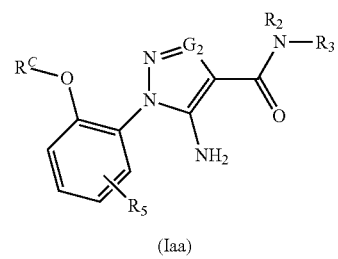

(Iaa)

Compound of Formula (Iaa) can be obtained by reacting intermediate of Formula (XII) via two routes a) or b) as depicted in the scheme 4b. Intermediate of Formula (XII) may be prepared by reacting compound of Formula (XIII) with BBr₃ in DCM or THF at 0° C. for 18 hrs.

In the particular case, wherein $R_4$ represents $—NR^aR^b$, compounds of Formula (Iab) maybe prepared following Scheme 4c:

Scheme 4c:

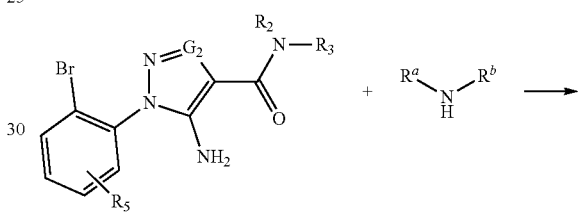

(XV)

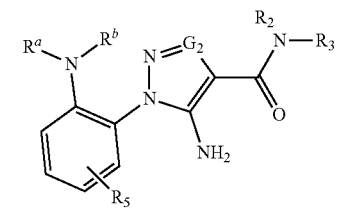

(Iab)

Synthesis of compound of Formula (Iab) is depicted in Scheme 4c. Reacting the corresponding commercially available amine with intermediate of Formula (XV) with CuI, potassium carbonate, DMSO at 100° C. for 16 hrs.

An alternative route for the synthesis of compound of Formula (Ia) is depicted in Scheme 4d.

Scheme 4d:

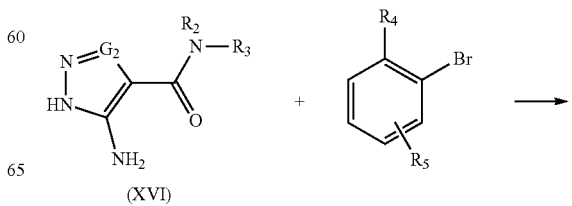

(XVI)

33

-continued

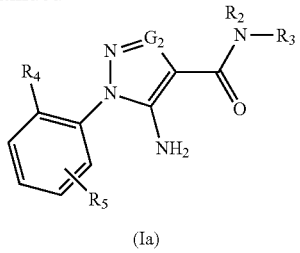

(Ia)

Compounds of Formula (Ia) may be obtained by reacting the corresponding commercially available brombenzene with intermediate of Formula (XVI), which is synthezised as described in Scheme 3, using CuI, potassium carbonate in dioxane at 100° C. for 18 hrs.

In a particular case wherein $R_4$ represents —O—CH$_2$—CO—NR$^a$R$^b$ group compounds of Formula (Iac) may be prepared is depicted in Scheme 4e.

Scheme 4e:

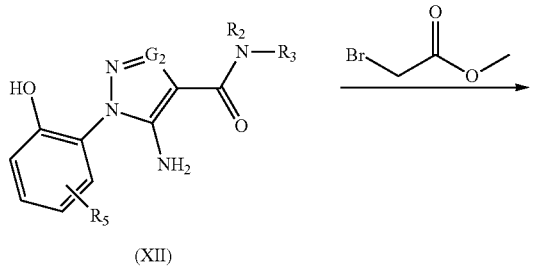

34

-continued

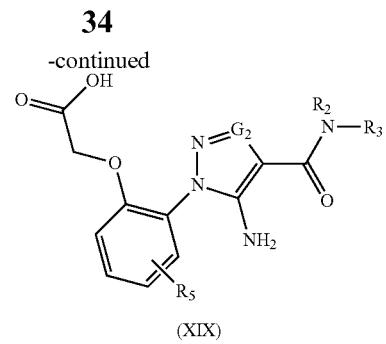

(XIX)

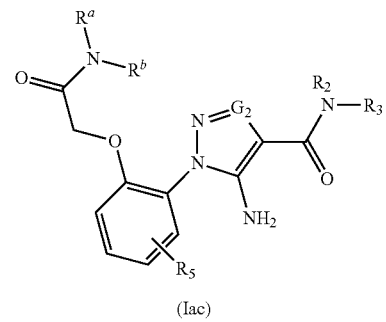

(Iac)

Compound of Formula (Iac) may be obtained by reacting intermediate of Formula (XIX) with the corresponding amine with HATU, DMF, DIEA at room temperature for 18 hrs. Intermediate of Formula (XIX) may be obtained by reacting intermediate of Formula (XII), which is described in Scheme 4b, with methyl bromoacetate using cesium carbonate, DMF at room temperature for 18 hrs or with LiOH, H$_2$O/THF at a temperature between 50 and 75° C. for 1 to 5 hrs.

The most convenient route for the preparation of compound of Formula (Ib), wherein G$_2$ represents a =N— is depicted in Scheme 5.

Scheme 5

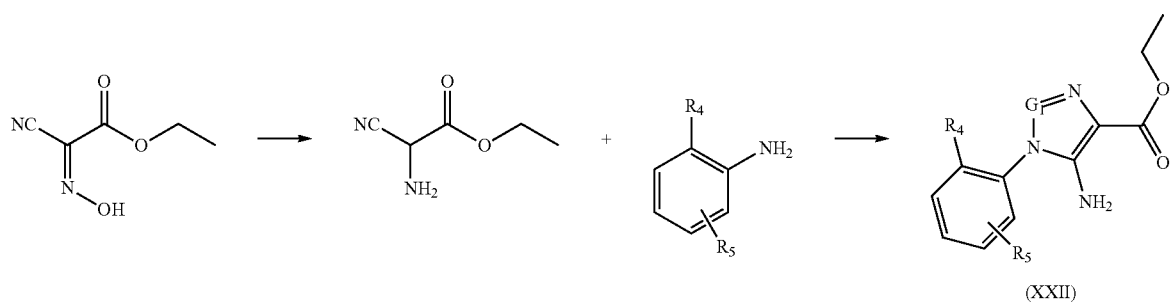

(XXII)

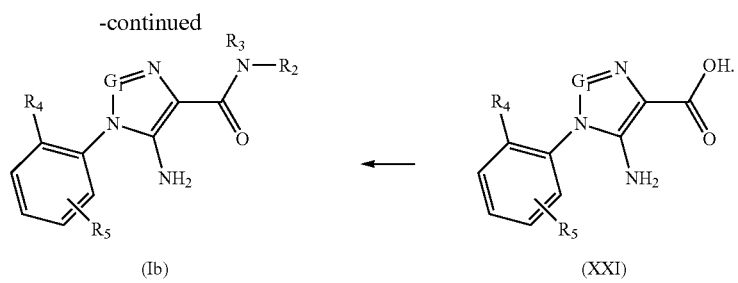

Compound of Formula (Ib) may be obtained by reacting intermediate of Formula (XXI) with the corresponding amine via sulfonyl chloride formation in DCM, DIEA at room temperature for 1 hr.

Intermediate of Formula (XXI) can be obtained by reacting the corresponding intermediate of Formula (XXII) with lithium hydroxide monohydrate in THF/MeOH/H$_2$O at a temperature between 50 and 80° C. for 2 to 6 hrs, or with sodium hydroxide 2M in THF/MeOH at a temperature between room temperature and 75° C. for 1 to 6 hrs.

Intermediate of Formula (XXII) can be obtained by reacting the corresponding aniline with ethyl 2-amino-2-cyanoacetate in acetonitrile.

The most convenient route for the preparation of compound of Formula (Ic) wherein both $G_1$ and $G_2$ represent a nitrogen atom is depicted in Scheme 6.

Scheme 6:

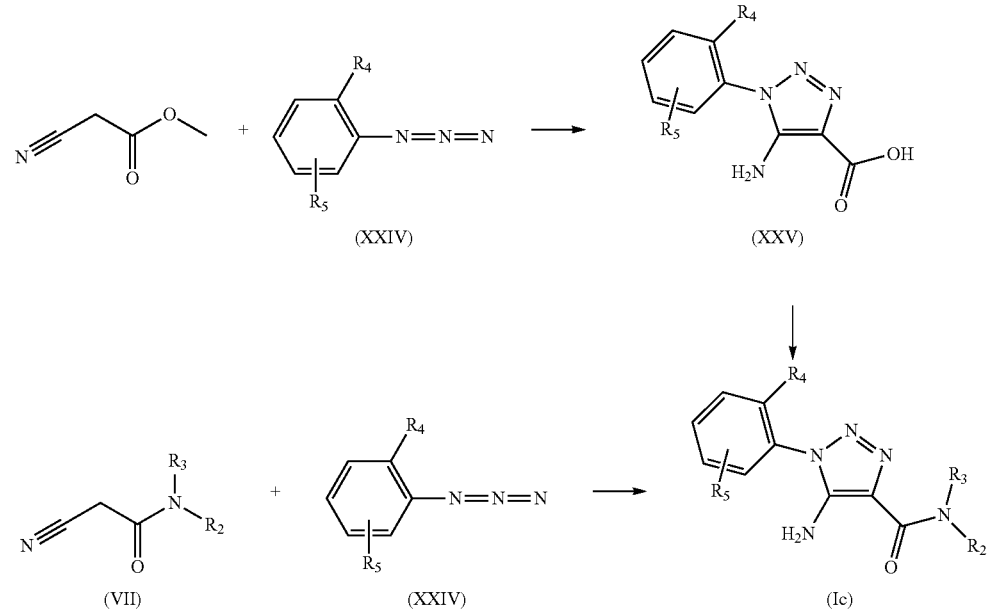

Compounds of Formula (Ic) may be prepared by reacting intermediates of Formula (VII) with intermediates of Formula (XXIV) using NaOMe, MeOH, toluene at a temperature between 40 and 60° C. for 15 min to 2 hrs and then 18 hrs at room temperature.

Alternatively, compounds of Formula (Ic) may be prepared by reacting intermediate of Formula (XXV) and the corresponding amine, either reacting with SOCl$_2$, MeCN, Et$_3$N or PyBOP, DMF, Et$_3$N. Intermediate of Formula (XXV) can be obtained by reacting intermediate of Formula (XXIV) with methyl 2-cyanoacetate in MeOH, toluene at room temperature for 18 hrs and then using sodium hydroxide in MeOH at room temperature for 18 hrs.

EXAMPLES

General.

Reagents, starting materials and solvents were purchased from commercial suppliers and used as received. Concentration refers to evaporation under vacuum using a Büchi rotatory evaporator. Spectroscopic data were recorded on either a Bruker Avance 400 MHz, 5 mm QNP probe, Bruker DPX 400 MHz, 5 mm QNP probe or Bruker Avance III 400 MHz, 5 mm BBFO Plus probe. HPLC-MS were performed on a Waters/Micromass ZQ, single quadrapole mass spectrometer. Waters 2795 HPLC system, with Waters 2996 DAD. Alternatively, HPLC-MS were performed on a Waters SQD2, single quadrapole mass spectrometer. Waters I class UPLC with SM-FTM sample manager, SO plate handler and Acquity system DAD.

The syntheses of the compounds of the invention and of the intermediates for use therein are illustrated by the following Examples (1-264) and including Preparation Examples (Preparations 1 to 107) which do not limit the scope of the invention in any way.

Intermediate 1. Ethyl 5-amino-1-(2-methoxyphenyl)-1H-pyrazole-4-carboxylate

A mixture of ethyl 2-cyano-3-ethoxyacrylate (0.96 g, 5.7 mmol), 2-methoxyphenylhydrazine hydrochloride (0.91 g, 5.2 mmol), NEt$_3$ (1.6 mL, 11.4 mmol) and EtOH (26 mL) was stirred at 80° C. for 1 hr. The reaction mixture was allowed to cool to r.t. and the solvent removed under reduced pressure. The crude product was purified by column chromatography (Biotage SNAP 25 g column, 0 to 50% EtOAc/isohexane) to give the title compound as an orange oil (0.94 g, 63%).

$^1$H NMR (ppm)(400 MHz, CDCl3): 1.36 (3H, t, J=7.1 Hz), 3.88 (3H, s), 4.30 (2H, q, J=7.1 Hz), 5.22 (2H, s), 7.06-7.12 (2H, m), 7.39-7.44 (2H, m), 7.82 (1H, s)

Intermediate 2. 5-Amino-1-(2-methoxyphenyl)-1H-pyrazole-4-carboxylic acid

A mixture of ethyl 5-amino-1-(2-methoxyphenyl)-1H-pyrazole-4-carboxylate (Intermediate 1; 0.94 g, 3.6 mmol), 2 M NaOH (aq) (7.2 mL, 14.4 mmol), MeOH (9 mL) and THF (9 mL) was stirred at 65° C. for 4 hr. The reaction mixture was acidified to approximately pH 4 with 4M HCl (aq). The resultant precipitate was collected by filtration. The crude product was triturated with Et$_2$O and dried under reduced pressure to give the title compound as a pale brown solid (0.53 g, 63%).

$^1$H NMR (ppm) (400 MHz, DMSO-d6): 3.85 (3H, s), 5.94 (2H, s), 7.10-7.15 (1H, m), 7.28 (1H, d, J=8.4 Hz), 7.35 (1H, dd, J=7.8, 1.7 Hz), 7.49-7.57 (1H, m), 7.64 (1H, s) (OH not observed)

Intermediate 3. Ethyl 5-amino-1-(o-tolyl)-1H-pyrazole-4-carboxylate

The title compound was prepared using a method analogous to the preparation of ethyl 5-amino-1-(2-methoxyphenyl)-1H-pyrazole-4-carboxylate (Intermediate 1). The crude product was purified by column chromatography (Biotage SNAP 100 g column, 0 to 10% EtOAc/DCM) to give the title compound as a yellow oil (3.82 g, 53%).

$^1$H NMR (ppm)(400 MHz, CDCl$_3$): 1.38 (3H, t, J=7.6 Hz), 2.18 (3H, s), 4.23-4.35 (2H, m), 4.98 (2H, s), 7.29-7.41 (4H, m), 7.79 (1H, s)

Intermediate 4. 5-Amino-1-(o-tolyl)-1H-pyrazole-4-carboxylic acid

The title compound was prepared from ethyl 5-amino-1-(o-tolyl)-1H-pyrazole-4-carboxylate (Intermediate 3) using a method analogous to the preparation of 5-amino-1-(2-methoxyphenyl)-1H-pyrazole-4-carboxylic acid (Intermediate 2).

The title compound was obtained as a white solid (0.49 g, 52%).

$^1$H NMR (ppm)(400 MHz, CDCl$_3$): 2.18 (3H, s), 5.04 (2H, s), 7.31-7.42 (4H, m), 7.86 (1H, s) (OH not observed)

Intermediate 5. Ethyl 5-(methylamino)-1-(o-tolyl)-1H-pyrazole-4-carboxylate

A mixture of ethyl 5-amino-1-(o-tolyl)-1H-pyrazole-4-carboxylate (Intermediate 4; 0.8 g, 2.0 mmol), cesium carbonate (1.0 g, 3.1 mmol) and iodomethane (0.19 mL, 3.1 mmol) in DMF was stirred at r.t. for 3 days. The mixture was extracted with EtOAc (75 mL) and washed with H$_2$O (2×100 mL). The organic layer was dried (MgSO$_4$), filtered and the solvent removed under reduced pressure. The crude product was purified by column chromatography (Biotage SNAP 50 g column, 20 to 60% EtOAc/isohexane) to give the title compound as a pale yellow solid (0.41 g, 48%).

$^1$H NMR (ppm)(400 MHz, CDCl$_3$): 1.36 (3H, t, J=7.2 Hz), 2.17 (3H, s), 2.41 (3H, d, J=5.6 Hz), 4.29 (2H, q, J=7.2 Hz), 6.26 (1H, s), 7.29-7.33 (4H, m), 7.78 (1H, s)

Intermediate 6. 5-(Methylamino)-1-(o-tolyl)-1H-pyrazole-4-carboxylic acid

The title compound was prepared from ethyl 5-(methylamino)-1-(o-tolyl)-1H-pyrazole-4-carboxylate (Intermediate 5) using a method analogous to the preparation of 5-amino-1-(2-methoxyphenyl)-1H-pyrazole-4-carboxylic acid (Intermediate 2).

The title compound was obtained as a yellow solid (0.41 g, >95%).

$^1$H NMR (ppm)(400 MHz, CDCl3): 2.19 (3H, s), 2.44 (3H, d, J=5.6 Hz), 6.28 (1H, s), 7.35-7.41 (4H, m), 7.84 (1H, s)

Intermediate 7. 1-Bromo-2-(2-methoxyethoxy)benzene

A mixture of 2-bromophenol (7.1 g, 41 mmol), 1-bromo-2-methoxyethane (5.7 mL, 61 mmol), K$_2$CO$_3$ (15.7 g, 123 mmol) and MeCN (100 mL) was stirred at 80° C. for 2 hrs. The reaction mixture was allowed to cool to r.t. The reaction mixture was diluted with H$_2$O (200 mL) and extracted with EtOAc (2×200 mL). The combined organic extracts were dried (MgSO$_4$), filtered and the solvent removed under reduced pressure to give the title compound as a colourless oil (9.4 g).

The crude product was used in subsequent reactions without further analysis.

Intermediate 8. tert-Butyl 1-(2-(2-methoxyethoxy)phenyl)-2-pivaloylhydrazinecarboxylate $^t$BuLi (1.5 M solution in pentane) (6.3 mL, 9.4 mmol) was added dropwise to a stirred solution of 1-bromo-2-(2-methoxyethoxy)benzene (Intermediate 7; 1.03 g, 4.5 mmol) in Et2O (20 mL) at −78° C. The reaction mixture was stirred at −78° C. for 0.25 hrs. A solution of di-tert-butylazodicarboxylate (1.43 g, 6.3 mmol) in Et$_2$O (20 mL) was added dropwise and the reaction mixture stirred at −78 C for 0.75 hrs. The reaction mixture was allowed to warm to r.t. and quenched by the careful addition of saturated NH$_4$Cl (aq) (25 mL). The mixture was extracted with EtOAc (2×50 mL). The combined organic extract was dried (MgSO$_4$), filtered and the solvent removed under reduced pressure. The crude product was purified by column chromatography (Biotage SNAP 50 g column, 0-30% EtOAc/DCM) to give the title compound as a brown oil (1.00 g)

The crude product was used in subsequent reactions without further analysis.

Intermediate 9. (2-(2-Methoxyethoxy)phenyl)hydrazine

A mixture of tert-butyl 1-(2-(2-methoxyethoxy)phenyl)-2-pivaloylhydrazinecarboxylate (0.98 g, 2.5 mmol) and HCl (4 M solution in dioxane) (6.3 mL, 25 mmol) was stirred at 100° C. for 0.25 hrs. The reaction mixture was allowed to cool to r.t. The reaction mixture was concentrated under reduced pressure. The crude product was purified by SPE (Isolute SCX-2 10 g column, 0 to 100% 7 M NH$_3$ in MeOH/DCM) to give the title compound as a brown oil (0.27 g).

The crude product was used in subsequent reactions without further analysis.

Intermediate 10. Ethyl 5-amino-1-(2-(2-methoxyethoxy)phenyl)-1H-pyrazole-4-carboxylate The title compound was prepared from (2-(2-methoxyethoxy)phenyl)hydrazine (Intermediate 9) using a method analogous to the preparation of ethyl 5-amino-1-(2-methoxyphenyl)-1H-pyrazole-4-carboxylate (Intermediate 1).

The crude product was purified by column chromatography (Biotage SNAP 50 g column, 0 to 80% EtOAc/isohexane) to give the title compound as a yellow oil (0.72 g, 54%).

$^1$H NMR (ppm)(400 MHz, CDCl$_3$): 1.36 (3H, t, J=7.1 Hz), 3.37 (3H, s), 3.64-3.71 (2H, m), 4.18-4.22 (2H, m), 4.31 (2H, q, J=7.1 Hz), 5.54 (2H, s), 7.03-7.13 (2H, m), 7.34-7.40 (1H, m), 7.47 (1H, dd, J=1.5, 7.8 Hz), 7.82 (1H, s)

Intermediate 11. 5-Amino-1-(2-(2-methoxyethoxy)phenyl)-1H-pyrazole-4-carboxylic acid The title compound was prepared from ethyl 5-amino-1-(2-(2-methoxyethoxy)phenyl)-1H-pyrazole-4-carboxylate (Intermediate 10) using a method analogous to the preparation of 5-amino-1-(2-methoxyphenyl)-1H-pyrazole-4-carboxylic acid (Intermediate 2).

The title compound was obtained as a brown solid (0.61 g, 92%).

$^1$H NMR (ppm)(400 MHz, CDCl3): 3.27 (3H, s), 3.66-3.72 (2H, m), 4.21-4.27 (2H, m), 5.96 (2H, s), 7.14 (1H, dd, J=8.0, 8.0 Hz), 7.32 (1H, d, J=8.0 Hz), 7.38 (1H, d, J=8.0 Hz), 7.51 (1H, dd, J=8.0, 8.0 Hz), 12.0 (1H, br s).

Intermediate 12. Ethyl 5-amino-3-methyl-1-(o-tolyl)-1H-pyrazole-4-carboxylate

The title compound was prepared using a method analogous to the preparation of ethyl 5-amino-1-(2-methoxyphenyl)-1H-pyrazole-4-carboxylate (Intermediate 1)

The crude product was purified by column chromatography (Biotage SNAP 100 g column, 10 to 90% EtOAc/isohexane) to give the title compound as a yellow oil (0.32 g).

The crude product was used in subsequent reactions without further analysis.

Intermediate 13. 5-Amino-3-methyl-1-(o-tolyl)-1H-pyrazole-4-carboxylic acid

The title compound was prepared from ethyl 5-amino-3-methyl-1-(o-tolyl)-1H-pyrazole-4-carboxylate using a method analogous to the preparation of 5-amino-1-(2-methoxyphenyl)-1H-pyrazole-4-carboxylic acid (Intermediate 2).

The title compound was obtained as an off-white solid (0.15 g).

The crude product was used in subsequent reactions without further analysis.

Intermediate 14. Ethyl 5-amino-1-(2-ethylphenyl)-3-methyl-1H-pyrazole-4-carboxylate The title compound was prepared using a method analogous to the preparation of ethyl 5-amino-1-(2-methoxyphenyl)-1H-pyrazole-4-carboxylate (Intermediate 1).

The crude product was purified by column chromatography (Biotage SNAP 50 g column, 0 to 40% EtOAc/DCM) to give the title compound as a yellow solid (0.60 g, 17%).

$^1$H NMR (ppm)(400 MHz, CDCl$_3$): 1.24-1.34 (6H, m), 2.37 (3H, s), 2.53-2.61 (2H, m), 4.17-4.25 (2H, m), 6.14 (1H, s), 6.70 (1H, d, J=7.8 Hz), 6.93 (1H, dd, J=7.5, 7.5 Hz), 7.15 (2H, d, J=7.3 Hz), 10.82 (1H, s)

Intermediate 15. 5-Amino-1-(2-ethylphenyl)-3-methyl-1H-pyrazole-4-carboxylic acid The title compound was prepared from ethyl 5-amino-1-(2-ethylphenyl)-3-methyl-1H-pyrazole-4-carboxylate using a method analogous to the preparation of 5-amino-1-(2-methoxyphenyl)-1H-pyrazole-4-carboxylic acid (Intermediate 2).

The title compound was obtained as a white solid (0.49 g, 52%).

$^1$H NMR (ppm)(400 MHz, CDCl$_3$): 1.11-1.15 (3H, m), 2.44 (3H, s), 2.49-2.54 (2H, m), 5.08 (2H, s), 7.26-7.34 (2H, m), 7.40-7.46 (2H, m) (OH not observed)

Intermediate 16. N-(4-Methoxybenzyl)-5-(trifluoromethoxy)pyridin-2-amine

A mixture of 2-chloro-5-(trifluoromethoxy)pyridine (0.99 g, 5 mmol), 4-methoxybenzylamine (2.6 mL, 20 mmol), DIEA (1.3 mL, 7.5 mmol), K$_2$CO$_3$ (1.0 g, 7.5 mmol) and DMF (13 mL) was stirred at 160° C. (microwave) for 2 hrs. The reaction mixture was concentrated under reduced pressure. The residue was dissolved in DCM (100 mL) and H$_2$O (25 mL). The organic layer was separated (phase separating cartridge) and the solvent was removed under reduced pressure. The crude product was purified by column chromatography (Biotage SNAP 50 g column, 0 to 15% EtOAc/isohexane). The product was triturated with Et$_2$O to give the title compound as a yellow oil (0.33 g, 40%).

$^1$H NMR (ppm)(400 MHz, CDCl$_3$): 3.80 (3H, s), 4.42 (2H, d, J=5.8 Hz), 4.91 (1H, s), 6.35 (1H, d, J=8.8 Hz), 6.90-6.87 (2H, m), 7.25-7.28 (3H, m), 8.04 (1H, d, J=2.8 Hz)

Intermediate 17. 5-(Trifluoromethoxy)pyridin-2-amine

A mixture of N-(4-methoxybenzyl)-5-(trifluoromethoxy)pyridin-2-amine (Intermediate 16; 1.2 g, 4 mmol), TFA (12 mL) and H$_2$O (1.2 mL) was stirred at 100° C. (microwave) for 0.5 hrs. The reaction mixture was concentrated under reduced pressure. The residue was dissolved in DCM (100 mL) and H$_2$O (25 mL). The organic layer was separated (phase separating cartridge) and the solvent was removed under reduced pressure. The crude product was purified by SPE (Isolute SCX-2 10 g column, 0 to 100% 7 M NH$_3$ in MeOH/DCM) to give the title compound as an off-white solid (0.46 g, 70%).

$^1$H NMR (ppm)(400 MHz, CDCl$_3$): 4.52-4.51 (2H, m), 6.49 (1H, d, J=9.6 Hz), 7.33-7.30 (1H, m), 8.01 (1H, d, J=2.8 Hz)

Intermediate 18. 5-Amino-1-(3-fluoro-2-methylphenyl)-1H-pyrazole-4-carboxylic acid A mixture of ethyl 2-cyano-3-ethoxyacrylate (0.85 g, 5.0 mmol), 3-fluoro-2-methylphenylhydrazine hydrochloride (0.88 g, 5.0 mmol), NEt$_3$ (1.4 mL, 10.0 mmol) and EtOH (25 mL) was stirred at 80° C. for 1 hr. The reaction mixture was allowed to cool to r.t. and the solvent removed under reduced pressure. The crude product was purified by column chromatography (Biotage SNAP 50 g column, 0 to 60% EtOAc/isohexane) to give a crude intermediate corresponding to the ethyl ester of the title compound. A mixture of the crude intermediate, 1 M LiOH (aq) (12 mL, 12 mmol) and MeOH (12 mL) was stirred at 65° C. for 5 hrs. The reaction mixture was concentrated under reduced pressure. The residue was dissolved in H$_2$O (20 mL) and washed with EtOAc (20 mL). The aqueous phase was acidified to approximately pH 4 with 4 M HCl (aq) and extracted with EtOAc (3×20 mL). The combined organic extracts were dried (MgSO$_4$), filtered and the solvent removed under reduced pressure to give the title compound as a yellow solid (1.08 g, 92%).

$^1$H NMR (ppm)(400 MHz, CDCl$_3$): 2.10 (3H, d, J=2.0 Hz), 5.09 (2H, s), 7.16 (1H, d, J=7.8 Hz), 7.20 (1H, dd, J=8.1, 8.1 Hz), 7.36-7.29 (1H, m), 7.86 (1H, s) (OH not observed)

Intermediate 19. 5-Amino-1-(2-fluorophenyl)-1H-pyrazole-4-carboxylic acid

The title compound was prepared using a method analogous to the preparation of 5-amino-1-(3-fluoro-2-methylphenyl)-1H-pyrazole-4-carboxylic acid (Intermediate 2).

The title compound was obtained as an orange solid (0.66 g, 59%).

$^1$H NMR (ppm)(400 MHz, CDCl$_3$): 5.29 (2H, s), 7.35-7.27 (2H, m), 7.56-7.44 (2H, m), 7.89 (1H, s) (OH not observed)

Intermediate 20. Ethyl 5-amino-1-(2-(2-methoxyethoxy)phenyl)-3-methyl-1H-pyrazole-4-carboxylate The title compound was prepared using a method analogous to the preparation of ethyl 5-amino-1-(2-methoxyphenyl)-1H-pyrazole-4-carboxylate (Intermediate 1).

The crude product was purified by column chromatography (Biotage SNAP 50 g column, 0 to 40% EtOAc/DCM then Biotage SNAP 50 g column, 0 to 90% EtOAc/isohexane) to give the title compound as a yellow solid (4.3 g).

The crude product was used in subsequent reactions without further analysis.

Intermediate 21. 5-Amino-1-(2-(2-methoxyethoxy)phenyl)-3-methyl-1H-pyrazole-4-carboxylic acid The title compound was prepared from ethyl 5-amino-1-(2-(2-methoxyethoxy)phenyl)-3-methyl-1H-pyrazole-4-carboxylate (Intermediate 20) using a method analogous to the preparation of 5-amino-1-(3-fluoro-2-methylphenyl)-1H-pyrazole-4-carboxylic acid (Intermediate 2).

The title compound was obtained as a white solid (0.36 g, 9%).

$^1$H NMR (ppm)(400 MHz, CDCl$_3$): 2.19 (3H, s), 3.12 (3H, s), 3.49-3.41 (2H, m), 3.95 (2H, dd, J=4.4, 4.4 Hz), 5.39 (2H, s), 6.90-6.76 (2H, m), 7.15-7.06 (1H, m), 7.23-7.20 (1H, m), 9.92 (1H, br s)

Intermediate 22. Methyl 5-amino-1-(2-methoxyphenyl)-1H-1,2,3-triazole-4-carboxylate A mixture of sodium methoxide (1.0 M solution in MeOH) (10 mL, 10 mmol) and methyl 2-cyanoacetate (0.99 g, 10 mmol) was stirred at 45° C. for 0.5 hrs. The reaction mixture was allowed to cool to r.t. 1-Azido-2-methoxybenzene (0.5 M solution in toluene) (20 mL, 20 mmol) was added and the reaction mixture was stirred at r.t. for 18 hrs. H$_2$O (20 mL) was added and the reaction mixture was stirred at r.t. for 0.5 hrs. The resultant precipitate was collected by filtration, washed with H$_2$O (2×20 mL), Et$_2$O (2×30 mL) and dried under reduced pressure to give the title compound as a white solid (1.24 g, 50%).

$^1$H NMR (ppm)(400 MHz, CDCl$_3$): 3.89 (3H, s), 3.97 (3H, s), 5.21 (2H, s), 7.10-7.17 (2H, m), 7.47-7.54 (2H, m)

Intermediate 23. 5-Amino-1-(2-methoxyphenyl)-1H-1,2,3-triazole-4-carboxylic acid A mixture of methyl 5-amino-1-(2-methoxyphenyl)-1H-1,2,3-triazole-4-carboxylate (6.82 g, 26 mmol), 2 M NaOH (aq) (200 mL, 400 mmol), MeOH (50 mL) and THF (50 mL) was stirred at r.t. for 1 hr. The reaction mixture was acidified to approximately pH 2-3 with 12 M HCl (aq). The reaction mixture was extracted with EtOAc (3×100 mL). The combined organic extracts were dried (MgSO$_4$), filtered and the solvent removed under reduced pressure. The crude product was triturated with MeOH and dried under reduced pressure to give the title compound as a white solid (6.30 g, >95%).

$^1$H NMR (ppm) (400 MHz, DMSO-d6): 3.86 (3H, s), 6.30 (2H, s), 7.16-7.21 (1H, m), 7.33 (1H, d, J=7.8 Hz), 7.45 (1H, dd, J=1.6, 7.7 Hz), 7.60-7.66 (1H, m), 12.59-12.66 (1H, m)

Intermediate 24. Methyl 5-amino-1-(o-tolyl)-1H-1,2,3-triazole-4-carboxylate

The title compound was prepared using a method analogous to the preparation of methyl 5-amino-1-(2-methoxyphenyl)-1H-1,2,3-triazole-4-carboxylate (Intermediate 22).

The title compound was obtained as a white solid (0.45 g, 39%).

$^1$H NMR (ppm)(400 MHz, CDCl$_3$): 2.16 (3H, s), 3.98 (3H, s), 5.02 (2H, s), 7.30-7.33 (1H, m), 7.36-7.51 (3H, m)

Intermediate 25. 5-Amino-1-(o-tolyl)-1H-1,2,3-triazole-4-carboxylic acid

The title compound was prepared from methyl 5-amino-1-(o-tolyl)-1H-1,2,3-triazole-4-carboxylate (Intermediate 24) using a method analogous to the preparation of 5-amino-1-(2-methoxyphenyl)-1H-1,2,3-triazole-4-carboxylic acid (Intermediate 23).

The title compound was obtained as a white solid (0.37 g, 90%).

$^1$H NMR (ppm)(400 MHz, CDCl$_3$): 2.17 (3H, s), 5.08 (2H, s), 7.32 (1H, d, J=8.3 Hz), 7.38-7.46 (2H, m), 7.47-7.52 (1H, m)

Intermediate 26. Methyl 5-amino-1-(3-fluoro-2-methylphenyl)-1H-1,2,3-triazole-4-carboxylate The title compound was prepared using a method analogous to the preparation of methyl 5-amino-1-(2-methoxyphenyl)-1H-1,2,3-triazole-4-carboxylate (Intermediate 22).

The title compound was obtained as a white solid (0.21 g, 25%).

$^1$H NMR (ppm)(400 MHz, DMSO-d6): 2.00 (3H, d, J=2.0 Hz), 3.86 (3H, s), 6.62 (2H, s), 7.29-7.34 (1H, m), 7.49-7.55 (2H, m)

m/z: [ES+] 251 ([M+H]+, C11H11FN4O2)

Intermediate 27. 5-Amino-1-(3-fluoro-2-methylphenyl)-1H-1,2,3-triazole-4-carboxylic acid The title compound was prepared from methyl 5-amino-1-(3-fluoro-2-methylphenyl)-1H-1,2,3-triazole-4-carboxylate (Intermediate 26) using a method analogous to the preparation of 5-amino-1-(2-methoxyphenyl)-1H-1,2,3-triazole-4-carboxylic acid (Intermediate 23).

The title compound was obtained as a white solid (0.14 g, 71%).

$^1$H NMR (ppm)(400 MHz, DMSO-d6): 2.01 (3H, d, J=1.8 Hz), 6.49 (2H, s), 7.28-7.34 (1H, m), 7.49-7.54 (2H, m), 12.68 (1H, s)

m/z: [ES+] 237 ([M+H]+, C10H9FN4O2)

Intermediate 28. N-(4-Bromophenyl)-2-cyanoacetamide

A mixture of 2-cyanoacetic acid (5.0 g, 59 mmol), $PCl_5$ (12.3 g, 59 mmol) and DCM (500 mL) was stirred at 40° C. for 2 hrs. The reaction mixture was allowed to cool to r.t. 4-Bromoaniline (11.9 g, 59 mmol) was added and the reaction mixture was stirred at 40° C. for 2 hrs. The reaction mixture was allowed to cool to r.t and concentrated under reduced pressure. $H_2O$ (250 mL) was added to the residue and the suspension stirred at r.t. for 0.5 hrs. The solid material was collected by filtration, washed with 1 M $NaHCO_3$ (aq) (250 mL) and $H_2O$ (250 mL) and dried under reduced pressure to give the title compound as a yellow solid (13.1 g, 93%).

$^1$H NMR (ppm)(400 MHz, DMSO-d6): 3.96 (2H, s), 7.57 (4H, s), 10.48 (1H, s)

Intermediate 29. N-(5-Chloropyridin-2-yl)-2-cyanoacetamide

A mixture of 2-cyanoacetic acid (1.0 g, 11.8 mmol), 5-chloropyridin-2-amine (0.83 g, 12.9 mmol), EDC (2.46 g, 12.9 mmol), 2-pyridinol 1-oxide (3.9 g, 35.4 mmol), $NEt_3$ (4.9 mL, 35.4 mmol) and DCM (25 mL) was stirred at r.t. for 16 hrs. The reaction mixture was diluted with 1 M HCl (aq) (30 mL) and extracted with EtOAc (2×30 mL). The combined organic extracts were dried ($MgSO_4$), filtered and the solvent removed under reduced pressure. The crude product was purified by column chromatography (Biotage SNAP 25 g column, 0 to 25% EtOAc/isohexane) to give the title compound as an off-white solid (0.10 g, 4%).

$^1$H NMR (ppm)(400 MHz, DMSO-d6) 4.03 (2H, s), 8.00 (1H, dd, J=2.7, 9.0 Hz), 8.10 (1H, d, J=8.8 Hz), 8.45 (1H, d, J=2.5 Hz), 11.06 (1H, s)

Intermediate 30. N-(4-Chlorophenyl)-2-cyanoacetamide

A mixture of methyl 2-cyanoacetate (22.2 g, 224 mmol), 4-chloroaniline (25.9 g, 202 mmol) and DMF (200 mL) was stirred at 100° C. for 72 hrs. The reaction mixture was concentrated under reduced pressure and the crude product triturated with Et2O to give the title compound as an off-white solid (10.1 g, 31%).

$^1$H NMR (ppm)(400 MHz, DMSO-d6): 3.90 (2H, s), 7.41-7.37 (2H, m), 7.59-7.56 (2H, m), 10.42 (1H, s)

Intermediate 31. 2-Cyano-N-(5-(trifluoromethyl)pyridin-2-yl)acetamide

The title compound was prepared using a method analogous to the preparation of N-(4-chlorophenyl)-2-cyanoacetamide (Intermediate 30).

The title compound was obtained as an off-white solid (6.80 g, 51%).

$^1$H NMR (ppm)(400 MHz, $CDCl_3$): 3.64 (2H, s), 7.98 (1H, d, J=7.2 Hz), 8.26 (1H, s), 8.47 (1H, s), 8.59 (1H, s)

Intermediate 32. N-(4-Chloro-2-methoxyphenyl)-2-cyanoacetamide

The title compound was prepared using a method analogous to the preparation N-(4-chlorophenyl)-2-cyanoacetamide (Intermediate 30).

The title compound was obtained an off-white solid (0.67 g, 93%).

$^1$H NMR (ppm)(400 MHz, $CDCl_3$): 3.56 (2H, s), 3.92 (3H, s), 6.90 (1H, s), 6.94-6.98 (1H, m), 8.21 (1H, d, J=8.8 Hz), 8.26 (1H, s)

Intermediate 33. 2-Cyano-N-(2-fluoro-4-(trifluoromethyl)phenyl)acetamide

The title compound was prepared using a method analogous to the preparation of N-(4-chlorophenyl)-2-cyanoacetamide (Intermediate 30).

The title compound was obtained as a white solid (1.29 g, 35%).

$^1$H NMR (ppm)(400 MHz, $CDCl_3$): 4.11 (2H, s), 7.66 (1H, d, J=8.6 Hz), 7.80-7.86 (1H, m), 8.29 (1H, dd, J=8.1, 8.1 Hz), 10.52 (1H, s)

Intermediate 34. 2-Cyano-N-(3-fluoro-5-(trifluoromethyl)pyridin-2-yl)acetamide The title compound was prepared from 2-amino-3-fluoro-5-trifluoromethylpyridine using a method analogous to the preparation of N-(4-chlorophenyl)-2-cyanoacetamide (Intermediate 30).

The crude product was purified by column chromatography (Biotage SNAP 25 g column, 20-80% EtOAC/ihexane) to give the title compound as a pale yellow powder (0.23 g, 45%)

$^1$H NMR (ppm) (400 MHz, CDCl3): 4.14 (4H, s), 5.30 (1H, s), 7.73 (2H, dd, J=1.8, 9.6 Hz), 8.12 (2H, s), 8.47 (2H, s)

Intermediate 35. 2-((5-(2,2,2-Trifluoroethoxy)pyridin-2-yl)amino)acetonitrile A stirred mixture of cyanoacetic acid (0.62 g, 7.3 mmol) and phosphorus pentachloride (1.52 g, 7.3 mmol) in DCM (100 mL) was heated to reflux for 1.5 hrs. A colourless soln. was produced. The mixture was cooled and 5-(2,2,2-trifluoroethoxy)pyridin-2-amine (1.40 g, 7.3 mmol) was added and the mixture re-heated to reflux for 5 hrs. The mixture was cooled and concentrated under reduced pressure and the residue treated with water (50 mL) and agitated using sonication for 0.2 hrs. DCM (10 mL) was added and the mixture stirred for 0.3 hrs and the precipitate collected by filtration, washed with water and dried under vacuum to give the title compound as a yellow solid (0.46 g, 24%).

$^1$H NMR (ppm) (400 MHz, DMSO): 4.00 (2H, s), 4.90 (2H, q, J=8.9 Hz), 7.66 (1H, dd, J=3.3, 9.1 Hz), 8.04 (1H, d, J=9.1 Hz), 8.23 (1H, d, J=2.8 Hz), 10.85 (1H, s)

Intermediate 36. 5-(2,2,2-Trifluoroethoxy)pyridin-2-amine

To a stirred mixture of 2-amino-5-hydroxypyridine (1.00 g, 9.0 mmol) and cesium carbonate (4.40 g, 13.5 mmol) in dry DMF (25 mL) was added dropwise 2,2,2-trifluoroethyl trifluoromethane sulfonate (2.29 g, 9.9 mmol). After stirring for 6 hrs the mixture was concentrated to dryness under reduced pressure and residue partitioned between EtOAc (100 mL) and H₂O (20 mL). The organic phase was dried (MgSO₄) and concentrated to dryness under reduced pressure and the residue purified by column chromatography (Biotage SNAP 25 g column, 20-80% EtOAC/ihexane) to give the title compound as a pale brown solid (1.22 g, 70%).

¹H NMR (ppm) (400 MHz, CDCl₃): 4.09-4.28 (4H, m), 6.49 (1H, d, J=8.8 Hz), 7.16 (1H, dd, J=2.9, 9.0 Hz), 7.83 (1H, d, J=2.8 Hz)

Intermediate 37. N-(4-Chloro-2-fluorophenyl)-2-cyanoacetamide

The title compound was prepared using a method analogous to the preparation of N-(4-chlorophenyl)-2-cyanoacetamide (Intermediate 30).

The title compound was obtained as an off-white solid (4.70 g, 88%).

¹H NMR (ppm)(400 MHz, CDCl₃): 4.05 (2H, s), 7.33-7.37 (1H, m), 7.58 (1H, d, 10.7 Hz), 7.98 (1H, dd, J=8.6, 8.6 Hz), 10.30 (1H, s)

Intermediate 38. 2-Cyano-N-(5-iodopyridin-2-yl)acetamide

The title compound was prepared using a method analogous to the preparation of N-(4-chlorophenyl)-2-cyanoacetamide (Intermediate 30).

The title compound was obtained as an off-white solid (8.94 g, 62%).

¹H NMR (ppm)(400 MHz, DMSO-d6): 4.03 (2H, s), 7.94 (1H, d, J=8.6 Hz), 8.21 (1H, dd, J=2.3, 8.8 Hz), 8.61 (1H, d, J=1.5 Hz), 11.00 (1H, s)

Intermediate 39. 2-Cyano-N-(6-(trifluoromethyl)pyridin-3-yl)acetamide

The title compound was prepared using a method analogous to the preparation of N-(4-chlorophenyl)-2-cyanoacetamide (Intermediate 30).

The title compound was obtained as an off-white solid (0.46 g, quantitative).

¹H NMR (ppm)(400 MHz, DMSO-d6): 4.07 (2H, s), 7.96 (1H, d, J=8.6 Hz), 8.34 (1H, dd, J=2.1, 8.5 Hz), 8.88 (1H, d, J=2.3 Hz), 10.97 (1H, s)

Intermediate 40. N-(4-Chlorophenyl)-2-cyano-3-ethoxyacrylamide

A mixture of N-(4-chlorophenyl)-2-cyanoacetamide (5.00 g, 25.5 mmol), triethyl orthoformate (7.50 g, 51 mmol) and acetic anhydride (0.75 mL, 8 mmol) was stirred at 125° C. for 18 hrs. The reaction mixture was allowed to cool to r.t. The solid material was collected by filtration, triturated with MeOH and dried under reduced pressure to give the title compound as an off-white solid (3.10 g, 48%).

¹H NMR (ppm)(400 MHz, DMSO-d6): 1.40 (3H, t, J=7.2 Hz), 4.46 (2H, q, J=7.2 Hz), 7.44 (2H, d, J=9.2 Hz), 7.67 (2H, d, J=8.6 Hz), 8.42 (1H, s), 9.98 (1H, s)

Intermediate 41. 2-Cyano-3-dimethylamino-N-(5-(trifluoromethyl)pyridin-2-yl)acrylamide A mixture of 2-cyano-N-(5-(trifluoromethyl)pyridin-2-yl)acetamide (1.54 g, 6.7 mmol), N,N-dimethylformamide dimethyl acetal (0.89 mL, 6.7 mmol) and xylene (10 mL) was stirred 140° C. for 1.5 hrs. The reaction mixture was allowed to cool to r.t. The solid material was collected by filtration, triturated with EtOH and dried under reduced pressure to give the title compound as an off-white solid (1.42 g, 75%).

¹H NMR (ppm)(400 MHz, DMSO-d6): 3.31 (3H, s), 3.35 (3H, s), 8.01 (1H, s), 8.27-8.16 (2H, m), 8.72 (1H, s), 9.58 (1H, s)

Intermediate 42. 2-Cyano-3-ethoxy-N-(5-(trifluoromethyl)pyridin-2-yl)pent-2-enamide A stirred mixture of 2-cyano-N-(5-(trifluoromethyl)pyridin-2-yl)acetamide (572 mg, 2.5 mmol), triethylorthopropionate (882 mg, 5.0 mmol) in acetic anhydride (1 mL) was heated to 75° C. for 0.2 hrs. The mixture was diluted with diisopropyl ether (10 mL) and the resultant precipitate collected by filtration, washed with a small volume of diisopopyl ether and dried under vacuum to give the crude title compound as a brown solid (0.39 g, 50%).

¹H NMR (ppm) (400 MHz, CDCl₃): 1.37 (3H, t), 1.63 (3H, t), 2.84 (2H, q, J=7.58 Hz), 4.45 (2H, q, J=6.56 Hz), 7.92 (1H, dd, J=2.1, 8.7 Hz), 8.39 (1H, d, J=8.8 Hz), 8.52 (1H, s), 9.77 (1H, s)

Intermediate 43. 2-Cyano-3-methoxy-4-methyl-N-(5-(trifluoromethyl)pyridin-2-yl)pent-2-enamide The title compound was prepared from 2-cyano-N-(5-(trifluoromethyl)pyridin-2-yl)acetamide using a method analogous to the preparation of 2-cyano-3-ethoxy-N-(5-(trifluoromethyl)pyridin-2-yl)pent-2-enamide (Intermediate 42).

The crude product was purified by column chromatography (Biotage SNAP 50 g column, 0 to 30% EtOAc/isohexane) to give the title compound as a white solid (0.045 g, 7%).

The product was used in subsequent reactions without further analysis.

Intermediate 44. 2-Cyano-3-dimethylamino-N-(2-fluoro-4-(trifluoromethyl)phenyl)but-2-enamide A mixture of 2-cyano-N-(2-fluoro-4-(trifluoromethyl)phenyl)acetamide (1.23 g, 5.0 mmol), ), N,N-dimethylformamide dimethyl acetal (0.82 mL, 5.0 mmol) and xylene (25 mL) was stirred 100° C. for 1 hr. The reaction mixture was allowed to cool to r.t. and concentrated under reduced pressure. The crude product was triturated with Et₂O and dried under reduced pressure to give the title compound as an off-white solid (0.89 g, 56%).

¹H NMR (ppm)(400 MHz, DMSO-d6): 2.41 (3H, s), 3.15 (6H, s), 7.59 (1H, d, J=8.3 Hz), 7.74 (1H, d, J=11.1 Hz), 8.11 (1H, dd, J=8.0, 8.0 Hz), 9.33 (1H, m)

Intermediate 45. N-(5-Chloropyridin-2-yl)-2-cyano-3-(dimethylamino)acrylamide The title compound was prepared from N-(5-chloropyridin-2-yl)-2-cyanoacetamide using a method analogous to the preparation of 2-cyano-3-(dimethylamino)-N-(5-(trifluoromethyl)pyridin-2-yl)acrylamide (Intermediate 41).

The title compound was obtained as a pale brown solid (5.87 g, 92%).

¹H NMR (ppm)(400 MHz, CDCl₃): 3.40 (3H, s), 3.26 (3H, s), 7.63 (1H, dd, J=2.5, 8.8 Hz), 7.87 (1H, s), 8.15 (1H, d, J=8.8 Hz), 8.22 (1H, d, J=2.0 Hz), 8.28 (1H, s)

Intermediate 46. 2-Cyano-3-(dimethylamino)-N-(5-iodopyridin-2-yl)acrylamide

The title compound was prepared from N-(5-iodopyridin-2-yl)-2-cyanoacetamide using a method analogous to the preparation of 2-cyano-3-(dimethylamino)-N-(5-(trifluoromethyl)pyridin-2-yl)acrylamide (Intermediate 41).

The title compound was obtained as an orange solid (4.41 g, 64%).

¹H NMR (ppm)(400 MHz, CDCl₃): 3.67 (6H, s), 7.93-7.97 (2H, m), 8.14 (1H, dd, J=2.3, 8.8 Hz), 8.55 (1H, d, J=1.8 Hz), 9.17 (1H, s)

Intermediate 47. N-(4-Chloro-2-fluorophenyl)-2-cyano-3-(dimethylamino)acrylamide The title compound was prepared from N-(4-chloro-2-fluorophenyl)-2-cyanoacetamide using a method analogous to the preparation of 2-cyano-3-(dimethylamino)-N-(5-(trifluoromethyl)pyridin-2-yl)acrylamide (Intermediate 41).

The title compound was obtained as an orange solid (3.07 g, 52%).

¹H NMR (ppm)(400 MHz, DMSO-d6): 3.35 (6H, d, J=10.6 Hz), 7.27-7.32 (1H, m), 7.51 (1H, dd, J=2.5, 10.6 Hz), 7.73 (1H, t, J=8.6 Hz), 7.89 (1H, s), 8.85 (1H, s)

Intermediate 48. N-(4-Chloro-2-methoxyphenyl)-2-cyano-3-(dimethylamino)acrylamide The title compound was prepared from N-(4-chloro-2-methoxyphenyl)-2-cyanoacetamide using a method analogous to the preparation of 2-cyano-3-(dimethylamino)-N-(5-(trifluoromethyl)pyridin-2-yl)acrylamide (Intermediate 41).

The crude product was purified by column chromatography (Biotage SNAP 50 g column, 20 to 80% EtOAc/isohexane) to give the title compound as a white solid (0.36 g, 43%).

¹H NMR (ppm)(400 MHz, CDCl₃): 3.23 (3H, s), 3.38 (3H, s), 3.90 (3H, s), 6.86 (1H, d, J=2.3 Hz), 6.93 (1H, dd, J=2.1, 8.7 Hz), 7.84 (1H, s), 8.27 (1H, d, J=8.6 Hz), 8.31 (1H, s)

Intermediate 49. 2-Cyano-3-dimethylamino-N-(5-(trifluoromethyl)pyridin-2-yl)but-2-enamide The title compound was prepared from 2-cyano-N-(5-(trifluoromethyl)pyridin-2-yl)acetamide using a method analogous to the preparation of 2-cyano-3-(dimethylamino)-N-(2-fluoro-4-(trifluoromethyl)phenyl)but-2-enamide (Intermediate 44).

The crude product was purified by trituration with EtOH to give the title compound as a white solid (1.1 g, 52%).

¹H NMR (ppm)(400 MHz, CDCl₃): 2.45 (3H, s), 3.21 (6H, s), 7.81 (1H, dd, J=2.3, 8.8 Hz), 8.22 (1H, d, J=8.8 Hz), 8.41 (1H, s), 8.47 (1H, s)

Intermediate 50. N-(5-Chloropyridin-2-yl)-2-cyano-3-(dimethylamino)but-2-enamide The title compound was prepared from N-(5-chloropyridin-2-yl)-2-cyanoacetamide using a method analogous to the preparation of 2-cyano-3-(dimethylamino)-N-(2-fluoro-4-(trifluoromethyl)phenyl)but-2-enamide (Intermediate 44).

The title compound was obtained as a purple solid (3.10 g, 78%).

¹H NMR (ppm)(400 MHz, CDC₁₃): 2.47 (3H, s), 3.22-3.19 (6H, m), 7.61 (1H, dd, J=1.9, 8.7 Hz), 8.11 (1H, d, J=8.8 Hz), 8.24-8.21 (2H, m)

Intermediate 51. 2-Cyano-3-dimethylamino-N-(3-fluoro-5-(trifluoromethyl)pyridin-2-yl)acrylamide The title compound was prepared from 2-cyano-N-(3-fluoro-5-(trifluoromethyl)pyridin-2-yl)acetamide using a method analogous to the preparation of 2-cyano-3-(dimethylamino)-N-(5-(trifluoromethyl)pyridin-2-yl)acrylamide (Intermediate 41).

The crude product was purified by trituration with isohexane to give the title compound as an off-white solid (0.16 g, 67%).

¹H NMR (ppm) (400 MHz, CDCl₃): 3.28 (3H, s), 3.42 (3H, s), 7.67 (1H, dd, J=1.8, 9.6 Hz), 7.91 (1H, s), 8.10 (1H, s), 8.50 (1H, s)

Intermediate 52. 3-Dimethylamino-2-((5-(2,2,2-trifluoroethoxy)pyridin-2-yl)amino)acrylonitrile A stirred mixture of 2-((5-(2,2,2-trifluoroethoxy)pyridin-2-yl)amino)acetonitrile (1.20 g, 4.6 mmol) and dimethylformamide dimethyl acetal (0.55 g, 4.6 mmol) in xylene (20 mL) was heated to reflux for 2 hrs. The cooled mixture was concentrated to dryness in vacuo and the residue was triturated in diethyl ether to afford the title compound as a yellow-green solid (1.27 g, 88%).

¹H NMR (ppm) (400 MHz, DMSO): 3.31 (6H, d, J=21.5 Hz), 4.88 (2H, q, J=8.9 Hz), 7.62 (1H, dd, J=3.0, 9.1 Hz), 7.96 (1H, s), 8.03 (1H, d, J=9.1 Hz), 8.18 (1H, d, J=2.8 Hz), 8.97 (1H, s)

Intermediate 53. N-(5-Chloropyridin-2-yl)-2-cyano-3-ethoxypent-2-enamide

The title compound was prepared from N-(5-chloropyridin-2-yl)-2-cyanoacetamide using a method analogous to the preparation of 2-cyano-3-ethoxy-N-(5-(trifluoromethyl)pyridin-2-yl)pent-2-enamide (Intermediate 42).

The crude product was purified by column chromatography (Biotage SNAP 50 g column, 0 to 50% EtOAc/isohexane) to give the title compound as a pale brown solid (1.05 g, 12%).

¹H NMR (ppm)(400 MHz, DMSO-d6): 1.26 (3H, t, J=7.5 Hz), 3.23 (2H, q, J=7.5 Hz), 7.29 (1H, d, J=9.8 Hz), 7.85 (1H, dd, J=2.1, 9.7 Hz), 8.59 (1H, d, J=1.8 Hz)

Intermediate 54. 2-Cyano-3-dimethylamino-N-(6-(trifluoromethyl)pyridin-3-yl)acrylamide The title compound was prepared using a method analogous to the preparation of 2-cyano-3-dimethylamino N-(4-chloro-2-methoxyphenyl)-2-cyanoacetamide using a method analogous to the preparation of 2-cyano-3-(dimethylamino)-N-(5-(trifluoromethyl)pyridin-2-yl)acrylamide (Intermediate 41).

The title compound was obtained as an off-white solid (0.16 g, 56%).

¹H NMR (ppm)(400 MHz, CDCl₃): 3.28 (3H, s), 3.42 (3H, s), 7.65 (1H, d, J=8.6 Hz), 7.79 (1H, s), 7.89 (1H, s), 8.27 (1H, dd, J=2.4, 8.5 Hz), 8.74 (1H, d, J=2.5 Hz).

Intermediate 55. di-tert-Butyl 1-(2-(1H-pyrazol-1-yl)phenyl)hydrazine-1,2-dicarboxylate The title compound was prepared using a method analogous to the preparation of tert-butyl 1-(2-(2-methoxyethoxy)phenyl)-2-pivaloylhydrazinecarboxylate (Intermediate 8).

The crude product was purified by column chromatography (Biotage SNAP 50 g column, 0 to 40% EtOAc/isohexane) to give the title compound as a colourless oil (1.31 g, 89%).

$^1$H NMR (ppm)(400 MHz, CDCl$_3$): 7.77-7.72 (2H, m), 7.44-7.37 (3H, m), 6.46-6.44 (1H, m), 1.56 (18H, s)

Intermediate 56. di-tert-Butyl 1-(2-((dimethylamino)methyl)phenyl)hydrazine-1,2-dicarboxylate The title compound was prepared using a method analogous to the preparation of tert-butyl 1-(2-(2-methoxyethoxy)phenyl)-2-pivaloylhydrazinecarboxylate (Intermediate 8).

The crude product was purified by column chromatography (Biotage SNAP 50 g column, 0 to 80% EtOAc/isohexane) to give the title compound as a colourless oil (0.72 g, 86%).

The product was used in subsequent reactions without further analysis.

Intermediate 57. di-tert-Butyl 1-(3-fluoro-2-(2-methoxyethoxy)phenyl)hydrazine-1,2-dicarboxylate The title compound was prepared using a method analogous to the preparation of tert-butyl 1-(2-(2-methoxyethoxy)phenyl)-2-pivaloylhydrazinecarboxylate (Intermediate 8).

The crude product was purified by column chromatography (Biotage SNAP 50 g column, 0 to 80% EtOAc/isohexane) to give the title compound as a colourless oil (1.4 g, 80%).

The product was used in subsequent reactions without further analysis.

Intermediate 58. 1-Bromo-3-fluoro-2-(2-methoxyethoxy)benzene

To a solution of 2-bromo-6-fluorophenol (1.0 g, 5.2 mmol) in MeCN (20 mL) was added K$_2$CO$_3$ (2.2 g, 15.7 mmol) followed by 1-bromo-2-methoxyethane (1.2 g, 7.9 mmol). The mixture was heated at 80° C. for 18 hrs then the mixture was cooled and water (50 mL) was added and the mixture extracted with DCM (2×75 mL). The combined extracts were dried (MgSO$_4$) then concentrated under reduced pressure to give the title compound as a colourless oil (1.09 g, 85%).

$^1$H NMR (ppm)(400 MHz, CDCl$_3$): 3.76 (2H, t, J=4.8 Hz), 3.45 (3H, s), 4.25 (2H, t, J=4.8 Hz), 6.95-6.88 (1H, m), 7.09-7.02 (1H, m), 7.34-7.29 (1H, m)

Intermediate 59. di-tert-Butyl 1-(2-morpholinophenyl)hydrazine-1,2-dicarboxylate The title compound was prepared using a method analogous to the preparation of tert-butyl 1-(2-(2-methoxyethoxy)phenyl)-2-pivaloylhydrazinecarboxylate (Intermediate 8).

The crude product was purified by column chromatography (Biotage SNAP 50 g column, 0 to 50% EtOAc/isohexane) to give the title compound as a colourless oil (0.61 g, 74%).

The product was used in subsequent reactions without further analysis.

Intermediate 60. 5-(2-(2-(Diphenylmethylene)hydrazinyl)phenyl)oxazole

A mixture of 5-(2-bromophenyl)oxazole (0.90 g, 4.0 mmol), benzophenone hydrazone (0.78 g, 4.0 mmol), NaOtBu (0.58 g, 6.0 mmol), Pd(AcO)$_2$ (0.045 mg, 0.2 mmol) and Xanthphos (0.116 g, 0.2 mmol) in toluene (20 mL) was stirred at 80° C. for 18 hrs. The reaction mixture was allowed to cool to r.t., filtered through Celite, and concentrated under reduced pressure.

The crude product was purified by silica gel chromatography (Biotage SNAP 100 g column, 0 to 25% EtOAc/isohexane) to give the title compound as a white solid (0.69 g, 51%).

$^1$H NMR (ppm)(400 MHz, CDCl$_3$): 6.88 (2H, m), 7.32-7.38 (5H, m), 7.39-7.42 (2H, m), 7.50 (1H, s), 7.57-7.67 (5H, m), 7.91 (1H, d, J=8.1 Hz), 8.53 (1H, s)

Intermediate 61. 1-(Diphenylmethylene)-2-(2-fluoro-3-methylphenyl)hydrazine

The title compound was prepared using a method analogous to 5-(2-(2-(diphenylmethylene) hydrazinyl)phenyl)oxazole (Intermediate 60).

The crude product was purified by silica gel chromatography (Biotage SNAP 25 g column, 0 to 15% EtOAc/isohexane) to give the title compound as a yellow solid (0.234 g, 77%).

$^1$H NMR (ppm)(CDCl3): 2.19 (3H, d, J=2.3 Hz), 6.62 (1H, dd, J=6.9, 6.9 Hz), 7.00 (1H, dd, J=7.8, 7.8 Hz), 7.29-7.36 (5H, m), 7.51-7.62 (6H, m), 7.66 (1H, d, J=2.8 Hz)

Intermediate 62. 5-(2-(2-(Diphenylmethylene)hydrazinyl)-6-fluorophenyl)oxazole The title compound was prepared using a method analogous to 5-(2-(2-(diphenylmethylene) hydrazinyl)phenyl)oxazole (Intermediate 60).

The crude product was purified by silica gel chromatography (Biotage SNAP 100 g column, 0 to 20% EtOAc/isohexane) to give the title compound as a yellow solid (1.5 g, 84%).

$^1$H NMR (ppm)(CDCl3): 6.65-6.59 (1H, m), 7.27-7.38 (8H, m), 7.58-7.66 (5H, m), 7.72 (1H, d, J=8.6 Hz), 9.02 (1H, s)

Intermediate 63. 5-(2-Bromo-6-fluorophenyl)oxazole

A mixture of 2-bromo-6-fluorobenzaldehyde (1.02 g, 5.0 mmol), 4-toluenesulfonylmethylisocyanide (1.07 g, 5.5 mmol) and K$_2$CO$_3$ (1.38 g, 10 mmol) in MeOH (25 mL) was stirred at 65° C. for 3 hrs. The mixture was allowed to cool to r.t. and the reaction mixture was concentrated under reduced pressure. The crude product was suspended in H$_2$O (10 mL), collected by filtration and dried under reduced pressure to give the title compound as a white solid (1.35 g, >95%).

$^1$H NMR (ppm)(CDCl$_3$): 7.12-7.18 (1H, m), 7.27-7.32 (1H, m), 7.42 (1H, s), 7.51 (1H, d, J=8.1 Hz), 8.04 (1H, s)

Intermediate 64. 1-((2-Bromophenyl)sulfonyl)pyrrolidine

To a solution of 2-bromobenzenesulfonyl chloride (1.0 g, 3.91 mmol) in dry dioxane (10 mL) at approximately 10° C.

was added dropwise pyrrolidine (0.65 mL, 7.81 mmol). The mixture was warmed to room temperature and stirred for 0.5 hrs. EtOAc (100 mL) was added and the organic layer was washed with $H_2O$ (3×30 mL) and brine (30 mL) passed through a phase separation cartridge and the solvent removed under reduced pressure to give the title compound as a yellow oil (1.24 g>95%).

$^1$H NMR (ppm)(400 MHz, $CDCl_3$): 1.89-1.94 (4H, m), 3.39-3.44 (4H, m), 7.35-7.46 (2H, m), 7.74 (1H, dd, J=1.3, 7.8 Hz), 8.12 (1H, dd, J=1.8, 7.8 Hz)

Intermediate 65. 1-((2-(2-(Diphenylmethylene)hydrazinyl)phenyl)sulfonyl)pyrrolidine The title compound was prepared from 1-((2-bromophenyl)sulfonyl)pyrrolidine using a method analogous to the preparation of 5-(2-(2-(diphenylmethylene)hydrazinyl)phenyl)oxazole (Intermediate 60).

The crude product was purified by column chromatography (Biotage SNAP 50 g column, 10 to 25% EtOAc/isohexane to give the title compound as a pale yellow solid (0.70 g, 46%).

$^1$H NMR (ppm)(400 MHz, $CDCl_3$): 1.70-1.72 (4H, m), 2.99-2.94 (4H, m), 6.82-6.87 (1H, m), 7.31-7.35 (5H, m), 7.49-7.65 (7H, m), 7.98 (1H, d, J=7.6 Hz), 9.60 (1H, s)

Intermediate 66. 2-(2-(Diphenylmethylene)hydrazinyl)-N-methyl-N-(pyridin-3-yl)benzenesulfonamide The title compound was prepared from 2-bromo-N-methyl-N-(pyridin-3-yl)benzenesulfonamide using a method analogous to the preparation of 5-(2-(2-(diphenylmethylene)hydrazinyl)phenyl)oxazole (Intermediate 60).

The crude product was purified by column chromatography (Biotage SNAP 50 g column, 20 to 60% EtOAc/isohexane to give the title compound as an orange solid (1.3 g, 71%).

$^1$H NMR (ppm)(400 MHz, $CDCl_3$): 3.01 (3H, s), 6.74-6.80 (1H, m), 7.13-7.20 (3H, m), 7.28-7.35 (6H, m), 7.49-7.61 (6H, m), 7.94 (1H, d, J=8.3 Hz), 8.27 (1H, d, J=2.3 Hz), 8.47 (1H, dd, J=1.4, 4.7 Hz), 9.43 (1H, s)

Intermediate 67. 2-Bromo-N-methyl-N-(pyridin-3-yl)benzenesulfonamide

To a solution of N-methylpyridin-3-amine (0.47 g, 4.35 mmol) in dry dioxane (5 mL) was added 2-bromobenzenesulfonyl chloride (1.1 g, 4.35 mmol) and pyridine (1.4 mL, 17.4 mmol) and the mixture was stirred at r.t. overnight. $H_2O$ (10 mL) was added and the mixture was extracted with EtOAc (60 mL). The organic layer was washed with $H_2O$ (2×20 mL) and brine (20 mL) passed through a phase separation cartridge and the solvent removed under reduced pressure to give the title compound as a golden yellow oil (1.35 g, 95%).

$^1$H NMR (ppm)(400 MHz, $CDCl_3$): 3.44 (3H, s), 7.24-7.30 (1H, m), 7.36-7.40 (2H, m), 7.67 (1H, ddd, J=1.5, 2.5, 8.3 Hz), 7.72-7.76 (1H, m), 7.93-7.96 (1H, m), 8.46 (2H, dd, J=5.3 Hz)

Intermediate 68. 2-Hydrazinyl-3-methylpyridine

A mixture of 2-bromo-3-methylpyridine (1.50 g, 8.7 mmol) and hydrazine monohydrate (4.3 mL, 87 mmol) was stirred at 100° C. for 20 hrs. The reaction mixture was allowed to cool to r.t. The resultant precipitate was collected by filtration and washed with $H_2O$. The solid material was dissolved in DCM (50 mL) and dried (phase separating cartridge). The solvent was removed under reduced pressure to give the title compound as a white solid (0.56 g, 52%).

$^1$H NMR (ppm)(400 MHz, $CDCl_3$): 2.08 (3H, s), 4.00-4.00 (2H, m), 5.63-5.49 (1H, m), 6.69-6.60 (1H, m), 7.30-7.22 (1H, m), 8.08 (1H, d, J=3.8 Hz)

Intermediate 69. 1-(2-Hydrazinylphenyl)-1H-pyrazole hydrochloride

The title compound was prepared from di-tert-butyl 1-(2-(1H-pyrazol-1-yl)phenyl)hydrazine-1,2-dicarboxylat using a method analogous to the preparation of 3-hydrazinyl-4-methylpyridine hydrochloride (Intermediate 68) to give the title compound as a yellow solid (0.63 g, 85%).

$^1$H NMR (ppm)(400 MHz, $CDCl_3$): 6.65-6.62 (1H, m), 7.21-7.14 (1H, m), 7.39-7.35 (1H, m), 7.48-7.40 (1H, m), 7.56 (1H, dd, J=1.3, 7.8 Hz), 7.90 (1H, d, J=1.8 Hz), 8.32 (1H, d, J=2.3 Hz), 10.65-10.55 (3H, m)

Intermediate 70. (2-Fluoro-6-methylphenyl)hydrazine hydrochloride

The title compound was prepared using a method analogous to the preparation 3-hydrazinyl-4-methylpyridine hydrochloride (Intermediate 68) to give the title compound as an off-white solid (0.069 g, 13%).

The crude product was used in subsequent reactions without further analysis.

Intermediate 71. 1-(2-Hydrazinylphenyl)-N,N-dimethylmethanamine

The title compound was prepared using a method analogous to the preparation of 3-hydrazinyl-4-methylpyridine hydrochloride (Intermediate 68).

The crude product was purified by SPE (Isolute SCX-2 10 g column, 0 to 100% 7 M NH3 in MeOH/DCM) to give the title compound as a yellow oil (0.17 g, >95%).

The crude product was used in subsequent reactions without further analysis.

Intermediate 72. (3-Fluoro-2-(2-methoxyethoxy)phenyl)hydrazine hydrochloride

The title compound was prepared from di-tert-butyl 1-(3-fluoro-2-(2-methoxyethoxy)phenyl)hydrazine-1,2-dicarboxylate using a method analogous to the preparation of 3-hydrazinyl-4-methylpyridine hydrochloride (Intermediate 68).

The crude product was purified trituration with iso-hexane to give the title compound as a yellow oil (0.48 g, 46%).

$^1$H NMR (ppm)(400 MHz, $CDCl_3$): 3.50 (3H, s), 3.72-3.66 (2H, m), 4.28 (2H, dd, J=3.8, 3.8 Hz), 6.78 (1H, t, J=9.5 Hz), 6.94-6.86 (1H, m), 7.14 (1H, d, J=8.1 Hz), 8.00 (1H, s), 10.18 (3H, s)

Intermediate 73. 4-(2-Hydrazinylphenyl)morpholine hydrochloride

The title compound was prepared using a method analogous to the preparation of 3-hydrazinyl-4-methylpyridine hydrochloride (Intermediate 68).

The crude product was purified trituration with $Et_2O$ to give the title compound as a white solid (0.33 g, 69%).

The crude product was used in subsequent reactions without further analysis Intermediate 74. 5-(2-Hydrazinyl-phenyl)oxazole A mixture of 5-(2-(2-(diphenylmethylene) hydrazinyl)phenyl)oxazole, HCl (4 M solution in dioxane) (15 mL) and $H_2O$ (0.5 mL) was stirred at r.t. for 48 hrs. The reaction mixture was concentrated under reduced pressure. The crude product was purified by SPE (Isolute SCX-2 10 g column, 0 to 100% 7 M NH3 in MeOH/DCM) to give the title compound as a white solid (0.19 g, 53%).

$^1$H NMR (ppm)(400 MHz, DMSO-d6): 7.16-7.23 (2H, m), 7.47-7.52 (1H, m), 7.58 (1H, s), 7.72 (1H, dd, J=1.4, 7.7 Hz), 8.13-8.14 (1H, m), 8.59 (1H, s), 10.24 (2H, s)

Intermediate 75. (2-Fluoro-3-methylphenyl)hydrazine hydrochloride

The title compound was prepared using a method analogous to 5-(2-hydrazinylphenyl)oxazole (Intermediate 74).

The crude compound was triturated in diethyl ether to give the title compound which was obtained as a white solid (0.19 g, 78%).

$^1$H NMR (ppm)(DMSO-d6): 2.28 (3H, d, J=2.0 Hz), 7.01-6.91 (2H, m), 7.11 (1H, dd, J=7.8, 7.8 Hz), 8.22 (1H, s), 10.13-10.03 (3H, m)

Intermediate 76. 5-(2-Fluoro-6-hydrazinylphenyl)oxazole

The title compound was prepared using a method analogous to 5-(2-hydrazinylphenyl)oxazole (Intermediate 74).

The crude product was purified by SCX (Biotage 20 g cartridge, load in DCM/MeOH 4/1 then elution with 25% of NH3 7M in MeOH in DCM) to give the title compound as a white solid (0.583 g, 60%).

$^1$H NMR (ppm)(CDCl$_3$): 3.61 (2H, s), 6.39 (1H, s), 6.56-6.52 (1H, m), 7.01 (1H, d, J=8.6 Hz), 7.38 (1H, d, J=3.3 Hz), 8.00 (1H, s)

Intermediate 77. 1-((2-Hydrazinylphenyl)sulfonyl)pyrrolidine hydrochloride

The title compound was prepared from 1-((2-(2-(diphenylmethylene)hydrazinyl)phenyl)sulfonyl)-pyrrolidine using a method analogous to the preparation of 5-(2-hydrazinylphenyl)oxazole (Intermediate 74).

The crude product was triturated in DCM/Et$_2$O and the resulting solid was filtered off, washed with Et$_2$O and dried in a vacuum oven to give the title compound as an orange solid (0.27 g, 56%).

$^1$H NMR (ppm)(400 MHz, DMSO-d6): 1.76-1.81 (4H, m), 3.28 (4H, dd, J=6.7, 6.7 Hz), 7.17-7.22 (1H, m), 7.28 (1H, d, J=7.6 Hz), 7.74-7.68 (1H, m), 7.78 (1H, dd, J=1.5, 7.8 Hz), 8.14 (1H, s), 10.41-10.46 (3H, m)

Intermediate 78. 2-Hydrazinyl-N-methyl-N-(pyridin-3-yl)benzenesulfonamide dihydrochloride The title compound was prepared from 2-(2-(diphenylmethylene)hydrazinyl)-N-methyl-N-(pyridin-3-yl)benzene-sulfonamide using a method analogous to the preparation of 5-(2-hydrazinylphenyl)oxazole (Intermediate 74).

The crude product was triturated in DCM/Et$_2$O and the resulting solid was filtered off, washed with Et$_2$O and dried in a vacuum oven to give the title compound as a beige solid (0.9 g, 87%).

$^1$H NMR (ppm)(400 MHz, DMSO-d6): 3.34 (3H, s), 7.15 (1H, dd, J=7.7, 7.7 Hz), 7.28 (1H, d, J=7.8 Hz), 7.57 (1H, dd, J=1.5, 8.1 Hz), 7.67-7.77 (2H, m), 7.93 (1H, s), 8.00 (1H, d, J=9.3 Hz), 8.66 (2H, dd, J=1.5, 3.5 Hz)

Intermediate 79. (2-Iodophenyl)hydrazine hydrochloride

NaNO$_2$ (3.0 g, 43.8 mmol) was slowly added to a suspension of 2-iodoaniline (8.0 g, 36.5 mmol) in concentrated HCl (40 mL) at 0° C. The reaction mixture was stirred at 0° C. for 1.5 hrs. A solution of SnCl$_2$ (17.3 g, 91.3 mmol) in 12 M HCl (10 mL) was added at 0° C. The reaction mixture was allowed to warm to r.t. and stirred for 18 hrs. The solid was collected by filtration and washed with H$_2$O and dried under reduced pressure to give the title compound as a light brown solid (5.9 g, 60%).

$^1$H NMR (ppm)(DMSO-d6): 6.85-6.80 (1H, m), 7.06 (1H, dd, J=1.3, 8.3 Hz), 7.46-7.41 (1H, m), 7.64 (1H, s), 7.84 (1H, dd, J=1.4, 7.7 Hz), 10.30-10.16 (3H, m)

Intermediate 80. (2-Bromo-6-fluorophenyl)hydrazine hydrochloride

The title compound was prepared using a method analogous to the preparation of (2-iodophenyl)hydrazine hydrochloride (0.089 g) (Intermediate 79).

The crude product was used in subsequent reactions without further analysis.

Intermediate 81. (2-Chloro-6-fluorophenyl)hydrazine hydrochloride

The title compound was prepared using a method analogous to the preparation of (2-iodophenyl)hydrazine hydrochloride (0.072 g) (Intermediate 79).

The crude product was used in subsequent reactions without further analysis.

Intermediate 82. (2-Methyl-5-(trifluoromethyl)phenyl)hydrazine hydrochloride The title compound was prepared using a method analogous to the preparation of (2-iodophenyl)hydrazine hydrochloride (Intermediate 79) to give the title compound as an off-white solid (0.088 g, 13%).

$^1$H NMR (ppm)(400 MHz, CDCl$_3$): 2.31 (3H, s), 7.27 (1H, d, J=7.6 Hz), 7.31 (1H, s), 7.40 (1H, d, J=7.8 Hz), 8.25 (1H, s), 10.41-10.23 (3H, m)

Intermediate 83. 3-(2-Hydrazinylphenyl)-5-methyl-1,2,4-oxadiazole hydrochloride The title compound was prepared using a method analogous to the preparation of (2-iodophenyl)hydrazine hydrochloride (Intermediate 79) to give the title compound as an off-white solid (0.088 g, 13%).

$^1$H NMR (ppm)(400 MHz, CDCl$_3$): 2.74 (3H, s), 7.22-7.15 (1H, m), 7.24 (1H, d, J=8.3 Hz), 7.66-7.59 (1H, m), 8.08 (1H, dd, J=1.5, 7.8 Hz), 8.35-8.34 (1H, m), 10.47 (3H, s)

Intermediate 84. (2-Bromo-3-fluorophenyl)hydrazine hydrochloride

The title compound was prepared using a method analogous to the preparation of (2-iodophenyl)hydrazine hydrochloride (Intermediate 79) to give the title compound as an off-white solid (0.1 g).

The crude product was used in subsequent reactions without further analysis.

Intermediate 85. (2-Bromo-6-fluorophenyl)hydrazine hydrochloride

The title compound was prepared using a method analogous to the preparation of (2-iodophenyl)hydrazine hydrochloride (Intermediate 79) to give the title compound as a yellow solid (0.15 g).

The crude product was used in subsequent reactions without further analysis.

Intermediate 86. (2-Chloro-6-fluorophenyl)hydrazine hydrochloride

The title compound was prepared using a method analogous to the preparation of (2-iodophenyl)hydrazine hydrochloride (Intermediate 79) to give the title compound as a brown solid (0.22 g).

The crude product was used in subsequent reactions without further analysis.

Intermediate 87. (2-Fluoro-6-methoxyphenyl)hydrazine hydrochloride

The title compound was prepared using a method analogous to the preparation of (2-iodophenyl)hydrazine hydrochloride (Intermediate 79) to give the title compound as an off-white solid (0.21 g).

The crude product was used in subsequent reactions without further analysis.

Intermediate 88. (2-Chloro-3-fluorophenyl)hydrazine hydrochloride

The title compound was prepared using a method analogous to the preparation of (2-iodophenyl)hydrazine hydrochloride (Intermediate 79) to give the title compound as an off-white solid (0.22 g).

The crude product was used in subsequent reactions without further analysis.

Intermediate 89. (2-Fluoro-6-methylphenyl)hydrazine hydrochloride

The title compound was prepared using a method analogous to the preparation of (2-iodophenyl)hydrazine hydrochloride (Intermediate 79) to give the title compound as a brown solid (0.19 g).

The crude product was used in subsequent reactions without further analysis.

Intermediate 90. (3-Fluoro-2-methoxyphenyl)hydrazine hydrochloride

The title compound was prepared using a method analogous to the preparation of (2-iodophenyl)hydrazine hydrochloride (Intermediate 79) to give the title compound as a brown solid (0.21 g).

The crude product was used in subsequent reactions without further analysis.

Intermediate 91. (2-Chloro-6-methylphenyl)hydrazine hydrochloride

The title compound was prepared using a method analogous to the preparation of (2-iodophenyl)hydrazine hydrochloride (Intermediate 79) to give the title compound as a brown solid (0.41 g).

The crude product was used in subsequent reactions without further analysis.

Intermediate 92. (2,6-Dichlorophenyl)hydrazine hydrochloride

The title compound was prepared using a method analogous to the preparation of (2-iodophenyl)hydrazine hydrochloride (Intermediate 79) to give the title compound as a brown solid (0.23 g).

The crude product was used in subsequent reactions without further analysis.

Intermediate 93. (2-(5-Chlorothiophen-2-yl)phenyl)hydrazine hydrochloride

The title compound was prepared using a method analogous to the preparation of (2-iodophenyl)hydrazine hydrochloride (Intermediate 79) to give the title compound as a yellow solid (0.25 g).

The crude product was used in subsequent reactions without further analysis.

Intermediate 94. 2-(5-Chlorothiophen-2-yl)aniline Hydrochloride

A mixture of N-Boc-2-aminobenzeneboronic acid (2.37 g, 10.0 mmol), 2-bromo-5-chlorothiophene (2.17 g, 11.0 mmol), sodium carbonate (2.12 g, 20.0 mmol) and tetrakistriphenylphosphine palladium (0.57 g, 0.5 mmol) in 10% aq dioxane (75 mL) were degassed with nitrogen for 10 mins and then heated at 100° C. for 8 hrs. The cooled mixture was filtered and the filtrate concentrated to under reduced pressure and the residue treated with water (75 mL) and extracted with DCM (3×40 mL). The combined extracts were dried (MgSO$_4$) and concentrated to dryness in vacuo. The crude product was purified by column chromatography (Biotage SNAP 100 g column, 20-100% DCM/ihexane) to give a mixture of the title compound and the N-BOC intermediate. The mixture was dissolved in diethyl ether (25 mL) and treated with a 4M soln. of HCl in dioxane (3 mL) and stirred at r.t. for 0.75 hrs. The precipitate was collected by filtration washed with diethyl ether and dried at 40° C. under vacuum to give the title compound as a colourless solid (1.35 g, 55%).

$^1$H NMR (ppm) (400 MHz, DMSO): 7.18 (1H, dd, J=7.2, 7.2 Hz) 7.27 (1H, d, J=3.8 Hz), 7.34 (1H, d, J=7.3 Hz), 7.36-7.45 (3H, m) (NH$_2$ not visible)

Intermediate 95. (3-Fluoro-2-iodophenyl)hydrazine hydrochloride

The title compound was prepared using a method analogous to the preparation of (2-iodophenyl)hydrazine hydrochloride (Intermediate 94) to give the title compound as a as a white solid (0.86 g).

The crude product was used in subsequent reactions without further analysis.

Intermediate 96. Ethyl 2-amino-2-cyanoacetate

A mixture of ethyl 2-cyano-2-(hydroxyimino)acetate (7.5 g, 52 mmol), saturated NaHCO$_3$ (aq) (50 mL) and H$_2$O (40 mL) was stirred at r.t. for 0.2 hrs. Sodium dithionate (23.0 g, 174 mmol) was added in two portions over a period of 0.3 hrs and the mixture was stirred at 35° C. for 0.75 hrs. The reaction mixture was allowed to cool to r.t. CaCl$_2$ (25 g, 225 mmol) was added and the mixture was then extracted with CHCl$_3$ (4×60 mL). The combined organic extracts were dried (MgSO$_4$) and concentrated under reduced pressure to give the title compound (3.0 g, 40%). The crude product was used in subsequent reactions without further analysis.

Intermediate 97. Ethyl 5-amino-1-(3-fluoro-2-methylphenyl)-1H-imidazole-4-carboxylate To a mixture of ethyl 2-amino-2-cyanoacetate (Intermediate 96; 4.20 g, 29.3 mmol) in acetonitrile (75 mL) was added trimethylorthoformate (3.11 g, 29.3 mmol) and the mixture heated to reflux for 1 hr. The mixture was cooled to r.t. and 3-fluoro-2-methylaniline (3.66 g, 29.3 mmol) was added and the mixture stirred for 18 hrs. The mixture was concentrated to dryness and the residue dissolved in EtOAc (100 mL) and successively washed with dil. aq. KHCO$_3$ (3×10 mL), water (2×10 mL) and brine (10 mL), dried (over MgSO$_4$) and concentrated to dryness under reduced pressure to afford a dark brown oil. The crude product was purified by column chromatography (Biotage SNAP 100 g column, 0.5 to 5% MeOH/DCM) to give the title compound as a yellow oil (0.93 g, 12%).
$^1$H NMR (ppm)(400 MHz, CDCl$_3$): 1.42 (3H, t, J=7.1 Hz), 2.08 (3H, d, J=2.3 Hz), 4.39 (2H, q, J=7.2 Hz), 4.84 (2H, s), 7.05 (1H, s), 7.09 (1H, d, J=7.8 Hz), 7.23 (1H, m), 7.30-7.37 (1H, m)

Intermediate 98. 5-Amino-1-(3-fluoro-2-methylphenyl)-1H-imidazole-4-carboxylic acid A mixture of ethyl 5-amino-1-(3-fluoro-2-methylphenyl)-1H-imidazole-4-carboxylate (Intermediate 97; 0.93 g, 3.54 mmol) and lithium hydroxide monohydrate (0.37 g, 8.8 mmol) in THF/MeOH/H$_2$O (1:1:1, v/v) (24 mL) was stirred at 80° C. for 4 hrs. The reaction mixture was allowed to cool to r.t. The solvent was removed under reduced pressure. The residue was treated with 1 M HCl (aq.) (3 mL). The resultant precipitate was collected by filtration, washed with H$_2$O and dried under reduced pressure to give the title compound as a white solid (0.82 g, 98%).
$^1$H NMR (ppm)(400 MHz, DMSO-d6): 2.03 (3H, d, J=2.0 Hz), 5.88 (2H, s), 7.24-7.29 (2H, m), 7.40-7.52 (2H, m) (COOH not visible)

Intermediate 99. Ethyl 5-amino-1-(2-methoxyphenyl)-1H-imidazole-4-carboxylate

The title compound was prepared from ethyl 2-amino-2-cyanoacetate (Intermediate 96) using a method analogous to the preparation of ethyl 5-amino-1-(3-fluoro-2-methylphenyl)-1H-imidazole-4-carboxylate (Intermediate 97)
The crude product was purified by column chromatography (Biotage SNAP 50 g column, 1 to 5% MeOH/DCM) to give the title compound as a yellow oil (1.14 g, 21%).

$^1$H NMR (ppm)(400 MHz, CDCl$_3$): 1.42 (3H, t, J=7.2 Hz), 3.86 (3H, s), 4.38 (2H, q, J=7.1 Hz), 4.96 (2H, s), 7.07-7.12 (3H, m), 7.28 (1H, dd, J=1.7, 8.1 Hz), 7.44-7.49 (1H, m)
m/z: [ES+] 262 ([M+H]+, C13H15N3O3)

Intermediate 100. 5-Amino-1-(2-methoxyphenyl)-1H-imidazole-4-carboxylic acid

The title compound was prepared from ethyl 5-amino-1-(2-methoxyphenyl)-1H-imidazole-4-carboxylate (Intermediate 97) using a method analogous to the preparation of 5-amino-1-(3-fluoro-2-methylphenyl)-1H-imidazole-4-carboxylic acid (Intermediate 98).
The title compound was obtained as a white solid (0.87 g, 94%).
$^1$H NMR (ppm)(400 MHz, DMSO-d6): 3.86 (3H, s), 5.80 (2H, s), 7.13-7.19 (1H, m), 7.32 (1H, d, J=7.6 Hz), 7.37-7.43 (2H, m), 7.55-7.61 (1H, m)
m/z: [ES+] 234 ([M+H]+, C11H11N3O3)

Intermediate 101. 5-Amino-1-(2-hydroxyphenyl)-3-methyl-N-(5-(trifluoromethyl)pyridin-2-yl)-1H-pyrazole-4-carboxamide The title compound was prepared from 5-amino-1-(2-methoxyphenyl)-3-methyl-N-(5-(trifluoromethyl)pyridin-2-yl)-1H-pyrazole-4-carboxamide using a method analogous to the preparation of 5-amino-1-(2-hydroxyphenyl)-N-(5-(trifluoromethyl)pyridin-2-yl)-1H-pyrazole-4-carboxamide (Example 109).
The title compound was obtained as a pale brown solid (0.25 g, 64%).
$^1$H NMR (ppm) (400 MHz, DMSO): 2.49 (3H, s), 6.05 (2H, s), 6.96-7.01 (1H, m), 7.11 (1H, dd, J=1.1, 8.2 Hz), 7.29-7.38 (2H, m), 8.23 (1H, dd, J=2.4, 9.0 Hz), 8.35 (1H, d, J=8.8 Hz), 8.75 (1H, s), 9.40 (1H, s), 10.31 (1H, s)

Intermediate 102. 5-Amino-3-ethyl-1-(2-hydroxyphenyl)-N-(5-(trifluoromethyl)pyridin-2-yl)-1H-pyrazole-4-carboxamide The title compound was prepared from 5-amino-3-ethyl-1-(2-methoxyphenyl)-N-(5-(trifluoromethyl)pyridin-2-yl)-1H-pyrazole-4-carboxamide using a method analogous to the preparation of 5-amino-1-(2-hydroxyphenyl)-N-(5-(trifluoromethyl)pyridin-2-yl)-1H-pyrazole-4-carboxamide (Example 109).
The title compound was obtained as a white solid (0.35 g, 100%).
$^1$H NMR (ppm) (400 MHz, DMSO): 1.22 (3H, t, J=7.4 Hz), 2.90 (2H, q, J=7.4 Hz), 6.92-6.96 (1H, m), 7.04-7.07 (1H, m), 7.25-7.34 (2H, m), 8.18 (1H, dd, J=2.3, 9.0 Hz), 8.31 (1H, d, J=8.8 Hz), 8.70-8.71 (1H, m), 9.45 (1H, s), 10.29-10.28 (1H, m) (NH$_2$ not visible)

Intermediate 103. 5-Amino-N-(5-chloropyridin-2-yl)-3-ethyl-1-(2-hydroxyphenyl)-1H-pyrazole-4-carboxamide The title compound was prepared from 5-amino-N-(5-chloropyridin-2-yl)-3-ethyl-1-(2-methoxyphenyl)-1H-pyrazole-4-carboxamide using a method analogous to the preparation of 5-amino-1-(2-hydroxyphenyl)-N-(5-(trifluoromethyl)pyridin-2-yl)-1H-pyrazole-4-carboxamide (Example 109).

The title compound was obtained as a white solid (0.25 g, 69%).

¹H NMR (ppm)(400 MHz, DMSO-d6) 1.21 (3H, t, J=7.4 Hz), 2.88 (2H, q, J=7.4 Hz), 6.87-6.94 (1H, m), 7.04 (1H, d, J=7.9 Hz), 7.24-7.31 (2H, m), 7.91 (1H, dd, J=2.6, 9.0 Hz), 8.17 (1H, d, J=8.9 Hz), 8.37 (1H, d, J=2.5 Hz), 9.16 (1H, s) (NH₂ and OH not visible)

Intermediate 104. 5-Amino-1-(3-fluoro-2-hydroxyphenyl)-N-(5-(trifluoromethyl)pyridin-2-yl)-1H-pyrazole-4-carboxamide The title compound was prepared from 5-amino-1-(3-fluoro-2-methoxyphenyl)-N-(5-(trifluoromethyl)pyridin-2-yl)-1H-pyrazole-4-carboxamide using a method analogous to the preparation of 5-amino-1-(2-hydroxyphenyl)-N-(5-(trifluoromethyl)pyridin-2-yl)-1H-pyrazole-4-carboxamide (Example 109).

The title compound was obtained as a brown solid (0.04 g, 62%).

¹H NMR (ppm)(400 MHz, DMSO-d6): 6.31-6.34 (2H, m), 6.81-6.87 (1H, m), 7.02-7.04 (1H, m), 7.20-7.27 (1H, m), 8.09 (1H, dd, J=2.4, 9.0 Hz), 8.30 (2H, d, J=6.8 Hz), 8.64 (1H, d, J=1.0 Hz), 10.60 (1H, s)

Intermediate 105. 5-Amino-1-(2-methoxyphenyl)-N-(5-(trifluoromethoxy)pyridin-2-yl)-1H-pyrazole-4-carboxamide The title compound was prepared from 5-amino-1-(2-methoxyphenyl)-H-pyrazole-4-carboxylic acid (Intermediate 2) using a method analogous to the preparation of 5-amino-N-(5-chloropyridin-2-yl)-1-(o-tolyl)-1H-pyrazole-4-carboxamide (Example 3).

The crude product was purified by silica gel chromatography (Biotage SNAP 50 g column, 0 to 100% EtOAc/isohexane) to give the title compound as a white solid (0.11 g, 16%).

¹H NMR (ppm)(400 MHz, CDCl₃): 3.89 (3H, s), 5.52 (2H, s), 7.08-7.14 (2H, m), 7.43-7.46 (2H, m), 7.59 (1H, dd, J=2.4, 9.2 Hz), 7.80 (1H, s), 8.04 (1H, s), 8.23 (1H, d, J=3.0 Hz), 8.36 (1H, d, J=9.1 Hz)

Intermediate 106. 5-Amino-1-(2-hydroxyphenyl)-N-(5-(trifluoromethoxy)pyridin-2-yl)-1H-pyrazole-4-carboxamide The title compound was prepared from 5-amino-1-(2-methoxyphenyl)-N-(5-(trifluoromethoxy)pyridin-2-yl)-1H-pyrazole-4-carboxamide using a method analogous to the preparation of 5-amino-1-(2-hydroxyphenyl)-N-(5-(trifluoromethyl)pyridin-2-yl)-1H-pyrazole-4-carboxamide (Example 109).

The title compound was obtained as a pale yellow solid (0.045 g).

The crude product was used in subsequent reactions without further analysis.

Intermediate 107. (2-Bromo-6-fluorophenyl)hydrazine hydrochloride

The title compound was prepared from 2-bromo-6-fluoroaniline using a method analogous to the preparation of (2-iodophenyl)hydrazine hydrochloride (1.19 g).

The crude product was used in subsequent reactions without further analysis.

Example 1. 5-Amino-N-(4-chlorophenyl)-1-(2-methoxyphenyl)-1H-pyrazole-4-carboxamide A mixture of 5-amino-1-(2-methoxyphenyl)-1H-pyrazole-4-carboxylic acid (Intermediate 2; 58 mg, 0.25 mmol), 4-chloroaniline (36 mg, 0.28 mmol), PyBOP (156 mg, 0.30 mmol), Et₃N (0.042 mL, 0.30 mmol) and DCM (1.25 mL) was stirred at r.t. for 16 hrs. The reaction mixture was diluted with H₂O (2.5 mL) and DCM (10 mL). The organic phase was separated (phase separating cartridge) and the solvent removed under reduced pressure. The crude product was purified by reverse phase preparative HPLC to give the title compound as an off-white solid (0.019 g, 22%).

¹H NMR (ppm)(400 MHz, CDCl₃): 3.88 (3H, s), 5.49 (2H, s), 7.06-7.13 (2H, m), 7.28-7.33 (3H, m), 7.41-7.49 (2H, m), 7.49-7.54 (2H, m), 7.75 (1H, s)

m/z: [ES+] 343, 345 ([M+H]+, C17H15ClN4O2)

Example 2. 5-Amino-N-(4-bromophenyl)-1-(2-methoxyphenyl)-1H-pyrazole-4-carboxamide The title compound was prepared from 5-amino-1-(2-methoxyphenyl)-1H-pyrazole-4-carboxylic acid (Intermediate 2) using a method analogous to the preparation of 5-amino-N-(4-chlorophenyl)-1-(2-methoxyphenyl)-1H-pyrazole-4-carboxamide (Example 1).

The crude product was purified by reverse phase preparative HPLC to give the title compound as a white solid (0.018 g, 19%).

¹H NMR (ppm)(400 MHz, CDCl₃): 3.88 (3H, s), 5.49 (2H, s), 7.06-7.13 (2H, m), 7.22-7.31 (1H, m), 7.41-7.50 (6H, m), 7.75 (1H, s)

m/z: [ES+] 387, 389 ([M+H]+, C17H15BrN4O2)

Example 3. 5-Amino-1-(2-methoxyphenyl)-N-(p-tolyl)-1H-pyrazole-4-carboxamide

The title compound was prepared from 5-amino-1-(2-methoxyphenyl)-H-pyrazole-4-carboxylic acid (Intermediate 2) using a method analogous to the preparation of 5-amino-N-(4-bromophenyl)-1-(2-methoxyphenyl)-1H-pyrazole-4-carboxamide (Example 1).

The crude product was purified by reverse phase preparative HPLC to give the title compound as a white solid (0.033 g, 41%).

¹H NMR (ppm)(400 MHz, CDCl₃): 2.33 (3H, s), 3.88 (3H, s), 5.49 (2H, s), 7.05-7.16 (4H, m), 7.07-7.42 (1H, m), 7.41-7.46 (4H, m), 7.73 (1H, s)

m/z: [ES+] 323 ([M+H]+, C18H18N4O2)

Example 4. 5-Amino-N-(5-chloropyridin-2-yl)-1-(o-tolyl)-1H-pyrazole-4-carboxamide A mixture of 5-amino-1-(o-tolyl)-1H-pyrazole-4-carboxylic acid (Intermediate 4; 0.54 g, 2.5 mmol), SOCl₂ (0.91 mL, 12.5 mmol) and MeCN (12.5 mL) was stirred at r.t. for 0.25 hrs. The reaction mixture was concentrated under reduced pressure. The residue was dissolved in a mixture of 2-amino-5-chloropyridine (0.36 g, 2.8 mmol), DIEA (1.3 mL, 7.5 mmol) and DCM (12.5 mL) and stirred at r.t. for 1 hr. The reaction mixture was diluted with DCM (50 mL) and H₂O (20 mL). The organic phase was separated (phase separating cartridge) and the solvent removed under reduced pressure. The crude product was purified by column chromatography (Biotage SNAP 25 g column, 0 to 50% EtOAc/isohexane). The product was triturated with Et2O to give the title compound as a pale yellow solid (0.095 g, 12%).

¹H NMR (ppm)(400 MHz, CDCl3): 2.18 (3H, s), 5.31 (2H, s), 7.30-7.45 (4H, m), 7.67 (1H, dd, J=8.9, 2.6 Hz), 7.77 (1H, s), 8.04 (1H, s), 8.22-8.30 (2H, m)
m/z: [ES+] 330, 328 ([M+H]+, C16H14ClN5O)

Example 5. 5-Amino-1-(o-tolyl)-N-(5-(trifluoromethyl)pyridin-2-yl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1)

The crude product was purified by reverse phase preparative HPLC to give the title compound as a pale yellow solid (0.06 g, 48%).

¹H NMR (ppm)(400 MHz, DMSO-d6): 2.13 (3H, s), 6.39 (2H, s), 7.35 (1H, d, J=7.6 Hz), 7.39-7.45 (1H, m), 7.48-7.50 (2H, m), 8.22 (1H, dd, J=2.5, 9.1 Hz), 8.43 (2H, s), 8.78 (1H, s), 10.75 (1H, s)
m/z: [ES+] 362 ([M+H]+, C17H14F3N5O)

Example 6. 5-Amino-N-(4-chloro-2-methyl-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.055 g, 47%).

¹H NMR (ppm)(400 MHz, CDCl3): 2.18 (3H, s), 2.33 (3H, s), 5.27 (2H, s), 7.10 (1H, s), 7.23-7.18 (2H, m), 7.42-7.30 (4H, m), 7.67 (1H, s), 7.78 (1H, d, J=8.1 Hz),
m/z: [ES+] 341, 343 ([M+H]+, C18H17ClN4O)

Example 7. 5-Amino-N-(4-chloro-2-fluoro-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a beige solid (0.072 g, 61%).

¹H NMR (ppm)(400 MHz, CDCl3): 2.18 (3H, s), 5.24-5.32 (2H, m), 7.14-7.20 (2H, m), 7.33-7.46 (5H, m), 7.74 (1H, s), 8.29-8.35 (1H, m)
m/z: [ES+] 345, 347 ([M+H]+, C17H14ClFN4O)

Example 8. 5-Amino-N-(4-chloro-2-cyano-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a beige solid (0.056 g, 46%).

¹H NMR (ppm)(400 MHz, CDCl3): 2.18 (3H, s), 5.28 (2H, s), 7.31-7.44 (4H, m), 7.53-7.58 (2H, m), 7.79 (2H, s), 8.49 (1H, d, J=8.6 Hz)
m/z: [ES+] 352, 354 ([M+H]+, C18H14ClN5O)

Example 9. 5-Amino-N-(4-chloro-2-methoxy-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a beige solid (0.036 g, 29%).

¹H NMR (ppm)(400 MHz, CDCl3): 2.17 (3H, s), 3.94 (3H, s), 5.27 (2H, s), 6.90 (1H, d, J=2.0 Hz), 6.97 (1H, dd, J=2.3, 8.6 Hz), 7.32-7.42 (4H, m), 7.73 (1H, s), 7.90 (1H, s), 8.35 (1H, d, J=8.6 Hz)
m/z: [ES+] 357, 359 ([M+H]+, C18H17ClN4O2)

Example 10. 5-Amino-N-(5-chloro-3-methyl-2-pyridyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a yellow solid (0.055 g, 47%).

¹H NMR (ppm)(400 MHz, CDCl3): 2.19 (3H, s), 2.36 (3H, s), 5.25 (2H, s), 7.31-7.35 (2H, m), 7.36-7.42 (2H, m), 7.55-7.58 (1H, m), 7.59 (1H, d, J=1.8 Hz), 7.74 (1H, s), 8.24 (1H, d, J=2.3 Hz)
m/z: [ES+] 342, 344 ([M+H]+, C17H16ClN5O)

Example 11. 5-Amino-N-[3-fluoro-5-(trifluoromethyl)-2-pyridyl]-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a yellow solid (0.067 g, 51%).

¹H NMR (ppm)(400 MHz, CDCl3): 2.18 (3H, s), 5.35 (2H, s), 7.13-7.43 (4H, m), 7.72 (1H, dd, J=1.8, 9.6 Hz), 7.79 (1H, s), 7.83 (1H, s), 8.53 (1H, s)
m/z: [ES+] 380 ([M+H]+, C17H13F4N5O)

Example 12. 5-Amino-N-(5-chloro-3-methoxy-2-pyridyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a yellow solid (0.059 g, 48%).

¹H NMR (ppm)(400 MHz, CDCl₃): 2.17 (3H, s), 3.96 (3H, s), 5.37 (2H, s), 7.18 (1H, s), 7.33 (2H, d, J=3.0 Hz), 7.35-7.42 (2H, m), 7.74 (1H, s), 7.99 (1H, s), 8.06 (1H, s)
m/z: [ES+] 358, 360 ([M+H]+, C17H16ClN5O2)

Example 13. 5-Amino-N-(4-chloro-2-(methylamino) phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by reverse phase preparative HPLC to give the title compound as a pale yellow solid (0.059 g, 49%).
¹H NMR (ppm)(400 MHz, DMSO-d6): 2.15 (3H, s), 2.78 (3H, d, J=4.8 Hz), 5.56-5.50 (1H, m), 6.13 (2H, s), 6.68-6.62 (2H, m), 7.15 (1H, d, J=8.1 Hz), 7.32 (1H, d, J=7.3 Hz), 7.50-7.40 (3H, m), 8.12 (1H, s), 9.05 (1H, s)
m/z: [ES+] 356 ([M+H]+, C18H18ClN5O)

Example 14. 5-Amino-N-(2-carbamoyl-4-chlorophenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by reverse phase preparative HPLC to give the title compound as a pale yellow solid (0.063 g, 50%).
¹H NMR (ppm)(400 MHz, DMSO-d6): 2.13 (3H, s), 6.28 (2H, s), 7.52-7.37 (3H, m), 7.76-7.60 (2H, m), 8.04-7.93 (2H, m), 8.52 (2H, s), 8.68 (1H, d, J=9.1 Hz), 12.37 (1H, s)
m/z: [ES+] 370 ([M+H]+, C18H16ClN5O2)

Example 15. 5-Amino-N-(2-cyano-4-(trifluoromethyl)phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by reverse phase preparative HPLC to give the title compound as a pale yellow solid (0.069 g, 53%).
¹H NMR (ppm)(400 MHz, CDCl₃): 2.19 (3H, s), 5.32 (2H, s), 7.44-7.32 (4H, m), 7.88-7.81 (3H, m), 7.97 (1H, s), 8.75 (1H, d, J=8.8 Hz)
m/z: [ES+] 386 ([M+H]+, C19H14F3N5O)

Example 16. 5-Amino-N-(2-methoxy-4-(trifluoromethyl)phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by reverse phase preparative HPLC to give the title compound as a pale yellow solid (0.06 g, 45%).
¹H NMR (ppm)(400 MHz, CDCl₃): 2.18 (3H, s), 4.01 (3H, s), 5.29 (2H, s), 7.12 (1H, s), 7.36-7.31 (2H, m), 7.43-7.36 (3H, m), 7.75 (1H, s), 8.09 (1H, s), 8.55 (1H, d, J=8.3 Hz)
m/z: [ES+] 391 ([M+H]+, C19H17F3N4O2)

Example 17. 5-Amino-N-(4-chloro-2-hydroxyphenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamid (Example 1).
The crude product was purified by column chromatography (Biotage SNAP 25 g column, 0 to 50% EtOAc/isohexane) to give title compound as a pale yellow solid (0.385 g, 16%).
¹H NMR (ppm)(400 MHz, DMSO-d6): 2.14 (3H, s), 6.20 (2H, s), 6.90 (1H, dd, J=2.4, 8.5 Hz), 6.97 (1H, d, J=2.3 Hz), 7.34 (1H, d, J=7.6 Hz), 7.45-7.39 (1H, m), 7.48 (2H, d, J=4.0 Hz), 7.64 (1H, d, J=8.6 Hz), 8.16 (1H, s), 9.16 (1H, s), 10.56 (1H, s)
m/z: [ES+] 343 ([M+H]+, C17H15ClN4O2)

Example 18. 5-Amino-N-(4-chloro-2-((dimethylamino)methyl)phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by reverse phase preparative HPLC to give the title compound as a yellow-brown solid (0.046 g, 40%).
¹H NMR (ppm)(400 MHz, CDCl₃): 2.19 (3H, s), 2.37 (6H, s), 3.56 (2H, s), 5.25-5.32 (2H, m), 7.10 (1H, d, J=2.3 Hz), 7.23-7.29 (1H, m), 7.31-7.42 (4H, m), 7.65 (1H, s), 8.34 (1H, d, J=8.8 Hz), 11.24 (1H, s)
m/z: [ES+] 383 ([M+H]+, C20H22ClN5O)

Example 19. 5-Amino-N-(4-chloro-2-(methoxymethyl)phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).
The crude product was purified by column chromatography (Biotage SNAP 10 g column 20 to 100% Et2O/isohexane) to give the title compound as a white solid (0.021 g, 19%).
¹H NMR (ppm)(400 MHz, CDCl₃): 2.19 (3H, s), 3.49 (3H, s), 4.58 (2H, s), 5.25-5.31 (2H, m), 7.18 (1H, d, J=2.5 Hz), 7.30-7.42 (5H, m), 7.67 (1H, s), 8.28 (1H, d, J=8.8 Hz), 9.08 (1H, s)
m/z: [ES+] 371 ([M+H]+, C19H19ClN4O2)

Example 20. 5-Amino-N-(4-bromo-2-methoxy-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.071 g, 52%).

$^1$H NMR (ppm)(400 MHz, CDCl$_3$): 2.18 (3H, s), 3.95 (3H, s), 5.26 (2H, s), 7.04 (1H, s), 7.11 (1H, d, J=8.6 Hz), 7.42-7.31 (4H, m), 7.73 (1H, s), 7.90 (1H, s), 8.31 (1H, d, J=8.6 Hz)

m/z: [ES+] 401 ([M+H]+, C18H17BrN4O2)

Example 21. 5-Amino-N-(4-chloro-2-fluoro-phenyl)-1-[2-(2-methoxyethoxy)phenyl]-1H-pyrazole-4-carboxamide The title compound was prepared from 5-amino-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.028 g, 38%).

$^1$H NMR (ppm)(400 MHz, CDCl$_3$): 3.37 (3H, s), 3.70 (2H, t, J=4.5 Hz), 4.22 (2H, t, J=4.5 Hz), 5.80 (2H, s), 7.04-7.18 (4H, m), 7.36-7.43 (1H, m), 7.44-7.50 (2H, m), 7.76 (1H, s), 8.36-8.30 (1H, m)

m/z: [ES+] 405 ([M+H]+, C19H18ClFN4O3)

Example 22. 5-Amino-N-(4-chloro-2-methoxy-phenyl)-1-[2-(2-methoxyethoxy)phenyl]-1H-pyrazole-4-carboxamide The title compound was prepared from 5-amino-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.022 g, 29%).

$^1$H NMR (ppm)(400 MHz, CDCl$_3$): 3.37 (3H, s), 3.69 (2H, t, J=4.4 Hz), 3.94 (3H, s), 4.22 (2H, t, J=4.5 Hz), 5.80 (2H, s), 6.90 (1H, d, J=2.3 Hz), 6.97 (1H, dd, J=2.0, 8.6 Hz), 7.03-7.14 (2H, m), 7.47 (1H, dd, J=1.5, 7.8 Hz), 7.75 (1H, s), 7.35-7.42 (1H, m), 7.89 (1H, s), 8.35 (1H, d, J=8.6 Hz)

m/z: [ES+] 417 ([M+H]+, C20H21ClN4O4)

Example 23. 5-Amino-N-(5-chloro-2-pyridyl)-1-[2-(2-methoxyethoxy)phenyl]-1H-pyrazole-4-carboxamide The title compound was prepared from 5-amino-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.012 g, 17%).

$^1$H NMR (ppm)(400 MHz, CDCl$_3$): 3.38 (3H, s), 3.68-3.72 (2H, m), 4.20-4.25 (2H, m), 5.84 (2H, s), 7.04-7.15 (2H, m), 7.36-7.43 (1H, m), 7.48 (1H, dd, J=1.5, 7.8 Hz), 7.67 (1H, dd, J=2.4, 9.0 Hz), 7.80 (1H, s), 8.02 (1H, s), 8.23-8.30 (2H, m)

m/z: [ES+] 388 ([M+H]+, C18H18ClN5O3)

Example 24. 5-Amino-N-[4-chloro-2-[[isopropyl(methyl)amino]methyl]phenyl]-1-(o-tolyl)-1H-pyrazole-4-carboxamide The title compound was prepared from 5-amino-1-(o-tolyl)-1H-pyrazole-4-carboxylic (Intermediate 4) acid using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.033 g, 24%).

$^1$H NMR (ppm)(400 MHz, CDCl$_3$): 1.11 (6H, d, J=6.6 Hz), 2.19 (3H, s), 2.31 (3H, s), 2.91-2.99 (1H, m), 3.70 (2H, s), 5.28 (2H, s), 7.11 (1H, d, J=2.3 Hz), 7.26 (1H, s), 7.31-7.34 (2H, m), 7.37-7.42 (2H, m), 7.68 (1H, s), 8.32 (1H, d, J=8.8 Hz), 11.28 (1H, s)

m/z: [ES+] 412 ([M+H]+, C22H26ClN5O)

Example 25. 5-Amino-N-[4-chloro-2-(pyrrolidin-1-ylmethyl)phenyl]-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a pale yellow solid (0.033 g, 24%).

$^1$H NMR (ppm)(400 MHz, CDCl$_3$): 1.92 (4H, dd, J=5.2, 5.2 Hz), 2.19 (3H, s), 2.63 (4H, s), 3.74 (2H, s), 5.28 (2H, s), 7.12 (1H, d, J=2.5 Hz), 7.26 (1H, s), 7.31-7.42 (4H, m), 7.61 (1H, s), 8.32 (1H, d, J=8.8 Hz), 11.30 (1H, s)

m/z: [ES+] 410 ([M+H]+, C22H24ClN5O)

Example 26. 5-Amino-N-[4-chloro-2-(morpholinomethyl)phenyl]-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.022 g, 15%).

$^1$H NMR (ppm)(400 MHz, CDCl$_3$): 2.20 (3H, s), 2.52-2.59 (4H, m), 3.62 (2H, s), 3.82 (4H, dd, J=4.3, 4.3 Hz), 5.29 (2H, s), 7.14 (1H, d, J=2.3 Hz), 7.27-7.36 (3H, m), 7.38-7.43 (2H, m), 7.77 (1H, s), 8.29 (1H, d, J=8.8 Hz), 10.46 (1H, s)

m/z: [ES+] 426 ([M+H]+, C22H24ClN5O2)

Example 27. 5-Amino-N-(4-cyanophenyl)-1-(o-tolyl)-1H-pyrazole-4-carboxamide

The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a light beige solid (0.007 g, 6%).

$^1$H NMR (ppm)(400 MHz, CDCl$_3$): 2.18 (3H, s), 5.30 (2H, s), 7.34 (2H, m), 7.38-7.44 (2H, m), 7.64 (2H, d, J=8.6 Hz), 7.72 (2H, s), 7.75 (1H, s) (one proton is obscured by CDCl3)

m/z: [ES+] 318 ([M+H]+, C18H15N5O)

Example 28. 5-Amino-N-(4-tert-butylphenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.058 g, 49%).

$^1$H NMR (ppm)(400 MHz, CDCl$_3$): 1.32 (9H, s), 2.18 (3H, s), 5.28 (2H, s), 7.27-7.34 (3H, m), 7.34-7.39 (4H, m), 7.45-7.49 (2H, m), 7.71 (1H, s)

m/z: [ES+] 318 ([M+H]+, C21H24N4O)

Example 29. 5-Amino-N-[4-chloro-2-[[(3R)-3-fluoropyrrolidin-1-yl]methyl]phenyl]-1-(o-tolyl)-1H-pyrazole-4-carboxamide The title compound was prepared from 5-amino-1-(o-tolyl)-1H-pyrazole-4-carboxylic (Intermediate 4) acid using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.016 g, 11%).

$^1$H NMR (ppm)(400 MHz, CDCl$_3$): 2.19 (3H, s), 2.19 (2H, s), 2.19-2.71 (1H, m), 3.01-3.16 (2H, m), 3.71-3.82 (2H, m), 5.18-5.33 (2H, m), 7.13 (1H, d, J=2.3 Hz), 7.27-7.34 (3H, m), 7.37-7.41 (2H, m), 7.72 (1H, s), 8.27 (1H, d, J=8.8 Hz), 10.79 (1H, s)

m/z: [ES+] 428 ([M+H]+, C22H23ClFN5O)

Example 30. 5-Amino-N-(4-chloro-2-phenyl-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.027 g, 20%).

$^1$H NMR (ppm)(400 MHz, CDCl$_3$): 2.14 (3H, s), 5.24 (2H, s), 7.10 (1H, s), 7.27-7.30 (2H, m), 7.32-7.41 (4H, m), 7.43-7.46 (3H, m), 7.48-7.50 (1H, m), 7.52-7.59 (2H, m), 8.42 (1H, d, J=8.8 Hz)

m/z: [ES+] 403 ([M+H]+, C23H19ClN4O)

Example 31. 5-Amino-1-[2-(2-methoxyethoxy)phenyl]-N-[4-(trifluoromethyl)phenyl]-1H-pyrazole-4-carboxamide The title compound was prepared from 5-amino-1-(2-(2-methoxyethoxy)phenyl)-1H-pyrazole-4-carboxylic (Intermediate 11) acid using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a pale yellow solid (0.030 g, 40%).

$^1$H NMR (ppm)(400 MHz, CDCl$_3$): 3.38 (3H, s), 3.73-3.68 (2H, m), 4.25-4.21 (2H, m), 5.83 (2H, s), 7.14-7.04 (2H, m), 7.45-7.38 (2H, m), 7.48 (1H, dd, J=1.8, 7.8 Hz), 7.60 (2H, d, J=8.6 Hz), 7.71 (2H, d, J=8.3 Hz), 7.78 (1H, s)

m/z: [ES+] 421 ([M+H]+, C20H19F3N4O3)

Example 32. 5-Amino-N-[2-fluoro-4-(trifluoromethyl)phenyl]-1-[2-(2-methoxyethoxy)phenyl]-1H-pyrazole-4-carboxamide The title compound was prepared from 5-amino-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.037 g, 47%).

$^1$H NMR (ppm)(400 MHz, CDCl$_3$): 3.38 (3H, s), 3.69-3.73 (2H, m), 4.21-4.25 (2H, m), 5.82 (2H, s), 7.05-7.15 (2H, m), 7.26 (2H, s), 7.37-7.51 (2H, m), 7.64 (1H, d, J=2.3 Hz), 7.79 (1H, s), 8.59 (1H, t, J=8.0 Hz)

m/z: [ES+] 439 ([M+H]+, C20H18F4N4O3)

Example 33. 5-Amino-N-(2-bromo-4-chloro-phenyl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.038 g, 28%).

$^1$H NMR (ppm)(400 MHz, CDCl$_3$): 2.18 (3H, s), 5.27 (2H, s), 7.29-7.36 (3H, m), 7.38-7.42 (2H, m), 7.58 (1H, d, J=2.3 Hz), 7.77 (1H, s), 7.85 (1H, s), 8.40 (1H, d, J=9.1 Hz)

m/z: [ES+] 405 ([M+H]+, C17H14BrClN4O)

Example 34. 5-Amino-1-[2-(2-methoxyethoxy)phenyl]-N-[2-methyl-4-(trifluoromethyl)phenyl]-1H-pyrazole-4-carboxamide The title compound was prepared from 5-amino-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.025 g, 32%).

$^1$H NMR (ppm)(400 MHz, CDCl$_3$): 2.40 (3H, s), 3.37 (3H, s), 3.68-3.73 (2H, m), 4.23 (2H, t, J=4.4 Hz), 5.81 (2H, s), 7.04-7.15 (2H, m), 7.29 (1H, s), 7.36-7.43 (1H, m), 7.47-7.52 (3H, m), 7.75 (1H, s), 8.17 (1H, d, J=8.3 Hz)

m/z: [ES+] 435 ([M+H]+, C21H21F3N4O3)

Example 35. 5-Amino-N-(4-chloro-2-methoxy-phenyl)-3-methyl-1-(o-tolyl)-1H-pyrazole-4-carboxamide The title compound was prepared from 5-amino-3-methyl-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.026 g, 32%).

$^1$H NMR (ppm)(400 MHz, CDCl$_3$): 2.18 (3H, s), 2.59 (3H, s), 3.94 (3H, s), 5.34 (2H, s), 6.90 (1H, d, J=2.0 Hz), 6.97 (1H, dd, J=2.1, 8.7 Hz), 7.30-7.40 (4H, m), 8.09 (1H, s), 8.41 (1H, d, J=8.6 Hz)

m/z: [ES+] 371 ([M+H]+, C19H19ClN4O2)

Example 36. 5-Amino-N-(4-chloro-2-methoxy-phenyl)-1-[2-(2-methoxyethoxy)phenyl]-3-methyl-1H-pyrazole-4-carboxamide The title compound was prepared from 5-amino-3-methyl-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide. (Example 1). The crude product was purified by reverse phase preparative HPLC to give the title compound as an off-white solid (0.036 g, 33%).

$^1$H NMR (ppm)(400 MHz, CDCl$_3$): 2.59 (3H, s), 3.37 (3H, s), 3.69 (2H, dd, J=4.2, 4.2 Hz), 3.94 (3H, s), 4.20 (2H, dd, J=4.3, 4.3 Hz), 5.87 (2H, s), 6.88-6.91 (1H, m), 6.97 (1H, d, J=8.8 Hz), 7.01-7.13 (2H, m), 7.36 (1H, dd, J=7.8, 7.8 Hz), 7.46 (1H, d, J=7.8 Hz), 8.09 (1H, s), 8.42 (1H, d, J=8.6 Hz)

m/z: [ES+] 431 ([M+H]+, C21H23ClN4O4)

Example 37. 5-Amino-1-[2-(2-methoxyethoxy)phenyl]-N-[2-methoxy-4-(trifluoromethyl)phenyl]-3-methyl-1H-pyrazole-4-carboxamide The title compound was prepared from 5-amino-3-methyl-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.011 g, 9%).

$^1$H NMR (ppm)(400 MHz, CDCl$_3$): 2.61 (3H, s), 3.38 (3H, s), 3.68-3.72 (2H, m), 4.00 (3H, s), 4.19-4.24 (2H, m), 5.90 (2H, s), 7.03-7.13 (3H, m), 7.29 (1H, s), 7.33-7.40 (1H, m), 7.46 (1H, dd, J=1.5, 7.8 Hz), 8.29 (1H, s), 8.61 (1H, d, J=8.6 Hz)

m/z: [ES+] 465 ([M+H]+, C22H23F3N4O4)

Example 38. 5-Amino-N-(2-fluoro-4-(trifluoromethyl)phenyl)-1-(2-(2-methoxyethoxy)phenyl)-3-methyl-1H-pyrazole-4-carboxamide The title compound was prepared from 5-amino-3-methyl-1-(2-(2-methoxyethoxy)phenyl)-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1). The crude product was purified by reverse phase preparative HPLC to give the title compound as a yellow solid (0.05 g, 43%).

$^1$H NMR (ppm)(400 MHz, CDCl$_3$): 2.61 (3H, s), 3.38 (3H, s), 3.70 (2H, dd, J=4.2, 4.2 Hz), 4.22 (2H, dd, J=4.2, 4.2 Hz), 5.85 (2H, s), 7.05 (1H, d, J=8.3 Hz), 7.11 (1H, dd, J=7.6, 7.6 Hz), 7.34-7.49 (4H, m), 7.88-7.91 (1H, m), 8.65 (1H, dd, J=8.1, 8.1 Hz)

m/z: [ES+] 453 ([M+H]+, C21H20F4N4O3)

Example 39. 5-Amino-N-[2-cyano-4-(trifluoromethyl)phenyl]-1-(2-ethylphenyl)-3-methyl-1H-pyrazole-4-carboxamide The title compound was prepared from 5-amino-1-(2-ethylphenyl)-3-methyl-1H-pyrazole-4-carboxylic acid (Intermediate 15) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.013 g, 10%).

$^1$H NMR (ppm)(400 MHz, CDCl$_3$): 1.15 (3H, t, J=7.2 Hz), 2.54 (2H, q, J=7.2 Hz), 2.71 (3H, s), 5.40 (2H, s), 7.30 (1H, s), 7.32-7.38 (1H, m), 7.47-7.41 (2H, m), 7.81-7.86 (2H, m), 8.16 (1H, s), 8.84 (1H, d, J=9.1 Hz)

m/z: [ES+] 414 ([M+H]+, C21H18F3N5O)

Example 40. 5-Amino-N-(4-bromo-2-methoxy-phenyl)-1-(2-ethylphenyl)-3-methyl-1H-pyrazole-4-carboxamide The title compound was prepared from 5-amino-1-(2-ethylphenyl)-3-methyl-1H-pyrazole-4-carboxylic acid (Intermediate 15) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.025 g, 18%).

$^1$H NMR (ppm)(400 MHz, CDCl$_3$): 1.13 (3H, t, J=7.6 Hz), 2.50-2.60 (5H, m), 3.94 (3H, s), 5.33 (2H, s), 7.04 (1H, s), 7.12 (1H, d, J=8.3 Hz), 7.28-7.35 (2H, m), 7.41 (2H, dd, J=8.5, 8.5 Hz), 8.11 (1H, s), 8.37 (1H, d, J=8.6 Hz)

m/z: [ES+] 429 ([M+H]+, C20H21BrN4O2)

Example 41. 5-Amino-N-(4-chloro-2-methoxy-phenyl)-1-(2-ethylphenyl)-3-methyl-1H-pyrazole-4-carboxamide The title compound was prepared from 5-amino-1-(2-ethylphenyl)-3-methyl-1H-pyrazole-4-carboxylic acid (Intermediate 15) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.032 g, 26%).

$^1$H NMR (ppm)(400 MHz, CDCl$_3$): 1.12 (3H, t, J=8.3 Hz), 2.52 (2H, q, J=7.5 Hz), 2.58 (3H, s), 3.94 (3H, s), 5.32 (2H, s), 6.90 (1H, d, J=2.0 Hz), 6.97 (1H, dd, J=2.1, 8.7 Hz), 7.27-7.35 (2H, m), 7.38-7.45 (2H, m), 8.09 (1H, s), 8.41 (1H, d, J=8.6 Hz)

m/z: [ES+] 385 ([M+H]+, C20H21ClN4O2)

Example 42. 5-Amino-N-(5-chloro-2-pyridyl)-1-(2-ethylphenyl)-3-methyl-1H-pyrazole-4-carboxamide The title compound was prepared from 5-amino-1-(2-ethylphenyl)-3-methyl-1H-pyrazole-4-carboxylic acid (Intermediate 15) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.014 g, 12%).

$^1$H NMR (ppm)(400 MHz, CDCl$_3$): 1.14 (3H, t, J=7.2 Hz), 2.52 (2H, q, J=7.6 Hz), 2.62 (3H, s), 5.35 (2H, s), 7.28-7.36 (2H, m), 7.39-7.46 (2H, m), 7.67 (1H, dd, J=2.4, 8.7 Hz), 8.03 (1H, s), 8.23-8.29 (2H, m)

m/z: [ES+] 356 ([M+H]+, C18H18ClN5O)

Example 43. 5-Amino-N-(4-chloro-2-fluoro-phenyl)-1-[2-(2-methoxyethoxy)phenyl]-3-methyl-1H-pyrazole-4-carboxamide The title compound was prepared from 5-amino-1-(2-(2-methoxyethoxy)phenyl)-1-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.041 g, 38%).

$^1$H NMR (ppm)(400 MHz, CDCl$_3$): 2.59 (3H, s), 3.38 (3H, s), 3.70 (2H, dd, J=4.4, 4.4 Hz), 4.21 (2H, dd, J=4.4, 4.4 Hz), 5.83 (2H, s), 7.02-7.18 (4H, m), 7.37 (1H, dd, J=7.8, 7.8 Hz), 7.46 (1H, d, J=7.8 Hz), 7.70-7.72 (1H, m), 8.45-8.38 (1H, m)

m/z: [ES+] 419 ([M+H]+, C20H20ClFN4O3)

Example 44. 5-Amino-N-[2-fluoro-4-(trifluoromethyl)phenyl]-3-methyl-1-(o-tolyl)-1H-pyrazole-4-carboxamide The title compound was prepared from 5-amino-3-methyl-1-(o-tolyl)-1H-pyrazole-4-carboxylic acid (Intermediate 13) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.038 g, 30%).

$^1$H NMR (ppm)(400 MHz, CDCl$_3$): 2.19 (3H, s), 2.61 (3H, s), 5.37 (2H, s), 7.30-7.47 (6H, m), 7.82 (1H, d, J=1.8 Hz), 8.64 (1H, dd, J=8.1, 8.1 Hz)

m/z: [ES+] 393 ([M+H]+, C19H16F4N4O)

Example 45. 5-Amino-1-(2-ethylphenyl)-3-methyl-N-[5-(trifluoromethyl)-2-pyridyl]-1H-pyrazole-4-carboxamide The title compound was prepared from 5-amino-1-(2-ethylphenyl)-3-methyl-1H-pyrazole-4-carboxylic acid (Intermediate 15) using a method analogous to the preparation of 5-amino-N-(5-chloropyridin-2-yl)-1-(o-tolyl)-1H-pyrazole-4-carboxamide (Example 1). The crude product was purified by reverse phase preparative HPLC to give the title compound as an off-white solid (0.009 g, 7%).

$^1$H NMR (ppm)(400 MHz, CDCl$_3$): 1.14 (3H, t, J=7.6 Hz), 2.52 (2H, q, J=8.0 Hz), 2.64 (3H, s), 5.38 (2H, s), 7.29 (1H, d, J=7.6 Hz), 7.34 (1H, t, J=7.3 Hz), 7.40-7.47 (2H, m), 7.92 (1H, d, J=8.3 Hz), 8.21 (1H, s), 8.42 (1H, d, J=8.6 Hz), 8.55 (1H, s)

m/z: [ES+] 390 ([M+H]+, C19H18F3N5O)

Example 46. 5-Amino-N-(5-chloro-2-pyridyl)-1-[2-(2-methoxyethoxy)phenyl]-3-methyl-1H-pyrazole-4-carboxamide The title compound was prepared from 5-amino-1-(2-(2-methoxyethoxy)phenyl)-3-methyl-1H-pyrazole-4-carboxylic acid (Intermediate 11) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.006 g, 6%).

$^1$H NMR (ppm)(400 MHz, CDCl$_3$): 2.48 (3H, s), 3.23 (3H, s), 3.53-3.57 (2H, m), 4.07 (2H, dd, J=4.5, 4.5 Hz), 5.72 (2H, s), 6.90 (1H, d, J=8.1 Hz), 6.95 (1H, dd, J=7.5, 7.5 Hz), 7.20-7.25 (1H, m), 7.30-7.33 (1H, m), 7.52 (1H, dd, J=2.5, 9.1 Hz), 7.93 (1H, s), 8.08-8.15 (2H, m)

m/z: [ES+] 402 ([M+H]+, C19H20ClN5O3)

Example 47. 5-Amino-1-(o-tolyl)-N-[4-(trifluoromethylsulfonyl)phenyl]-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.044 g, 31%).

$^1$H NMR (ppm)(400 MHz, CDCl$_3$): 2.18 (3H, s), 5.34 (2H, s), 7.30-7.44 (4H, m), 7.62 (1H, s), 7.78 (1H, s), 7.89-7.93 (2H, m), 7.97-8.02 (2H, m)

m/z: [ES+] 425 ([M+H]+, C18H15F3N4O3S)

Example 48. 5-Amino-N-[4-bromo-2-(difluoromethoxy)phenyl]-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.048 g, 32%).

$^1$H NMR (ppm)(400 MHz, CDCl$_3$): 2.18 (3H, s), 5.27 (2H, s), 6.58 (1H, t, J=72.9 Hz), 7.25-7.43 (6H, m), 7.71 (2H, s), 8.36-8.40 (1H, m)

m/z: [ES+] 437 ([M+H]+, C18H15BrF2N4O2)

Example 49. 5-Amino-N-(4-chloro-2-fluoro-phenyl)-3-methyl-1-(o-tolyl)-1H-pyrazole-4-carboxamide The title compound was prepared from 5-amino-3-methyl-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a cream solid (0.032 g, 28%).

$^1$H NMR (ppm)(400 MHz, CDCl3): 2.18 (3H, s), 2.59 (3H, s), 5.34 (2H, s), 7.13-7.20 (2H, m), 7.28-7.41 (4H, m), 7.61 (1H, d, J=1.8 Hz), 8.37-8.43 (1H, m)

m/z: [ES+] 359 ([M+H]+, C18H16ClFN4O)

Example 50. 5-Amino-N-(5-methylpyridin-2-yl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a pale yellow solid (0.013 g, 14%).

$^1$H NMR (ppm)(400 MHz, CDCl$_3$): 2.18 (3H, s), 2.31 (3H, s), 5.30 (2H, s), 7.32-7.35 (2H, m), 7.37-7.41 (2H, m), 7.53 (1H, dd, J=2.4, 8.5 Hz), 7.76 (1H, s), 7.97 (1H, s), 8.12 (1H, d, J=2.5 Hz), 8.16 (1H, d, J=8.6 Hz)

m/z: [ES+] 308 ([M+H]+, C17H17N5O)

Example 51. 5-Amino-N-(5-cyanopyridin-2-yl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an orange solid (0.015 g, 16%).

$^1$H NMR (ppm)(400 MHz, CDCl$_3$): 2.18 (3H, s), 5.34 (2H, s), 7.30-7.43 (4H, m), 7.78 (1H, s), 7.94 (1H, dd, J=2.1, 8.7 Hz), 8.16 (1H, s), 8.44 (1H, d, J=8.8 Hz), 8.58 (1H, d, J=1.5 Hz)

m/z: [ES+] 319 ([M+H]+, C17H14N6O)

Example 52. 5-Amino-N-(5-bromopyridin-2-yl)-1-(o-tolyl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a white solid (0.022 g, 20%).

$^1$H NMR (ppm)(400 MHz, CDCl$_3$): 2.17 (3H, s), 5.31 (2H, s), 7.31-7.42 (4H, m), 7.76 (1H, s), 7.80 (1H, dd, J=2.5, 8.8 Hz), 8.00 (1H, s), 8.23 (1H, d, J=8.8 Hz), 8.34 (1H, d, J=1.8 Hz)

m/z: [ES+] 372, 374 ([M+H]+, C16H14BrN5O)

Example 53. 5-Amino-1-(o-tolyl)-N-(5-(trifluoromethoxy)pyridin-2-yl)-1H-pyrazole-4-carboxamide The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a white solid (0.023 g, 20%).

$^1$H NMR (ppm)(400 MHz, CDCl$_3$): 2.18 (3H, s), 5.31 (2H, s), 7.32-7.43 (4H, m), 7.59 (1H, dd, J=2.8, 9.1 Hz), 7.78 (1H, s), 8.06 (1H, s), 8.23 (1H, d, J=2.8 Hz), 8.36 (1H, d, J=9.1 Hz)

m/z: [ES+] 378 ([M+H]+, C17H14F3N5O)

Example 54. 5-Amino-1-(2-methoxyphenyl)-N-[5-(2,2,2-trifluoroethoxy)-2-pyridyl]pyrazole-4-carboxamide The title compound was prepared from 5-amino-1-(2-methoxyphenyl)-1H-pyrazole-4-carboxylic acid (Intermediate 2) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a yellow solid (0.008 g, 9%).

$^1$H NMR (ppm)(400 MHz, CDCl$_3$): 3.89 (3H, s), 4.39 (2H, q, J=8.0 Hz), 5.51 (2H, s), 7.07-7.14 (2H, m), 7.35 (1H, dd, J=3.0, 9.1 Hz), 7.42-7.47 (2H, m), 7.79 (1H, s), 7.98 (1H, s), 8.05 (1H, d, J=2.8 Hz), 8.27 (1H, d, J=9.3 Hz)

m/z: [ES+] 408 ([M+H]+, C16H15F3N5O3)

Example 55. 5-Amino-1-(3-fluoro-2-methylphenyl)-N-(5-(trifluoromethoxy)pyridin-2-yl)-1H-pyrazole-4-carboxamide The title compound was prepared from 5-amino-1-(3-fluoro-2-methylphenyl)-1H-pyrazole-4-carboxylic acid (Intermediate 18) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.011 g, 6%).

$^1$H NMR (ppm)(DMSO-d6): 2.04 (3H, d, J=2.0 Hz), 6.48 (2H, s), 7.24 (1H, d, J=7.6 Hz), 7.41-7.48 (2H, m), 7.94-7.98 (1H, m), 8.35 (1H, d, J=9.3 Hz), 8.42 (1H, s), 8.49 (1H, d, J=2.8 Hz), 10.58 (1H, s)

m/z: [ES+] 396 ([M+H]+, C17H13F4N5O2)

Example 56. 5-Amino-N-(5-bromopyridin-2-yl)-1-(2-fluorophenyl)-1H-pyrazole-4-carboxamide The title compound was prepared from 5-amino-1-(2-fluorophenyl)-1H-pyrazole-4-carboxylic acid (Intermediate 19) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as a pale brown solid (0.009 g, 10%).

$^1$H NMR (ppm)(400 MHz, CDCl$_3$): 5.56 (2H, s), 7.27-7.33 (2H, m), 7.45-7.57 (2H, m), 7.79-7.83 (2H, m), 8.03 (1H, s), 8.23 (1H, d, J=9.1 Hz), 8.34 (1H, d, J=2.0)

m/z: [ES+] 374/376 ([M+H]+, C15H11BrF3N5O)

Example 57. (5-Amino-1-(3-fluoro-2-methylphenyl)-1H-pyrazol-4-yl)(5-chloroindolin-1-yl)methanone The title compound was prepared from 5-amino-1-(3-fluoro-2-methylphenyl)-1H-pyrazole-4-carboxylic acid (Intermediate 18) using a method analogous to the preparation 5-amino-N-(5-chloropyridin-2-yl)-1-(o-tolyl)-1H-pyrazole-4-carboxamide (Example 1).

The crude product was purified by reverse phase preparative HPLC to give the title compound as an off white solid (0.041 g, 37%).

$^1$H NMR (ppm)(DMSO-d6): 2.04 (3H, d, J=1.8 Hz), 3.28 (2H, t, J=8.5 Hz), 4.47 (2H, t, J=8.6 Hz), 6.61 (2H, s), 7.23-7.28 (2H, m), 7.37 (1H, d, J=2.3 Hz), 7.39-7.49 (2H, m), 7.99 (1H, s), 8.13 (1H, d, J=8.6 Hz)

m/z: [ES+] 371 ([M+H]+, C19H16ClFN4O)

Example 58. 5-Amino-1-(3-fluoro-2-methylphenyl)-N-(4-(trifluoromethyl)phenyl)-1H-pyrazole-4-carboxamide The title compound was prepared from 5-amino-1-(3-fluoro-2-methylphenyl)-1H-pyrazole-4-carboxylic acid (Intermediate 18) using a method analogous to the preparation of 5-amino-N-(5-chloropyridin-2-yl)-1-(o-tolyl)-1H-pyrazole-4-carboxamide (Example 1).

The crude product was purified by column chromatography (Biotage SNAP 10 g column 20-100% Et$_2$O/isohexane) to give the title compound as a pale yellow solid (0.028 g, 34%).

$^1$H NMR (ppm)(400 MHz, CDCl$_3$): 2.10 (3H, s), 5.35 (2H, s), 7.16 (1H, d, J=7.8 Hz), 7.21 (1H, dd, J=8.8, 8.8 Hz), 7.29-7.37 (1H, m), 7.41 (1H, s), 7.61 (2H, d, J=8.6 Hz), 7.71 (2H, d, J=8.6 Hz), 7.76 (1H, s)

m/z: [ES+] 379 ([M+H]+, C18H14F4N4O)

Example 59. (5-Amino-1-(o-tolyl)-1H-pyrazol-4-yl)(5-chloroindolin-1-yl)methanone The title compound was prepared from 5-amino-1-(o-tolyl)-1H-pyrazole-4-carboxylic acid (Intermediate 4) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.045 g, 43%).

$^1$H NMR (ppm)(DMSO-d6): 2.14 (3H, s), 3.28 (2H, t, J=8.5 Hz), 4.47 (2H, t, J=8.6 Hz), 6.48 (2H, s), 7.26 (1H, dd, J=2.4, 8.7 Hz), 7.36-7.38 (2H, m), 7.40-7.48 (1H, m), 7.49-7.51 (2H, m), 7.97 (1H, s), 8.13 (1H, d, J=8.6 Hz)

m/z: [ES+] 353 ([M+H]+, C19H17ClN4O)

Example 60. [5-Amino-1-(2-fluorophenyl)pyrazol-4-yl]-(5-chloroindolin-1-yl)methanone The title compound was prepared from 5-amino-1-(2-fluorophenyl)-1H-pyrazole-4-carboxylic acid (Intermediate 19) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.023 g, 23%).

$^1$H NMR (ppm)(DMSO-d6): 3.29 (2H, t, J=8.3 Hz), 4.47 (2H, t, J=8.4 Hz), 6.76 (2H, s), 7.26 (1H, dd, J=2.3, 8.6 Hz), 7.36-7.38 (1H, m), 7.41-7.47 (1H, m), 7.50-7.66 (3H, m), 8.00 (1H, s), 8.13 (1H, d, J=8.6 Hz)

m/z: [ES+] 357 ([M+H]+, C18H14ClFN4O)

Example 61. (5-Amino-1-(2-methoxyphenyl)-1H-pyrazol-4-yl)(5-chloroindolin-1-yl)methanone The title compound was prepared from 5-amino-1-(2-methoxyphenyl)-1H-pyrazole-4-carboxylic acid (Intermediate 2) using a method analogous to the preparation of 5-amino-N-(5-chloropyridin-2-yl)-1-(o-tolyl)-1H-pyrazole-4-carboxamide (Example 1).

The crude product was purified by reverse phase preparative HPLC to give the title compound as an off-white solid (0.011 g, 10%).

$^1$H NMR (ppm)(DMSO-d6): 3.28 (2H, t, J=8.5 Hz), 3.86 (3H, s), 4.46 (2H, t, J=8.6 Hz), 6.42 (2H, s), 7.13-7.17 (1H, m), 7.23-7.31 (2H, m), 7.36-7.39 (2H, m), 7.53-7.58 (1H, m), 7.93 (1H, s), 8.13 (1H, d, J=8.6 Hz)

m/z: [ES+] 369 ([M+H]+, C19H17ClN4O2)

Example 62. 5-Amino-N-(4-bromophenyl)-1-(o-tolyl)-1H-1,2,3-triazole-4-carboxamide A mixture of N-(4-bromophenyl)-2-cyanoacetamide (Intermediate 28; 0.10 g, 0.41 mmol) and sodium methoxide (1 M solution in MeOH) (0.41 mL, 0.41 mmol) was stirred at 45° C. for 0.25 hrs. The reaction mixture was allowed to cool to r.t. 1-Azido-2-methylbenzene (0.5 M solution in toluene) (0.82 mL, 0.41 mmol) was added and the mixture stirred at 45° C. for 0.25 hrs. The mixture was allowed to cool to r.t. and stirred for 16 hrs. The reaction mixture was concentrated under reduced pressure. The crude product was purified by reverse phase preparative HPLC to give the title compound as an off-white solid (0.053 g, 35%).

$^1$H NMR (ppm)(400 MHz, DMSO-d6): 2.14 (3H, s), 6.48 (2H, s), 7.44-7.52 (2H, m), 7.54-7.57 (4H, m), 7.88-7.91 (2H, m), 10.42 (1H, s)

m/z: [ES+] 372, 374 ([M+H]+, C16H14BrN5O)

Example 63. 5-Amino-1-(2-methoxyphenyl)-N-(5-(trifluoromethyl)pyridin-2-yl)-1H-1,2,3-triazole-4-carboxamide A mixture of 5-amino-1-(2-methoxyphenyl)-1H-1,2,3-triazole-4-carboxylic acid (Intermediate 23; 0.075 g, 0.32 mmol), 5-(trifluoromethyl)pyridin-2-amine (0.057 g, 0.35 mmol) SOCl$_2$ (0.12 mL, 1.6 mmol) and MeCN (2 mL) was stirred at r.t. for 0.25 hrs. The reaction mixture was concentrated under reduced pressure. The residue was dissolved in a mixture of NEt$_3$ (0.09 mL, 0.64 mmol) and DCM (2 mL) and stirred at r.t. for 1 hr. The reaction mixture was concentrated under reduced pressure. The crude product was purified by reverse phase preparative HPLC to give the title compound as a pale brown solid (0.037 g, 31%).

$^1$H NMR (ppm)(400 MHz, DMSO-d6): 6.61 (2H, s), 3.88 (3H, s), 7.18-7.23 (1H, m), 7.36 (1H, d, J=7.6 Hz), 7.50 (1H, dd, J=1.6, 7.7 Hz), 7.63-7.68 (1H, m), 8.30 (1H, dd, J=2.4, 9.0 Hz), 8.42 (1H, d, J=8.8 Hz), 8.81 (1H, d, J=0.8 Hz), 9.93 (1H, s)

m/z: [ES+] 379 ([M+H]+, C16H13F3N6O2)

Example 64. 5-Amino-1-(2-methoxyphenyl)-N-(p-tolyl)-1H-1,2,3-triazole-4-carboxamide A mixture of 5-amino-1-(2-methoxyphenyl)-1H-1,2,3-triazole-4-carboxylic acid (Intermediate 23; 0.5 g, 2.1 mmol), PyBOP (1.31 g, 2.5 mmol), p-methylaniline (0.47 g, 2.3 mmol), Et$_3$N (0.44 mL, 3.2 mmol) and DMF (10 mL) was stirred at r.t. for 16 hrs. The reaction mixture was diluted with H$_2$O (50 mL) and extracted with EtOAc (2×75 mL). The combined organic extracts were washed with H$_2$O (2×50 mL) and saturated NaCl (aq) (50 mL). The organic extract was dried (MgSO$_4$), filtered and concentrated under reduced pressure. The crude product was purified by reverse phase preparative HPLC to give the title compound as an off-white solid (0.037 g, 54%).

$^1$H NMR (ppm)(400 MHz, DMSO-d6): 2.33 (3H, s), 3.87 (3H, s), 6.35 (2H, s), 7.15-7.22 (3H, m), 7.35 (1H, d, J=7.6 Hz), 7.49 (1H, dd, J=1.6, 7.7 Hz), 7.62-7.67 (1H, m), 7.76 (2H, d, J=8.6 Hz), 10.08 (1H, s)

m/z: [ES+] 324 ([M+H]+, C17H17N5O2)

Example 65. 5-Amino-1-(2-methoxyphenyl)-N-(4-(trifluoromethyl)phenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-Amino-1-(2-methoxyphenyl)-N-(p-tolyl)-1H-1,2,3-triazole-4-carboxamide (Example 64).

The crude product was purified by reverse phase preparative HPLC to give the title compound as an off-white solid (0.012 g, 15%).

$^1$H NMR (ppm)(400 MHz, DMSO-d6): 3.88 (3H, s), 6.47 (2H, s), 7.18-7.23 (1H, m), 7.36 (1H, d, J=7.6 Hz), 7.50 (1H, dd, J=1.6, 7.7 Hz), 7.62-7.68 (1H, m), 7.74 (2H, d, J=8.6 Hz), 8.14 (2H, d, J=8.3 Hz), 10.60 (1H, s)

m/z: [ES+] 378 ([M+H]+, C17H14F3N5O2)

Example 66. 5-Amino-1-(2-methoxyphenyl)-N-(4-(trifluoromethoxy)phenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-Amino-1-(2-methoxyphenyl)-N-(p-tolyl)-1H-1,2,3-triazole-4-carboxamide (Example 64). The crude product was purified by reverse phase preparative HPLC to give the title compound as an off-white solid (0.043 g, 52%).

$^1$H NMR (ppm)(400 MHz, DMSO-d6): 3.88 (3H, s), 6.42 (2H, s), 7.18-7.23 (1H, m), 7.34-7.40 (3H, m), 7.50 (1H, dd, J=1.8, 7.8 Hz), 7.62-7.67 (1H, m), 8.00-8.04 (2H, m), 10.45 (1H, s)

m/z: [ES+] 394 ([M+H]+, C17H14F3N5O3)

Example 67. 5-Amino-N-(4-isopropylphenyl)-1-(2-methoxyphenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-Amino-1-(2-methoxyphenyl)-N-(p-tolyl)-1H-1,2,3-triazole-4-carboxamide (Example 64). The crude product was purified by reverse phase preparative HPLC to give the title compound as an off-white solid (0.046 g, 62%).

$^1$H NMR (ppm)(400 MHz, DMSO-d6): 1.26 (6H, d, J=6.8 Hz), 2.85-2.97 (1H, m), 3.88 (3H, s), 6.35 (2H, s), 7.17-7.26 (3H, m), 7.33-7.36 (1H, m), 7.49 (1H, dd, J=1.6, 7.7 Hz), 7.62-7.67 (1H, m), 7.78 (2H, d, J=8.6 Hz), 10.09 (1H, s)

m/z: [ES+] 352 ([M+H]+, C19H21N5O2)

Example 68. 5-Amino-N-(5-chloropyridin-2-yl)-1-(2-methoxyphenyl)-1H-1,2,3-triazole-4-carboxamide The title compound was prepared from N-(5-chloropyridin-2-yl)-2-cyanoacetamide (Intermediate 29) using a method analogous to the preparation of 5-amino-N-(4-bromophenyl)-1-(o-tolyl)-1H-1,2,3-triazole-4-carboxamide (Example 62).

The crude product was purified by reverse phase preparative HPLC to give the title compound as a yellow solid (0.023 g, 16%).

$^1$H NMR (ppm)(400 MHz, DMSO-d6): 3.87 (3H, s), 6.54 (2H, s), 7.17-7.23 (1H, m), 7.35 (1H, d, J=7.6 Hz), 7.49 (1H, dd, J=1.5, 7.8 Hz), 7.62-7.68 (1H, m), 8.02 (1H, dd, J=2.5, 8.8 Hz), 8.25 (1H, d, J=8.8 Hz), 8.47 (1H, d, J=2.0 Hz), 9.70 (1H, s)

m/z: [ES+] 345, 347 ([M+H]+, C15H13ClN6O2)

Example 69. 5-Amino-1-(2-methoxyphenyl)-N-(4-phenoxyphenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-Amino-1-(2-methoxyphenyl)-N-(p-tolyl)-1H-1,2,3-triazole-4-carboxamide (Example 64). The crude product was purified by reverse phase preparative HPLC to give the title compound as a brown solid (0.047 g, 42%).

$^1$H NMR (ppm)(400 MHz, CDCl3): 3.90 (3H, s), 5.32 (2H, s), 7.00-7.16 (7H, m), 7.31-7.36 (2H, m), 7.48-7.56 (2H, m), 7.62-7.65 (2H, m), 8.66 (1H, s)

m/z: [ES+] 402 ([M+H]+, C22H19N5O3)

Example 70. 5-Amino-1-(2-methoxyphenyl)-N-(4-(1,1,2,2-tetrafluoroethoxy)phenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-amino-N-(4-bromophenyl)-1-(o-tolyl)-1H-1,2,3-triazole-4-carboxamide (Example 62).

The crude product was purified by reverse phase preparative HPLC to give the title compound as a yellow oil (0.047 g, 39%).

$^1$H NMR (ppm)(400 MHz, CDCl3): 3.91 (3H, s), 5.32 (2H, s), 5.91 (1H, tt, J=2.8, 52.8 Hz), 7.12-7.24 (4H, m), 7.48-7.56 (2H, m), 7.68-7.71 (2H, m), 8.72 (1H, s)

m/z: [ES+] 426 ([M+H]+, C18H15F4N5O3)

Example 71. 5-Amino-N-(4-(benzyloxy)phenyl)-1-(2-methoxyphenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-amino-N-(4-bromophenyl)-1-(o-tolyl)-1H-1,2,3-triazole-4-carboxamide (Example 62).

The crude product was purified by reverse phase preparative HPLC to give the title compound as a yellow oil (0.039 g, 34%).

$^1$H NMR (ppm)(400 MHz, CDCl3): 3.90 (3H, s), 5.07 (2H, s), 5.30 (2H, s), 6.99 (2H, d, J=9.1 Hz), 7.13 (1H, d, J=8.0 Hz), 7.16 (1H, d, J=7.3 Hz), 7.30-7.35 (1H, m), 7.39 (2H, dd, J=7.5, 7.5 Hz), 7.44 (2H, d, J=7.3 Hz), 7.48-7.59 (4H, m), 8.59 (1H, s)

m/z: [ES+] 416 ([M+H]+, C23H21N5O3)

Example 72. 5-Amino-N-(4-benzylphenyl)-1-(2-methoxyphenyl)-1H-1,2,3-triazole-4-carboxamide The title compound was prepared from 5-amino-1-(2-methoxyphenyl)-1H-1,2,3-triazole-4-carboxylic acid (Intermediate 23) using a method analogous to the preparation of 5-amino-N-(4-bromophenyl)-1-(o-tolyl)-1H-1,2,3-triazole-4-carboxamide (Example 62).

The crude product was purified by reverse phase preparative HPLC to give the title compound as a yellow oil (0.036 g, 54%).

$^1$H NMR (ppm)(400 MHz, CDCl3): 3.90 (3H, s), 3.98 (2H, s), 5.31 (2H, s), 7.11-7.23 (7H, m), 7.27-7.32 (2H, m), 7.48-7.55 (2H, m), 7.58 (2H, d, J=8.3 Hz), 8.64 (1H, s)

m/z: [ES+] 400 ([M+H]+, C23H21N5O2)

Example 73. 5-Amino-N-(5-chloropyridin-2-yl)-1-(o-tolyl)-1H-1,2,3-triazole-4-carboxamide The title compound was prepared from 5-amino-1-(o-tolyl)-1H-1,2,3-triazole-4-carboxylic acid (Intermediate 25) using a method analogous to the preparation of 5-amino-1-(2-methoxyphenyl)-N-(5-(trifluoromethyl)pyridin-2-yl)-1H-1,2,3-triazole-4-carboxamide (Example 63).

The crude product was purified by reverse phase preparative HPLC to give the title compound as a white solid (0.033 g, 29%).

¹H NMR (ppm)(400 MHz, DMSO-d6): 2.14 (3H, s), 6.60 (2H, s), 7.44-7.52 (2H, m), 7.55-7.60 (2H, m), 8.02 (1H, dd, J=2.7, 9.0 Hz), 8.25 (1H, d, J=8.8 Hz), 8.47 (1H, d, J=2.5 Hz), 9.75 (1H, s)

m/z: [ES+] 329, 331 ([M+H]+, C15H13ClN6O)

Example 74. 5-Amino-1-(o-tolyl)-N-(5-(trifluoromethyl)pyridin-2-yl)-1H-1,2,3-triazole-4-carboxamide The title compound was prepared from 5-amino-1-(o-tolyl)-1H-1,2,3-triazole-4-carboxylic acid (Intermediate 25) using a method analogous to the preparation of 5-amino-1-(2-methoxyphenyl)-N-(5-(trifluoromethyl)pyridin-2-yl)-1H-1,2,3-triazole-4-carboxamide (Example 63).

The crude product was purified by reverse phase preparative HPLC to give the title compound as a pale brown solid (0.028 g, 23%).

¹H NMR (ppm)(400 MHz, CDCl3): 2.20 (3H, s), 5.17 (2H, s), 7.33-7.36 (1H, m), 7.39-7.53 (3H, m), 7.94 (1H, dd, J=2.3, 8.8 Hz), 8.44 (1H, d, J=8.6 Hz), 8.61 (1H, s), 9.49 (1H, s)

m/z: [ES+] 363 ([M+H]+, C16H13F3N6O)

Example 75. 5-Amino-N-(5-chloropyridin-2-yl)-1-(3-fluoro-2-methylphenyl)-1H-1,2,3-triazole-4-carboxamide The title compound was prepared from N-(5-chloropyridin-2-yl)-2-cyanoacetamide (Intermediate 29) using a method analogous to the preparation of 5-amino-N-(4-bromophenyl)-1-(o-tolyl)-1H-1,2,3-triazole-4-carboxamide (Example 62).

The crude product was purified by reverse phase preparative HPLC to give the title compound as a pale brown solid (0.161 g, 31%).

¹H NMR (ppm)(400 MHz, DMSO-d6): 2.04 (3H, s), 6.73 (2H, s), 7.33-7.37 (1H, m), 7.51-7.56 (2H, m), 8.02 (1H, dd, J=2.8, 8.8 Hz), 8.24 (1H, d, J=8.8 Hz), 8.47 (1H, d, J=2.8 Hz), 9.76 (1H, s)

m/z: [ES+] 347 ([M+H]+, C15H12ClFN6O)

Example 76. 5-Amino-1-(3-fluoro-2-methylphenyl)-N-(5-(trifluoromethyl)pyridin-2-yl)-1H-1,2,3-triazole-4-carboxamide The title compound was prepared from 5-amino-1-(3-fluoro-2-methylphenyl)-1H-1,2,3-triazole-4-carboxylic acid (Intermediate 27) using a method analogous to the preparation of 5-amino-1-(2-methoxyphenyl)-N-(5-(trifluoromethyl)pyridin-2-yl)-1H-1,2,3-triazole-4-carboxamide (Example 63).

The crude product was purified by reverse phase preparative HPLC to give the title compound as a pale brown solid (0.003 g, 3%).

¹H NMR (ppm)(400 MHz, CDCl3): 2.12 (3H, s), 5.21 (2H, s), 7.18 (1H, d, J=7.8 Hz), 7.29 (1H, dd, J=8.6, 8.6 Hz), 7.37-7.44 (1H, m), 7.95 (1H, dd, J=2.3, 8.8 Hz), 8.43 (1H, d, J=8.8 Hz), 8.60-8.62 (1H, m), 9.47 (1H, s)

m/z: [ES+] 381 ([M+H]+, C16H12F4N6O)

Example 77. 5-Amino-N-(4-chlorophenyl)-1-(2,6-dimethylphenyl)-1H-pyrazole-4-carboxamide A mixture of N-(4-chlorophenyl)-2-cyano-3-ethoxyacrylamide (Intermediate 30; 75 mg, 0.30 mmol), (2,6-dimethylphenyl)hydrazine (41 mg, 0.30 mmol), Et3N (0.08 mL, 0.60 mmol) and EtOH (2 mL) was stirred at 60° C. for 18 hrs. The reaction mixture was allowed to cool to r.t. and concentrated under reduced pressure. The crude product was purified by reverse phase preparative HPLC to give the title compound as a pale brown solid (0.051 g, 50%).

¹H NMR (ppm)(400 MHz, CDCl3): 2.07 (6H, s), 5.19 (2H, s), 7.18 (2H, d, J=7.6 Hz), 7.31-7.27 (3H, m), 7.35 (1H, s), 7.55-7.51 (2H, m), 7.77 (1H, s)

m/z: [ES+] 341 ([M+H]+, C18H17ClN4O)

Example 78. 5-Amino-1-(2-chlorophenyl)-N-(4-chlorophenyl)pyrazole-4-carboxamide The title compound was prepared from N-(4-chlorophenyl)-2-cyano-3-ethoxyacrylamide (Intermediate 30) and (2-chlorophenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.025 g, 24%).

¹H NMR (ppm)(400 MHz, CDCl3): 5.39 (2H, s), 7.37-7.34 (3H, m), 7.46-7.54 (5H, m), 7.58-7.61 (1H, m), 7.76 (1H, s)

m/z: [ES+] 347, 349, 351 ([M+H]+, C16H12Cl2N4O)

Example 79. 5-Amino-N-(4-chlorophenyl)-1-(o-tolyl)pyrazole-4-carboxamide

The title compound was prepared from N-(4-chlorophenyl)-2-cyano-3-ethoxyacrylamide (Intermediate 30) and o-tolylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.039 g, 40%).

¹H NMR (ppm)(400 MHz, CDCl3): 2.17 (3H, s), 5.25-5.31 (2H, m), 7.29-7.35 (4H, m), 7.24-7.38 (1H, m), 7.36-7.43 (2H, m), 7.53 (2H, d, J=8.8 Hz), 7.72 (1H, s)

m/z: [ES+] 327, 329 ([M+H]+, C17H15ClN4O)

Example 80. 5-Amino-N-(4-chlorophenyl)-1-[2-(trifluoromethyl)phenyl]pyrazole-4-carboxamide The title compound was prepared from N-(4-chlorophenyl)-2-cyano-3-ethoxyacrylamide (Intermediate 30) and (2-(trifluoromethyl)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.027 g, 24%).

¹H NMR (ppm)(400 MHz, CDCl3): 5.31 (2H, s), 7.25 (1H, s), 7.30-7.34 (2H, m), 7.47-7.55 (3H, m), 7.69 (1H, dd, J=7.6, 7.6 Hz), 7.74 (1H, s), 7.75-7.77 (1H, m), 7.88-7.91 (1H, m)

m/z: [ES+] 381, 383 ([M+H]+, C17H12ClF3N4O)

Example 81. 5-Amino-N-(4-chlorophenyl)-1-(2,3-dichlorophenyl)-1H-pyrazole-4-carboxamide The title compound was prepared from N-(4-chlorophenyl)-2-cyano-3-ethoxyacrylamide (Intermediate 30) and (2,3-dichlorophenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.042 g, 37%).

$^1$H NMR (ppm)(400 MHz, CDCl$_3$): 5.41 (2H, s), 7.33-7.30 (3H, m), 7.42-7.38 (2H, m), 7.54-7.51 (2H, m), 7.64 (1H, dd, J=2.3, 7.3 Hz), 7.76 (1H, s)

m/z: [ES+] 381, 383, 385 ([M+H]+, C16H11Cl3N4O)

Example 82. 5-Amino-N-(4-chlorophenyl)-1-(2-fluorophenyl)pyrazole-4-carboxamide The title compound was prepared from N-(4-chlorophenyl)-2-cyano-3-ethoxyacrylamide (Intermediate 30) and (2-fluorophenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.037 g, 37%).

$^1$H NMR (ppm)(400 MHz, CDCl$_3$): 5.54 (2H, s), 7.25 (1H, s), 7.27-7.35 (4H, m), 7.44-7.50 (1H, m), 7.50-7.54 (3H, m), 7.76 (1H, s)

m/z: [ES+] 331, 333 ([M+H]+, C16H12ClFN4O)

Example 83. 5-Amino-N-(4-chlorophenyl)-1-[3-(trifluoromethyl)phenyl]pyrazole-4-carboxamide The title compound was prepared from N-(4-chlorophenyl)-2-cyano-3-ethoxyacrylamide (Intermediate 31) and (3-(trifluoromethyl)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.065 g, 57%).

$^1$H NMR (ppm)(400 MHz, CDCl3): 5.66 (2H, s), 7.30-7.34 (3H, m), 7.51-7.54 (2H, m), 7.66-7.68 (2H, m), 7.75 (1H, s), 7.78-7.82 (1H, m), 7.88-7.90 (1H, m)

m/z: [ES+] 381, 383 ([M+H]+, C17H12ClF3N4O)

Example 84. 5-Amino-1-(2-ethylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl) (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.035 g, 37%).

$^1$H NMR (ppm)(400 MHz, CDCl$_3$): 1.13 (3H, t, J=7.6 Hz), 2.51 (2H, q, J=7.6 Hz), 5.32 (2H, s), 7.26 (1H, s), 7.28-7.37 (2H, m), 7.41-7.50 (1H, m), 7.80 (1H, s), 7.92 (1H, dd, J=2.0, 8.8 Hz), 8.19 (1H, s), 8.43 (1H, d, J=8.8 Hz), 8.56 (1H, s)

m/z: [ES+] 376 ([M+H]+, C18H16F3N5O)

Example 85. 5-Amino-1-(2-chlorophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.004 g, 12%).

$^1$H NMR (ppm)(400 MHz, CDCl$_3$): 5.44 (2H, s), 7.45-7.51 (3H, m), 7.61 (1H, d, J=7.6 Hz), 7.84 (1H, s), 7.93 (1H, d, J=8.3 Hz), 8.19 (1H, s), 8.43 (1H, d, J=8.8 Hz), 8.56 (1H, s)

m/z: [ES+] 382, 384 ([M+H]+, C16H11ClF3N5O)

Example 86. 5-Amino-1-(2-isopropylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.011 g, 11%).

$^1$H NMR (ppm)(400 MHz, CDCl$_3$): 1.19 (6H, d, J=6.8 Hz), 2.73-2.84 (1H, m), 5.31 (2H, s), 7.32-7.37 (2H, m), 7.50-7.52 (2H, m), 7.80 (1H, s), 7.93 (1H, dd, J=2.1, 8.7 Hz), 8.20 (1H, s), 8.43 (1H, d, J=8.8 Hz), 8.55 (1H, s)

m/z: [ES+] 390 ([M+H]+, C19H18F3N5O)

Example 87. 5-Amino-1-[2-(trifluoromethoxy)phenyl]-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.049 g, 44%).

$^1$H NMR (ppm)(400 MHz, CDCl$_3$): 5.54 (2H, s), 7.46-7.53 (2H, m), 7.55-7.60 (2H, m), 7.84 (1H, s), 7.93 (1H, dd, J=2.1, 8.7 Hz), 8.22 (1H, s), 8.42 (1H, d, J=8.8 Hz), 8.55 (1H, s)

m/z: [ES+] 432 ([M+H]+, C17H11F6N5O2)

Example 88. 5-Amino-1-[2-(2-methoxyethoxy)phenyl]-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and (2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.013 g, 3%).

$^1$H NMR (ppm)(400 MHz, CDCl$_3$): 3.38 (3H, s), 3.69-3.73 (2H, m), 4.22-4.26 (2H, m), 5.88 (2H, s), 7.06-7.15 (2H, m), 7.37-7.43 (1H, m), 7.49 (1H, dd, J=1.8, 7.8 Hz), 7.83 (1H, s), 7.92 (1H, dd, J=2.5, 8.8 Hz), 8.19 (1H, s), 8.43 (1H, d, J=8.8 Hz), 8.55 (1H, s)

m/z: [ES+] 422 ([M+H]+, C19H18F3N5O3)

Example 89. 5-Amino-N-(5-chloropyridin-2-yl)-1-(2-ethylphenyl)-1H-pyrazole-4-carboxamide The title compound was prepared from N-(5-chloropyridin-2-yl)-2-cyano-3-(dimethylamino)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.019 g, 19%).

$^1$H NMR (ppm)(400 MHz, CDCl$_3$): 1.13 (3H, t, J=7.6 Hz), 2.51 (2H, q, J=7.6 Hz), 5.30 (2H, s), 7.39-7.28 (2H, m), 7.50-7.41 (2H, m), 7.70-7.65 (1H, m), 7.77 (1H, s), 8.02 (1H, s), 8.30-8.24 (2H, m)

m/z: [ES+] 342 ([M+H]+, C17H16ClN5O)

Example 90. 5-Amino-1-(2-(methoxymethyl)phenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.007 g, 7%).

$^1$H NMR (ppm)(400 MHz, CDCl$_3$): 3.36 (3H, s), 4.32 (2H, s), 5.57 (2H, s), 7.36 (1H, d, J=7.6 Hz), 7.56-7.44 (2H, m), 7.64 (1H, d, J=7.6 Hz), 7.81 (1H, s), 7.93 (1H, dd, J=1.8, 8.8 Hz), 8.22 (1H, s), 8.43 (1H, d, J=8.6 Hz), 8.57-8.56 (1H, m)

m/z: [ES+] 392 ([M+H]+, C18H16F3N5O2)

Example 91. 5-Amino-N-(5-chloropyridin-2-yl)-1-(2-methoxyphenyl)-1H-pyrazole-4-carboxamide The title compound was prepared from N-(5-chloropyridin-2-yl)-2-cyano-3-(dimethylamino)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.009 g, 9%).

$^1$H NMR (ppm)(400 MHz, CDCl$_3$): 3.89 (3H, s), 5.52 (2H, s), 7.14-7.07 (2H, m), 7.45 (2H, dd, J=7.6, 7.6 Hz), 7.67 (1H, dd, J=2.5, 8.8 Hz), 7.79 (1H, s), 8.02 (1H, s), 8.30-8.23 (2H, m)

m/z: [ES+] 344 ([M+H]+, C16H14ClN5O2)

Example 92. 5-Amino-1-(2-chlorophenyl)-N-(5-chloropyridin-2-yl)-1H-pyrazole-4-carboxamide The title compound was prepared from N-(5-chloropyridin-2-yl)-2-cyano-3-(dimethylamino)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.031 g, 30%).

$^1$H NMR (ppm)(400 MHz, CDCl$_3$): 5.42 (2H, s), 7.52-7.44 (3H, m), 7.60 (1H, d, J=7.6 Hz), 7.67 (1H, dd, J=2.0, 8.8 Hz), 7.81 (1H, s), 8.04 (1H, s), 8.29-8.23 (2H, m)

m/z: [ES+] 349 ([M+H]+, C15H11Cl2N5O)

Example 93. 5-Amino-N-(4-chloro-2-methoxyphenyl)-1-(2-methoxyphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.015 g, 22%).

$^1$H NMR (ppm)(400 MHz, CDCl$_3$): 3.88 (3H, s), 3.94 (3H, s), 5.48 (2H, s), 6.90 (1H, d, J=2.0 Hz), 6.96 (1H, dd, J=2.3, 8.6 Hz), 7.14-7.07 (2H, m), 7.47-7.42 (2H, m), 7.75 (1H, s), 7.88 (1H, s), 8.34 (1H, d, J=8.6 Hz).

m/z: [ES+] 373 ([M+H]+, C18H17ClN4O3)

Example 94. 5-Amino-N-(4-chloro-2-methoxyphenyl)-1-(2-ethylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.034 g, 51%).

$^1$H NMR (ppm)(400 MHz, CDCl$_3$): 1.12 (3H, t, J=7.6 Hz), 2.51 (2H, q, J=7.6 Hz), 3.94 (3H, s), 5.25 (2H, s), 6.90 (1H, d, J=2.3 Hz), 6.97 (1H, dd, J=2.1, 8.7 Hz), 7.38-7.28 (2H, m), 7.47-7.39 (2H, m), 7.73 (1H, s), 7.90 (1H, s), 8.35 (1H, d, J=8.8 Hz)

m/z: [ES+] 371 ([M+H]+, C19H19ClN4O2)

Example 95. 1-(2-(1H-Pyrazol-1-yl)phenyl)-5-amino-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) and 1-(2-hydrazinylphenyl)-1H-pyrazole hydrochloride using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.043 g, 40%).

$^1$H NMR (ppm)(400 MHz, CDCl$_3$): 5.24 (2H, s), 6.33 (1H, dd, J=2.1, 2.1 Hz), 7.20 (1H, d, J=2.5 Hz), 7.55 (2H, d, J=4.0 Hz), 7.70-7.62 (2H, m), 7.85-7.79 (2H, m), 7.91 (1H, dd, J=2.0, 8.6 Hz), 8.11 (1H, s), 8.37 (1H, d, J=8.8 Hz), 8.54 (1H, s)

m/z: [ES+] 414 ([M+H]+, C19H14F3N7O)

Example 96. 5-Amino-1-(2-bromophenyl)-N-(5-chloropyridin-2-yl)-1H-pyrazole-4-carboxamide The title compound was prepared from N-(5-chloropyridin-2-yl)-2-cyano-3-(dimethylamino)acrylamide (Intermediate 29) and a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.047 g, 40%).

$^1$H NMR (ppm)(400 MHz, CDCl$_3$): 5.39 (2H, s), 7.44-7.38 (1H, m), 7.52-7.46 (2H, m), 7.68 (1H, dd, J=2.5, 8.8 Hz), 7.80-7.75 (2H, m), 8.00 (1H, s), 8.29-8.23 (2H, m)

m/z: [ES+] 392, 394 ([M+H]+, C15H11BrClN5O)

Example 97. 5-Amino-N-(4-chloro-2-methoxyphenyl)-1-(5-fluoro-2-methylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 55-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.041 g, 61%).

$^1$H NMR (ppm)(400 MHz, CDCl$_3$): 2.14 (3H, s), 3.94 (3H, s), 5.31 (2H, s), 6.90 (1H, d, J=2.0 Hz), 6.97 (1H, dd, J=2.0, 8.6 Hz), 7.17-7.06 (2H, m), 7.37-7.31 (1H, m), 7.73 (1H, s), 7.89 (1H, s), 8.34 (1H, d, J=8.6 Hz)

m/z: [ES+] 375 ([M+H]+, C18H16ClFN4O2)

Example 98. 5-Amino-N-(4-chloro-2-methoxyphenyl)-1-(4-fluoro-2-methylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 55-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.024 g, 36%).

$^1$H NMR (ppm)(400 MHz, CDCl$_3$): 2.16 (3H, s), 3.94 (3H, s), 5.26 (2H, s), 6.92-6.89 (1H, m), 6.96 (1H, d, J=8.3 Hz), 7.10-7.00 (2H, m), 7.34-7.29 (1H, m), 7.72 (1H, s), 7.89 (1H, s), 8.34 (1H, d, J=8.6 Hz).

m/z: [ES+] 375 ([M+H]+, C18H16ClFN4O2)

Example 99. 5-Amino-N-(4-chloro-2-methoxyphenyl)-1-(3-fluoro-2-methylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 55-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.02 g, 15%).

$^1$H NMR (ppm)(400 MHz, CDCl3): 2.09 (3H, s), 3.95 (3H, s), 5.31 (2H, s), 6.92-6.90 (1H, m), 6.97 (1H, dd, J=1.8, 8.6 Hz), 7.23-7.14 (2H, m), 7.36-7.28 (1H, m), 7.73 (1H, s), 7.89 (1H, s), 8.34 (1H, d, J=8.6 Hz)

m/z: [ES+] 375 ([M+H]+, C18H16ClFN4O2)

Example 100. 5-Amino-N-(4-chloro-2-methoxyphenyl)-1-(2,3-dimethylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.65 g, 65%).

$^1$H NMR (ppm)(400 MHz, CDCl$_3$): 2.02 (3H, s), 2.35 (3H, s), 3.94 (3H, s), 5.23 (2H, s), 6.90 (1H, d, J=2.0 Hz), 6.97 (1H, dd, J=2.1, 8.7 Hz), 7.19-7.14 (1H, m), 7.23 (1H, dd, J=7.8, 7.8 Hz), 7.29 (1H, d, J=7.1 Hz), 7.72 (1H, s), 7.90 (1H, s), 8.35 (1H, d, J=8.6 Hz)

m/z: [ES+] 371 ([M+H]+, C19H19ClN4O2)

Example 101. 5-Amino-N-(4-chloro-2-methoxyphenyl)-1-(2,5-dimethylphenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.067 g, 67%).

$^1$H NMR (ppm)(400 MHz, CDCl$_3$): 2.12 (3H, s), 2.36 (3H, s), 3.94 (3H, s), 5.25 (2H, s), 6.90 (1H, d, J=2.0 Hz), 6.96 (1H, dd, J=2.0, 8.6 Hz), 7.13 (1H, s), 7.25-7.17 (2H, m), 7.71 (1H, s), 7.89 (1H, s), 8.35 (1H, d, J=8.6 Hz)

m/z: [ES+] 371 ([M+H]+, C19H19ClN4O2)

Example 102. 5-Amino-1-(2-bromophenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation of 5-amino-1-(4-methylpyridin-3-yl)-N-(5-(trifluoromethyl)pyridin-2-yl)-1H-pyrazole-4-carboxamide (Example 77).

The crude product was purified by column chromatography (Biotage SNAP 50 g column, 10% to 90% EtOAc/isohexane) then trituration with diethyl ether to give the title compound as a white solid (0.84 g, 37%).

$^1$H NMR (ppm)(400 MHz, CDCl3): 5.42 (2H, s), 7.45-7.38 (1H, m), 7.52-7.47 (2H, m), 7.79 (1H, d, J=8.1 Hz), 7.83 (1H, s), 7.93 (1H, dd, J=1.8, 8.8 Hz), 8.19 (1H, s), 8.42 (1H, d, J=8.8 Hz), 8.56 (1H, s)

m/z: [ES+] 426, 428 ([M+H]+, C16H11BrF3N5O)

Example 103. 5-Amino-N-(4-chloro-2-methoxyphenyl)-1-(2-chlorophenyl)-1H-pyrazole-4-carboxamide The title compound was prepared from N-(4-chloro-2-methoxyphenyl)-2-cyano-3-(dimethylamino)acrylamide (Intermediate 32) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.03 g, 4%).

$^1$H NMR (ppm)(400 MHz, DMSO-d6): 3.93 (3H, s), 6.36 (2H, s), 7.05 (1H, dd, J=2.3, 8.3 Hz), 7.20 (1H, d, J=2.3 Hz), 7.64-7.57 (3H, m), 7.79-7.73 (2H, m), 8.18 (1H, s), 8.95 (1H, s)

m/z: [ES+] ([M+H]+, C17H14Cl2N4O2)

Example 104. 5-Amino-1-(2-methyl-5-(trifluoromethyl)phenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) and (2-methyl-5-(trifluoromethyl)phenyl)hydrazine hydrochloride using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as an off-white solid (0.034 g, 26%).

$^1$H NMR (ppm)(400 MHz, CDCl$_3$): 2.26 (3H, s), 5.38 (2H, s), 7.54 (1H, d, J=8.1 Hz), 7.64 (1H, s), 7.69 (1H, d, J=7.8 Hz), 7.83 (1H, s), 7.94 (1H, dd, J=2.1, 9.0 Hz), 8.20 (1H, s), 8.42 (1H, d, J=8.8 Hz), 8.56 (1H, s)

m/z: [ES+] 430 ([M+H]+, C18H13F6N5O)

Example 105. 5-Amino-1-[2-(5-methyl-1,2,4-oxadiazol-3-yl)phenyl]-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 3-(2-hydrazinylphenyl)-5-methyl-1,2,4-oxadiazole hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.008 g, 7%).

$^1$H NMR (ppm)(400 MHz, CDCl$_3$): 2.57 (3H, s), 5.33 (2H, s), 7.59-7.54 (1H, m), 7.70-7.66 (2H, m), 7.78 (1H, s), 7.95-7.91 (1H, m), 8.17-8.13 (1H, m), 8.21 (1H, s), 8.42 (1H, d, J=8.8 Hz), 8.55 (1H, s)

m/z: [ES+] 430 ([M+H]+, C19H14F3N7O2)

Example 106. 5-Amino-1-(2-fluoro-6-methylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and (2-fluoro-6-methylphenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.012 g, 12%).

$^1$H NMR (ppm)(400 MHz, CDCl$_3$): 1.41 (3H, s), 5.22 (2H, s), 6.94-7.00 (1H, m), 7.03 (1H, d, J=7.7 Hz), 7.22-7.29 (1H, m), 7.71 (1H, s), 7.78 (1H, dd, J=2.0, 8.8 Hz), 8.02 (1H, s), 8.28 (1H, d, J=8.8 Hz), 8.42 (1H, s)

m/z: [ES+] 380 ([M+H]+, C17H13F4N5O)

Example 107. 5-Amino-1-(2-(oxazol-5-yl)phenyl)-N-(5-(trifluoromethyl)pyridin-2-yl)-1H-pyrazole-4-carboxamide The title compound was prepared from N-(5-chloropyridin-2-yl)-2-cyano-3-(dimethylamino)acrylamide (Intermediate 31) and 5-(2-hydrazinylphenyl)oxazole using a method analogous to the preparation of preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.016 g, 16%).

$^1$H NMR (ppm)(400 MHz, DMSO-d6): 6.24 (1H, s), 6.46 (2H, s), 7.54 (1H, dd, J=1.3, 7.8 Hz), 7.62-7.67 (1H, m), 7.74-7.78 (1H, m), 8.00 (1H, dd, J=1.4, 8.0 Hz), 8.23 (1H, dd, J=2.4, 9.0 Hz), 8.44 (1H, d, J=8.8 Hz), 8.51 (2H, d, J=3.3 Hz), 8.78-8.80 (1H, m), 10.82 (1H, s)

m/z: [ES+] 415 ([M+H]+, C19H13F3N6O2)

Example 108. 5-Amino-1-[2-(dimethylaminomethyl)phenyl]-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 1-(2-hydrazinylphenyl)-N,N-dimethylmethanamine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale brown solid (68 mg, 37%).

$^1$H NMR (ppm)(400 MHz, CDCl$_3$): 2.25 (6H, s), 3.31 (2H, s), 6.59 (2H, m), 7.30-7.35 (1H, m), 7.43-7.47 (3H, m), 7.81 (1H, s), 7.92 (1H, dd, J=1.9, 8.7 Hz), 8.19 (1H, s), 8.44 (1H, d, J=8.8 Hz), 8.54-8.56 (1H, m)

m/z: [ES+] 404 ([M+H]+C19H19F3N6O)

Example 109. 5-Amino-N-(4-chloro-2-methoxyphenyl)-1-[3-fluoro-2-(2-methoxyethoxy)phenyl]pyrazole-4-carboxamide The title compound was prepared from N-(4-chloro-2-methoxyphenyl)-2-cyano-3-(dimethylamino)acrylamide (Intermediate 32) and (3-fluoro-2-(2-methoxyethoxy)phenyl)-hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale yellow solid (68 mg, 58%).

$^1$H NMR (ppm)(400 MHz, CDCl$_3$): 3.28 (3H, s), 3.52 (2H, dd, J=4.4, 4.4 Hz), 3.94 (3H, s), 4.13 (2H, dd, J=4.2, 4.2 Hz), 5.79 (2H, s), 6.90 (1H, d, J=1.5 Hz), 6.97 (1H, d, J=8.6 Hz), 7.15-7.24 (2H, m), 7.27-7.31 (1H, m), 7.76 (1H, s), 7.89 (1H, s), 8.35 (1H, d, J=8.6 Hz)

m/z: [ES+] 434 ([M+H]+C20H20ClFN4O4)

Example 110. 5-Amino-N-(5-chloro-2-pyridyl)-1-[3-fluoro-2-(2-methoxyethoxy)phenyl]-pyrazole-4-carboxamide The title compound was prepared from N-(5-chloropyridin-2-yl)-2-cyano-3-(dimethylamino)acrylamide (Intermediate 29) and (3-fluoro-2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (39 mg, 21%).

$^1$H NMR (ppm)(400 MHz, CDCl$_3$): 3.27 (3H, s), 3.52 (2H, dd, J=4.2, 4.2 Hz), 4.14 (2H, dd, J=4.0, 4.0 Hz), ), 5.84

(2H, s), 7.16-7.24 (2H, m), 7.29 (1H, d, J=7.3 Hz), 7.68 (1H, dd, J=1.8, 8.8 Hz), 7.80 (1H, s), 7.98 (1H, s), 8.24-8.30 (2H, m)

m/z: [ES+] 405 ([M+H]+C18H17ClFN5O3)

Example 111. 5-Amino-N-(5-chloro-2-pyridyl)-1-[2-(di methylaminomethyl)-phenyl]-pyrazole-4-carboxamide The title compound was prepared from N-(5-chloropyridin-2-yl)-2-cyano-3-(dimethylamino)acrylamide (Intermediate 29) and 1-(2-hydrazinylphenyl)-N,N-dimethylmethanamine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale yellow solid (49 mg, 29%).

$^1$H NMR (ppm)(400 MHz, CDCl3): 2.23 (6H, dd, J=6.7, 6.7 Hz), 3.30 (2H, m), 6.49-6.53 (2H, m), 7.32 (1H, d, J=4.3 Hz), 7.43 (3H, d, J=6.1 Hz), 7.63-7.71 (1H, m), 7.74-7.78 (1H, m), 8.00 (1H, s), 8.21-8.30 (2H, m)

m/z: [ES+] 370 ([M+H]+C18H17ClFN5O3)

Example 112. 5-Amino-1-[3-fluoro-2-(2-methoxyethoxy)phenyl]-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and (3-fluoro-2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale brown solid (56 mg, 28%).

$^1$H NMR (ppm)(400 MHz, CDCl$_3$): 3.27 (3H, s), 3.55-3.51 (2H, m), 4.16 (2H, dd, J=4.2, 4.2 Hz), 5.87 (2H, s), 7.16-7.25 (2H, m), 7.30 (1H, s), 7.83 (1H, s), 7.92 (1H, d, J=8.8 Hz), 8.15 (1H, s), 8.42 (1H, d, J=8.8 Hz), 8.55 (1H, s)

m/z: [ES+] 439 ([M+H]+C19H17F4N5O3)

Example 113. 5-Amino-1-[3-fluoro-2-(2-methoxyethoxy)phenyl]-3-methyl-N-[5-(trifluoromethyl)-2-pyridyl]pyrazole-4-carboxamide The title compound was prepared from 2-cyano-3-dimethylamino-N-(5-(trifluoromethyl)pyridin-2-yl)but-2-enamide (Intermediate 31) and (3-fluoro-2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (14 mg, 11%).

$^1$H NMR (ppm)(400 MHz, CDCl$_3$): 2.65 (3H, s), 3.29 (3H, s), 3.54 (2H, dd, J=4.4, 4.4 Hz), 4.15 (2H, dd, J=4.2, 4.2 Hz), 5.93 (2H, s), 7.14-7.21 (2H, m), 7.30 (1H, s), 7.92 (1H, d, J=8.8 Hz), 8.24 (1H, s), 8.42 (1H, d, J=8.8 Hz), 8.55 (1H, s)

Example 114. 5-Amino-3-ethyl-1-(2-methoxyphenyl)-N-(5-(trifluoromethyl)pyridin-2-yl)-1H-pyrazole-4-carboxamide The title compound was prepared from N-(5-chloropyridin-2-yl)-2-cyano-3-(dimethylamino)acrylamide (Intermediate 31) and 1-(2-hydrazinylphenyl)-N,N-dimethylmethanamine hydrochloride using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 25 g column 10-70% EtOAc in ihexane) to give the title compound as a white solid (0.15 g, 59%).

$^1$H NMR (ppm) (400 MHz, CDCl$_3$): 1.47 (3H, t, J=7.4 Hz), 3.00 (2H, q, J=7.5 Hz), 3.89 (3H, s), 5.60 (2H, s), 7.05-7.14 (2H, m), 7.43 (2H, m), 7.91 (1H, d, J=8.8 Hz), 8.25 (1H, s), 8.43 (1H, d, J=8.8 Hz), 8.53-8.56 (1H, m)

m/z: [ES+] 406 ([M+H]+C19H18F3N5O2)

Example 115. 5-Amino-1-(2-(2-methoxyethoxy)phenyl)-3-methyl-N-(2-methyl-4-(trifluoromethyl)phenyl)-1H-pyrazole-4-carboxamide The title compound was prepared from 2-cyano-3-dimethylamino-N-(2-fluoro-4-(trifluoromethyl)phenyl)but-2-enamide (Intermediate 33) and (2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale brown solid (0.166 g, 25%).

$^1$H NMR (ppm)(400 MHz, CDCl$_3$): 2.61 (3H, s), 3.38 (3H, s), 3.73-3.67 (2H, m), 4.19-4.25 (2H, m), 5.85 (2H, s), 7.02-7.14 (2H, m), 7.34-7.50 (4H, m), 7.92 (1H, s), 8.65 (1H, t, J=8.0 Hz)

m/z: [ES+] 453 ([M+H]+, C21H20F4N4O3)

Example 116. 5-Amino-1-(2-bromo-3-fluorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide and using a method analogous to the preparation of 5-amino-1-(4-methylpyridin-3-yl)-N-(5-(trifluoromethyl)pyridin-2-yl)-1H-pyrazole-4-carboxamide.

The crude product was purified by reverse phase preparative HPLC to give the title compound as an off-white solid (0.019 g, 17%).

$^1$H NMR (ppm)(400 MHz, CDCl$_3$): 2.65 (3H, s), 5.51 (2H, s), 7.28-7.34 (2H, m), 7.44-7.51 (1H, m), 7.93 (1H, d, J=8.6 Hz), 8.21 (1H, s), 8.41 (1H, d, J=8.8 Hz), 8.55 (1H, s)

m/z: [ES+] 458 ([M+H]+, C17H12BrF4N5O)

Example 117. 5-Amino-1-(2-bromo-6-fluorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.016 g, 14%).

$^1$H NMR (ppm)(400 MHz, CDCl$_3$): 2.65 (3H, s), 5.54 (2H, s), 7.13-7.18 (1H, m), 7.21-7.24 (1H, m), 7.73 (1H, dd, J=5.6, 8.8 Hz), 7.93 (1H, d, J=9.3 Hz), 8.20 (1H, s), 8.41 (1H, d, J=8.8 Hz), 8.56 (1H, s)

m/z: [ES+] 458 ([M+H]+, C17H12BrF4N5O)

Example 118. 5-Amino-1-(2-chloro-6-fluorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.018 g, 17%).

$^1$H NMR (ppm)(400 MHz, CDCl$_3$): 2.66 (3H, s), 5.51 (2H, s), 7.22 (1H, d, J=8.3 Hz), 7.38-7.50 (2H, m), 7.92 (1H, d, J=8.8 Hz), 8.20 (1H, s), 8.41 (1H, d, J=8.6 Hz), 8.55 (1H, s)

m/z: [ES+] 414 ([M+H]+, C17H12ClF4N5O)

Example 119. 5-Amino-1-(2-bromo-3-fluorophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off white solid (0.015 g, 13%).

$^1$H NMR (ppm)(400 MHz, CDCl$_3$): 2.63 (3H, s), 5.48 (2H, s), 7.27-7.31 (2H, m), 7.44-7.51 (1H, m), 7.68 (1H, dd, J=2.5, 8.8 Hz), 8.02 (1H, s), 8.23-8.28 (2H, m)

m/z: [ES+] 424 ([M+H]+, C16H12BrClFN5O)

Example 120. 5-Amino-1-(2-chloro-6-fluorophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off white solid (0.014 g, 13%).

$^1$H NMR (ppm)(400 MHz, CDCl$_3$): 2.64 (3H, s), 5.47 (2H, s), 7.20-7.25 (1H, m), 7.38-7.47 (2H, m), 7.67 (1H, dd, J=2.4, 9.0 Hz), 8.03 (1H, s), 8.23-8.28 (2H, m)

m/z: [ES+] 380 ([M+H]+, C16H12Cl2FN5O)

Example 121. 5-Amino-1-(2-bromophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off white solid (0.018 g, 16%).

$^1$H NMR (ppm)(400 MHz, CDCl$_3$): 2.63 (3H, s), 5.44 (2H, s), 7.36-7.42 (1H, m), 7.45-7.50 (2H, m), 7.67 (1H, d, J=8.3 Hz), 7.76 (1H, d, J=8.1 Hz), 8.04 (1H, s), 8.23-8.29 (2H, m)

m/z: [ES+] 406 ([M+H]+, C16H13BrClN5O)

Example 122. 5-Amino-1-(3-fluoro-2-methylphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.023 g, 6%).

$^1$H NMR (ppm)(400 MHz, CDCl$_3$): 2.11 (3H, d, J=2.1 Hz), 2.64 (3H, s), 5.43 (2H, s), 7.14-7.21 (2H, m), 7.29-7.35 (1H, m), 7.92 (1H, dd, J=2.5, 8.8 Hz), 8.20 (1H, s), 8.41 (1H, d, J=8.8 Hz), 8.55-8.55 (1H, m)

m/z: [ES+] 394 ([M+H]+, C18H15F4N5O)

Example 123. 5-Amino-1-(2-methoxyphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.008 g, 8%).

$^1$H NMR (ppm)(400 MHz, CDCl$_3$): 2.65 (3H, s), 3.88 (3H, s), 5.57 (2H, s), 7.09 (2H, dd, J=7.6, 13.9 Hz), 7.43 (2H, d, J=7.6 Hz), 7.91 (1H, dd, J=2.1, 8.7 Hz), 8.22 (1H, s), 8.42 (1H, d, J=8.6 Hz), 8.53-8.55 (1H, m)

m/z: [ES+] 392 ([M+H]+, C18H16F3N5O2)

Example 124. 5-Amino-N-(5-chloro-2-pyridyl)-1-(2-methoxyphenyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.009 g, 9%).

$^1$H NMR (ppm)(400 MHz, CDCl$_3$): 2.63 (3H, s), 3.88 (3H, s), 5.56 (2H, s), 7.06-7.11 (2H, m), 7.40-7.46 (2H, m), 7.66 (1H, dd, J=2.5, 8.8 Hz), 8.04 (1H, s), 8.22-8.29 (2H, m)

m/z: [ES+] 358 ([M+H]+, C17H16ClN5O2)

Example 125. 5-Amino-1-(2-bromo-6-fluorophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.044 g, 38%)

$^1$H NMR (ppm)(400 MHz, CDCl$_3$): 5.48 (2H, s), 7.14-7.21 (1H, m), 7.26 (1H, s), 7.74 (1H, dd, J=5.4, 9.0 Hz), 7.82 (1H, s), 7.93 (1H, d, J=8.8 Hz), 8.16 (1H, s), 8.42 (1H, d, J=8.8 Hz), 8.56 (1H, s)

m/z: [ES+] 444 ([M+H]+, C16H10BrF4N5O)

Example 126. 5-Amino-1-(2-chloro-6-fluorophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.018 g, 17%).

$^1$H NMR (ppm)(400 MHz, CDCl$_3$): 5.30 (2H, s), 7.11 (1H, m), 7.26-7.28 (1H, d), 7.32-7.38 (1H, m), 7.73 (1H, s), 7.77-7.80 (1H, m), 8.01 (1H, s), 8.28 (1H, d, J=8.8 Hz), 8.40-8.43 (1H, m)

m/z: [ES+] 400 ([M+H]+, C16H10ClF4N5O)

Example 127. 5-Amino-N-(5-chloropyridin-2-yl)-1-(3-fluoro-2-methylphenyl)-1H-pyrazole-4-carboxamide The title compound was prepared from N-(5-chloropyridin-2-yl)-2-cyano-3-(dimethylamino)acrylamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 25 g column, 0 to 100% EtOAc/isohexane). The product was triturated with Et2O and dried under reduced pressure to give the title compound as a pale yellow solid (0.025 g, 18%).

$^1$H NMR (ppm)(400 MHz, DMSO-d6): 6.72 (2H, s), 7.45-7.47 (1H, m), 7.59-7.71 (2H, m), 8.22 (1H, dd, J=2.5, 9.1 Hz), 8.42-8.47 (2H, m), 8.78 (1H, d, J=2.5 Hz), 10.78 (1H, s)

m/z: [ES+] 346 ([M+H]+, C16H13ClFN5O)

Example 128. 5-Amino-1-(2-bromo-6-fluorophenyl)-N-(5-chloro-2-pyridyl)pyrazole-4-carboxamide The title compound was prepared from 2-cyano-3-dimethylamino-N-(5-(trifluoromethyl)pyridin-2-yl)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.042 g, 34%).

$^1$H NMR (ppm)(400 MHz, CDCl$_3$): 5.45 (2H, s), 7.17 (1H, ddd, J=2.9, 7.6, 9.0 Hz), 7.23-7.24 (1H, d) 7.66-7.77 (2H, m), 7.80 (1H, s), 8.00 (1H, s), 8.24-8.29 (2H, m)

m/z: [ES+] 410 ([M+H]+, C15H10BrClFN5O)

Example 129. 5-Amino-1-(2-fluoro-6-methoxyphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.007 g, 7%).

$^1$H NMR (ppm)(400 MHz, CDCl$_3$): 2.65 (3H, s), 3.87 (3H, s), 5.44 (2H, s), 6.84-6.92 (2H, m), 7.40-7.47 (1H, m), 7.89-7.94 (1H, m), 8.21 (1H, s), 8.41 (1H, d, J=8.8 Hz), 8.54 (1H, s)

m/z: [ES+] 410 ([M+H]+, C18H15F4N5O2)

Example 130. 5-Amino-1-(2-chloro-3-fluorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.008 g, 8%).

$^1$H NMR (ppm)(400 MHz, CDCl$_3$): 2.65 (3H, s), 5.54 (2H, s), 7.30-7.37 (2H, m), 7.39-7.46 (1H, m), 7.93 (1H, d, J=8.8 Hz), 8.20 (1H, s), 8.41 (1H, d, J=8.6 Hz), 8.56 (1H, s)

m/z: [ES+] 414 ([M+H]+, C17H12ClF4N5O)

Example 131. 5-Amino-N-(5-chloro-2-pyridyl)-1-(2-fluoro-6-methoxyphenyl)-3-methyl-pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off white solid (0.007 g, 7%).

$^1$H NMR (ppm)(400 MHz, CDCl$_3$): 2.63 (3H, s), 3.86 (3H, s), 5.42 (2H, s), 6.83-6.92 (2H, m), 7.39-7.46 (1H, m), 7.66 (1H, dd, J=2.4, 9.0 Hz), 8.00-8.05 (1H, m), 8.22-8.29 (2H, m)

m/z: [ES+] 376 ([M+H]+, C17H15ClFN5O2)

Example 132. 5-Amino-1-(2-chloro-3-fluorophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.016 g, 15%).

¹H NMR (ppm)(400 MHz, CDCl₃): 2.63 (3H, s), 5.52 (2H, s), 7.28-7.36 (2H, m), 7.38-7.45 (1H, m), 7.68 (1H, dd, J=2.0, 9.1 Hz), 8.02 (1H, s), 8.23-8.28 (2H, m)
m/z: [ES+] 380 ([M+H]+, C16H12Cl2FN5O)

Example 133. 5-Amino-N-(5-chloro-2-pyridyl)-1-(2-fluoro-6-methylphenyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.011 g, 11%).

¹H NMR (ppm)(400 MHz, CDCl3): 2.19 (3H, s), 2.63 (3H, s), 5.39 (2H, s), 7.06-7.18 (2H, m), 7.34-7.41 (1H, m), 7.67 (1H, dd, J=2.5, 8.8 Hz), 8.02 (1H, s), 8.23-8.29 (2H, m)
m/z: [ES+] 361 ([M+H]+, C17H15ClFN5O)

Example 134. 5-Amino-3-ethyl-1-(o-tolyl)-N-[5-trifluoromethyl-2-pyridyl]pyrazole-4-carboxamide The title compound was prepared from 2-cyano-3-ethoxy-N-(5-(trifluoromethyl)pyridin-2-yl)pent-2-enamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.014 g, 11%).

¹H NMR (ppm)(400 MHz, CDCl₃): 1.46 (3H, t, J=7.5 Hz), 2.18 (3H, s), 3.00 (2H, q, J=7.5 Hz), 5.40 (2H, s), 7.30-7.35 (2H, m), 7.38 (2H, s), 7.92 (1H, d, J=8.6 Hz), 8.22 (1H, s), 8.42 (1H, d, J=8.6 Hz), 8.55 (1H, s)
m/z: [ES+] 390 ([M+H]+, C19H18F3N5O)

Example 135. 5-Amino-3-ethyl-1-(2-(2-methoxyethoxy)phenyl)-N-(5-(trifluoromethyl)pyridin-2-yl)-1H-pyrazole-4-carboxamide The title compound was prepared from 2-cyano-3-ethoxy-N-(5-(trifluoromethyl)pyridin-2-yl)pent-2-enamide (Intermediate 31) and (2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 25 g column 20-65% EtOAc in isohexane) to give a colourless solid (0.049 g, 34%).

¹H NMR (ppm)(400 MHz, CDCl₃): 1.46 (3H, dd, J=7.5, 7.5 Hz), 3.00 (2H, q, J=7.4 Hz), 3.38 (3H, s), 3.71 (2H, dd, J=4.3, 4.3 Hz), 4.22 (2H, dd, J=4.3, 4.3 Hz), 5.89 (2H, s), 7.05 (1H, d, J=8.3 Hz), 7.11 (1H, dd, J=7.7, 7.7 Hz), 7.37 (1H, dd, J=7.8, 7.8 Hz), 7.48 (1H, d, J=7.8 Hz), 7.91 (1H, d, J=8.3 Hz), 8.31 (1H, s), 8.43 (1H, d, J=8.6 Hz), 8.55 (1H, s)
m/z: [ES+] 450 ([M+H]+, C21H22F3N5O3)

Example 136. 5-Amino-1-(2-chloro-6-fluorophenyl)-N-(5-chloro-2-pyridyl)pyrazole-4-carboxamide The title compound was prepared from N-(5-chloropyridin-2-yl)-2-cyano-3-(dimethylamino)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.020 g, 18%).

¹H NMR (ppm)(400 MHz, CDCl3): 5.42 (2H, s), 7.22-7.25 (1H, m), 7.40-7.50 (2H, m), 7.68 (1H, dd, J=2.4, 8.7 Hz), 7.88 (1H, s), 8.11 (1H, s), 8.23-8.30 (2H, m)
m/z: [ES+] 366 ([M+H]+, C15H10Cl2FN5O)

Example 137. 5-Amino-N-(5-chloro-2-pyridyl)-1-(3-fluoro-2-methylphenyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.050 g, 15%).

¹H NMR (ppm)(400 MHz, CDCl₃): 2.10 (3H, d, J=2.1 Hz), 2.62 (3H, s), 5.41 (2H, s), 7.13-7.20 (2H, m), 7.28-7.34 (1H, m), 7.67 (1H, dd, J=2.5, 8.9 Hz), 8.02 (1H, s), 8.24-8.28 (2H, m)
m/z: [ES+] 360 ([M+H]+, C17H15ClFN5O)

Example 138. 5-Amino-1-(2-ethylphenyl)-N-(3-fluoro-5-(trifluoromethyl)pyridin-2-yl)-1H-pyrazole-4-carboxamide A stirred mixture of 2-cyano-3-dimethylamino-N-(3-fluoro-5-(trifluoromethyl)pyridin-2-yl)acrylamide (Intermediate 34; 95 mg, 0.31 mmol), 2-ethylphenylhydrazine hydrochloride (81 mg, 0.47 mmol) and DIPEA (120 mg, 0.93 mmol) in ethanol (2 mL) was heated to 80° C. for 48 hrs.

The mixture was cooled and concentrated to dryness in vacuo and the crude product was purified by reverse phase preparative HPLC to give the title compound as an orange-brown powder (0.019 g, 15%).

¹H NMR (ppm)(400 MHz, CDCl3): 1.13 (3H, dd, J=7.6, 7.6 Hz), 2.51 (2H, q, J=7.6 Hz), 5.34 (2H, s), 7.28-7.38 (2H, m), 7.41-7.48 (2H, m), 7.71 (1H, dd, J=1.8, 9.6 Hz), 7.79 (1H, s), 7.82-7.87 (1H, m), 8.53 (1H, s)
m/z: [ES+] 394 ([M+H]+, C18H15F4N5O)

Example 139. 5-Amino-1-(o-tolyl)-N-(5-(2,2,2-trifluoroethoxy)pyridin-2-yl)-1H-pyrazole-4-carboxamide The title compound was prepared from 2-cyano-3-dimethylamino-N-(5-(2,2,2-trifluoroethoxy)pyridin-2-yl)acrylamide (Intermediate 35) and 2-methylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream powder (0.062 g, 44%).

¹H NMR (ppm)(400 MHz, CDCl₃): 2.18 (3H, s), 4.39 (2H, q, J=8.0 Hz), 5.30 (2H, s), 7.32-7.43 (5H, m), 7.77 (1H, s), 8.02 (1H, s), 8.05 (1H, d, J=2.5 Hz), 8.27 (1H, d, J=9.1 Hz)
m/z: [ES+] 392 ([M+H]+, C18H16F3N5O2)

Example 140. 5-Amino-1-(2-ethylphenyl)-N-(5-(2,2,2-trifluoroethoxy)pyridin-2-yl)-1H-pyrazole-4-carboxamide The title compound was prepared from 2-cyano-3-dimethylamino-N-(5-(2,2,2-trifluoroethoxy)pyridin-2-yl)acrylamide (Intermediate 35) using a method analogous to the preparation 5-amino-N-(4-chlorophenyl)-1-(2,6-dimethylphenyl)-1H-pyrazole-4-carboxamide.

The crude product was purified by reverse phase preparative HPLC to give the title compound as give a pale yellow powder (0.045 g, 37%).

$^1$H NMR (ppm)(400 MHz, CDCl$_3$): 1.13 (3H, t, J=7.6, 7.6 Hz), 2.51 (2H, q, J=7.6 Hz), 4.39 (2H, q, J=8.0 Hz), 5.29 (2H, s), 7.28-7.37 (3H, m), 7.41-7.48 (2H, m), 7.76 (1H, s), 8.00 (1H, s), 8.05 (1H, d, J=2.8 Hz), 8.27 (1H, d, J=9.1 Hz), m/z: [ES+] 406 ([M+H]+, C19H18F3N5O2)

Example 141. 5-Amino-1-(2-(2-methoxyethoxy)phenyl)-N-(5-(2,2,2-trifluoroethoxy)pyridin-2-yl)-1H-pyrazole-4-carboxamide The title compound was prepared from 2-cyano-3-dimethylamino-N-(5-(2,2,2-trifluoroethoxy)pyridin-2-yl)acrylamide (Intermediate 35) and (2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale brown solid (0.018 g, 14%).

$^1$H NMR (ppm)(400 MHz, CDCl$_3$): 3.37 (3H, s), 3.68-3.72 (2H, m), 4.21-4.24 (2H, m), 4.39 (2H, q, J=8.0 Hz), 5.83 (2H, s), 7.05-7.14 (2H, m), 7.33-7.42 (2H, m), 7.48 (1H, dd, J=1.8, 7.8 Hz), 7.80 (1H, s), 8.00 (1H, s), 8.05 (1H, d, J=2.5 Hz), 8.27 (1H, d, J=9.1 Hz)

m/z: [ES+] 452 ([M+H]+, C20H20F3N5O4)

Example 142. 5-Amino-1-(3-fluoro-2-methylphenyl)-N-(5-(2,2,2-trifluoroethoxy)pyridin-2-yl)-1H-pyrazole-4-carboxamide The title compound was prepared from 2-cyano-3-dimethylamino-N-(5-(2,2,2-trifluoroethoxy)pyridin-2-yl)acrylamide (Intermediate 35) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale brown solid (0.049 g, 40%).

$^1$H NMR (ppm) (400 MHz, CDCl$_3$): 2.10 (3H, d, J=2.0 Hz), 4.39 (2H, q, J=8.0 Hz), 5.34 (2H, s), 7.15-7.23 (2H, m), 7.29-7.37 (2H, m), 7.77 (1H, s), 8.01 (1H, s), 8.05 (1H, d, J=2.8 Hz), 8.26 (1H, d, J=9.1 Hz)

m/z: [ES+] 410 ([M+H]+, C18H15F4N5O2)

Example 143. 5-Amino-3-ethyl-1-(3-fluoro-2-methylphenyl)-N-[5-trifluoromethyl-2-pyridyl]pyrazole-4-carboxamide The title compound was prepared from 2-cyano-3-ethoxy-N-(5-(trifluoromethyl)pyridin-2-yl)pent-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by to flash chromatography on silica (Biotage 25 g SNAP, 0-70% ethyl acetate/isohexane) give the title compound as a pale orange solid (0.217 g, 63%).

$^1$H NMR (ppm)(400 MHz, DMSO): 1.21 (3H, t, J=7.5 Hz), 2.00 (3H, d, J=2.0 Hz), 2.90 (2H, q, J=7.5 Hz), 6.23 (2H, s), 7.19 (1H, d, J=7.5 Hz), 7.34-7.45 (2H, m), 8.18 (1H, dd, J=2.4, 9.0 Hz), 8.29 (1H, d, J=8.8 Hz), 8.70-8.71 (1H, m), 9.40 (1H, s)

m/z: [ES+] 408 ([M+H]+, C19H17F4N5O)

Example 144. 5-Amino-N-(5-chloro-2-pyridyl)-3-ethyl-1-(3-fluoro-2-methylphenyl)pyrazole-4-carboxamide The title compound was prepared from N-(5-chloropyridin-2-yl)-2-cyano-3-ethoxypent-2-enamide (Intermediate 29) using a method analogous to the preparation of 5-amino-N-(4-chlorophenyl)-1-(2,6-dimethylphenyl)-1H-pyrazole-4-carboxamide (Example 77).

The crude product precipitated out of solution to give the title compound as a pale pink solid (0.144 g, 54%).

$^1$H NMR (ppm)(400 MHz, DMSO): 1.21 (3H, t, J=7.5 Hz), 2.00 (3H, d, J=1.9 Hz), 2.89 (2H, q, J=7.4 Hz), 6.18 (2H, s), 7.18 (1H, d, J=7.5 Hz), 7.33-7.44 (2H, m), 7.91 (1H, dd, J=2.6, 8.9 Hz), 8.16 (1H, d, J=9.0 Hz), 8.37 (1H, d, J=2.3 Hz), 9.10 (1H, s)

m/z: [ES+] 374 ([M+H]+, C18H17ClFN5O)

Example 145. 5-Amino-1-(3-fluoro-2-methylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a white solid (0.070 g, 19%).

$^1$H NMR (ppm)(400 MHz, CDCl$_3$): 2.10 (3H, d, J=2.1 Hz), 5.38 (2H, s), 7.15-7.24 (2H, m), 7.30-7.37 (1H, m), 7.80 (1H, s), 7.93 (1H, dd, J=2.3, 8.9 Hz), 8.14 (1H, s), 8.42 (1H, d, J=8.7 Hz), 8.56 (1H, s)

m/z: [ES+] 380 ([M+H]+, C17H13F4N5O)

Example 146. 5-Amino-N-(4-chloro-2-fluorophenyl)-1-(2-methoxyphenyl)-1H-pyrazole-4-carboxamide The title compound was prepared from N-(4-chloro-2-fluorophenyl)-2-cyano-3-(dimethylamino)acrylamide (Intermediate 37) using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 25 g column, 0 to 50% EtOAc/isohexane). The product was triturated with Et2O and dried under reduced pressure to give the title compound as a pale yellow solid (0.063 g, <5%).

$^1$H NMR (ppm)(400 MHz, DMSO-d6): 3.89 (3H, s), 5.48 (2H, s), 7.07-7.18 (4H, m), 7.42-7.45 (3H, m), 7.76 (1H, s), 8.29-8.34 (1H, m)

m/z: [ES+] 361 ([M+H]+, C17H14ClFN4O2)

Example 147. 5-Amino-1-(3-fluoro-2-methylphenyl)-N-(5-iodopyridin-2-yl)-1H-pyrazole-4-carboxamide The title compound was prepared from 2-cyano-3-dimethylamino-N-(5-iodopyridin-2-yl)acrylamide (Intermediate 38) using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 25 g column, 0 to 100% EtOAc/isohexane). The product was triturated with Et2O and dried under reduced pressure to give the title compound as a pale yellow solid (0.108 g, 25%).

$^1$H NMR (ppm)(400 MHz, CDCl$_3$): 2.09 (3H, d, J=2.0 Hz), 5.35 (2H, s), 7.15-7.22 (2H, m), 7.29-7.36 (1H, m), 7.77 (1H, s), 7.95-8.01 (2H, m), 8.14 (1H, d, J=8.6 Hz), 8.48 (1H, d, J=1.5 Hz)

m/z: [ES+] 438 ([M+H]+, C16H13FIN5O)

Example 148. 5-Amino-N-(5-chloropyridin-2-yl)-1-(2-fluorophenyl)-1H-pyrazole-4-carboxamide The title compound was prepared from N-(5-chloropyridin-2-yl)-2-cyano-3-(dimethylamino)acrylamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.027 g, 16%).

$^1$H NMR (ppm)(DMSO-d6): 6.62 (2H, s), 7.40-7.45 (1H, m), 7.48-7.65 (3H, m), 7.95 (1H, dd, J=2.7, 9.0 Hz), 8.27 (1H, d, J=9.1 Hz), 8.41-8.45 (2H, m), 10.49 (1H, s)

m/z: [ES+] 332 ([M+H]+, C15H11ClFN5O)

Example 149. 5-amino-1-(2-fluorophenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.045 g, 25%).

$^1$H NMR (ppm)(DMSO-d6): 6.68 (2H, s), 7.41-7.46 (1H, m), 7.49-7.66 (3H, m), 8.22 (1H, dd, J=2.5, 8.8 Hz), 8.42-8.46 (2H, m), 8.78 (1H, d, J=2.5 Hz), 10.77 (1H, s)

m/z: [ES+] 366 ([M+H]+, C16H11F4N5O)

Example 150. 5-Amino-3-methyl-1-(2-(oxazol-5-yl)phenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) and 5-(2-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.014 g, 12%).

$^1$H NMR (ppm)(DMSO-d6): 2.53 (3H, s), 6.24 (2H, s), 6.32 (1H, s), 7.52 (1H, dd, J=1.0, 7.8 Hz), 7.62-7.67 (1H, m), 7.73-7.78 (1H, m), 8.01 (1H, dd, J=1.4, 8.0 Hz), 8.24 (1H, dd, J=2.3, 8.8 Hz), 8.35 (1H, d, J=8.8 Hz), 8.53 (1H, s), 8.76-8.79 (1H, m), 9.54 (1H, s)

m/z: [ES+] 429 ([M+H]+, C20H15F3N6O2)

Example 151. 5-Amino-3-ethyl-1-(2-fluorophenyl)-N-(5-(trifluoromethyl)pyridin-2-yl)-1H-pyrazole-4-carboxamide The title compound was prepared from 2-cyano-3-ethoxy-N-(5-(trifluoromethyl)pyridin-2-yl)pent-2-enamide (Intermediate 31) using a method analogous to the 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.254 g, 43%).

$^1$H NMR (ppm)(CDCl$_3$): 1.47 (3H, t, J=7.6 Hz), 3.00 (2H, q, J=7.5 Hz), 5.64 (2H, s), 7.28-7.34 (2H, m), 7.43-7.49 (1H, m), 7.51-7.57 (1H, m), 7.92 (1H, dd, J=2.4, 8.7 Hz), 8.22 (1H, s), 8.42 (1H, d, J=8.8 Hz), 8.55 (1H, d, J=0.8 Hz)

m/z: [ES+] 394 ([M+H]+, C18H15F4N5O)

Example 152. 5-Amino-N-(5-chloropyridin-2-yl)-3-ethyl-1-(2-fluorophenyl)-1H-pyrazole-4-carboxamide The title compound was prepared from N-(4-chlorophenyl)-2-cyano-3-ethoxyacrylamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale brown solid (0.049 g, 27%).

$^1$H NMR (ppm)(400 MHz, CDCl$_3$): 1.45 (3H, t, J=7.5 Hz), 2.98 (2H, q, J=7.5 Hz), 7.23-7.34 (2H, m), 5.62 (2H, s), 7.43-7.56 (2H, m), 7.67 (1H, dd, J=2.7, 9.0 Hz), 8.05 (1H, s), 8.23-8.29 (2H, m)

m/z: [ES+] 360 ([M+H]+, C17H15ClFN5O)

Example 153. 5-Amino-1-(2-fluorophenyl)-3-methyl-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation 5-amino-1-(4-methylpyridin-3-yl)-N-(5-(trifluoromethyl)pyridin-2-yl)-1H-pyrazole-4-carboxamide.

The crude product was purified by reverse phase preparative HPLC to give the title compound as a pale brown solid (0.042 g, 22%).

$^1$H NMR (ppm)(400 MHz, CDCl$_3$): 2.65 (3H, s), 5.64 (2H, s), 7.26 (1H, s), 7.28-7.34 (1H, m), 7.45-7.55 (2H, m), 7.92 (1H, dd, J=2.3, 8.8 Hz), 8.20 (1H, s), 8.41 (1H, d, J=8.8 Hz), 8.54 (1H, d, J=0.8 Hz)

m/z: [ES+] 380 ([M+H]+, C17H13F4N5O)

Example 154. 5-Amino-N-(5-chloropyridin-2-yl)-1-(2-fluorophenyl)-3-methyl-1H-pyrazole-4-carboxamide The title compound was prepared from N-(5-chloropyridin-2-yl)-2-cyano-3-(dimethylamino)but-2-enamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale brown solid (0.042 g, 22%).

$^1$H NMR (ppm)(400 MHz, CDCl$_3$): 2.63 (3H, s), 5.61 (2H, s), 7.27-7.33 (2H, m), 7.43-7.54 (2H, m), 7.67 (1H, dd, J=2.5, 8.8 Hz), 8.02 (1H, s), 8.23-8.28 (2H, m)

m/z: [ES+] 346 ([M+H]+, C16H13ClFN5O)

Example 155. 5-Amino-N-(5-chloropyridin-2-yl)-1-(2-fluoro-3-methylphenyl)-1H-pyrazole-4-carboxamide The title compound was prepared from N-(5-chloropyridin-2-yl)-2-cyano-3-(dimethylamino)acrylamide (Intermediate 29) using a method analogous to the preparation 5-amino-N-(4-chlorophenyl)-1-(2,6-dimethylphenyl)-1H-pyrazole-4-carboxamide.

The crude product was purified by reverse phase preparative HPLC to give the title compound which was obtained as a white solid (0.052 g, 30%).

$^1$H NMR (ppm)(DMSO-d6): 2.38 (3H, d, J=1.5 Hz), 6.59 (2H, s), 7.30 (1H, dd, J=7.7, 7.7 Hz), 7.34-7.40 (1H, m), 7.49 (1H, dd, J=6.7, 6.7 Hz), 7.95 (1H, dd, J=2.8, 9.1 Hz), 8.27 (1H, d, J=9.6 Hz), 8.40 (1H, s), 8.44 (1H, d, J=2.0 Hz), 10.48 (1H, s)

m/z: [ES+] 346 ([M+H]+, C16H13ClFN5O)

Example 156. 5-Amino-1-(2-fluoro-3-methylphenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation 55-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.030 g, 17%).

$^1$H NMR (ppm)(DMSO-d6): 2.38 (3H, d, J=1.5 Hz), 6.65 (2H, s), 7.31 (1H, dd, J=7.7, 7.7 Hz), 7.35-7.40 (1H, m), 7.47-7.52 (1H, m), 8.22 (1H, dd, J=2.4, 9.0 Hz), 8.42-8.46 (2H, m), 8.77-8.79 (1H, m), 10.76 (1H, s)

m/z: [ES+] 380 ([M+H]+, C17H13F4N5O)

Example 157. 5-Amino-N-(5-chloropyridin-2-yl)-1-(2-iodophenyl)-1H-pyrazole-4-carboxamide The title compound was prepared from N-(5-chloropyridin-2-yl)-2-cyano-3-(dimethylamino)acrylamide (Intermediate 29) using a method analogous to the preparation of 5-amino-N-(4-chlorophenyl)-1-(2,6-dimethylphenyl)-1H-pyrazole-4-carboxamide (Example 77).

The crude product was purified by column chromatography (Biotage SNAP 25 g column, 2 to 60% EtOAc/isohexane) then suspended in diethyl ether and collated by filtration to give the title compound (0.9 g, 34%). An analytically pure sample was obtained from purification by reverse phase preparative HPLC.

$^1$H NMR (ppm)(DMSO-d6): 6.29 (2H, s), 7.26-7.21 (1H, m), 7.36 (1H, dd, J=1.5, 7.8 Hz), 7.52-7.47 (1H, m), 7.82 (1H, dd, J=2.7, 9.0 Hz), 7.97 (1H, dd, J=1.3, 8.1 Hz), 8.15 (1H, d, J=9.6 Hz), 8.26 (1H, s), 8.32 (1H, d, J=2.8 Hz), 10.34 (1H, s)

m/z: [ES+] 440 ([M+H]+, C15H11ClIN5O)

Example 158. 5-Amino-N-(5-chloropyridin-2-yl)-1-(3-fluoro-2-(oxazol-5-yl)phenyl)-3-methyl-1H-pyrazole-4-carboxamide The title compound was prepared from N-(5-chloropyridin-2-yl)-2-cyano-3-(dimethylamino)but-2-enamide (Intermediate 29) and 5-(2-fluoro-6-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.017 g, 10%).

$^1$H NMR (ppm)(CDCl$_3$): 2.59 (3H, s), 5.38 (2H, s), 7.20 (1H, d, J=2.5 Hz), 7.33 (1H, d, J=7.8 Hz), 7.35-7.40 (1H, m), 7.49-7.56 (1H, m), 7.67 (1H, dd, J=2.4, 9.0 Hz), 7.86 (1H, s), 8.01 (1H, s), 8.22-8.25 (2H, m)

m/z: [ES+] 413 ([M+H]+, C19H14ClFN6O2)

Example 159. 5-Amino-1-(3-fluoro-2-(oxazol-5-yl)phenyl)-3-methyl-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)but-2-enamide (Intermediate 31) and 5-(2-fluoro-6-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.042 g, 19%).

$^1$H NMR (ppm)(CDCl$_3$): 2.61 (3H, s), 5.41 (2H, s), 7.21 (1H, d, J=2.5 Hz), 7.32-7.40 (2H, m), 7.50-7.57 (1H, m), 7.86 (1H, s), 7.92 (1H, dd, J=2.5, 8.8 Hz), 8.18 (1H, s), 8.39 (1H, d, J=8.8 Hz), 8.55 (1H, s)

m/z: [ES+] 447 ([M+H]+, C20H14F4N6O2)

Example 160. 5-Amino-N-(5-chloropyridin-2-yl)-1-(3-fluoro-2-(oxazol-5-yl)phenyl)-1H-pyrazole-4-carboxamide The title compound was prepared from N-(5-chloropyridin-2-yl)-2-cyano-3-(dimethylamino)acrylamide (Intermediate 29) and 5-(2-fluoro-6-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.027 g, 14%).

$^1$H NMR (ppm)(CDCl$_3$): 5.32 (2H, s), 7.22 (1H, d, J=2.5 Hz), 7.33-7.42 (2H, m), 7.51-7.58 (1H, m), 7.68 (1H, dd, J=2.4, 8.7 Hz), 7.74 (1H, s), 7.84 (1H, s), 7.98 (1H, s), 8.23-8.26 (2H, m), m/z: [ES+] 399 ([M+H]+, C18H12ClFN6O2)

Example 161. 5-Amino-1-(3-fluoro-2-(oxazol-5-yl)phenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) and 5-(2-fluoro-6-hydrazinylphenyl)oxazole using a method analogous to the preparation 5-amino- N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.064 g, 30%).

$^1$H NMR (ppm)(CDCl$_3$): 5.35 (2H, s), 7.23 (1H, d, J=2.5 Hz), 7.34-7.43 (2H, m), 7.52-7.58 (1H, m), 7.77 (1H, s), 7.84 (1H, s), 7.93 (1H, dd, J=2.3, 8.8 Hz), 8.16 (1H, s), 8.40 (1H, d, J=8.6 Hz), 8.56 (1H, d, J=0.8 Hz)

m/z: [ES+] 433 ([M+H]+, C19H12F4N6O2)

Example 162. 5-Amino-3-ethyl-1-(3-fluoro-2-(oxazol-5-yl)phenyl)-N-(5-(trifluoromethyl)pyridin-2-yl)-1H-pyrazole-4-carboxamide The title compound was prepared from 2-cyano-3-ethoxy-N-(5-(trifluoromethyl)pyridin-2-yl)pent-2-enamide (Intermediate 31) and 5-(2-fluoro-6-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by silica gel chromatography (Biotage SNAP 25 g column, 5 to 100% EtOAc/isohexane) to give the title compound as a yellow solid (0.142 g, 62%).

$^1$H NMR (ppm)(CDCl$_3$): 1.39 (3H, t, J=7.5 Hz), 2.95 (2H, q, J=7.5 Hz), 5.44 (2H, s), 7.19 (1H, d, J=2.5 Hz), 7.33-7.40 (2H, m), 7.50-7.57 (1H, m), 7.85 (1H, s), 7.92 (1H, dd, J=2.3, 8.8 Hz), 8.20 (1H, s), 8.40 (1H, d, J=8.8 Hz), 8.54-8.57 (1H, m)

m/z: [ES+] 360 ([M+H]+, C21H16F4N6O2)

Example 163. 5-Amino-3-ethyl-1-(2-(oxazol-5-yl)phenyl)-N-(5-(trifluoromethyl)pyridin-2-yl)-1H-pyrazole-4-carboxamide The title compound was prepared from 2-cyano-3-ethoxy-N-(5-(trifluoromethyl)pyridin-2-yl)pent-2-enamide (Intermediate 31) and 5-(2-hydrazinylphenyl)oxazole using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.051 g, 23%).

$^1$H NMR (ppm)(CDCl$_3$): 1.47 (3H, t, J=7.5 Hz), 3.03 (2H, q, J=7.5 Hz), 5.36 (2H, s), 6.36 (1H, s), 7.45 (1H, dd, J=1.0, 7.8 Hz), 7.50-7.55 (1H, m), 7.60-7.65 (1H, m), 7.90 (1H, s), 7.90-7.98 (2H, m), 8.24 (1H, s), 8.41 (1H, d, J=8.6 Hz), 8.56-8.58 (1H, m)

m/z: [ES+] 443 ([M+H]+, C21H17F3N6O2)

Example 164. 5-Amino-1-(2-iodophenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by column chromatography (Biotage SNAP 25 g column, 2 to 60% EtOAc/isohexane) then suspended in diethyl ether and collated by filtration to give the title compound (1.1 g, 58%). An analytically pure sample was obtained from purification by reverse phase preparative HPLC.

$^1$H NMR (ppm)(DMSO-d6): 6.48 (2H, s), 7.39-7.34 (1H, m), 7.49 (1H, dd, J=1.5, 7.8 Hz), 7.65-7.60 (1H, m), 8.10 (1H, dd, J=1.3, 7.8 Hz), 8.22 (1H, dd, J=2.5, 8.8 Hz), 8.47-8.42 (2H, m), 8.79-8.77 (1H, m), 10.75 (1H, s)

m/z: [ES+] 474 ([M+H]+, C16H11F3IN5O)

Example 165. 5-Amino-1-(2-iodophenyl)-3-methyl-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation of 5-amino-N-(4-chlorophenyl)-1-(2,6-dimethylphenyl)-1H-pyrazole-4-carboxamide (Example 77).

The crude product was purified by column chromatography (Biotage SNAP 25 g column, 2 to 60% EtOAc/isohexane) then suspended in diethyl ether and collated by filtration to give the title compound (0.61 g, 31%). An analytically pure sample was obtained from purification by reverse phase preparative HPLC.

$^1$H NMR (ppm)(DMSO-d6): 2.51 (3H, s), 6.33 (2H, s), 7.38-7.33 (1H, m), 7.46 (1H, dd, J=1.5, 7.8 Hz), 7.64-7.59 (1H, m), 8.09 (1H, dd, J=1.3, 7.8 Hz), 8.23 (1H, dd, J=2.4, 9.0 Hz), 8.34 (1H, d, J=8.8 Hz), 8.75 (1H, s), 9.30 (1H, s)

m/z: [ES+] 488 ([M+H]+, C17H13F3IN5O)

Example 166. 5-Amino-N-(5-chloropyridin-2-yl)-1-(2-(oxazol-5-yl)phenyl)-1H-pyrazole-4-carboxamide The title compound was prepared from N-(5-chloropyridin-2-yl)-2-cyano-3-(dimethylamino)acrylamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound which was obtained as a white solid (0.012 g, 9%).

$^1$H NMR (ppm)(CDCl$_3$): 5.20 (2H, s), 6.27 (1H, s), 7.39 (1H, dd, J=1.3, 7.8 Hz), 7.44-7.49 (1H, m), 7.55-7.63 (2H, m), 7.78 (1H, s), 7.82 (1H, s), 7.90 (1H, dd, J=1.4, 8.0 Hz), 7.97 (1H, s), 8.17-8.20 (2H, m)

m/z: [ES+] 381 ([M+H]+, C18H13ClN6O2)

Example 167. 5-Amino-1-(2-chloro-3-fluorophenyl)-N-(5-chloropyridin-2-yl)-1H-pyrazole-4-carboxamide The title compound was prepared from N-(5-chloropyridin-2-yl)-2-cyano-3-(dimethylamino)acrylamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a yellow solid (0.094 g, 17%).

$^1$H NMR (ppm)(400 MHz, DMSO-d6): 6.65 (2H, s), 7.44-7.47 (1H, m), 7.58-7.71 (2H, m), 7.95 (1H, dd, J=2.7, 9.0 Hz), 8.27 (1H, d, J=9.1 Hz), 8.42-8.45 (2H, m), 10.50 (1H, s)

m/z: [ES+] 366 ([M+H]+, C15H10Cl2FN5O)

Example 168. 5-Amino-1-(2-chloro-3-fluorophenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a yellow solid (0.111 g, 19%).

$^1$H NMR (ppm)(400 MHz, DMSO-d6): 6.72 (2H, s), 7.45-7.47 (1H, m), 7.59-7.71 (2H, m), 8.22 (1H, dd, J=2.5, 9.1 Hz), 8.42-8.47 (2H, m), 8.78 (1H, d, J=2.5 Hz), 10.78 (1H, s)

m/z: [ES+] 400 ([M+H]+, C15H10ClF4N5O)

Example 169. 5-Amino-1-(2-(5-chlorothiopheN-2-yl)phenyl)-N-(5-(trifluoromethyl)pyridin-2-yl)-1H-pyrazole-4-carboxamide The title compound was prepared from 2-cyano-3-dimethylamino-N-(5-(trifluoromethyl)pyridin-2-yl)acrylamide (Intermediate 31) and (2-(5-chlorothiopheN-2-yl)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale yellow solid (0.012 g, 7%).

$^1$H NMR (ppm)(400 MHz, CDCl$_3$): 5.24 (2H, s), 6.68 (1H, d, J=4.0 Hz), 6.80 (1H, d, J=3.8 Hz), 7.43 (1H, dd, J=1.5, 7.8 Hz), 7.46-7.51 (1H, m), 7.53-7.58 (1H, m), 7.67 (1H, dd, J=1.3, 7.8 Hz), 7.82 (1H, s), 7.92 (1H, dd, J=2.3, 8.8 Hz), 8.18 (1H, s), 8.40 (1H, d, J=8.8 Hz), 8.55-8.57 (1H, m)

m/z: [ES+] 464 ([M+H]+, C20H13ClF3N5OS)

Example 170. 5-Amino-N-(5-chloropyridin-2-yl)-1-(2-(pyrrolidin-1-ylsulfonyl)phenyl)-1H-pyrazole-4-carboxamide The title compound was prepared from N-(5-chloropyridin-2-yl)-2-cyano-3-(dimethylamino)acrylamide (Intermediate 31) and 1-((2-hydrazinylphenyl)sulfonyl)pyrrolidine hydrochloride using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as a beige solid (0.085 g, 20%).

$^1$H NMR (ppm)(400 MHz, CDCl$_3$): 1.80-1.85 (4H, m), 3.07-3.15 (4H, m), 5.55 (2H, s), 7.35 (1H, dd, J=1.5, 7.6 Hz), 7.64-7.74 (3H, m), 7.78 (1H, s), 7.99 (1H, s), 8.19 (1H, dd, J=1.5, 7.8 Hz), 8.24-8.29 (2H, m)

m/z: [ES+] 447, 449 ([M+H]+, C19H19ClN6O3S)

Example 171. 5-Amino-N-(5-chloropyridin-2-yl)-1-(2-(N-methyl-N-(pyridin-3-yl)sulfamoyl)phenyl)-1H-pyrazole-4-carboxamide The title compound was prepared from N-(5-chloropyridin-2-yl)-2-cyano-3-(dimethylamino)acrylamide (Intermediate 29) and 2-hydrazinyl-N-methyl-N-(pyridin-3-yl)benzenesulfonamide dihydrochloride using a method analogous to the preparation of 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (0.067 g, 49%).

$^1$H NMR (ppm)(400 MHz, CDCl$_3$): 3.10 (3H, s), 5.53 (2H, s), 7.21 (1H, dd, J=4.8, 7.6 Hz), 7.39 (1H, dd, J=1.0, 7.8 Hz), 7.53-7.58 (1H, m), 7.61-7.75 (4H, m), 7.86 (1H, dd, J=1.5, 8.1 Hz), 7.98 (1H, s), 8.24-8.29 (2H, m), 8.47 (1H, dd, J=1.5, 4.8 Hz), 8.50 (1H, d, J=2.0 Hz)

m/z: [ES+] 484, 486 ([M+H]+, C21H18ClN7O3S)

Example 172. 5-Amino-1-(2-bromophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.007 g, 6%).

$^1$H NMR (ppm)(400 MHz, CDCl$_3$): 2.66 (3H, s), 5.47 (2H, s), 7.37-7.42 (1H, m), 7.44-7.51 (2H, m), 7.75-7.79 (1H, m), 7.91-7.95 (1H, m), 8.22 (1H, s), 8.42 (1H, d, J=8.8 Hz), 8.55 (1H, s)

m/z: [ES+] 440/442 ([M+H]+, C17H13BrF3N5O)

Example 173. 5-Amino-N-(5-chloro-2-pyridyl)-1-(2-fluoro-6-methylphenyl)pyrazole-4-carboxamide The title compound was prepared from N-(5-chloropyridin-2-yl)-2-cyano-3-(dimethylamino)acrylamide (Intermediate 29) and 2-fluoro-6-methylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a grey solid (0.043 g, 41%).

$^1$H NMR (ppm)(400 MHz, CDCl$_3$): 2.38 (3H, s), 5.53 (2H, s), 7.20 (2H, m), 7.32 (2H, m), 7.68 (1H, d, J=8.6 Hz), 7.79 (1H, s), 7.96 (1H, s), 8.25 (1H, s)

m/z: [ES+] 346 ([M+H]+, C16H13ClFN5O)

Example 174. 5-Amino-N-(5-chloro-2-pyridyl)-1-(2-fluoro-6-methoxyphenyl)pyrazole-4-carboxamide The title compound was prepared from N-(5-chloropyridin-2-yl)-2-cyano-3-(dimethylamino)acrylamide (Intermediate 29) and 2-fluoro-6-methoxyphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as an off-white solid (0.003 g, 3%).

$^1$H NMR (ppm)(400 MHz, CDCl$_3$): 3.87 (3H, s), 5.37 (2H, s), 6.89 (2H, m), 7.41-7.48 (1H, m), 7.67 (1H, dd, J=2.5, 8.8 Hz), 7.83 (1H, s), 7.97 (1H, s), 8.29-8.23 (2H, m)

m/z: [ES+] 362 ([M+H]+, C16H13ClFN5O2)

Example 175. 5-Amino-1-(2-chlorophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (0.023 g, 2%).

$^1$H NMR (ppm)(400 MHz, CDCl$_3$): 2.63 (3H, s), 5.48 (2H, s), 7.2-7.50 (3H, m), 7.59 (1H, dd, J=1.8, 5.8 Hz), 7.67 (1H, dd, J=2.5, 8.8 Hz), 8.03 (1H, s), 8.23-8.28 (2H, m)

m/z: [ES+] 362 ([M+H]+, C16H13Cl2N5O)

Example 176. 5-Amino-1-(2-chlorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.005 g, 5%).

$^1$H NMR (ppm)(400 MHz, CDCl$_3$): 2.65 (3H, s), 5.51 (2H, s), 7.44-7.51 (3H, m), 7.57-7.61 (1H, m), 7.92 (1H, dd, J=2.3, 8.8 Hz), 8.21 (1H, s), 8.42 (1H, d, J=8.8 Hz), 8.55 (1H, s)

m/z: [ES+] 396 ([M+H]+, C17H13ClF3N5O)

Example 177. 5-Amino-3-methyl-1-(2-morpholinophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 4-(2-hydrazinylphenyl)morpholine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.006 g, 4%).

$^1$H NMR (ppm)(400 MHz, CDCl$_3$): 2.66 (3H, s), 2.90 (4H, dd, J=4.5, 4.5 Hz), 3.74 (4H, dd, J=4.5, 4.5 Hz), 6.15 (2H, s), 7.10 (1H, d, J=8.1 Hz), 7.14-7.20 (1H, m), 7.37-7.47 (2H, m), 7.93 (1H, dd, J=2.0, 8.8 Hz), 8.23 (1H, s), 8.43 (1H, d, J=8.8 Hz), 8.55 (1H, s)

m/z: [ES+] 447 ([M+H]+, C21H21F3N6O2)

Example 178. 5-Amino-1-(2-bromo-6-fluorophenyl)-N-(5-chloro-2-pyridyl)-3-methyl-pyrazole-4-carboxamide The title compound was prepared from N-(5-chloropyridin-2-yl)-2-cyano-3-(dimethylamino)but-2-enamide (Intermediate 29) and 2-bromo-6-fluorophenylhydrazine hydrochloride using a method analogous to the preparation 5-amino-N-(4-chlorophenyl)-1-(2,6-dimethylphenyl)-1H-pyrazole-4-carboxamide.

The crude product was purified by reverse phase preparative HPLC to give the title compound as a pale brown solid (0.017 g, 13%).

$^1$H NMR (ppm)(400 MHz, CDCl$_3$): 2.63 (3H, s), 5.51 (2H, s), 7.11-7.18 (1H, m), 7.23 (1H, dd, J=2.7, 8.2 Hz), 7.66-7.74 (2H, m), 8.02 (1H, s), 8.26 (2H, d, J=9.3 Hz)

m/z: [ES+] 424/426 ([M+H]+, C16H12BrClFN5O)

Example 179. 5-Amino-3-isopropyl-1-(o-tolyl)-N-[5-(trifluoromethyl)-2-pyridyl]pyrazole-4-carboxamide The title compound was prepared from 2-cyano-3-methoxy-4-methyl-N-(5-(trifluoromethyl)pyridin-2-yl)pent-2-enamide (Intermediate 29) using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a pale yellow solid (0.032 g, 57%).

$^1$H NMR (ppm)(400 MHz, CDCl$_3$): 1.48 (6H, d, J=6.8 Hz), 2.17 (3H, s), 3.35-3.26 (1H, m), 5.39 (2H, s), 7.33-7.39 (4H, m), 7.92 (1H, d, J=8.6 Hz), 8.29 (1H, s), 8.43 (1H, d, J=8.6 Hz), 8.54-8.57 (1H, m)

m/z: [ES+] 404 ([M+H]+, C20H20F3N5O)

Example 180. 5-Amino-1-(2-fluoro-6-methylphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 2-fluoro-6-methylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale brown solid (0.006 g, 6%).

$^1$H NMR (ppm) (400 MHz, CDCl$_3$): 2.20 (3H, s), 2.65 (3H, s), 5.42 (2H, s), 7.10 (1H, dd, J=9.0, 9.0 Hz), 7.16 (1H, d, J=7.6 Hz), 7.35-7.42 (1H, m), 7.92 (1H, dd, J=2.3, 8.8 Hz), 8.20 (1H, s), 8.42 (1H, d, J=8.8 Hz), 8.55 (1H, s)

m/z: [ES+] 394 ([M+H]+, C18H15F4N5O)

Example 181. 5-Amino-1-(2-fluoro-6-methoxyphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 2-fluoro-6-methoxyphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale brown solid (0.004 g, 4%).

$^1$H NMR (ppm) (400 MHz, CDCl$_3$): 3.87 (3H, s), 5.40 (2H, s), 6.90 (2H, dd, J=8.3, 15.9 Hz), 7.42-7.49 (1H, m), 7.86 (1H, s), 7.92 (1H, d, J=8.8 Hz), 8.12-8.16 (1H, m), 8.42 (1H, d, J=8.8 Hz), 8.55 (1H, s)

m/z: [ES+] 396 ([M+H]+, C17H13F4N5O2)

Example 182. 5-Amino-1-[2-(2-methoxyethoxy)phenyl]-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and (2-(2-methoxyethoxy)phenyl)hydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.007 g, 6%).

$^1$H NMR (ppm)(400 MHz, CDCl$_3$): 2.64 (3H, s), 3.38 (3H, s), 3.70 (2H, dd, J=4.5, 4.5 Hz), 4.22 (2H, dd, J=4.4, 4.4 Hz), 5.89 (2H, s), 7.05 (1H, d, J=8.3 Hz), 7.11 (1H, dd, J=7.7, 7.7 Hz), 7.36-7.41 (1H, m), 7.47 (1H, dd, J=1.5, 7.8 Hz), 7.91 (1H, d, J=8.6 Hz), 8.27 (1H, s), 8.42 (1H, d, J=8.8 Hz), 8.56-8.53 (1H, m)

m/z: [ES+] 436 ([M+H]+, C20H20F3N5O3)

Example 183. 5-Amino-1-(3-fluoro-2-methoxyphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 3-fluoro-2-methoxyphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale brown solid (0.004 g, 4%).

$^1$H NMR (ppm) (400 MHz, CDCl$_3$): 3.87 (3H, d, J=1.5 Hz), 5.78 (2H, s), 7.16-7.24 (2H, m), 7.27-7.31 (1H, m), 7.84 (1H, s), 7.93 (1H, dd, J=2.3, 8.8 Hz), 8.18 (1H, s), 8.43 (1H, d, J=8.8 Hz), 8.56 (1H, s)

m/z: [ES+] 396 ([M+H]+, C17H13F4N5O2)

Example 184. 5-Amino-N-(5-chloro-2-pyridyl)-1-(3-fluoro-2-methoxyphenyl)pyrazole-4-carboxamide The title compound was prepared from N-(5-chloropyridin-2-yl)-2-cyano-3-(dimethylamino)acrylamide (Intermediate 29) and 3-fluoro-2-methoxyphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as give a pale yellow solid (0.004 g, 3%).

$^1$H NMR (ppm) (400 MHz, CDCl$_3$): 3.86 (3H, s), 5.75 (2H, s), 7.16-7.24 (2H, m), 7.27-7.30 (1H, m), 7.68 (1H, dd, J=2.5, 8.8 Hz), 7.81 (1H, s), 8.01 (1H, s), 8.23-8.30 (2H, m)

m/z: [ES+] 362 ([M+H]+, C16H13ClFN5O2)

Example 185. 5-Amino-1-(2,6-difluorophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 2,6-difluorophenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.040 g, 42%).

$^1$H NMR (ppm) (400 MHz, CDCl$_3$): 5.53 (2H, s), 7.15 (2H, dd, J=8.1, 8.1 Hz), 7.47-7.56 (1H, m), 7.88 (1H, s), 7.94 (1H, d, J=8.9 Hz), 8.14 (1H, s), 8.42 (1H, d, J=8.8 Hz), 8.56 (1H, s)

m/z: [ES+] 384 ([M+H]+, C16H10F5N5O)

Example 186. 5-Amino-1-(2,6-dimethylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 2,6-dimethylphenylhydrazine hydrochloride using a method analogous to the 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.028 g, 30%).

$^1$H NMR (ppm) (400 MHz, CDCl$_3$): 2.09 (6H, s), 5.25 (2H, s), 7.20 (2H, d, J=7.6 Hz), 7.31 (1H, dd, J=7.6, 7.6 Hz), 7.83 (1H, s), 7.91-7.95 (1H, m), 8.17 (1H, s), 8.43 (1H, d, J=8.8 Hz), 8.56 (1H, s)

m/z: [ES+] 376 ([M+H]+, C18H16F3N5O)

Example 187. 5-Amino-1-(2,6-difluorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 2,6-difluorophenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a buff solid (0.021 g, 22%).

$^1$H NMR (ppm) (400 MHz, CDCl$_3$): 2.65 (3H, s), 5.56 (2H, s), 7.11-7.15 (2H, m), 7.40-7.44 (1H, m), 7.91 (1H, d, J=8.9 Hz), 8.28 (1H, s), 8.40 (1H, d, J=7.3 Hz), 8.68 (1H, s)

m/z: [ES+] 398 ([M+H]+, C17H12F5N5O)

Example 188. 5-Amino-1-(2,6-dimethylphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 2,6-dimethylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (0.019 g, 19%).

$^1$H NMR (ppm) (400 MHz, CDCl$_3$): 2.09 (6H, s), 2.65 (3H, s), 5.30 (2H, s), 7.18 (2H, d, J=7.6 Hz), 7.26-7.31 (1H, m), 7.92 (1H, dd, J=2.0, 8.8 Hz), 8.22 (1H, s), 8.43 (1H, d, J=8.8 Hz), 8.54-8.57 (1H, m)

m/z: [ES+] 390 ([M+H]+, C19H18F3N5O)

Example 189. 5-Amino-1-(2-chloro-6-methylphenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 2-chloro-6-methylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.005 g, 5%).

$^1$H NMR (ppm) (400 MHz, CDCl$_3$): 2.16 (3H, s), 2.66 (3H, s), 5.38 (2H, s), 7.26-7.29 (1H, m), 7.35 (1H, m), 7.41 (1H, m), 7.93 (1H, d, J=8.6 Hz), 8.22 (1H, s), 8.42 (1H, d, J=8.8 Hz), 8.54 (1H, s)

m/z: [ES+] 410 ([M+H]+, C18H15ClF3N5O)

Example 190. 5-Amino-1-(2,6-dichlorophenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 2,6-dichlorophenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a yellow solid (0.015 g, 14%).

$^1$H NMR (ppm) (400 MHz, CDCl$_3$): 5.39 (2H, s), 7.42-7.47 (1H, m), 7.53 (2H, d, J=8.1 Hz), 7.89 (1H, s), 7.91-7.95 (1H, m), 8.16 (1H, s), 8.43 (1H, d, J=8.8 Hz), 8.56 (1H, s)

m/z: [ES+] 416 ([M+H]+, C16H10Cl2F3N5O)

Example 191. 5-Amino-1-(2-chloro-6-methylphenyl)-N-[5-trifluoromethyl-2-pyridyl]pyrazole-4-carboxamide The title compound was prepared from 2-cyano-3-dimethylamino-N-(5-(trifluoromethyl)pyridin-2-yl)acrylamide (Intermediate 31) and 2-chloro-6-methylphenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a brown solid (0.004 g, 4%).

$^1$H NMR (ppm) (400 MHz, CDCl$_3$): 2.16 (3H, s), 5.32 (2H, s), 7.30 (1H, d, J=7.7 Hz), 7.35-7.45 (2H, m), 7.86 (1H, s), 7.94 (1H, d, J=8.6 Hz), 8.18 (1H, s), 8.43 (1H, d, J=8.8 Hz), 8.56 (1H, s)

m/z: [ES+] 396 ([M+H]+, C17H13ClF3N5O)

Example 192. 5-Amino-1-(2,6-dichlorophenyl)-3-methyl-N-[5-trifluoromethyl-2-pyridyl]pyrazole-4-carboxamide The title compound was prepared from 2-cyano-3-dimethylamino-N-(5-(trifluoromethyl)pyridin-2-yl)but-2-enamide (Intermediate 31) and 2,6-dichloro-phenylhydrazine hydrochloride using a method analogous to the preparation 5-amino-N-(4-chlorophenyl)-1-(2,6-dimethylphenyl)-1H-pyrazole-4-carboxamide (Example 77).

The crude product was purified by reverse phase preparative HPLC to give the title compound as a cream solid (0.010 g, 9%).

$^1$H NMR (ppm) (400 MHz, CDCl$_3$): 2.67 (3H, s), 5.45 (2H, s), 7.39-7.45 (1H, m), 7.51 (2H, d, J=7.8 Hz), 7.93 (1H, d, J=8.7 Hz), 8.22 (1H, m), 8.42 (1H, d, J=8.7 Hz), 8.55 (1H, s)

m/z: [ES+] 430 ([M+H]+, C17H12Cl2F3N5O)

Example 193. 5-Amino-1-(2-bromo-3-methylphenyl)-N-(5-chloropyridin-2-yl)-1H-pyrazole-4-carboxamide The title compound was prepared from 2-cyano-3-dimethylamino-N-(5-(5-chloropyridin-2-yl)acrylamide (Intermediate 29) and (2-bromo-6-fluorophenyl)hydrazine hydrochloride (Intermediate 107) using a method analogous to the preparation 5-amino-N-(4-chlorophenyl)-1-(2,6-dimethylphenyl)-1H-pyrazole-4-carboxamide (Example 77).

The crude product was purified by column chromatography (Biotage SNAP 50 g column, 25 to 75% EtOAc/isohexane). The product was triturated with Et2O to give the title compound as a pale brown solid (0.31 g, 23%).

$^1$H NMR (ppm)(400 MHz, DMSO-d6): 2.52 (3H, s), 5.35 (2H, s), 7.29 (1H, dd, J=1.5, 7.6 Hz), 7.35-7.42 (2H, m), 7.67 (1H, dd, J=2.5, 8.8 Hz), 7.78 (1H, s), 8.00 (1H, s), 8.24-8.29 (2H, m)

m/z: [ES+] 406 ([M+H]+, C16H13BrClN5O)

Example 194. 1-([1,1'-Biphenyl]-2-yl)-5-amino-N-(5-chloropyridin-2-yl)-1H-pyrazole-4-carboxamide A mixture of 5-amino-N-(5-chloropyridin-2-yl)-1-(2-iodophenyl)-1H-pyrazole-4-carboxamide (Example 157; 0.088 g, 0.2 mmol), 4,4,5,5-tetramethyl-2-phenyl-1,3,2-dioxaborolane (0.082 g, 0.4 mmol), K$_2$CO$_3$ (0.083 g, 0.6 mmol) followed by [1,1'-bis(diphenylphosphino)ferrocene]dichloropalladium(II), complex with dichloromethane (0.016 g, 0.02 mmol), 1,4-dioxane (4 mL) and H$_2$O (1 mL) was stirred at 90° C. for 18 hrs. The mixture was concentrated under reduced pressure and dissolved in H$_2$O (2 mL) and EtOAc (3 mL). The layers were separated and the aqueous phase was extracted with EtOAc (2 mL). The combined organic extracts were dried (MgSO$_4$) and concentrated under reduced pressure. The crude product was purified by reverse phase preparative HPLC to give the title compound as a white solid (0.025 g, 32%).

$^1$H NMR (ppm)(400 MHz, DMSO-d6): 6.21 (2H, s), 7.23-7.25 (2H, m), 7.59-7.64 (2H, m), 7.30-7.38 (3H, m), 7.49 (1H, d, J=7.8 Hz), 7.66-7.71 (1H, m), 7.92 (1H, dd, J=2.8, 9.1 Hz), 8.21 (1H, d, J=9.6 Hz), 8.26 (1H, s), 8.42 (1H, d, J=2.0 Hz), 10.36 (1H, s)

m/z: [ES+] 390 ([M+H]+, C21H16ClN5O)

Example 195. 5-Amino-1-(2-(2-methoxypyridin-4-yl)phenyl)-N-(5-(trifluoromethyl)pyridin-2-yl)-1H-pyrazole-4-carboxamide The title compound was prepared from 5-amino-1-(2-iodophenyl)-N-(5-(trifluoromethyl)pyridin-2-yl)-1H-pyrazole-4-carboxamide (Example 164) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.036 g, 26%).

$^1$H NMR (ppm)(400 MHz, DMSO-d6): 3.86 (3H, s), 6.40 (2H, s), 6.76 (1H, dd, J=1.5, 5.3 Hz), 6.68 (1H, s), 7.53-7.57 (1H, m), 7.68-7.73 (3H, m), 8.13 (1H, d, J=5.3 Hz), 8.20 (1H, d, J=9.1 Hz), 8.34 (1H, s), 8.37-8.43 (1H, m), 8.77 (1H, s), 10.68 (1H, s)

m/z: [ES+] 455 ([M+H]+, C22H17F3N6O2)

Example 196. 5-Amino-N-(5-chloropyridin-2-yl)-1-(2-(pyridin-3-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.026 g, 33%).

¹H NMR (ppm)(400 MHz, DMSO-d6): 6.31 (2H, s), 7.38-7.41 (1H, m), 7.54-7.61 (2H, m), 7.65-7.73 (3H, m), 7.92 (1H, dd, J=2.7, 9.0 Hz), 8.21 (1H, d, J=9.1 Hz), 8.28 (1H, s), 8.42 (2H, dd, J=1.8, 7.6 Hz), 8.51 (1H, dd, J=1.5, 4.8 Hz), 10.39 (1H, s)

m/z: [ES+] 391 ([M+H]+, C20H15ClN6O)

Example 197. 5-Amino-N-(5-chloropyridin-2-yl)-1-(2-(2-methoxypyridin-4-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.007 g, 8%).

¹H NMR (ppm)(400 MHz, DMSO-d6): 3.74 (3H, s), 6.21 (2H, s), 6.55 (1H, s), 6.63 (1H, dd, J=1.5, 5.3 Hz), 7.40-7.43 (1H, m), 7.55-7.59 (3H, m), 7.80 (1H, dd, J=2.7, 9.0 Hz), 7.99 (1H, d, J=5.3 Hz), 8.10 (1H, d, J=9.6 Hz), 8.17 (1H, s), 8.30 (1H, d, J=3.3 Hz), 10.28 (1H, s), m/z: [ES+] 421 ([M+H]+, C21H17ClN6O2)

Example 198. 5-Amino-N-(5-chloropyridin-2-yl)-1-(2-(1-methyl-1H-pyrazol-4-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.032 g, 41%).

¹H NMR (ppm)(400 MHz, DMSO-d6): 3.83 (3H, s), 6.17 (2H, s), 7.03 (1H, s), 7.38 (1H, dd, J=1.3, 7.8 Hz), 7.42-7.48 (1H, m), 7.53 (1H, s), 7.58-7.63 (1H, m), 7.80 (1H, dd, J=1.3, 8.1 Hz), 7.95 (1H, dd, J=2.8, 9.1 Hz), 8.43 (1H, s), 8.26 (1H, d, J=9.1 Hz), 8.45 (1H, d, J=2.8 Hz), 10.49 (1H, s)

m/z: [ES+] 394 ([M+H]+, C19H16ClN7O)

Example 199. 5-Amino-3-methyl-1-(2-(pyridin-3-yl)phenyl)-N-(5-(trifluoromethyl)pyridin-2-yl)-1H-pyrazole-4-carboxamide The title compound was prepared from 5-amino-1-(2-iodophenyl)-3-methyl-N-(5-(trifluoromethyl)pyridin-2-yl)-1H-pyrazole-4-carboxamide (Example 165) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.035 g, 40%).

¹H NMR (ppm)(400 MHz, DMSO-d6): 2.42 (3H, s), 6.18 (2H, s), 7.42-7.46 (1H, m), 7.54 (1H, d, J=7.6 Hz), 7.62-7.73 (4H, m), 8.20 (1H, dd, J=2.4, 9.0 Hz), 8.28 (1H, d, J=8.8 Hz), 8.47 (1H, d, J=1.8 Hz), 8.55 (1H, dd, J=1.6, 4.9 Hz), 8.73 (1H, s), 9.24 (1H, s)

m/z: [ES+] 439 ([M+H]+, C22H17F3N6O)

Example 200. 5-Amino-1-(2-(2-methoxypyridin-4-yl)phenyl)-3-methyl-N-(5-(trifluoromethyl)pyridin-2-yl)-1H-pyrazole-4-carboxamide The title compound was prepared from 5-amino-1-(2-iodophenyl)-3-methyl-N-(5-(trifluoromethyl)pyridin-2-yl)-1H-pyrazole-4-carboxamide (Example 165) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.021 g, 22%).

¹H NMR (ppm)(400 MHz, DMSO-d6): 2.44 (3H, s), 3.88 (3H, s), 6.21 (2H, s), 6.74-6.78 (2H, m), 7.50-7.54 (1H, m), 7.66-7.73 (3H, m), 8.13 (1H, d, J=5.1 Hz), 8.21 (1H, dd, J=2.4, 9.0 Hz), 8.29 (1H, d, J=8.8 Hz), 8.74 (1H, d, J=1.5 Hz), 9.26 (1H, s)

m/z: [ES+] 469 ([M+H]+, C23H19F3N6O2)

Example 201. 5-Amino-1-(2-(pyridin-3-yl)phenyl)-N-(5-(trifluoromethyl)pyridin-2-yl)-1H-pyrazole-4-carboxamide The title compound was prepared from 5-amino-N-(5-chloropyridin-2-yl)-1-(2-iodophenyl)-1H-pyrazole-4-carboxamide (Example 164) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.030 g, 35%).

¹H NMR (ppm)(400 MHz, DMSO-d6): 6.39 (2H, s), 7.55-7.61 (2H, m), 7.71-7.77 (4H, m), 8.20 (1H, dd, J=2.9, 8.5 Hz), 8.34-8.40 (2H, m), 8.49 (1H, d, J=1.8 Hz), 8.61 (1H, dd, J=1.5, 5.1 Hz), 8.76 (1H, s), 10.68 (1H, s)

m/z: [ES+] 425 ([M+H]+, C21H15F3N6O)

Example 202. 5-Amino-1-(2-(pyridin-4-yl)phenyl)-N-(5-(trifluoromethyl)pyridin-2-yl)-1H-pyrazole-4-carboxamide The title compound was prepared from 5-amino-1-(2-iodophenyl)-N-(5-(trifluoromethyl)pyridin-2-yl)-1H-pyrazole-4-carboxamide (Example 164) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.014 g, 17%).

¹H NMR (ppm)(400 MHz, DMSO-d6): 6.41 (2H, s), 7.18-7.21 (2H, m), 7.55-7.59 (1H, m), 7.69-7.76 (3H, m), 8.20 (1H, dd, J=2.7, 8.7 Hz), 8.33 (1H, s), 8.39 (1H, d, J=8.8 Hz), 8.56 (2H, d, J=6.1 Hz), 8.75 (1H, d, J=1.0 Hz), 10.68 (1H, s)

m/z: [ES+] 425 ([M+H]+, C21H15F3N6O)

Example 203. 5-Amino-1-(2-(5-fluoropyridin-3-yl)phenyl)-N-(5-(trifluoromethyl)pyridin-2-yl)-1H-pyrazole-4-carboxamide The title compound was prepared from 5-amino-1-(2-iodophenyl)-N-(5-(trifluoromethyl)pyridin-2-yl)-1H-pyrazole-4-carboxamide (Example 164) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.019 g, 21%).

1H NMR (ppm)(400 MHz, DMSO-d6): 6.41-6.42 (2H, m), 7.51 (1H, ddd, J=1.8, 2.8, 9.9 Hz), 7.59 (1H, dd, J=2.0, 6.6 Hz), 7.70-7.78 (3H, m), 8.18-8.25 (2H, m), 8.35-8.40 (2H, m), 8.55 (1H, d, J=2.5 Hz), 8.76 (1H, s), 10.69 (1H, s)

m/z: [ES+] 443 ([M+H]+, C21H14F4N6O)

Example 204. 5-Amino-N-(5-chloropyridin-2-yl)-1-(2-(6-methoxypyridin-3-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.021 g, 25%).

$^1$H NMR (ppm)(400 MHz, DMSO-d6): 3.88 (3H, s), 6.28 (2H, s), 6.81 (1H, d, J=8.6 Hz), 7.44-7.52 (2H, m), 7.60-7.70 (3H, m), 7.92 (1H, dd, J=2.7, 9.0 Hz), 8.05 (1H, d, J=2.0 Hz), 8.22 (1H, d, J=9.6 Hz), 8.31 (1H, s), 8.43 (1H, d, J=2.0 Hz), 10.40 (1H, s)

m/z: [ES+] 421 ([M+H]+, C21H17ClN6O2)

Example 205. 1-(2-(1H-Pyrazol-4-yl)phenyl)-5-amino-N-(5-chloropyridin-2-yl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as an off white solid (0.02 g, 26%).

$^1$H NMR (ppm)(400 MHz, DMSO-d6): 6.16 (2H, s), 7.28 (1H, s), 7.35 (1H, s), 7.39 (1H, dd, J=1.4, 7.9 Hz), 7.42-7.47 (1H, m), 7.58-7.63 (1H, m), 7.88 (1H, dd, J=1.3, 7.8 Hz), 7.95 (1H, dd, J=2.8, 9.1 Hz), 8.26 (1H, d, J=8.3 Hz), 8.45 (2H, d, J=3.3 Hz), 10.51 (1H, s), 12.91 (1H, s)

m/z: [ES+] 380 ([M+H]+, C18H14ClN7O)

Example 206. 5-Amino-N-(5-chloropyridin-2-yl)-1-(3-fluoro-2-(2-methoxypyridin-4-yl)phenyl)-1H-pyrazole-4-carboxamide The title compound was prepared from 5-amino-N-(5-chloropyridin-2-yl)-1-(3-fluoro-2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.034 g, 39%).

$^1$H NMR (ppm)(400 MHz, CDCl3): 3.93 (3H, s), 5.30 (2H, s), 6.70-6.75 (2H, m), 7.34-7.40 (2H, m), 7.52-7.56 (1H, m), 7.85 (1H, dd, J=2.5, 9.3 Hz), 8.02 (1H, s), 8.16-8.19 (2H, m), 8.50 (1H, d, J=9.1 Hz), 10.1 (1H, s)

m/z: [ES+] 439 ([M+H]+, C21H16ClFN6O2)

Example 207. 5-Amino-N-(5-chloropyridin-2-yl)-1-(2-hydroxyphenyl)-1H-pyrazole-4-carboxamide A mixture of 5-amino-N-(5-chloropyridin-2-yl)-1-(2-methoxyphenyl)-1H-pyrazole-4-carboxamide (Example 92; 0.46, 1.34 mmol), boron tribromide (1.0 M in DCM) (6.7 mL, 6.7 mmol) and THF (10 mL) was stirred at 0° C. for 3 hrs. 1 M Na2CO3 (aq) (10 mL) was added and the organic phase was separated. The aqueous phase was extracted with DCM (10 mL). The combined organic extracts were dried (MgSO4) and concentrated under reduced pressure. The crude product was purified by chromatography (Biotage SNAP 50 g column, 50 to 100% EtOAc/isohexane) to give the title compound as a white solid (0.35 g, 79%).

$^1$H NMR (ppm)(MeOD): 6.84-6.88 (1H, m), 6.92-6.95 (1H, m), 7.22 (2H, dd, J=7.5, 7.5 Hz), 7.68 (1H, dd, J=2.7, 9.0 Hz), 8.00 (1H, s), 8.11 (1H, d, J=8.8 Hz), 8.19 (1H, d, J=2.5 Hz), 8.45 (1H, s) (NH and OH not visible).

m/z: [ES+] 330 ([M+H]+, C15H12ClN5O2)

Example 208. 5-Amino-1-(2-hydroxyphenyl)-N-(5-(trifluoromethyl)pyridin-2-yl)-1H-pyrazole-4-carboxamide A mixture of 5-amino-1-(2-methoxyphenyl)-N-(5-(trifluoromethyl)pyridin-2-yl)-1H-pyrazole-4-carboxamide (Intermediate 106; 0.75 g, 2.0 mmol) boron tribromide (1.0 M in DCM) (6.0 mL, 6.0 mmol) in DCM (20 mL) was stirred at 0° C. to r.t. for 16 hrs. The mixture was diluted with 10% w/v KHCO3 (aq) (20 mL). The reaction mixture was concentrated under reduced pressure to approximately half the original volume. Et2O (10 ml) was added and the solid material was collected by filtration, washed with H2O (10 ml) and dried under reduced pressure to give the title product as an off-white solid (0.70 g, 96%).

$^1$H NMR (ppm)(400 MHz, DMSO): 6.32 (2H, m), 6.92-6.97 (1H, m); 7.06-7.09 (1H, m), 7.29-7.36 (2H, m), 8.21 (1H, dd, J=2.4, 9.0 Hz), 8.40 (1H, s), 8.44 (1H, d, J=8.8 Hz), 8.77 (1H, d, J=2.5 Hz)

m/z: [ES+] 364 ([M+H]+, C16H12F3N5O2)

Example 209. 5-Amino-N-(5-chloropyridin-2-yl)-1-(2-ethoxyphenyl)-1H-pyrazole-4-carboxamide A mixture of PPh3 (0.06 g, 0.23 mmol), di-tert-butyl azodicarboxylate (0.055 g, 0.23 mmol), EtOH (0.011 g, 0.23 mmol) and THF (1 mL) was stirred at r.t. for 5 mins. A solution of 5-amino-N-(5-chloropyridin-2yl)-1-(2-hydroxyphenyl)-1H-pyrazole-4-carboxamide (Example 207; 0.050 g, 0.15 mmol) in THF (1 mL) was added and the mixture was stirred at r.t. for 18 hrs. The reaction mixture was concentrated under reduced pressure and the crude product was purified by reverse phase preparative HPLC to give the title compound as a white solid (0.003 g, 6%).

$^1$H NMR (ppm)(400 MHz, CDCl3): 1.36 (3H, t, J=6.9 Hz), 4.13 (2H, q, J=7.0 Hz), 5.61 (2H, s), 7.06-7.13 (2H, m), 7.37-7.48 (2H, m), 7.67 (1H, dd, J=2.4, 9.0 Hz), 7.79 (1H, s), 8.00 (1H, s), 8.23-8.30 (2H, m), 8.23-8.30 (2H, m)

m/z: [ES+] 358 ([M+H]+, C17H16ClN5O2)

Example 210. 5-Amino-N-(5-chloropyridin-2-yl)-1-(2-(2-(dimethylamino)ethoxy)phenyl)-1H-pyrazole-4-carboxamide The title compound was prepared from 5-amino-N-(5-chloropyridin-2-yl)-1-(2-hydroxyphenyl)-1H-pyrazole-4-carboxamide (Example 207) using a method analogous to the preparation of 5-amino-N-(5-chloropyridin-2-yl)-1-(2-ethoxyphenyl)-1H-pyrazole-4-carboxamide (Example 209).

The crude product was purified by reverse phase preparative HPLC to give the title compound as a white solid (0.005 g, 8%).

$^1$H NMR (ppm)(400 MHz, CDCl$_3$): 2.36 (6H, s), 2.88 (2H, t, J=5.0 Hz), 4.22-4.27 (2H, m), 5.19 (2H, s), 7.01 (1H, d, J=8.1 Hz), 7.04-7.10 (1H, m), 7.35-7.41 (2H, m), 7.63 (1H, dd, J=2.5, 9.1 Hz), 8.11 (1H, s), 7.75 (1H, s), 8.19 (1H, d, J=2.3 Hz), 8.23 (1H, d, J=8.9 Hz)

m/z: [ES+] 401 ([M+H]+, C19H21ClN6O2)

Example 211. (R)-5-Amino-N-(5-chloropyridin-2-yl)-1-(2-((tetrahydrofuraN-3-yl)oxy)phenyl)-1H-pyrazole-4-carboxamide The title compound was prepared from 5-amino-N-(5-chloropyridin-2-yl)-1-(2-hydroxyphenyl)-1H-pyrazole-4-carboxamide (Example 207) using a method analogous to the preparation of 5-amino-N-(5-chloropyridin-2-yl)-1-(2-ethoxyphenyl)-1H-pyrazole-4-carboxamide (Example 209).

The crude product was purified by reverse phase preparative HPLC to give the title compound as a white solid (0.003 g, 5%).

$^1$H NMR (ppm)(400 MHz, CDCl$_3$): 2.10-2.18 (2H, m), 3.83-3.98 (4H, m), 4.91-4.96 (1H, m), 5.62 (2H, s), 7.02 (1H, d, J=8.1 Hz), 7.12-7.17 (1H, m), 7.40-7.49 (2H, m), 7.65-7.71 (1H, m), 7.78 (1H, s), 8.00 (1H, s), 8.23-8.30 (2H, m)

m/z: [ES+] 400 ([M+H]+, C19H18ClN5O3)

Example 212. 5-Amino-N-(5-chloropyridin-2-yl)-1-(2-((1-methylpiperidiN-4-yl)oxy)phenyl)-1H-pyrazole-4-carboxamide The title compound was prepared from 5-amino-N-(5-chloropyridin-2-yl)-1-(2-hydroxyphenyl)-1H-pyrazole-4-carboxamide (Example 207) using a method analogous to the preparation of 5-amino-N-(5-chloropyridin-2-yl)-1-(2-ethoxyphenyl)-1H-pyrazole-4-carboxamide (Example 209).

The crude product was purified by reverse phase preparative HPLC to give the title compound as a white solid (0.004 g, 6%).

$^1$H NMR (ppm)(400 MHz, CDCl$_3$): 1.96-2.02 (2H, m), 2.18-2.25 (2H, m), 2.49 (3H, s), 2.65-2.74 (2H, m), 2.97-2.98 (2H, m), 4.63 (1H, s), 5.54 (2H, s), 7.12 (1H, d, J=8.9 Hz), 7.16-7.21 (1H, m), 7.44-7.51 (2H, m), 7.70 (1H, dd, J=2.4, 9.0 Hz), 7.84 (1H, s), 8.23-8.28 (2H, m), 8.42 (1H, s)

m/z: [ES+] 427 ([M+H]+, C21H23ClN6O2)

Example 213. 5-Amino-1-(2-(benzyloxy)phenyl)-N-(5-chloropyridin-2-yl)-1H-pyrazole-4-carboxamide The title compound was prepared from 5-amino-N-(5-chloropyridin-2-yl)-1-(2-hydroxyphenyl)-1H-pyrazole-4-carboxamide (Example 207) using a method analogous to the preparation of 5-amino-N-(5-chloropyridin-2-yl)-1-(2-ethoxyphenyl)-1H-pyrazole-4-carboxamide (Example 209.

The crude product was purified by reverse phase preparative HPLC to give the title compound as a white solid (0.003 g, 5%).

$^1$H NMR (ppm)(400 MHz, CDCl$_3$): 5.13 (2H, s), 5.55 (2H, s), 7.10-7.17 (2H, m), 7.28-7.33 (5H, m), 7.37-7.43 (1H, m), 7.44-7.49 (1H, m), 7.67 (1H, dd, J=2.3, 8.8 Hz), 7.80 (1H, s), 8.00 (1H, s), 8.23-8.29 (2H, m)

m/z: [ES+] 420 ([M+H]+, C22H18ClN5O2)

Example 214. 5-Amino-1-(2-isopropoxyphenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-N-(5-chloropyridin-2-yl)-1-(2-ethoxyphenyl)-1H-pyrazole-4-carboxamide (Example 209).

The crude product was purified by reverse phase preparative HPLC to give the title compound as a white solid (0.003 g, 5%).

$^1$H NMR (ppm)(400 MHz, CDCl$_3$): 1.28 (6H, d, J=6.1 Hz), 4.45-4.55 (1H, m), 5.71 (2H, s), 7.08-7.15 (2H, m), 7.37-7.43 (1H, m), 7.47 (1H, dd, J=1.6, 7.7 Hz), 7.85 (1H, s), 7.93 (1H, dd, J=2.1, 8.7 Hz), 8.32 (1H, s), 8.45 (1H, d, J=8.8 Hz), 8.55-8.56 (1H, m)

m/z: [ES+] 406 ([M+H]+, C19H18F3N5O2)

Example 215. 5-Amino-N-(4-chloro-2-(2-(dimethylamino)ethoxy)phenyl)-1-(o-tolyl)-1H-pyrazole-4-carboxamide A mixture of PPh$_3$ (0.047 g, 0.18 mmol), di-tert-butyl azodicarboxylate (0.041 g, 0.18 mmol), 2-(dimethylamino)ethanol (0.016 g, 0.18 mmol) in THF (1 mL) was stirred at r.t. for 5 mins. A solution of 5-amino-N-(4-chloro-2-hydroxy-phenyl)-1-(o-tolyl)-1H-pyrazole-4-carboxamide (Example 17; 0.040 g, 0.12 mmol) in THF (1 mL) was added and the reaction mixture was stirred at r.t. for 18 hrs. The reaction mixture was concentrated under reduced pressure and the residue was purified by reverse phase preparative HPLC to give the title compound as a white solid (0.020 g, 40%).

$^1$H NMR (ppm)(400 MHz, CDCl$_3$): 2.18 (3H, s), 2.35 (6H, s), 2.66 (2H, t, J=5.2 Hz), 4.18 (2H, t, J=5.3 Hz), 5.27 (2H, s), 6.98-7.04 (2H, m), 7.31-7.35 (2H, m), 7.36-7.41 (2H, m), 7.80 (1H, s), 8.38 (1H, d, J=8.8 Hz), 8.82 (1H, s)

m/z: [ES+] 414 ([M+H]+, C21H24ClN5O2)

Example 216. (R)-5-Amino-N-(4-chloro-2-((tetrahydrofuraN-3-yl)oxy)phenyl)-1-(o-tolyl)-1H-pyrazole-4-carboxamide The title compound was prepared from 5-amino-N-(4-chloro-2-hydroxy-phenyl)-1-(o-tolyl)-1H-pyrazole-4-carboxamide using a method analogous to the preparation of 5-amino-N-(4-chloro-2-(2-(dimethylamino)ethoxy)phenyl)-1-(o-tolyl)-1H-pyrazole-4-carboxamide.

The crude product was purified by reverse phase preparative HPLC to give the title compound as a white solid (0.027 g, 55%).

1H NMR (ppm)(400 MHz, CDCl3): 2.18 (3H, s), 2.20-2.37 (2H, m), 3.91-4.14 (4H, m), 4.97-5.02 (1H, m), 5.25 (2H, s), 6.88 (1H, d, J=2.3 Hz), 7.01 (1H, dd, J=2.1, 8.7 Hz), 7.31-7.41 (4H, m), 7.71 (1H, s), 7.98 (1H, s), 8.38 (1H, d, J=8.6 Hz)

m/z: [ES+] 413 ([M+H]+, C21H21ClN4O3)

Retention time (min.) 3.40 (basic)

Example 217. 5-Amino-N-(4-chloro-2-ethoxyphenyl)-1-(o-tolyl)-1H-pyrazole-4-carboxamide The title compound was prepared from 5-amino-N-(4-chloro-2-hydroxy-phenyl)-1-(o-tolyl)-1H-pyrazole-4-carboxamide (Example 17) using a method analogous to the preparation of 5-amino-N-(4-chloro-2-(2-(dimethylamino)ethoxy)phenyl)-1-(o-tolyl)-1H-pyrazole-4-carboxamide (Example 215).

The crude product was purified by reverse phase preparative HPLC to give the title compound as a white solid (0.031 g, 70%).

$^1$H NMR (ppm)(400 MHz, CDCl$_3$): 1.52 (3H, t, J=7.0 Hz), 2.18 (3H, s), 4.14 (2H, q, J=7.0 Hz), 5.26 (2H, s), 6.88 (1H, d, J=2.3 Hz), 6.95 (1H, dd, J=2.0, 8.6 Hz), 7.30-7.42 (4H, m), 7.69 (1H, s), 7.98 (1H, s), 8.35 (1H, d, J=8.6 Hz)

m/z: [ES+] 371 ([M+H]+, C19H19ClN4O2)

Example 218. 5-Amino-N-(4-chloro-2-(2-methoxyethoxy)phenyl)-1-(o-tolyl)-1H-pyrazole-4-carboxamide The title compound was prepared from 5-amino-N-(4-chloro-2-hydroxy-phenyl)-1-(o-tolyl)-1H-pyrazole-4-carboxamide (Example 17) using a method analogous to the preparation of 5-amino-N-(4-chloro-2-(2-(dimethylamino)ethoxy)phenyl)-1-(o-tolyl)-1H-pyrazole-4-carboxamide (Example 215).

The crude product was purified by reverse phase preparative HPLC to give the title compound as a white solid (0.027 g, 56%).

$^1$H NMR (ppm)(400 MHz, CDCl$_3$): 2.16 (3H, s), 3.46 (3H, s), 3.73-3.76 (2H, m), 5.24 (2H, s), 4.18-4.21 (2H, m), 6.95 (1H, d, J=2.5 Hz), 6.99 (1H, dd, J=2.3, 8.6 Hz), 7.29-7.33 (2H, m), 7.74 (1H, s), 7.34-7.39 (2H, m), 8.24 (1H, s), 8.37 (1H, d, J=8.8 Hz)

m/z: [ES+] 401 ([M+H]+, C20H21ClN4O3)

Example 219. 5-Amino-N-(4-chloro-2-((1-methylpiperidiN-4-yl)oxy)phenyl)-1-(o-tolyl)-1H-pyrazole-4-carboxamide The title compound was prepared from 5-amino-N-(4-chloro-2-hydroxy-phenyl)-1-(o-tolyl)-1H-pyrazole-4-carboxamide (Example 17) using a method analogous to the preparation of 5-amino-N-(4-chloro-2-(2-(dimethylamino)ethoxy)phenyl)-1-(o-tolyl)-1H-pyrazole-4-carboxamide (Example 215).

The crude product was purified by reverse phase preparative HPLC to give the title compound as a white solid (0.016 g, 30%).

$^1$H NMR (ppm)(400 MHz, CDCl$_3$): 1.91-1.99 (2H, m), 2.06-2.13 (2H, m), 2.18 (3H, s), 2.33 (3H, s), 2.42 (2H, s), 2.66 (2H, s), 4.44-4.49 (1H, m), 5.27 (2H, s), 6.91 (1H, d, J=2.0 Hz), 6.96 (1H, dd, J=2.1, 8.7 Hz), 7.31-7.35 (2H, m), 7.36-7.43 (2H, m), 7.70 (1H, s), 8.02 (1H, s), 8.38 (1H, d, J=8.8 Hz)

m/z: [ES+] 440 ([M+H]+, C23H26ClN5O2)

Example 220. 5-Amino-1-(2-((2-methoxyethyl)amino)phenyl)-N-(5-(trifluoromethyl)pyridin-2-yl)-1H-pyrazole-4-carboxamide A mixture of 5-amino-1-(2-bromophenyl)-N-[5-(trifluoromethyl)pyridin-2-yl]-1H-pyrazole-4-carboxamide (Example 102; 0.1 g, 0.26 mmol), 2-methoxyethanamine (0.25 g, 3.2 mmol), CuI (0.005 g, 0.026 mmol), proline (0.006 g, 0.052 mmol), K$_2$CO$_3$ (0.11 g, 0.78 mmol) and DMSO (2 mL) was stirred at 100° C. for 16 hrs. The mixture was allowed to cool to r.t and the solvent was removed under reduced pressure. The crude product was purified by reverse phase preparative HPLC to give the title compound as a white solid (0.002 g, 2%).

$^1$H NMR (ppm)(400 MHz, CDCl$_3$): 3.29-3.32 (2H, m), 3.34 (3H, s), 3.57 (2H, t, J=5.5 Hz), 4.60-4.62 (1H, m), 5.57 (2H, s), 6.78-6.87 (2H, m), 7.21 (1H, d, J=7.3 Hz), 7.31-7.35 (1H, m), 7.86 (1H, s), 7.93 (1H, d, J=8.8 Hz), 8.20 (1H, s), 8.40-8.45 (1H, m), 8.56 (1H, s)

m/z: [ES+] 421 ([M+H]+, C19H19F3N6O2)

Example 221. 5-Amino-1-(2-((2-methoxyethyl)(methyl)amino)phenyl)-N-(5-(trifluoromethyl)pyridin-2-yl)-1H-pyrazole-4-carboxamide The title compound was prepared from 5-amino-1-(2-bromophenyl)-N-[5-(trifluoromethyl)pyridin-2-yl]-1H-pyrazole-4-carboxamide (Example 102) using a method analogous to the preparation of 5-amino-1-(2-((2-methoxyethyl)amino)phenyl)-N-(5-(trifluoromethyl)pyridin-2-yl)-1H-pyrazole-4-carboxamide (Example 220).

The crude product was purified by reverse phase preparative HPLC to give the title compound as a white solid (0.004 g, 4%).

$^1$H NMR (ppm)(400 MHz, CDCl$_3$): 2.61 (3H, s), 6.25 (2H, s), 3.18 (2H, t, J=5.1 Hz), 3.28 (3H, s), 3.49 (2H, t, J=5.1 Hz), 7.09-7.13 (2H, m), 7.32-7.38 (1H, m), 7.42 (1H, dd, J=1.6, 8.2 Hz), 7.85 (1H, s), 7.92 (1H, dd, J=1.9, 9.0 Hz), 8.19 (1H, s), 8.44 (1H, d, J=8.8 Hz), 8.55 (1H, s)

m/z: [ES+] 435 ([M+H]+, C20H21F3N6O2)

Example 222. 5-Amino-1-(2-(3-methoxypyrrolidin-1-yl)phenyl)-N-(5-(trifluoromethyl)pyridin-2-yl)-1H-pyrazole-4-carboxamide The title compound was prepared from 5-amino-1-(2-bromophenyl)-N-[5-(trifluoromethyl)pyridin-2-yl]-1H-pyrazole-4-carboxamide (Example 102) using a method analogous to the preparation of 5-amino-1-(2-((2-methoxyethyl)amino)phenyl)-N-(5-(trifluoromethyl)pyridin-2-yl)-1H-pyrazole-4-carboxamide (Example 220).

The crude product was purified by reverse phase preparative HPLC to give the title compound as a white solid (0.002 g, 2%).

$^1$H NMR (ppm)(400 MHz, 400 MHz, CDCl$_3$): 1.93-2.01 (2H, m), 2.98 (1H, d, J=10.4 Hz), 3.03-3.10 (2H, m), 3.19-3.24 (1H, m), 3.26 (3H, s), 3.89-3.92 (1H, m), 5.59 (2H, s), 6.86-6.92 (2H, m), 7.24 (1H, s), 7.30-7.36 (1H, m), 7.80 (1H, s), 7.91-7.95 (1H, m), 8.14 (1H, s), 8.42 (1H, d, J=8.8 Hz), 8.54-8.57 (1H, m)

m/z: [ES+] 447 ([M+H]+, C21H21F3N6O2)

Example 223. 5-Amino-1-(2-(4-methoxypiperidiN-1-yl)phenyl)-N-(5-(trifluoromethyl)pyridin-2-yl)-1H-pyrazole-4-carboxamide The title compound was prepared from 5-amino-1-(2-bromophenyl)-N-[5-(trifluoromethyl)pyridine-2-yl]-1H-pyrazole-4-carboxamide (Example 102) using a method analogous to the preparation of 5-amino-1-(2-((2-methoxyethyl)amino)phenyl)-N-(5-(trifluoromethyl)pyridin-2-yl)-1H-pyrazole-4-carboxamide (Example 220).

The crude product was purified by reverse phase preparative HPLC to give the title compound as a white solid (0.003 g, <5%).

$^1$H NMR (ppm)(400 MHz, 400 MHz, CDCl$_3$): 1.64 (2H, m), 1.89-1.92 (2H, m), 2.72 (2H, dd, J=9.0, 9.0 Hz), 3.06-3.10 (2H, m), 3.31 (4H, m), 6.15 (2H, s), 7.11-7.19 (2H, m), 7.35-7.41 (1H, m), 7.44 (1H, d, J=7.6 Hz), 7.87-7.89 (1H, m), 7.94 (1H, d, J=8.8 Hz), 8.18 (1H, s), 8.41-8.60 (2H, m)

m/z: [ES+] 461 ([M+H]+, C22H23F3N6O2)

Example 224. 5-Amino-1-(2-((3-methyloxetan-3-yl)methoxy)phenyl)-N-(5-(trifluoromethyl)pyridin-2-yl)-1H-pyrazole-4-carboxamide A mixture of (3-methyloxeta-3-yl)methanol (0.021 g, 0.21 mmol), Et$_3$N (0.021 g, 0.21 mmol), MsCl (0.024 g, 0.21 mmol) and DCM (1 mL) was stirred at 0° C. for 1 hr. The mixture was diluted with DCM (5 mL) and washed with a saturated NaHCO$_3$ (aq) (5 mL). The organic layer was separated (phase separation cartridge) and concentrated under reduced pressure. The residue was dissolved in DMF (1 mL). 5-Amino-1-(2-hydroxyphenyl)-N-(5-(trifluoromethyl)pyridin-2-yl)-1H-pyrazole-4-carboxamide (Example 208; 0.05 g, 0.14 mmol) and K$_2$CO$_3$ (0.078 g, 0.21 mmol) were added and the reaction mixture was stirred at 80° C. for 1 hr. The reaction mixture was allowed to cool to r.t., filtered through Celite and the solvent removed under reduced pressure. The crude product was purified by reverse phase preparative HPLC to give the title compound as a white solid (0.002 g, <5%).

$^1$H NMR (ppm)(400 MHz, CDCl$_3$): 1.29 (3H, s), 4.11 (2H, s), 4.36 (2H, d, J=6.1 Hz), 4.46 (2H, d, J=5.8 Hz), 5.52 (2H, s), 7.12-7.18 (2H, m), 7.44-7.49 (2H, m), 7.80 (1H, s), 7.92 (1H, dd, J=2.0, 8.8 Hz), 8.17 (1H, s), 8.42 (1H, d, J=8.8 Hz), 8.55 (1H, s)

m/z: [ES+] 448 ([M+H]+, C21H20F3N5O3)

Example 225. 1-(2-(2-(1H-Imidazol-1-yl)ethoxy)phenyl)-5-amino-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.003 g, 3%).

$^1$H NMR (ppm)(400 MHz, 400 MHz, CDCl$_3$): 4.25 (4H, s), 5.37 (2H, s), 6.82 (1H, s), 7.01 (2H, d, J=9.9 Hz), 7.16 (1H, dd, J=7.6, 7.6 Hz), 7.44 (3H, d, J=7.6 Hz), 7.88 (1H, s), 7.93 (1H, dd, J=1.8, 8.8 Hz), 8.46 (1H, d, J=8.8 Hz), ), 8.53 (1H, s), 8.56 (1H, s)

m/z: [ES+] 458 ([M+H]+, C21H18F3N7O2)

Example 226. 5-Amino-1-(2-((tetrahydro-2H-pyraN-4-yl)oxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.002 g, 2%).

$^1$H NMR (ppm)(400 MHz, CDCl$_3$): 1.65-1.75 (2H, m), 1.88-1.96 (2H, m), 3.45-3.53 (2H, m), 3.70-3.78 (2H, m), 4.44-4.49 (1H, m), 5.67 (2H, s), 7.11-7.20 (2H, m), 7.40-7.45 (1H, m), 7.49 (1H, dd, J=1.6, 8.0 Hz), 7.82 (1H, s), 7.93 (1H, dd, J=1.9, 9.0 Hz), 8.15 (1H, s), 8.43 (1H, d, J=8.6 Hz), 8.57 (1H, s)

m/z: [ES+] 448 ([M+H]+, C21H20F3N5O3)

Example 227. 5-Amino-1-(2-((tetrahydrofuraN-3-yl)oxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.009 g, 10%).

$^1$H NMR (ppm)(400 MHz, CDCl$_3$): 2.09-2.19 (2H, m), 3.83-4.00 (4H, m), 4.95 (1H, s), 5.64 (2H, s), 7.03 (1H, d, J=8.3 Hz), 7.15 (1H, dd, J=7.7, 7.7 Hz), 7.42 (1H, dd, J=8.0, 8.0 Hz), 7.48 (1H, d, J=7.8 Hz), 7.81 (1H, s), 7.92 (1H, d, J=8.8 Hz), 8.16 (1H, s), 8.43 (1H, d, J=8.8 Hz), 8.55 (1H, s)

m/z: [ES+] 434 ([M+H]+, C20H18F3N5O3)

Example 228. 5-Amino-1-(2-((4-methylmorpholiN-2-yl)methoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.016 g, 16%).

$^1$H NMR (ppm)(400 MHz, CDCl$_3$): 1.93 (1H, dd, m), 2.07-2.14 (1H, m), 2.25 (3H, s), 2.67 (2H, dd, J=10.9, 29.3 Hz), 3.65-3.70 (1H, m), 3.89 (2H, d, J=9.1 Hz), 4.07-4.11 (2H, m), 5.82 (2H, s), 7.06 (1H, d, J=7.8 Hz), 7.13 (1H, dd, J=7.6, 7.6 Hz), 7.41 (1H, dd, J=7.8, 7.8 Hz), 7.48 (1H, d, J=7.6 Hz), 7.82 (1H, s), 7.92 (1H, d, J=8.8 Hz), 8.15 (1H, s), 8.43 (1H, d, J=8.6 Hz), 8.54-8.57 (1H, m)

m/z: [ES+] 477 ([M+H]+, C22H23F3N6O3)

Example 229. 1-(2-(2-(1H-Pyrazol-1-yl)ethoxy)phenyl)-5-amino-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.021 g, 22%).

$^1$H NMR (ppm)(400 MHz, CDCl$_3$): 4.44 (4H, s), 5.30 (2H, s), 6.23 (1H, s), 7.00 (1H, d, J=8.3 Hz), 7.11 (1H, dd, J=7.5, 7.5 Hz), 7.28 (s, 1H), 7.41 (2H, dd, J=7.8, 7.8 Hz), 7.49 (1H, s), 7.81 (1H, s), 7.94 (1H, d, J=8.3 Hz), 8.16 (1H, s), 8.45 (1H, d, J=8.8 Hz), 8.56 (1H, s)

m/z: [ES+] 458 ([M+H]+, C21H18F3N7O2)

Example 230. 5-Amino-1-(2-((1-methylpiperidin-3-yl)methoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-(2-((3-methyloxetaN-3-yl)methoxy)phenyl)-N-(5-(trifluoromethyl)pyridin-2-yl)-1H-pyrazole-4-carboxamide (Example 224).

The crude product was purified by reverse phase preparative HPLC to give the title compound as a white solid (0.032 g, 32%).

$^1$H NMR (ppm)(400 MHz, CDCl$_3$): 0.98-1.06 (1H, m), 1.51-176 (4H, m), 1.89 (1H, dd, J=10.6, 10.6 Hz), 2.02-2.10 (1H, m), 2.20 (3H, s), 2.66 (1H, d, J=10.6 Hz), 2.76 (1H, d, J=10.6 Hz), 3.83-3.98 (2H, m), 5.54 (2H, s), 7.05-7.14 (2H, m), 7.39-7.47 (2H, m), 7.79 (1H, s), 7.89-7.93 (1H, m), 8.13 (1H, s), 8.42 (1H, d, J=8.8 Hz), 8.55 (1H, s)

m/z: [ES+] 475 ([M+H]+, C23H25F3N6O2)

Example 231. 5-Amino-1-(2-(2-amino-2-oxoethoxy)phenyl)-N-(5-(trifluoromethyl)pyridin-2-yl)-1H-pyrazole-4-carboxamide A mixture of 5-amino-1-(2-hydroxyphenyl)-N-(5-(trifluoromethyl)pyridin-2-yl)-1H-pyrazole-4-carboxamide (Example 208; 0.029 g, 0.80 mmol), 2-bromoacetamide (0.12 g, 1.20 mmol) and Cs$_2$CO$_3$ (0.39 g, 0.88 mmol) and DMF (5 mL) was stirred at r.t. for 18 hrs. The reaction mixture was concentrated under reduced pressure. H$_2$O (10 mL) was added and the mixture extracted with DCM (2×30 mL). The combined extracts were dried (MgSO$_4$) and the solvent removed under reduced pressure. The crude product was purified by column chromatography (Biotage SNAP 25 g column, 1 to 7% MeOH/DCM) to give the title compound as a colourless solid (0.24 g, 72%.)

$^1$H NMR (ppm) (400 MHz, DMSO-d6): 4.77 (2H, s), 6.77 (2H, s), 7.16-7.19 (2H, m), 7.43 (1H, dd, J=1.6, 8.0 Hz), 7.48-7.53 (1H, m), 7.63 (1H, s), 7.67 (1H, s), 8.22 (1H, dd, J=2.5, 9.1 Hz), 8.44 (2H, d, J=7.8 Hz), 8.76-8.79 (1H, m), 10.75 (1H, s).

m/z: [ES+] 421 ([M+H]+, C18H15F3N6O3)

Example 232. 5-Amino-1-(2-(2-amino-2-oxoethoxy)phenyl)-3-ethyl-N-(5-(trifluoromethyl)pyridin-2-yl)-1H-pyrazole-4-carboxamide The title compound was prepared from 5-amino-3-ethyl-1-(2-hydroxyphenyl)-N-(5-(trifluoromethyl)pyridin-2-yl)-1H-pyrazole-4-carboxamide (Intermediate 101) using a method analogous to the preparation of 5-amino-1-[2-(2-amino-2-oxo-ethoxy)phenyl]-N-[5-(trifluoromethyl)-2-pyridyl]-1H-pyrazole-4-carboxamide (Example 231).

The crude product was purified by reverse phase preparative HPLC to give the title compound as an off-white solid (0.030 g, 31%).

$^1$H NMR (ppm)(400 MHz, CDCl$_3$): 1.44 (3H, t, J=7.3 Hz), 3.00 (2H, q, J=7.5 Hz), 4.61 (2H, s), 5.49 (1H, d, J=1.0 Hz), 5.62 (2H, s), 7.09-7.12 (1H, m), 7.15-7.20 (1H, m), 7.30-7.51 (2H, m), 7.54 (1H, s), 7.92 (1H, dd, J=2.5, 8.8 Hz), 8.20 (1H, s), 8.41 (1H, d, J=8.8 Hz), 8.55 (1H, s)

m/z: [ES+] 449 ([M+H]+, C20H19F3N6O3)

Example 233. 5-Amino-1-(2-(2-amino-2-oxoethoxy)phenyl)-N-(5-(trifluoromethoxy)pyridin-2-yl)-1H-pyrazole-4-carboxamide The title compound was prepared from 5-amino-1-(2-hydroxyphenyl)-N-(5-(trifluoromethoxy)pyridin-2-yl)-1H-pyrazole-4-carboxamide (Intermediate 106) using a method analogous to the preparation of 5-amino-1-[2-(2-amino-2-oxo-ethoxy)phenyl]-N-[5-(trifluoromethyl)pyridin-2-yl]-1H-pyrazole-4-carboxamide (Example 231).

The crude product was purified by reverse phase preparative HPLC to give the title compound as a white solid (0.032 g, 62%).

$^1$H NMR (ppm)(400 MHz, CDCl$_3$): 4.60 (2H, s), 5.47 (1H, s), 5.54 (2H, s), 7.10 (1H, dd, J=1.0, 8.3 Hz), 7.17-7.22 (1H, m), 7.30 (1H, s), 7.45-7.53 (2H, m), 7.60 (1H, dd, J=2.4, 9.0 Hz), 7.82 (1H, s), 8.08 (1H, s), 8.23 (1H, d, J=3.0 Hz), 8.34 (1H, d, J=9.3 Hz)

m/z: [ES+] 437 ([M+H]+, C18H15F3N6O4)

Example 234. 5-Amino-1-(2-(2-amino-2-oxoethoxy)-3-fluorophenyl)-N-(5-(trifluoromethyl)pyridin-2-yl)-1H-pyrazole-4-carboxamide The title compound was prepared from 5-amino-3-(3-fluoro-2-hydroxyphenyl)-N-(5-(trifluoromethyl)pyridin-2-yl)-1H-pyrazole-4-carboxamide (Intermediate 104) using a method analogous to the preparation of 5-amino-1-[2-(2-amino-2-oxo-ethoxy)phenyl]-N-[5-(trifluoromethyl)-2-pyridyl]-1H-pyrazole-4-carboxamide (Example 231).

The crude product was purified by reverse phase preparative HPLC to give the title compound as a white solid (0.027 g, 61%).

$^1$H NMR (ppm)(400 MHz, DMSO-d6): 4.56 (2H, d, J=2.3 Hz), 6.72 (2H, s), 7.26-7.30 (2H, m), 7.40 (1H, s), 7.46-7.56 (2H, m), 8.22 (1H, dd, J=2.4, 9.0 Hz), 8.42-8.47 (2H, m), 8.78 (1H, d, J=2.5 Hz), 10.77 (1H, s)

m/z: [ES+] 439 ([M+H]+, C18H14F4N6O3)

Example 235. 5-Amino-1-(2-(2-amino-2-oxoethoxy)phenyl)-N-(5-chloropyridin-2-yl)-3-ethyl-1H-pyrazole-4-carboxamide The title compound was prepared from 5-amino-N-(5-chloropyridin-2-yl)-3-ethyl-1-(2-hydroxyphenyl)-1H-pyrazole-4-carboxamide (Intermediate 103) using a method analogous to the preparation of 5-amino-1-[2-(2-amino-2-oxo-ethoxy)phenyl]-N-[5-(trifluoromethyl)-2-pyridyl]-1H-pyrazole-4-carboxamide (Example 231).

The crude product was purified by reverse phase preparative HPLC to give the title compound as a white solid (0.015 g, 8%)

$^1$H NMR (ppm) (400 MHz, DMSO-d6): 1.43 (3H, t, J=7.5 Hz), 2.98 (2H, q, J=7.5 Hz), 4.61 (2H, s), 5.47 (1H, s), 5.59 (2H, s), 7.10 (1H, d, J=8.3 Hz), 7.17 (1H, dd, J=7.6, 7.6 Hz), 7.50-7.43 (2H, m), 7.60-7.59 (1H, m), 7.68 (1H, dd, J=2.7, 8.8 Hz), 8.03 (1H, s), 8.27-8.24 (2H, m)

m/z: [ES+] 415 ([M+H]+, C19H19ClN6O3)

Example 236. 5-Amino-1-(2-(2-(methylamino)-2-oxoethoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-[2-(2-amino-2-oxo-ethoxy)phenyl]-N-[5-(trifluoromethyl)pyridin-2-yl]-1H-pyrazole-4-carboxamide (Example 231).

The crude product was purified by reverse phase preparative HPLC to give the title compound as a white solid (0.037 g, 57%).

$^1$H NMR (ppm)(400 MHz, CDCl$_3$): 2.82 (3H, d, J=5.1 Hz), 4.60 (2H, s), 5.58 (2H, s), 7.08-7.10 (1H, m), 7.16-7.21 (1H, m), 7.29-7.32 (1H, m), 7.44-7.52 (2H, m), 7.86 (1H, s), 7.94 (1H, dd, J=2.3, 8.8 Hz), 8.20 (1H, s), 8.42 (1H, d, J=8.8 Hz), 8.56 (1H, d, J=0.8 Hz)

m/z: [ES+] 435 ([M+H]+, C19H17F3N6O3)

Example 237. 5-Amino-1-(2-((2,2-di methyl-1,3-dioxolaN-4-yl)methoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-[2-(2-amino-2-oxo-ethoxy)phenyl]-N-[5-(trifluoromethyl)pyridin-2-yl]-1H-pyrazole-4-carboxamide (Example 231).

The crude product was purified by column chromatography (Biotage SNAP 10 g column, 10 to 75% EtOAc in isohexane) to give a pale brown oil (0.044 g, 37%).

$^1$H NMR (ppm)(400 MHz, 400 MHz, CDCl$_3$): 1.36 (6H, d, J=12.4 Hz), 3.80 (1H, dd, J=5.6, 8.6 Hz), 4.02-4.15 (3H, m), 4.36-4.43 (1H, m), 5.67 (2H, s), 7.10-7.17 (2H, m), 7.41-7.48 (2H, m), 7.81 (1H, s), 7.92 (1H, dd, J=2.4, 8.7 Hz), 8.16 (1H, s), 8.42 (1H, d, J=8.8 Hz), 8.56 (1H, d, J=1.5 Hz)

m/z: [ES+] 478 ([M+H]+, C22H22F3N5O4)

Example 238. 5-Amino-1-(2-(2-amino-1-fluoro-2-oxoethoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide using a method analogous to the preparation of 5-amino-1-[2-(2-amino-2-oxo-ethoxy)phenyl]-N-[5-(trifluoromethyl)pyridin-2-yl]-1H-pyrazole-4-carboxamide.

The crude product was purified by reverse phase preparative HPLC to give the title compound as a pale brown solid (0.035 g, 40%).

$^1$H NMR (ppm)(400 MHz, DMSO): 6.30-6.44 (1H, d), 6.54 (2H, s), 7.34-7.39 (1H, m), 7.47-7.52 (2H, m), 7.64-7.59 (1H, m), 7.77 (1H, s), 7.92 (1H, s), 8.22 (1H, dd, J=2.5, 8.8 Hz), 8.43-, 8.45 (2H, m), 8.79 (1H, s), 10.77 (1H, s)

m/z: [ES+] 439 ([M+H]+, C18H14F4N6O3)

Example 239. 5-Amino-1-(2-(2-amino-2-oxoethoxy)phenyl)-3-methyl-N-(5-(trifluoromethyl)pyridin-2-yl)-1H-pyrazole-4-carboxamide The title compound was prepared from 5-amino-3-methyl-1-(2-hydroxyphenyl)-N-(5-(trifluoromethyl)-pyridin-2-yl)-1H-pyrazole-4-carboxamide (Intermediate 101) using a method analogous to the preparation of 5-amino-1-[2-(2-amino-2-oxo-ethoxy)phenyl]-N-[5-(trifluoromethyl)pyridin-2-yl]-1H-pyrazole-4-carboxamide (Example 231).

The crude product was purified by reverse phase preparative HPLC to give the title compound as a pale yellow-brown solid (0.013 g, 16%).

$^1$H NMR (ppm)(400 MHz, CDCl$_3$): 2.64 (3H, s), 4.61 (2H, s), 5.51 (1H, s), 5.62 (2H, s), 7.10 (1H, d, J=8.3 Hz), 7.15-7.20 (1H, m), 7.43-7.51 (3H, m), 7.93 (1H, dd, J=2.4, 8.7 Hz), 8.19 (1H, s), 8.40 (1H, d, J=8.8 Hz), 8.55 (1H, s)

m/z: [ES+] 435 ([M+H]+, C19H17F3N6O3)

Example 240. 5-Amino-1-(2-(2,2,3,3,3-pentafluoropropoxy)phenyl)-N-(5-(trifluoromethyl)pyridin-2-yl)-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) and 2,2,3,3,3-pentafluoropropyl trifluoromethanesulfonate using a method analogous to the preparation of 5-amino-1-[2-(2-amino-2-oxo-ethoxy)phenyl]-N-[5-(trifluoromethyl)pyridin-2-yl]-1H-pyrazole-4-carboxamide (Example 231).

The crude product was purified by reverse phase preparative HPLC to give the title compound as a grey solid (0.037 g, 55%).

$^1$H NMR (ppm)(400 MHz, CDCl$_3$): 4.38-4.45 (2H, m), 5.53 (2H, s), 7.14 (1H, d, J=7.8 Hz), 7.25-7.29 (1H, m), 7.50 (2H, dd, J=7.6, 7.6 Hz), 7.82 (1H, s), 7.93 (1H, dd, J=2.3, 8.8 Hz), 8.19 (1H, s), 8.43 (1H, d, J=8.8 Hz), 8.56 (1H, s)

m/z: [ES+] 496 ([M+H]+, C19H13F8N5O2)

Example 241. 5-Amino-1-(2-(2,2,2-trifluoroethoxy)phenyl)-N-(5-(trifluoromethyl)pyridin-2-yl)-1H-pyrazole-4-carboxamide A mixture of 5-amino-1-(2-hydroxyphenyl)-N-(5-(trifluoromethyl)pyridin-2-yl)-1H-pyrazole-4-carboxamide (Example 208; 0.050 g, 0.14 mmol), 2,2,2-trifluoroethyl trifluoromethanesulfonate (0.097 g, 0.42 mmol) and K$_2$CO$_3$ (0.023 g, 0.17 mmol) in DMF (2 mL) was stirred at 80° C. for 48 hrs. The reaction mixture was allowed to cool to r.t. The solvent was removed under reduced pressure and the crude product was purified by reverse phase preparative HPLC to give the title compound as a colourless liquid (0.006 g, 9%).

$^1$H NMR (ppm)(400 MHz, CDCl$_3$): 4.35 (2H, q, J=8.0 Hz), 5.58 (2H, s), 7.15 (1H, d, J=8.3 Hz), 7.23-7.31 (1H, m), 7.46-7.53 (2H, m), 7.84 (1H, s), 7.93 (1H, dd, J=2.3, 8.8 Hz), 8.24 (1H, s), 8.44 (1H, d, J=8.8 Hz), 8.55 (1H, d, J=0.8 Hz)

m/z: [ES+] 446 ([M+H]+, C18H13F6N5O2)

Example 242. 5-Amino-1-[2-(oxetan-3-yloxy)phenyl]-N-[5-(trifluoromethyl)pyridin-2-yl]-1H-pyrazole-4-carboxamide A mixture of 5-amino-1-(2-hydroxyphenyl)-N-(5-(trifluoromethyl)pyridin-2-yl)-1H-pyrazole-4-carboxamide (Example 208; 0.05 g, 0.14 mmol) 3-iodooxetane (0.039 g, 0.21 mmol), K$_2$CO$_3$ (0.028 g, 0.21 mmol) and DMF (1 mL) was stirred at 80° C. for 1 hr. The reaction mixture was allowed to cool to r.t. and the solvent was removed under reduced pressure. The crude product reverse phase preparative HPLC to give the title compound as a white solid (0.023 g, 39%).

$^1$H NMR (ppm)(400 MHz, CDCl3): 4.68-4.74 (2H, m), 4.93 (2H, dd, J=6.8, 6.8 Hz), 5.21-5.28 (1H, m), 5.60 (2H, s), 6.66 (1H, d, J=8.3 Hz), 7.17 (1H, dd, J=7.7, 7.7 Hz), 7.40

(1H, dd, J=8.0, 8.0 Hz), 7.48 (1H, d, J=7.8 Hz), 7.83 (1H, s), 7.93 (1H, d, J=8.6 Hz), 8.19 (1H, s), 8.43 (1H, d, J=8.8 Hz), 8.56 (1H, s)
m/z: [ES+] 420 ([M+H]+, C19H16F3N5O3)

Example 243. 5-Amino-1-[2-[(5-methylisoxazol-3-yl)methoxy]phenyl]-N-[5-(trifluoromethyl)pyridin-2-yl]-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-[2-(oxetaN-3-yloxy)phenyl]-N-[5-(trifluoromethyl)pyridin-2-yl]-1H-pyrazole-4-carboxamide (Example 242).

The crude product was purified by reverse phase preparative HPLC to give the title compound as a white solid (0.004 g, 6%).

$^1$H NMR (ppm)(400 MHz, 400 MHz, CDCl$_3$): 2.40 (3H, s), 5.21 (2H, s), 5.68 (2H, s), 5.96 (1H, s), 7.13-7.17 (2H, m), 7.39-7.48 (2H, m), 7.82 (1H, s), 7.92 (1H, dd, J=2.1, 8.7 Hz), 8.15 (1H, s), 8.43 (1H, d, J=8.6 Hz), 8.53-8.56 (1H, m)
m/z: [ES+] 459 ([M+H]+, C21H17F3N6O3)

Example 244. 5-Amino-1-[2-(3-methoxypropoxy)phenyl]-N-[5-(trifluoromethyl)pyridin-2-yl]-1H-pyrazole-4-carboxamide The title compound was prepared from 5-amino-1-(2-hydroxyphenyl)-N-(5-(trifluoromethyl)pyridin-2-yl)-1H-pyrazole-4-carboxamide (Example 208) using a method analogous to the preparation of 5-amino-1-[2-(oxetaN-3-yloxy)phenyl]-N-[5-(trifluoromethyl)pyridin-2-yl]-1H-pyrazole-4-carboxamide (Example 242).

The crude product was purified by reverse phase preparative HPLC to give the title compound as a white solid (0.032 g, 52%).

$^1$H NMR (ppm)(400 MHz, CDCl$_3$): 1.94-2.02 (2H, m), 3.29 (3H, s), 3.43 (2H, dd, J=5.9, 5.9 Hz), 4.16 (2H, dd, J=6.1, 6.1 Hz), 5.63 (2H, s), 7.09-7.14 (2H, m), 7.39-7.47 (2H, m), 7.83 (1H, s), 7.92 (1H, dd, J=2.0, 8.8 Hz), 8.27 (1H, s), 8.44 (1H, d, J=8.8 Hz), 8.53-8.56 (1H, m)
m/z: [ES+] 436 ([M+H]+, C20H20F3N5O3)

Example 245. 5-Amino-1-(2-(2-hydroxyethoxy)phenyl)-N-(5-(trifluoromethyl)pyridin-2-yl)-1H-pyrazole-4-carboxamide A mixture of 5-amino-1-(2-hydroxyphenyl)-N-(5-(trifluoromethyl)pyridin-2-yl)-1H-pyrazole-4-carboxamide (Example 208; 0.094 g, 0.26 mmol), 2-bromoethyl acetate (0.072 g, 0.43 mmol), Cs$_2$CO$_3$ (0.18 g, 0.54 mmol) in DMF (2 mL) was stirred at r.t. for 48 hrs. The reaction mixture was concentrated under reduced pressure. The residue was dissolve in a mixture of DCM (10 mL) and H$_2$O (10 mL). The organic phase was separated (phase separation cartridge) and the solvent removed under reduced pressure. The residue was dissolved in a mixture of THF/MeOH/H$_2$O (1:1:1, v/v) (6 mL) and LiOH.H$_2$O (0.022 g, 0.52 mmol). The reaction mixture was stirred at r.t. for 18 hrs. The reaction mixture was concentrated under reduced pressure and the crude product was purified by reverse phase preparative HPLC to give the title compound as an off-white solid (0.041 g, 39%).

$^1$H NMR (ppm)(400 MHz, CDCl$_3$): 3.83-3.87 (2H, m), 4.21-4.24 (2H, m), 5.61 (2H, s), 7.10-7.15 (2H, m), 7.42-7.48 (2H, m), 7.85 (1H, s), 7.92 (1H, dd, J=2.3, 8.8 Hz), 8.27 (1H, s), 8.41 (1H, d, J=8.8 Hz), 8.55 (1H, d, J=0.8 Hz) (OH not visible in 1H NMR spectra)
m/z: [ES+] 408 ([M+H]+, C18H16F3N5O3)

Example 246. 5-Amino-1-(2-(2-hydroxyethoxy)phenyl)-3-methyl-N-(5-(trifluoromethyl)pyridin-2-yl)-1H-pyrazole-4-carboxamide The title compound was prepared from 5-amino-3-methyl-1-(2-hydroxyphenyl)-N-(5-(trifluoromethyl)pyridin-2-yl)-1H-pyrazole-4-carboxamide (Intermediate 101) using a method analogous to the preparation of 5-amino-1-(2-(2-hydroxyethoxy)phenyl)-N-(5-(trifluoromethyl)pyridin-2-yl)-1H-pyrazole-4-carboxamide (Example 245).

The crude product was purified by reverse phase preparative HPLC to give the title compound as a pale yellow solid (0.031 g, 34%).

$^1$H NMR (ppm)(400 MHz, CDCl$_3$): 2.64 (3H, s), 3.79-3.86 (3H, m), 4.22-4.25 (2H, m), 5.64 (2H, s), 7.10-7.14 (2H, m), 7.39-7.46 (2H, m), 7.92 (1H, dd, J=2.3, 8.8 Hz), 8.20 (1H, s), 8.41 (1H, d, J=8.8 Hz), 8.54 (1H, s)
m/z: [ES+] 422 ([M+H]+, C19H18F3N5O3)

Example 247. 5-Amino-N-(5-chloropyridin-2-yl)-3-ethyl-1-(2-(2-hydroxyethoxy)phenyl)-1H-pyrazole-4-carboxamide The title compound was prepared from 5-amino-N-(5-chloropyridin-2-yl)-3-ethyl-1-(2-hydroxyphenyl)-1H-pyrazole-4-carboxamide (Intermediate 103) using a method analogous to the preparation of 5-amino-1-(2-(2-hydroxyethoxy)phenyl)-N-(5-(trifluoromethyl)pyridin-2-yl)-1H-pyrazole-4-carboxamide (Example 245).

The crude product was purified by reverse phase preparative HPLC to give the title compound as a pale yellow solid (0.051 g, 26%).

$^1$H NMR (ppm)(400 MHz, CDCl$_3$): 1.22 (3H, t, J=7.5 Hz), 2.89 (2H, q, J=7.5 Hz), 3.69 (2H, q, J=4.8 Hz), 4.16 (2H, t, J=5.0 Hz), 4.93 (1H, t, J=5.1 Hz), 5.97 (2H, s), 7.11-7.07 (1H, m), 7.27 (1H, d, J=8.1 Hz), 7.34 (1H, dd, J=1.7, 7.8 Hz), 7.42-7.47 (1H, m), 7.91 (1H, dd, J=2.6, 8.9 Hz), 8.17 (1H, d, J=8.8 Hz), 8.37 (1H, d, J=2.4 Hz), 9.22 (1H, s)
m/z: [ES+] 402 ([M+H]+, C19H20ClN5O3)

Example 248. 5-Amino-N-(5-chloropyridin-2-yl)-1-(2-(2-hydroxyethoxy)phenyl)-1H-pyrazole-4-carboxamide The title compound was prepared from 5-amino-N-(5-chloropyridin-2-yl)-1-(2-hydroxyphenyl)-1H-pyrazole-4-carboxamide (Example 207) using a method analogous to the preparation of 5-amino-1-(2-(2-hydroxyethoxy)phenyl)-N-(5-(trifluoromethyl)pyridin-2-yl)-1H-pyrazole-4-carboxamide (Example 245).

The crude product was purified by reverse phase preparative HPLC to give the title compound as a pale yellow solid (0.039 g, 40%).

$^1$H NMR (ppm)(400 MHz, DMSO-d6): 3.65-3.71 (2H, m), 4.15 (2H, t, J=5.0 Hz), 4.91 (1H, s), 6.25 (2H, s), 7.09 (1H, dd, J=7.3, 7.3 Hz), 7.27 (1H, d, J=7.9 Hz), 7.34 (1H, dd, J=1.7, 7.8 Hz), 7.42-7.48 (1H, m), 7.90 (1H, dd, J=2.7, 9.0 Hz), 8.22 (1H, d, J=8.9 Hz), 8.35 (1H, s), 8.39 (1H, d, J=2.4 Hz), 10.43 (1H, s)
m/z: [ES+] 374 ([M+H]+, C17H16ClN5O3)

Example 249. 5-Amino-3-ethyl-1-(2-(2-hydroxy-ethoxy)phenyl)-N-(5-(trifluoromethyl)pyridin-2-yl)-1H-pyrazole-4-carboxamide The title compound was prepared from 5-amino-3-ethyl-1-(2-hydroxyphenyl)-N-(5-(trifluoromethyl)-pyridin-2-yl)-1H-pyrazole-4-carboxamide (Intermediate 102) using a method analogous to the preparation of 5-amino-1-(2-(2-hydroxyethoxy)phenyl)-N-(5-(trifluoromethyl)pyridin-2-yl)-1H-pyrazole-4-carboxamide (Example 245).

The crude product was purified by reverse phase preparative HPLC to give the title compound as a pale yellow solid (0.23 g, 58%).

$^1$H NMR (ppm)(400 MHz, DMSO-d6): 1.22 (3H, t, J=7.5 Hz), 2.91 (2H, q, J=7.4 Hz), 3.69 (2H, q, J=4.9 Hz), 4.16 (2H, t, J=5.0 Hz), 4.93 (1H, t, J=5.1 Hz), 6.02 (2H, s), 7.07-7.11 (1H, m), 7.28 (1H, d, J=7.9 Hz), 7.35 (1H, dd, J=1.7, 7.8 Hz), 7.42-7.48 (1H, m), 8.18 (1H, dd, J=2.3, 9.0 Hz), 8.31 (1H, d, J=8.9 Hz), 8.70-8.72 (1H, m), 9.51 (1H, s)

m/z: [ES+] 436 ([M+H]+, C20H20F3N5O3)

Example 250. 5-Amino-1-(2-(difluoromethoxy)phenyl)-N-(5-(trifluoromethyl)pyridin-2-yl)-1H-pyrazole-4-carboxamide A mixture of 5-amino-1-(2-hydroxyphenyl)-N-(5-trifluoromethylpyridin-2-yl)-1H-pyrazole-4-carboxamide (Example 208; 0.080 g, 0.22 mmol), ethyl 2-bromo-2,2-difluoro acetate (0.049 g, 0.24 mmol), Cs$_2$CO$_3$ (0.14 g, 0.44 mmol) and DMF (2 mL) was stirred at r.t for 48 hr. The reaction mixture was concentrated under reduced pressure. The residue was suspended in H$_2$O (5 mL) and extracted with EtOAc (3×5 mL). The combined organic extracts were dried (MgSO$_4$), filtered and the solvent removed under reduced pressure. The crude product was purified by reverse phase preparative HPLC to give the title compound as give a pale yellow solid (0.024 g, 25%).

$^1$H NMR (ppm)(400 MHz, CDCl$_3$): 5.54 (2H, s), 6.46 (1H, t, J=71.4 Hz), 6.49 (1H, s), 7.40-7.45 (2H, m), 7.50-7.56 (2H, m), 7.82 (1H, s), 7.93 (1H, dd, J=2.3, 8.8 Hz), 8.17 (1H, s), 8.42 (1H, d, J=8.6 Hz), 8.55 (1H, d, J=0.8 Hz)

m/z: [ES+] 414 ([M+H]+, C17H12F5N5O2)

Example 251. 5-Amino-1-(3-fluoro-2-methylphenyl)-N-(5-(trifluoromethyl)pyridin-2-yl)-1H-imidazole-4-carboxamide A mixture of 5-amino-1-(3-fluoro-2-methylphenyl)-1H-imidazole-4-carboxylic acid ((Intermediate 97; 0.07 g, 0.3 mmol), SOCl$_2$ (0.18 g, 1.5 mmol) and MeCN (2 mL) was stirred at r.t. for 1 hr. The reaction mixture was concentrated under reduced pressure. The residue was dissolved in a mixture of 5-(trifluoromethyl)pyridin-2-amine (0.073 mg, 0.45 mmol) and DIEA (0.21 mL, 1.2 mmol) and DCM (3 mL) and stirred at r.t. for 18 hrs. The solvent was removed under reduced pressure and the crude product was purified by reverse phase preparative HPLC to give the title compound which was obtained as an off-white solid (0.021 g, 18%).

$^1$H NMR (ppm)(400 MHz, CDCl$_3$): 2.11 (3H, d, J=2.0 Hz), 4.98 (2H, s), 7.05 (1H, s), 7.12 (1H, d, J=7.8 Hz), 7.21-7.27 (1H, m), 7.32-7.39 (1H, m), 7.90 (1H, dd, J=2.5, 8.8 Hz), 8.46 (1H, d, J=8.8 Hz), 8.56 (1H, d, J=0.8 Hz), 9.36 (1H, s)

m/z: [ES+] 380 ([M+H]+, C17H13F4N5O)

Example 252. 5-Amino-N-(5-chloropyridin-2-yl)-1-(3-fluoro-2-methylphenyl)-1H-imidazole-4-carboxamide The title compound was prepared from 5-amino-1-(3-fluoro-2-methylphenyl)-1H-imidazole-4-carboxylic acid (Intermediate 97) using a method analogous to the preparation 5-amino-1-(3-fluoro-2-methylphenyl)-N-(5-(trifluoromethyl)pyridin-2-yl)-1H-imidazole-4-carboxamide (Example 251).

The crude product was purified by reverse phase preparative HPLC to give the title compound which was obtained as an off-white solid (0.032 g, 31%).

$^1$H NMR (ppm)(400 MHz, CDCl$_3$): 2.10 (3H, d, J=2.3 Hz), 4.94 (2H, s), 7.03 (1H, s), 7.11 (1H, d, J=7.6 Hz), 7.21-7.26 (1H, m), 7.32-7.38 (1H, m), 7.65 (1H, dd, J=2.5, 8.8 Hz), 8.26 (1H, d, J=2.5 Hz), 8.31 (1H, d, J=8.8 Hz), 9.19 (1H, s)

m/z: [ES+] 346 ([M+H]+, C16H13ClFN5O)

Example 253. 5-Amino-N-(4-bromophenyl)-1-(2-methoxyphenyl)-1H-imidazole-4-carboxamide The title compound was prepared from 5-amino-1-(2-methoxyphenyl)-1H-imidazole-4-carboxylic acid (Intermediate 100) using a method analogous to the preparation 5-amino-1-(3-fluoro-2-methylphenyl)-N-(5-(trifluoromethyl)pyridin-2-yl)-1H-imidazole-4-carboxamide (Example 251).

The crude product was purified by reverse phase preparative HPLC to give the title compound as an off-white solid (0.052 g, 45%).

$^1$H NMR (ppm)(400 MHz, CDCl$_3$): 3.87 (3H, s), 5.03 (2H, s), 7.09-7.13 (3H, m), 7.31 (1H, dd, J=1.8, 8.1 Hz), 7.42-7.49 (3H, m), 7.57-7.60 (2H, m), 8.57 (1H, s)

m/z: [ES+] 387, 389 ([M+H]+, C17H15BrN4O2)

Example 254. 5-Amino-N-(4-chlorophenyl)-1-(2-methoxyphenyl)-1H-imidazole-4-carboxamide The title compound was prepared from 5-amino-1-(2-methoxyphenyl)-1H-imidazole-4-carboxylic acid (Intermediate 100) using a method analogous to the preparation 5-amino-1-(3-fluoro-2-methylphenyl)-N-(5-(trifluoromethyl)pyridin-2-yl)-1H-imidazole-4-carboxamide (Example 251).

The crude product was purified by reverse phase preparative HPLC to give the title compound as an off-white solid (0.027 g, 32%).

$^1$H NMR (ppm)(400 MHz, CDCl$_3$): 3.87 (3H, s), 5.03 (2H, s), 7.09-7.13 (3H, m), 7.27-7.33 (3H, m), 7.45-7.51 (1H, m), 7.61-7.64 (2H, m), 8.58 (1H, s)

m/z: [ES+] 343 ([M+H]+, C17H15ClN4O2)

Example 255. 5-Amino-1-(2-methoxyphenyl)-N-(4-(trifluoromethyl)phenyl)-1H-imidazole-4-carboxamide The title compound was prepared from 5-amino-1-(2-methoxyphenyl)-1H-imidazole-4-carboxylic acid (Intermediate 100) using a method analogous to the preparation 5-amino-1-(3-fluoro-2-methylphenyl)-N-(5-(trifluoromethyl)pyridin-2-yl)-1H-imidazole-4-carboxamide (Example 251).

The crude product was purified by reverse phase preparative HPLC to give the title compound as an off-white solid (0.025 g, 27%).

¹H NMR (ppm)(400 MHz, CDCl₃): 3.88 (3H, s), 5.06 (2H, s), 7.10-7.14 (3H, m), 7.32 (1H, dd, J=1.6, 8.0 Hz), 7.46-7.52 (1H, m), 7.58 (2H, d, J=8.6 Hz), 7.80 (2H, d, J=8.3 Hz), 8.73 (1H, s)

m/z: [ES+] 377 ([M+H]+, C18H15F3N4O2)

Example 256. 5-Amino-1-(2-(6-aminopyridin-3-yl)phenyl)-N-(5-chloropyridin-2-yl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.0017 g, 18%).

¹H NMR (ppm)(400 MHz, DMSO-d6): 6.00 (2H, s), 6.16 (2H, s), 6.38 (1H, d, J=8.8 Hz), 7.16 (1H, dd, J=2.5, 8.6 Hz), 7.44 (1H, dd, J=1.0, 7.8 Hz), 7.66-7.50 (3H, m), 7.76 (1H, d, J=2.0 Hz), 7.92 (1H, dd, J=2.7, 9.0 Hz), 8.23 (1H, d, J=9.1 Hz), 8.32 (1H, s), 8.43 (1H, d, J=2.0 Hz), 10.40 (1H, s)

m/z: [ES+] 406 ([M+H]+, C20H16ClN7O)

Example 257. 5-Amino-1-(2-(6-aminopyridin-3-yl)phenyl)-N-(5-(trifluoromethyl)pyridin-2-yl)-1H-pyrazole-4-carboxamide The title compound was prepared from 5-amino-1-(2-iodophenyl)-N-(5-(trifluoromethyl)pyridin-2-yl)-1H-pyrazole-4-carboxamide (Example 164) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.050 g, 54%).

¹H NMR (ppm)(400 MHz, DMSO-d6): 6.00 (2H, s), 6.23 (2H, s), 6.39 (1H, d, J=8.6 Hz), 7.17 (1H, dd, J=2.5, 8.6 Hz), 7.44 (1H, dd, J=1.0, 7.8 Hz), 7.66-7.51 (3H, m), 7.76 (1H, d, J=1.8 Hz), 8.20 (1H, dd, J=2.4, 9.0 Hz), 8.36 (1H, s), 8.40 (1H, d, J=8.8 Hz), 8.76 (1H, d, J=0.8 Hz), 10.68 (1H, s), m/z: [ES+] 440 ([M+H]+, C21H16F3N7O)

Example 258. 5-Amino-N-(5-chloropyridin-2-yl)-1-(2-(6-(dimethylamino)pyridin-3-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.022 g, 22%).

¹H NMR (ppm)(400 MHz, DMSO-d6): 3.04 (6H, s), 6.21 (2H, s), 6.61 (1H, d, J=8.8 Hz), 7.29 (1H, dd, J=2.5, 8.8 Hz), 7.46-7.43 (1H, m), 7.57-7.52 (1H, m), 7.67-7.58 (2H, m), 7.93 (1H, dd, J=2.7, 9.0 Hz), 7.98 (1H, d, J=2.0 Hz), 8.23 (1H, d, J=9.1 Hz), 8.33 (1H, s), 8.43 (1H, d, J=2.0 Hz), 10.41 (1H, s)

m/z: [ES+] 434 ([M+H]+, C22H20ClN7O)

Example 259. 5-Amino-N-(5-chloropyridin-2-yl)-1-(2-(5-methoxypyridin-3-yl)phenyl)-1H-pyrazole-4-carboxamide The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.02 g, 21%).

¹H NMR (ppm)(400 MHz, DMSO-d6): 3.78 (3H, s), 6.30 (2H, s), 7.12 (1H, dd, J=1.8, 2.8 Hz), 7.57 (1H, d, J=7.1 Hz), 7.74-7.66 (3H, m), 7.92 (1H, dd, J=2.7, 9.0 Hz), 8.04 (1H, d, J=1.8 Hz), 8.24-8.20 (2H, m), 8.30 (1H, s), 8.43 (1H, d, J=2.8 Hz), 10.41 (1H, s)

m/z: [ES+] 421 ([M+H]+, C21H17ClN6O2)

Example 260. 5-Amino-1-(2-(2-(4-methylpiperaziN-1-yl)-2-oxoethoxy)phenyl)-N-(5-(trifluoromethyl)pyridin-2-yl)-1H-pyrazole-4-carboxamide The title compound was prepared from 2-(2-(5-amino-4-((5-(trifluoromethyl)pyridin-2-yl)carbamoyl)-1H-pyrazol-1-yl)phenoxy)acetic acid using a method analogous to the preparation of 5-amino-1-(2-(2-oxo-2-(pyrrolidin-1-yl)ethoxy)phenyl)-N-(5-(trifluoromethyl)pyridin-2-yl)-1H-pyrazole-4-carboxamide (Example 222).

The crude product was purified by reverse phase preparative HPLC to give the title compound as a pale yellow solid (0.004 g, 3%).

¹H NMR (ppm)(400 MHz, DMSO-d6): 8.55 (1H, d, J=1.0 Hz), 8.42 (1H, d, J=8.8 Hz), 8.18 (1H, s), 7.91 (1H, dd, J=2.1, 8.7 Hz), 7.81 (1H, s), 7.48 (1H, dd, J=1.5, 7.8 Hz), 7.43-7.38 (1H, m), 7.17-7.12 (1H, m), 6.88 (1H, s), 6.36 (2H, s), 4.88 (2H, s), 3.65-3.64 (4H, m), 2.49-2.49 (7H, m)

m/z: [ES+] 504 ([M+H]+, C23H24F3N7O3)

Example 261. tert-Butyl 3-(2-(5-amino-4-((5-chloropyridin-2-yl)carbamoyl)-1H-pyrazol-1-yl)phenyl)-5,6-dihydropyridine-1(2H)-carboxylate The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.026 g, 21%).

¹H NMR (ppm)(400 MHz, DMSO-d6): 1.43 (9H, s), 2.15-2.14 (2H, m), 3.41 (2H, dd, J=5.7, 5.7 Hz), 3.83-3.82 (2H, m), 5.32 (2H, s), 5.74 (1H, s), 7.50-7.37 (4H, m), 7.67 (1H, dd, J=2.7, 8.7 Hz), 7.72 (1H, s), 7.97 (1H, s), 8.27-8.24 (2H, m)

m/z: [ES+] 495 ([M+H]+, C25H27ClN6O3)

Example 262. tert-Butyl 5-(2-(5-amino-4-((5-chloropyridin-2-yl)carbamoyl)-1H-pyrazol-1-yl)phenyl)-3,4-dihydropyridine-1(2H)-carboxylate The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.005 g, 4%).

$^1$H NMR (ppm)(400 MHz, DMSO-d6): 1.33-1.24 (1H, m), 1.54 (9H, s), 1.81-1.77 (2H, m), 1.94 (1H, s), 3.51-3.49 (2H, m), 5.36 (2H, s), 7.38-7.34 (2H, m), 7.44-7.41 (2H, m), 7.67 (1H, dd, J=2.4, 8.7 Hz), 7.76 (1H, s), 8.02 (1H, s), 8.28-8.23 (2H, m). NH not observed m/z: [ES+] 495 ([M+H]+, C25H27ClN6O3)

Example 263. tert-Butyl 4-(2-(5-amino-4-((5-chloropyridin-2-yl)carbamoyl)-1H-pyrazol-1-yl)phenyl)-5,6-dihydropyridine-1 (2H)-carboxylate The title compound was prepared from 5-amino-N-(5-chloropyridin-2-yl)-1-(2-iodophenyl)-1H-pyrazole-4-carboxamide (Example 157) using a method analogous to the preparation of 1-([1,1'-biphenyl]-2-yl)-5-amino-N-(5-chloropyridin-2-yl)-1H-pyrazole-4-carboxamide (Example 194).

The crude product was purified by reverse phase preparative HPLC to give the title compound as a white solid (0.032 g, 26%).

$^1$H NMR (ppm)(400 MHz, DMSO-d6): 1.44 (9H, s), 2.03-2.00 (2H, m), 3.43 (2H, s), 3.97-3.91 (2H, m), 5.34 (2H, s), 5.68-5.65 (1H, m), 7.49-7.36 (4H, m), 7.67 (1H, dd, J=2.4, 9.0 Hz), 7.73 (1H, s), 7.98 (1H, s), 8.27-8.24 (2H, m)

m/z: [ES+] 495 ([M+H]+, C25H27ClN6O3)

Example 264. 5-Amino-1-(2-(2-oxo-2-(pyrrolidin-1-yl)ethoxy)phenyl)-N-(5-(trifluoromethyl)pyridin-2-yl)-1H-pyrazole-4-carboxamide To a solution of 2-(2-(5-amino-4-((5-(trifluoromethyl)pyridin-2-yl)carbamoyl)-1H-pyrazol-1-yl)phenoxy)acetic acid (0.065 g, 0.16 mmol) in DMF (2 mL) was added HATU (0.091 g, 0.24 mmol) and DIEA (0.057 mL, 0.32 mmol) and the mixture was stirred at r.t. for 0.25 hrs, then pyrrolidine (0.013 mL, 0.16 mmol) was added and the mixture stirred for 18 hrs. The mixture was diluted with DCM (5 mL) then washed with H$_2$O (3×5 mL). The organic phase was dried (MgSO$_4$) concentrated and the residue purified by reverse phase preparative HPLC to give the title compound as a white solid (0.006 g, 8%).

$^1$H NMR (ppm)(400 MHz, DMSO-d6): 1.96-1.88 (2H, m), 2.10-2.03 (2H, m), 3.46 (2H, t, J=6.8 Hz), 3.52 (2H, t, J=7.0 Hz), 4.82 (2H, s), 6.68 (2H, s), 6.83-6.80 (1H, m), 7.13-7.08 (1H, m), 7.38-7.32 (1H, m), 7.52-7.47 (1H, m), 7.79 (1H, s), 7.90 (1H, dd, J=2.4, 8.7 Hz), 8.10 (1H, s), 8.43 (1H, d, J=8.8 Hz), 8.53 (1H, d, J=1.5 Hz)

m/z: [ES+] 475 ([M+H]+, C22H21F3N6O3)

Biological Testing

Assay Procedure Nav1.7 and Nav1.5 Screening Assay

Cell Lines

Stable cell lines expressing the full-length protein of the voltage-gated sodium channels Nav1.7 or Nav1.5, with or without one beta-1, beta-2, beta-3, or beta-4 subunit, are created by transfected CHO cells or HEK293 cells, or any other suitable cell line, with a vector construct containing the complete open reading frame under a suitable promoter, as well known in the art.

In Vitro Electrophysiology

Electrophysiological studies are performed with an IonWorks Quattro (Molecular Devices Corp.) automated patch-clamp electrophysiology platform as described by (Schroeder K et al. *Journal of Biomolecular Screening* 2003, 8 (1), 50-64). Buffers for the experiments have the following composition (mM): Internal solution; K-gluconate 100, KCl 40, MgCl$_2$ 3.2, HEPES 5, EGTA 3, pH 7.3. To this amphotericin B is added to final concentration of 0.1 mg/ml to generate access solution. External solution; Dulbecco's Phosphate buffered saline (D-PBS) NaCl 137.93, KCl 2.67, KH$_2$PO$_4$ 1.47, Na$_2$HPO$_4$ 8.06, CaCl$_2$ 0.90, MgCl$_2$ 0.49. Prior to the experiment the cells expressing the voltage-gated ion channel of interest are detached from the tissue culture flasks, centrifuged and resuspended in D-PBS. Compounds are prepared and serially diluted in DMSO and finally diluted 1:100 in D-PBS. Cells are exposed to compounds through the pipetting system integrated into the platform and the voltage-gated ion channel of interest is activated with specific voltage stimulation protocols. The following voltage stimulation protocol is used for testing compounds against the voltage-gated sodium channel Nav1.7; from a holding potential of −100 mV a train of eight 60 ms depolarising steps to −20 mV at a frequency of 14 Hz are employed followed by a further step to −20 mV for 2000 ms. After which the voltage is returned to −100 mV for 10 ms before another voltage step to −20 mV for 60 ms is applied. The following voltage stimulation protocol is used for testing compounds against the voltage-gated sodium channel Nav1.5; from a holding potential of −120 mV a train of twenty-six 120 ms depolarising steps to −20 mV at a frequency of 5 Hz are employed. Recordings are made before and after compound addition with the compound incubation time being 5 minutes.

Percent block was calculated for each concentration in duplicate for peak 1 and peak 10 and peak 1 and 25 for Nav 1.7 and Nav 1.5 respectively in order to assess compound activity at close and inactivated states and IC$_{50}$ curves were fitted to percent block as a function of concentration.

The results are shown in Table 1.

TABLE 1

| Example | Na$_v$ 1.7 IC$_{50}$ (µM) | Na$_v$ 1.5 IC$_{50}$ (µM) |
|---|---|---|
| 1 | 0.7 | 21 |
| 7 | 0.3 | >33 |
| 38 | 0.7 | >33 |
| 55 | 0.5 | >33 |
| 57 | 0.8 | >33 |
| 61 | 0.9 | 28 |
| 75 | 0.8 | >33 |
| 114 | 0.4 | >33 |
| 115 | 0.7 | >33 |
| 137 | 0.6 | >33 |
| 140 | 1 | >33 |
| 143 | 0.3 | 10 |
| 153 | 0.4 | >33 |
| 196 | 0.7 | 17 |
| 197 | 1 | >33 |
| 208 | 0.3 | >33 |
| 251 | 0.2 | — |
| 254 | 1.9 | >33 |

It can be seen from Table 1 that the compounds of Formula (I) are potent "activity". Preferred compounds of the invention possess an IC$_{50}$ value for Nav1.7 inhibition less than 5 µM, preferably less than 3 µM and most preferably less than 1 µM. On the other hand, compounds of Formula (I) exhibit a high selectivity with respect to Nav1.5.

Combinations

The compounds of the present invention may also be combined with other active compounds, such as those mentioned above, in the treatment of a pathological condition or disease as hereinabove described.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other(s) later in the day. Or in another scenario, one or two actives could be administered twice daily and the other(s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the compounds of the invention together with one or more other therapeutic agents for use in the treatment of a pathological condition or disease as hereinabove described.

The invention also encompasses the use of a combination of the compounds of the invention together with one or more other therapeutic agents for the manufacture of a formulation or medicament for treating these diseases.

The invention also provides a method of treatment of a pathological condition or disease as hereinabove described comprising administering a therapeutically effective amount of a combination of the compounds of the invention together with one or more other therapeutic agents, such as (a) Opioid receptor agonists such as but not restricted to morphine, phentanyl, hydromorphone or hydrocodone,
(b) Opioid receptor partial agonists such as but not restricted to meptazinol,
(c) NSAIDS such as but not restricted to acetyl salicilic acid, ibuprofen, naproxen, aceclofenac or diclofenac,
(d) COX-2 inhibitors such as but not restricted to rofecoxib or celecoxib,
(e) Ion channel modulators such as but not restricted to ziconotide or gabapentin,
(f) Centrally acting agents such as but not restricted to flupirtine or neofam,
(g) Agents for neuropathic pain such as but not restricted to carbamazepine, gabapentine, duloxetine or pregabaline,
(h) Agents for cancer pain such as but not restricted to calcitonine, lexidronam or oxycodone for pain patients
(i) Anti-fibrotics such as but not restricted to pirfenidone, nintenadib for patients with idiopathic pulmonary fibrosis,
(j) Prostacyclin analogues such as but not restricted to epoprostenol, beraprost, treprostinil or iloprost
(k) Endothelin antagonists such as but not restricted to bosentac, sitaxentan, ambrisentan or macitentan,
(l) Phosphodiesterase V inhibitors such as but not restricted to sildenafil or taldenafil,
(m) Guanylate cyclase stimulators such as but not restricted to riociguat for patients with pulmonary hypertension,
(n) Oral and inhaled corticosteroids such as but not restricted to fluticasone,
(o) Phosphodiesterase IV inhibitors like roflumilast,
(p) Beta2-adrenoceptor agonists such as but not restricted to salbutamol, salmeterol, indacaterol or olodaterol,
(q) Muscarinic antagonists such as but not restricted to ipratropium, tiotropium, aclidinium, glycopyrronium or umeclidinium,
(r) Xantines such as but not restricted to teophyline,
(s) Mast cell stabilizers such as but not restricted to tranilast and tazonilast,
(t) Leukotriene modifiers such as but not restricted to montelukast, zafirlukast and zileuton,
(u) Th2 cytokine inhibitors such as but not restricted to suplatast,
(v) Thromboxane antagonists/thromboxane synthase inhibitors such as but not restricted to ozagrel and seratrodast,
(w) Anti-IgE therapy compounds such as but not restricted to xolair for patients with asthma
(x) Histamine antagonists such as but not restricted to ebastine, cetiricine and loratadine,
(y) Antiinflammatory agents (such as NSAIDs, corticosteroids, calcineurin inhibitors, anti-TNF, anti-IL17, anti-IL12/IL13, anti-IL5, anti IL4/IL-13, anti-IL31 or anti-IgE antibodies,
(z) JAK inhibitors such as but not restricted to ruxolitinib or tofacitinib,
(aa) Syk inhibitors,
(ab) Immunosupressants;
(ac) Antipruritic agents such as kappa opioid agonists, mu opioid agonists, neurokinin receptor 1 antagonists such as but not restricted to aprepitant, 5-HT3 antagonists and, cannabinoids for patients with dermatological diseases,
(ac) Anti-tussive agents, Decongestants, Mucolytics, Expectorants, or Proton Pump Inhibitors, for simultaneous, separate or sequential use in the treatment of the human or animal body.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the amino-substituted heterocyclic derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a amino-substituted heterocyclic derivative of the invention together with instructions for simultaneous, concurrent, separate or sequential use in combination with another active compound useful in the treatment of above mentioned diseases.

Another execution of the present invention consists of a package comprising an amino-substituted heterocyclic derivative of the invention and another active compound useful in the treatment of these diseases.

Pharmaceutical Compositions

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The present invention also provides pharmaceutical compositions which comprise, as an active ingredient, at least a compound of Formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

i) Oral Administration

The compounds of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.001-50 mg, more preferably 0.01-5 mg of active ingredient or the equivalent amount of a pharmaceutically acceptable salt thereof. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e. g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even stricter.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient(s) and a suitable propellant such as a fluorocarbon or hydrogen-containing chlorofluorocarbon or mixtures thereof, particularly hydrofluoroalkanes, e. g. dichlorodifluoromethane, trichlorofluoromethane, dichlorotetra-fluoroethane, especially 1,1, 1, 2-tetrafluoroethane, 1,1, 1,2, 3,3, 3-heptafluoro-n-propane or a mixture thereof. Carbon dioxide or other suitable gas may also be used as propellant.

The aerosol composition may be excipient free or may optionally contain additional formulation excipients well known in the art such as surfactants (eg. oleic acid or lecithin) and cosolvens (eg. ethanol). Pressurised formulations will generally be retained in a canister (eg. an aluminium canister) closed with a valve (eg. a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

iv) Nasal Mucosal Administration

The compounds of the invention may also be administered via the nasal mucosal.

Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the pharmaceutical compositions of the invention are made up in a form suitable for oral, inhalation or topical administration.

The pharmaceutical formulations may conveniently be presented in unit dosage form and may be prepared by any of the methods well known in the art of pharmacy.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Formulation Examples

The following preparations forms are cited as formulation examples:

Formulation Example 1 (Oral Suspension)

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2 (Hard Gelatine Capsule for Oral Administration)

| Ingredient | Amount |
| --- | --- |
| Active Compound | 1 mg |
| Lactose | 150 mg |
| Magnesium stearate | 3 mg |

Formulation Example 3 (Gelatin Cartridge for Inhalation)

| Ingredient | Amount |
| --- | --- |
| Active Compound (micronized) | 0.2 mg |
| Lactose | 25 mg |

Formulation Example 4 (Formulation for Inhalation with a DPI)

| Ingredient | Amount |
| --- | --- |
| Active Compound (micronized) | 15 mg |
| Lactose | 3000 mg |

Formulation Example 5 (Formulation for a MDI)

| Ingredient | Amount |
| --- | --- |
| Active Compound (micronized) | 10 g |
| 1,1,1,2,3,3,3-heptafluoro-n-propane | q.s. to 200 mL |

Formulation Example 6 (Topical Formulation)

| Ingredient | Amount |
| --- | --- |
| Active compound | 1% |
| Cetyl alcohol | 3% |
| Stearyl alcohol | 4% |
| Glyceryl monostearate | 4% |
| Sorbitan monostearate | 0.8% |
| Sorbitan monostearate POE | 0.8% |
| Liquid Vaseline | 0.8% |
| Glycerine | 15% |
| Preservative | 0.2% |
| Purified water | add to 100% |

Modifications, which do not affect, alter, change or modify the essential aspects of the compounds, combinations or pharmaceutical compositions described, are included within the scope of the present invention.

The invention claimed is:

1. A compound of Formula (I), or a pharmaceutically acceptable salt, N-oxide, or isotopically-labeled derivative thereof:

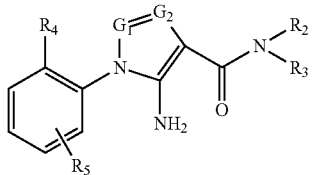

Formula (I)

wherein:

$G_1$ is —N— or —CH—;

$G_2$ is —N— or —$CR_1$, wherein $R_1$ is chosen from a hydrogen atom and a linear or branched $C_{1-4}$ alkyl group, with the proviso that at least one of $G_1$ and $G_2$ is —N—;

$R_2$ is a is a hydrogen atom and $R_3$ is a group of Formula (i):

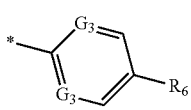

Formula (i)

wherein each $G_3$ is independently —N— or —$CR_7$, wherein $R_7$ is chosen from a hydrogen atom, a halogen atom, a hydroxyl group, a cyano group, a phenyl group, a linear or branched C1A alkyl group, a linear or branched ($C_{1-4}$ alkoxy)-($C_{1-4}$ alkyl) group, —O—$(CH_2)_{1-2}$—$NR^a R^b$, —$NR^a R^b$, —CO—$NR^a R^b$, —$OR^c$ and —$CH_2$—$R^d$;

$R_6$ is chosen from a halogen atom, a cyano group, a linear or branched $C_{1-4}$ alkyl group, a lineal linear or branched $C_{1-4}$ haloalkyl group, a linear or branched $C_{1-4}$ haloalkoxy group, —$SO_2$—$CF_3$ group, a O-phenyl group, a benzyl group and a —O-benzyl group;

or $R_2$ and $R_3$ together with the nitrogen atom to which they are attached form the group of Formula (ii):

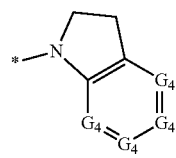

Formula (ii)

wherein each $G_4$ is independently —$CR^8$— or —N—, wherein $R^8$ is chosen from a hydrogen atom and a halogen atom;

$R_4$ is chosen from a halogen atom, a hydroxyl group, a linear or branched $C_{1-4}$ alkyl group, a linear or branched $C_{1-4}$ haloalkyl group, a linear or branched ($C_{1-4}$ alkyl)-($C_{1-4}$ alkoxy) group, a linear or branched ($C_{1-4}$ alkoxy)-($C_{1-4}$ alkyl) group, a linear or branched ($C_{1-4}$ alkoxy)-($C_{1-4}$ alkoxy) group, —$O_{(0-1)}$$(CH_2)_{(0-2)}$—$NR^a R^b$ group, —O—$(CH_2)_{(0-2)}$$R^c$ group, —O—$(CHR^f)_1$—CO—$NR^a R^b$ group, —$SO_2$—$NR^a R^b$ group, a $C_{6-6}$ aryl group, a monocyclic 5- to 8-membered heteroaryl group containing at least one heteroatom chosen from N, O and S, wherein the heteroaryl ring is optionally substituted with one or more substituents chosen from a halogen atom, a $C_{1-2}$ alkyl group, a $C_{1-2}$ alkoxy group and amino group optionally substituted with one or two $C_{1-2}$ alkyl groups, and a 4- to 6-membered saturated or non-saturated heterocyclyl group containing at least one heteroatom chosen from N, O and S, wherein the heterocyclyl ring is optionally substituted with one or more substituents chosen from a $C_{1-2}$ alkyl group, a $C_{1-2}$ alkoxy group and —C(O)O—$R^e$ group, wherein $R^e$ represents a linear or branched $C_{1-4}$ alkyl group, and wherein $R^f$ is a hydrogen atom, a halogen atom or a linear or branched $C_{1-4}$ alkyl group;

$R_5$ is chosen from a hydrogen atom, a halogen atom, a linear or branched $C_{1-4}$ alkyl group and a linear or branched $C_{1-4}$ haloalkyl group;

$R^a$ and $R^b$ are independently chosen from a hydrogen atom, a linear or branched $C_{1-4}$ alkyl group, a linear or branched ($C_{1-4}$ alkoxy)-($C_{1-4}$ alkyl) group and a 5- to 8-membered monocyclic heteroaryl group containing at least one heteroatom chosen from N, S and O, or $R^a$ and $R^b$ together with nitrogen atom to which they are attached form a 3- to 6-membered heterocyclyl group optionally containing a further heteroatom chosen from N, S and O, wherein the heterocyclyl group is optionally substituted with one or more substituents chosen from a $C_{1-2}$ alkyl group;

$R^c$ is chosen from a linear or branched $C_{1-4}$ alkyl group, a linear or branched $C_{1-4}$ hydroxyalkyl group, a linear or branched $C_{1-4}$ haloalkyl group, a linear or branched ($C_{1-4}$ alkoxy)-($C_{1-4}$ alkyl) group, a linear or branched ($C_{1-4}$ alkyl)-($C_{1-4}$ alkoxy) group, a $C_{6-8}$ aryl group, a monocyclic 5- to 8-membered heteroaryl group containing at least one heteroatom chosen from N, O and S, and a 4- to 6-membered heterocyclyl group containing at least one heteroatom chosen from N, O and S, wherein the heterocyclyl ring is optionally substituted with one or more substituents chosen from a $C_{1-2}$ alkyl group and a $C_{1-2}$ alkoxy group;

$R^d$ is chosen from —$NR^aR^b$ group, a 4- to 6-membered heterocyclyl group containing at least one heteroatom chosen from N, O and S, wherein the heterocyclyl group is optionally substituted with one or more substituents chosen from a halogen atom;

with the proviso that the compound is not chosen from:
5-amino-N-(4-ethylphenyl)-1-(2-methylphenyl)-1H-1,2,3-triazole-4-carboxamide,
5-amino-N-(2,4-dimethylphenyl)-1-(2-methylphenyl)-1H-1,2,3-triazole-4-carboxamide,
5-amino-1-(2,5-dimethylphenyl)-N-(4-fluorophenyl)-1H-1,2,3-triazole-4-carboxamide,
5-amino-N-(2,4-dichlorophenyl)-1-(2-methylphenyl)-1H-1,2,3-triazole-4-carboxamide,
5-amino-1-(2-methylphenyl)-N-(4-methylphenyl)-1H-1,2,3-triazole-4-carboxamide,
5-amino-N-(4-chlorophenyl)-1-(2-methylphenyl)-1H-1,2,3-triazole-4-carboxamide,
5-amino-N-(4-fluorophenyl)-1-(2-methylphenyl)-1H-1,2,3-triazole-4-carboxamide,
5-amino-N-(4-bromophenyl)-1-(2-methoxyphenyl)-1H-1,2,3-triazole-4-carboxamide,
5-amino-N-(2,4-difluorophenyl)-1-(2-methoxyphenyl)-1H-1,2,3-triazole-4-carboxamide,
5-amino-1-(2-methoxyphenyl)-N-(4-methylphenyl)-1H-1,2,3-triazole-4-carboxamide, and
5-amino-N-(4-fluorophenyl)-1-(2-methoxyphenyl)-1H-1,2,3-triazole-4-carboxamide.

2. The compound according to claim 1, wherein $R_6$ is chosen from a halogen atom, a cyano group, a linear or branched $C_{1-4}$ alkyl group, a linear or branched $C_{1-4}$ haloalkyl group, a linear or branched $C_{1-4}$ haloalkoxy group, —$SO_2$—$CF_3$ group, a benzyl group and —O-benzyl group; and $R^f$ is a linear or branched $C_{1-4}$ alkyl group.

3. The compound according to claim 1, wherein, in Formula (ii), $G_4$ is a —$CR^8$, wherein $R^8$ is chosen from a hydrogen atom and a halogen atom.

4. The compound according to claim 1, wherein $R_2$ is a hydrogen atom and $R_3$ is a group of Formula (i), wherein each $G_3$ s independently —N— or —$CR_7$, wherein $R_7$ is chosen from a hydrogen atom, a cyano group, a linear or branched $C_{1-4}$ alkyl group, a ($C_{1-2}$ alkoxy)-($C_{1-2}$ alkyl) group, and —$OR^c$, wherein $R^c$ is chosen from a $C_{1-2}$ alkyl group and a $C_{1-2}$ haloalkyl group.

5. The compound according to claim 4, wherein $R_2$ is a hydrogen atom and $R_3$ is a group of Formula (i), wherein $G_3$ is a —N— group.

6. The compound according to claim 4, wherein $R_2$ is a hydrogen atom and $R_3$ is a group of Formula (i), wherein one $G_3$ is a —N— group and the other $G_3$ is a —$CR_7$ group.

7. The compound according to claim 1, wherein $R_6$ is selected chosen from a halogen atom, a cyano group, a linear or branched $C_{1-4}$ alkyl group, a linear or branched $C_{1-4}$ haloalkyl group and a linear or branched $C_{1-4}$ haloalkoxy group.

8. The compound according to claim 7, wherein $R_6$ is chosen from a chlorine, a bromine atom, a methyl group, an ethyl group and a —$CF_3$ group.

9. The compound according to claim 1, wherein both $G_1$ and $G_2$ are —N— group.

10. The compound according to claim 1, wherein $G_1$ is a —N— group while $G_2$ is a —$CR_1$— group, wherein $R_1$ is chosen from a hydrogen atom, a methyl group and an ethyl group.

11. The compound according to claim 1, wherein $R_4$ is chosen from a halogen atom, a hydroxyl group, a linear or branched $C_{1-4}$ alkyl group, a linear or branched $C_{1-4}$ haloalkyl group, a $C_{6-8}$ aryl group, —$O_{(0-1)}$—$(CH_2)_{(O-2)}$—$NR^aR^b$ group, —O—$(CH_2)_{(0-2)}R^c$ group, —O—$(CH_2)_1$—CO—$NR^aR^b$ group, wherein $R^a$ and $R^b$ are independently chosen from a hydrogen atom and a linear or branched $C_{1-4}$ alkyl group, and wherein $R^c$ is chosen from a linear or branched $C_{1-4}$ alkyl group, a linear or branched ($C_{1-4}$ alkoxy)-($C_{1-4}$ alkyl) group, and a linear or branched $C_{1-4}$ haloalkyl group.

12. The compound according to claim 11, wherein $R_4$ is chosen from a fluorine atom, a hydroxyl group, a methyl group, —O—$R^c$ group and —O—$(CH_2)_1$—CO—$NR^aR^b$ group, wherein both $R^a$ and $R^b$ are hydrogen and wherein $R^c$ is selected chosen from a methyl group and a methoxyethyl group.

13. The compound according to claim 1, wherein $R_5$ is chosen from a hydrogen atom and a halogen atom.

14. The compound according to claim 1, having the following Formula (II)

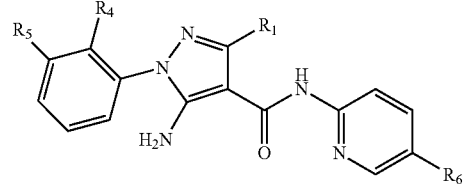

Formula (II)

wherein:
$R_1$ is chosen from a hydrogen atom, a methyl group and an ethyl group;
$R_4$ is chosen from a fluorine atom, a hydroxyl group, a methyl group, a —O—$R^c$ group and a —O—$(CH_2)_1$—CO—$NR^aR^b$ group, wherein both $R^a$ and $R^b$ are hydrogen and wherein $R^c$ is chosen from a methyl group and a methoxyethyl group;
$R_5$ is chosen from a hydrogen atom and a fluorine atom;
$R_6$ is chosen from a chlorine atom, a methyl group and a —$CF_3$ group.

15. The compound according to claim 1, wherein the compound is chosen from:
5-Amino-N-(4-chlorophenyl)-1-(2-methoxyphenyl)-1H-pyrazole-4-carboxamide,
5-Amino-N-(4-bromophenyl)-1-(2-methoxyphenyl)-1H-pyrazole-4-carboxamide,
5-Amino-1-(2-methoxyphenyl)-N-(p-tolyl)-1H-pyrazole-4-carboxamide,
5-Amino-N-(5-chloropyridin-2-yl)-1-(o-tolyl)-1H-pyrazole-4-carboxamide,
5-Amino-1-(o-tolyl)-N-(5-(trifluoromethyl)pyridin-2-yl)-1H-pyrazole-4-carboxamide,
5-Amino-N-(4-chloro-2-methyl-phenyl)-1-(o-tolyl)-pyrazole-4-carboxamide,
5-Amino-N-(4-chloro-2-fluoro-phenyl)-1-(o-tolyl)-1H-pyrazole-4-carboxamide,
5-Amino-N-(4-chloro-2-cyano-phenyl)-1-(o-tolyl)-1H-pyrazole-4-carboxamide, 5-Amino-N-(4-chloro-2-methoxy-phenyl)-1-(o-tolyl)-1H-pyrazole-4-carboxamide,
5-Amino-N-(5-chloro-3-methyl-2-pyridyl)-1-(o-tolyl)-1H-pyrazole-4-carboxamide,
5-Amino-N-[3-fluoro-5-(trifluoromethyl)-2-pyridyl]-1-(o-tolyl)-1H-pyrazole-4-carboxamide,
5-Amino-N-(5-chloro-3-methoxy-2-pyridyl)-1-(o-tolyl)-1H-pyrazole-4-carboxamide,
5-Amino-N-(4-chloro-2-(methylamino)phenyl)-1-(o-tolyl)-1H-pyrazole-4-carboxamide,
5-Amino-N-(2-carbamoyl-4-chlorophenyl)-1-(o-tolyl)-1H-pyrazole-4-carboxamide,
5-Amino-N-(2-cyano-4-(trifluoromethyl)phenyl)-1-(o-tolyl)-1H-pyrazole-4-carboxamide,
5-Amino-N-(2-methoxy-4-(trifluoromethyl)phenyl)-1-(o-tolyl)-1H-pyrazole-4-carboxamide,
5-Amino-N-(4-chloro-2-hydroxyphenyl)-1-(o-tolyl)-1H-pyrazole-4-carboxamide,
5-Amino-N-(4-chloro-2-((dimethylamino)methyl)phenyl)-1-(o-tolyl)-1H-pyrazole-4-carboxamide,
5-Amino-N-(4-chloro-2-(methoxymethyl)phenyl)-1-(o-tolyl)-1H-pyrazole-4-carboxamide,
5-Amino-N-(4-bromo-2-methoxy-phenyl)-1-(o-tolyl)-1H-pyrazole-4-carboxamide,
5-Amino-N-(4-chloro-2-fluoro-phenyl)-1-[2-(2-methoxyethoxy)phenyl]-1H-pyrazole-4-carboxamide,
5-Amino-N-(4-chloro-2-methoxy-phenyl)-1-[2-(2-methoxyethoxy)phenyl]-1H-pyrazole-4-carboxamide,
5-Amino-N-(5-chloro-2-pyridyl)-1-[2-(2-methoxyethoxy)phenyl]-1H-pyrazole-4-carboxamide,
5-Amino-N-[4-chloro-2-[[isopropyl(methyl)amino]methyl]phen y]-1-(o-tolyl)-1H-pyrazole-4-carboxamide,
5-Amino-N-[4-chloro-2-(pyrrolidin-1-ylmethyl)phenyl]-1-(o-tolyl)-1H-pyrazole-4-carboxamide,
5-Amino-N-[4-chloro-2-(morpholinomethyl)phenyl]-1-(o-tolyl)-1H-pyrazole-4-carboxamide,
5-Amino-N-(4-cyanophenyl)-1-(o-tolyl)-1H-pyrazole-4-carboxamide,
5-Amino-N-(4-tert-butylphenyl)-1-(o-tolyl)-1H-pyrazole-4-carboxamide,
5-Amino-N-[4-chlor-2-[[(3R)-3-fluoropyrrolidin-1-yl]methyl]phenyl]-1-(o-tolyl)-1H-pyrazole-4-carboxamide,
5-Amino-N-(4-chloro-2-phenyl-phenyl)-1-(o-tolyl)-1H-pyrazole-4-carboxamide,
5-Amino-1-[2-(2-methoxyethoxy)phenyl]-N-[4-(trifluoromethyl)phenyl]-1H-pyrazole-4-carboxamide,
5-Amino-N-[2-fluoro-4-(trifluoromethyl)phenyl]-1-[2-(2-methoxyethoxy)phenyl]-1H-pyrazole-4-carboxamide,
5-Amino-N-(2-bromo-4-chloro-phenyl)-1-(o-tolyl)-1H-pyrazole-4-carboxamide,
5-Amino-1-[2-(2-methoxyethoxy)phenyl]-N-[2-methyl-4-(trifluoromethyl)phenyl]-1H-pyrazole-4-carboxamide,
5-Amino-N-(4-chloro-2-methoxy-phenyl)-3-methyl-1-(o-tolyl)-1H-pyrazole-4-carboxamide,
5-Amino-N-(4-chloro-2-methoxy-phenyl)-1-[2-(2-methoxyethoxy)phenyl]-3-methyl-1H-pyrazole-4-carboxamide,
5-Amino-1-[2-(2-methoxyethoxy)phenyl]-N-[2-methoxy-4-(trifluoromethyl)phenyl]-3-methyl-1H-pyrazole-4-carboxamide,
5-Amino-N-(2-fluoro-4-(trifluoromethyl)phenyl)-1-(2-(2-methoxyethoxy)phenyl)-3-methyl-1H-pyrazole-4-carboxamide,
5-Amino-N-[2-cyano-4-(trifluoromethyl)phenyl]-1-(2-ethylphenyl)-3-methyl-1H-pyrazole-4-carboxamide,
5-Amino-N-(4-bromo-2-methoxy-phenyl)-1-(2-ethylphenyl)-3-methyl-1H-pyrazole-4-carboxamide,
5-Amino-N-(4-chloro-2-methoxy-phenyl)-1-(2-ethylphenyl)-3-methyl-1H-pyrazole-4-carboxamide,
5-Amino-N-(5-chloro-2-pyridyl)-1-(2-ethylphenyl)-3-methyl-1H-pyrazole-4-carboxamide,
5-Amino-N-(4-chloro-2-fluoro-phenyl)-1-[2-(2-methoxyethoxy)phenyl]-3-methyl-1H-pyrazole-4-carboxamide,
5-Amino-N-[2-fluoro-4-(trifluoromethyl)phenyl]-3-methyl-1-(o-tolyl)-1H-pyrazole-4-carboxamide,
5-Amino-1-(2-ethylphenyl)-3-methyl-N-[5-(trifluoromethyl)-2-pyridyl]-1H-pyrazole-4-carboxamide,
5-Amino-N-(5-chloro-2-pyridyl)-1-[2-(2-methoxyethoxy)phenyl]-3-methyl-1H-pyrazole-4-carboxamide,
5-Amino-1-(o-tolyl)-N-[4-(trifluoromethylsulfonyl)phenyl]-1H-pyrazole-4-carboxamide,
5-Amino-N-[4-bromo-2-(difluoromethoxy)phenyl]-1-(o-tolyl)-1H-pyrazole-4-carboxamide,
5-Amino-N-(4-chloro-2-fluoro-phenyl)-3-methyl-1-(o-tolyl)-1H-pyrazole-4-carboxamide,
5-Amino-N-(5-methylpyridin-2-yl)-1-(o-tolyl)-1H-pyrazole-4-carboxamide,
5-Amino-N-(5-cyanopyridin-2-yl)-1-(o-tolyl)-1H-pyrazole-4-carboxamide,
5-Amino-N-(5-bromopyridin-2-yl)-1-(o-tolyl)-1H-pyrazole-4-carboxamide,
5-Amino-1-(o-tolyl)-N-(5-(trifluoromethoxy)pyridin-2-yl)-1H-pyrazole-4-carboxamide,
5-Amino-1-(2-methoxyphenyl)-N-[5-(2,2,2-trifluoroethoxy)-2-pyridyl]pyrazol e-4-carboxamide,
5-Amino-1-(3-fluoro-2-methylphenyl)-N-(5-(trifluoromethoxy)pyridin-2-yl)-1H-pyrazole-4-carboxamide,
5-Amino-N-(5-bromopyridin-2-yl)-1-(2-fluorophenyl)-1H-pyrazole-4-carboxamide,
(5-Amino-1-(3-fluoro-2-methylphenyl)-1H-pyrazol-4-yl)(5-chloroindolin-1-yl)methanone,
5-Amino-1-(3-fluoro-2-methylphenyl)-N-(4-(trifluoromethyl)phenyl)-1H-pyrazole-4-carboxamide,
(5-Amino-1-(o-tolyl)-1H-pyrazol-4-yl)(5-chloroindolin-1-yl)methanone,
[5-Amino-1-(2-fluorophenyl)pyrazol-4-yl](5-chloroindolin-1-yl)methanone,
(5-Amino-1-(2-methoxyphenyl)-H-pyrazol-4-yl)(5-chloroindolin-1-yl)methanone,
5-Amino-N-(4-bromophenyl)-1-(o-tolyl)-1H-1,2,3-triazole-4-carboxamide,
5-Amino-1-(2-methoxyphenyl)-N-(5-(trifluoromethyl)pyridin-2-yl)-1H-1,2,3-triazole-4-carboxamide,
5-Amino-1-(2-methoxyphenyl)-N-(p-tolyl)-1H-1,2,3-triazole-4-carboxamide,
5-Amino-1-(2-methoxyphenyl)-N-(4-(trifluoromethyl)phenyl)-1H-1,2,3-triazole-4-carboxamide,
5-Amino-1-(2-methoxyphenyl)-N-(4-(trifluoromethoxy)phenyl)-1H-1,2,3-triazole-4-carboxamide,
5-Amino-N-(4-isopropylphenyl)-1-(2-methoxyphenyl)-1H-1,2,3-triazole-4-carboxamide,
5-Amino-N-(5-chloropyridin-2-yl)-1-(2-methoxyphenyl)-1H-1,2,3-triazole-4-carboxamide,
5-Amino-1-(2-methoxyphenyl)-N-(4-phenoxyphenyl)-1H-1,2,3-triazole-4-carboxamide,
5-Amino-1-(2-methoxyphenyl)-N-(4-(1,1,2,2-tetrafluoroethoxy)phenyl)-1H-1,2,3-triazole-4-carboxamide,
5-Amino-N-(4-(benzyloxy)phenyl)-1-(2-methoxyphenyl)-1H-1,2,3-triazole-4-carboxamide, 5-Amino-N-(4-benzylphenyl)-1-(2-methoxyphenyl)-1H-1,2,3-triazole-4-carboxamide,
5-Amino-N-(5-chloropyridin-2-yl)-1-(o-tolyl)-1H-1,2,3-triazole-4-carboxamide,
5-Amino-1-(o-tolyl)-N-(5-(trifluoromethyl)pyridin-2-yl)-1H-1,2,3-triazole-4-carboxamide,
5-Amino-N-(5-chloropyridin-2-yl)-1-(3-fluoro-2-methylphenyl)-1H-1,2,3-triazole-4-carboxamide,
5-Amino-1-(3-fluoro-2-methylphenyl)-N-(5-(trifluoromethyl)pyridin-2-yl)-1H-1,2,3-triazole-4-carboxamide,
5-Amino-N-(4-chlorophenyl)-1-(2,6-dimethylphenyl)-1H-pyrazole-4-carboxamide,
5-Amino-1-(2-chlorophenyl)-N-(4-chlorophenyl)pyrazole-4-carboxamide,
5-Amino-N-(4-chlorophenyl)-1-(o-tolyl)pyrazole-4-carboxamide,
5-Amino-N-(4-chlorophenyl)-1-[2-(trifluoromethyl)phenyl]pyrazole-4-carboxamide,
5-Amino-N-(4-chlorophenyl)-1-(2,3-dichlorophenyl)-1H-pyrazole-4-carboxamide,
5-Amino-N-(4-chlorophenyl)-1-(2-fluorophenyl)pyrazole-4-carboxamide,
5-Amino-N-(4-chlorophenyl)-1-[3-(trifluoromethyl)phenyl]pyrazole-4-carboxamide,
5-Amino-1-(2-ethylphenyl-N-[5-trifluoromethyl-2-pyridyl]pyrazole-4-carboxamide,
5-Amino-1-(2-chlorophenyl)-N-[5-trifluoromethyl-2-pyridyl]pyrazole-4-carboxamide,
5-Amino-1-(2-isopropylphenyl)-N-[5-trifluoromethyl-2-pyridyl]pyrazole-4-carboxamide,
5-Amino-1-[2-(trifluoromethoxy)phenyl]-N-[5-trifluoromethyl-2-pyridyl]pyrazole-4-carboxamide,
5-Amino-1-[2-(2-methoxyethoxy)phenyl]-N-[5-trifluoromethyl-2-pyridyl]pyrazole-4-carboxamide,
5-Amino-N-(5-chloropyridin-2-yl)-1-(2-ethylphenyl)-1H-pyrazole-4-carboxamide,
5-Amino-1-(2-(methoxymethyl)phenyl)-N-(5-(trifluoromethyl)pyridin-2-yl)-1H-pyrazole-4-carboxamide,
5-Amino-N-(5-chloropyridin-2-yl)-1-(2-methoxyphenyl)-1H-pyrazole-4-carboxamide,
5-Amino-1-(2-chlorophenyl)-N-(5-chloropyridin-2-yl)-1H-pyrazole-4-carboxamide,
5-Amino-N-(4-chloro-2-methoxyphenyl)-1-(2-methoxyphenyl)-1H-pyrazole-4-carboxamide,
5-Amino-N-(4-chloro-2-methoxyphenyl)-1-(2-ethylphenyl)-1H-pyrazole-4-carboxamide,
1-(2-(1H-Pyrazol-1-yl)phenyl)-5-amino-N-(5-(trifluoromethyl)pyridin-2-yl)-1H-pyrazole-4-carboxamide,
5-Amino-1-(2-bromophenyl)-N-(5-chloropyridin-2-yl)-1H-pyrazole-4-carboxamide,
5-Amino-N-(4-chloro-2-methoxyphenyl)-1-(5-fluoro-2-methylphenyl)-1H-pyrazole-4-carboxamide,
5-Amino-N-(4-chloro-2-methoxyphenyl)-1-(4-fluoro-2-methylphenyl)-1H-pyrazole-4-carboxamide,
5-Amino-N-(4-chloro-2-methoxyphenyl)-1-(3-fluoro-2-methylphenyl)-1H-pyrazole-4-carboxamide,
5-Amino-N-(4-chloro-2-methoxyphenyl)-1-(2,3-dimethylphenyl)-1H-pyrazole-4-carboxamide,
5-Amino-N-(4-chloro-2-methoxyphenyl)-1-(2,5-dimethylphenyl)-1H-pyrazole-4-carboxamide,
5-Amino-1-(2-bromophenyl)-N-(5-(trifluoromethyl)pyridin-2-yl)-1H-pyrazole-4-carboxamide,
5-Amino-N-(4-chloro-2-methoxyphenyl)-1-(2-chlorophenyl)-1H-pyrazole-4-carboxamide,
5-Amino-1-(2-methyl-5-(trifluoromethyl)phenyl)-N-(5-(trifluoromethyl)pyridin-2-yl)-1H-pyrazole-4-carboxamide,
5-Amino-1-[2-(5-methyl-1,2,4-oxadiazol-3-yl)phenyl]-N-[5-trifluoromethyl-2-pyridyl]pyrazole-4-carboxamide,
5-Amino-1-(2-fluoro-6-methylphenyl)-N-[5-trifluoromethyl-2-pyridyl]pyrazole-4-carboxamide,
5-Amino-1-(2-(oxazol-5-yl)phenyl)-N-(5-(trifluoromethyl)pyridin-2-yl)-1H-pyrazole-4-carboxamide,
5-Amino-1-[2-(dimethylaminomethyl)phenyl]-N-[5-trifluoromethyl-2-pyridyl]pyrazole-4-carboxamide,
5-Amino-N-(4-chloro-2-methoxyphenyl)-1-[3-fluoro-2-(2-methoxyethoxy)phenyl]pyrazole-4-carboxamide,
5-Amino-N-(5-chloro-2-pyridyl)-1-[3-fluoro-2-(2-methoxyethoxy)phenyl]-pyrazole-4-carboxamide,
5-Amino-N-(5-chloro-2-pyridyl)-1-[2-(dimethylaminomethyl)-phenyl]-pyrazole-4-carboxamide,
5-Amino-1-[3-fluoro-2-(2-methoxyethoxy)phenyl]-N-[5-trifluoromethyl-2-pyridyl]pyrazole-4-carboxamide,
5-Amino-1-[3-fluoro-2-(2-methoxyethoxy)phenyl]-3-methyl-N-[5-(trifluoromethyl)-2-pyridyl]pyrazole-4-carboxamide,
5-Amino-3-ethyl-1-(2-methoxyphenyl)-N-(5-(trifluoromethyl)pyridin-2-yl)-1H-pyrazole-4-carboxamide,
5-Amino-1-(2-(2-methoxyethoxy)phenyl)-3-methyl-N-(2-methyl-4-(trifluoromethyl)phenyl)-1H-pyrazole-4-carboxamide,
5-Amino-1-(2-bromo-3-fluorophenyl)-3-methyl-N-[5-trifluoromethyl-2-pyridyl]pyrazole-4-carboxamide,
5-Amino-1-(2-bromo-6-fluorophenyl)-3-methyl-N-[5-trifluoromethyl-2-pyridyl]pyrazole-4-carboxamide,
5-Amino-1-(2-chloro-6-fluorophenyl)-3-methyl-N-[5-trifluoromethyl-2-pyridyl]pyrazole-4-carboxamide,
5-Amino-1-(2-bromo-3-fluorophenyl)-N-(5-chloro-2-pyridyl)-3-methyl-pyrazole-4-carboxamide,
5-Amino-1-(2-chloro-6-fluorophenyl)-N-(5-chloro-2-pyridyl)-3-methyl-pyrazole-4-carboxamide,
5-Amino-1-(2-bromophenyl)-N-(5-chloro-2-pyridyl)-3-methyl-pyrazole-4-carboxamide,
5-Amino-1-(3-fluoro-2-methylphenyl)-3-methyl-N-[5-trifluoromethyl-2-pyridyl]pyrazole-4-carboxamide,
5-Amino-1-(2-methoxyphenyl)-3-methyl-N-[5-trifluoromethyl-2-pyridyl]pyrazole-4-carboxamide,
5-Amino-N-(5-chloro-2-pyridyl)-1-(2-methoxyphenyl)-3-methyl-pyrazole-4-carboxamide,
5-Amino-1-(2-bromo-6-fluorophenyl)-N-[5-trifluoromethyl-2-pyridyl]pyrazole-4-carboxamide,
5-Amino-1-(2-chloro-6-fluorophenyl)-N-[5-trifluoromethyl-2-pyridyl]pyrazole-4-carboxamide,
5-Amino-N-(5-chloropyridin-2-yl)-1-(3-fluoro-2-methylphenyl)-1H-pyrazole-4-carboxamide,
5-Amino-1-(2-bromo-6-fluorophenyl)-N-(5-chloro-2-pyridyl)pyrazole-4-carboxamide,
5-Amino-1-(2-fluoro-6-methoxyphenyl)-3-methyl-N-[5-trifluoromethyl-2-pyridyl]pyrazole-4-carboxamide,
5-Amino-1-(2-chloro-3-fluorophenyl)-3-methyl-N-[5-trifluoromethyl-2-pyridyl]pyrazole-4-carboxamide,
5-Amino-N-(5-chloro-2-pyridyl)-1-(2-fluoro-6-methoxyphenyl)-3-methyl-pyrazole-4-carboxamide,
5-Amino-1-(2-chloro-3-fluorophenyl)-N-(5-chloro-2-pyridyl)-3-methyl-pyrazole-4-carboxamide,
5-Amino-N-(5-chloro-2-pyridyl)-1-(2-fluoro-6-methylphenyl)-3-methyl-pyrazole-4-carboxamide,
5-Amino-3-ethyl-1-(o-tolyl)-N-[5-trifluoromethyl-2-pyridyl]pyrazole-4-carboxamide,
5-Amino-3-ethyl-1-(2-(2-methoxyethoxy)phenyl)-N-(5-(trifluoromethyl)pyridin-2-yl)-1H-pyrazole-4-carboxamide, 5-Amino-1-(2-chloro-6-fluorophenyl)-N-(5-chloro-2-pyridyl)pyrazole-4-carboxamide,
5-Amino-N-(5-chloro-2-pyridyl)-1-(3-fluoro-2-methylphenyl)-3-methyl-pyrazole-4-carboxamide,
5-Amino-1-(2-ethylphenyl)-N-(3-fluoro-5-(trifluoromethyl)pyridin-2-yl)-1H-pyrazole-4-carboxamide,
5-Amino-1-(o-tolyl)-N-(5-(2,2,2-trifluoroethoxy)pyridin-2-yl)-1H-pyrazole-4-carboxamide,
5-Amino-1-(2-ethylphenyl)-N-(5-(2,2,2-trifluoroethoxy)pyridin-2-yl)-1H-pyrazole-4-carboxamide,
5-Amino-1-(2-(2-methoxyethoxy)phenyl)-N-(5-(2,2,2-trifluoroethoxy)pyridin-2-yl)-1H-pyrazole-4-carboxamide,
5-Amino-1-(3-fluoro-2-methylphenyl)-N-(5-(2,2,2-trifluoroethoxy)pyridin-2-yl)-1H-pyrazole-4-carboxamide,
5-Amino-3-ethyl-1-(3-fluoro-2-methylphenyl)-N-[5-trifluoromethyl-2-pyridyl]pyrazole-4-carboxamide,
5-Amino-N-(5-chloro-2-pyridyl)-3-ethyl-1-(3-fluoro-2-methylphenyl)pyrazole-4-carboxamide,
5-Amino-1-(3-fluoro-2-methylphenyl)-N-[5-trifluoromethyl-2-pyridyl]pyrazole-4-carboxamide,
5-Amino-N-(4-chloro-2-fluorophenyl)-1-(2-methoxyphenyl)-1H-pyrazole-4-carboxamide,
5-Amino-1-(3-fluoro-2-methylphenyl)-N-(5-iodopyridin-2-yl)-1H-pyrazole-4-carboxamide,
5-Amino-N-(5-chloropyridin-2-yl)-1-(2-fluorophenyl)-1H-pyrazole-4-carboxamide,
5-amino-1-(2-fluorophenyl)-N-(5-(trifluoromethyl)pyridin-2-yl)-1H-pyrazole-4-carboxamide,
5-Amino-3-methyl-1-(2-(oxazol-5-yl)phenyl)-N-(5-(trifluoromethyl)pyridin-2-yl)-1H-pyrazole-4-carboxamide,
5-Amino-3-ethyl-1-(2-fluorophenyl)-N-(5-(trifluoromethyl)pyridin-2-yl)-1H-pyrazole-4-carboxamide,
5-Amino-N-(5-chloropyridin-2-yl)-3-ethyl-1-(2-fluorophenyl)-1H-pyrazole-4-carboxamide,
5-Amino-1-(2-fluorophenyl)-3-methyl-N-(5-(trifluoromethyl)pyridin-2-yl)-1H-pyrazole-4-carboxamide,
5-Amino-N-(5-chloropyridin-2-yl)-1-(2-fluorophenyl)-3-methyl-1H-pyrazole-4-carboxamide,
5-Amino-N-(5-chloropyridin-2-yl)-1-(2-fluoro-3-methylphenyl)-1H-pyrazole-4-carboxamide,
5-Amino-1-(2-fluoro-3-methylphen yl)-N-(5-(trifluoromethyl)pyridin-2-yl)-1H-pyrazole-4-carboxamide,
5-Amino-N-(5-chloropyridin-2-yl)-1-(2-iodophenyl)-1H-pyrazole-4-carboxamide,
5-Amino-N-(5-chloropyridin-2-yl)-1-(3-fluoro-2-(oxazol-5-yl)phenyl)-3-methyl-1H-pyrazole-4-carboxamide,
5-Amino-1-(3-fluoro-2-(oxazol-5-yl)phenyl)-3-methyl-N-(5-(trifluoromethyl)pyridin-2-yl)-1H-pyrazole-4-carboxamide,
5-Amino-N-(5-chloropyridin-2-yl)-1-(3-fluoro-2-(oxazol-5-yl)phenyl)-1H-pyrazole-4-carboxamide,
5-Amino-1-(3-fluoro-2-(oxazol-5-yl)phenyl)-N-(5-(trifluoromethyl)pyridin-2-yl)-1H-pyrazole-4-carboxamide,
5-Amino-3-ethyl-1-(3-fluoro-2-(oxazol-5-yl)phenyl)-N-(5-(trifluoromethyl)pyridin-2-yl)-1H-pyrazole-4-carboxamide,
5-Amino-3-ethyl-1-(2-(oxazol-5-yl)phenyl)-N-(5-(trifluoromethyl)pyridin-2-yl)-1H-pyrazole-4-carboxamide,
5-Amino-1-(2-iodophenyl)-N-(5-((trifluoromethyl)pyridin-2-yl)-1H-pyrazole-4-carboxamide,
5-Amino-1-(2-iodophenyl)-3-methyl-N-(5-(trifluoromethyl)pyridin-2-yl)-1H-pyrazole-4-carboxamide,
5-Amino-N-(5-chloropyridin-2-yl)-1-(2-(oxazol-5-yl)phenyl)-1H-pyrazole-4-carboxamide,
5-Amino-1-(2-chloro-3-fluorophenyl)-N-(5-chloropyridin-2-yl)-1H-pyrazole-4-carboxamide,
5-Amino-1-(2-chloro-3-fluorophenyl)-N-(5-(trifluoromethyl)pyridin-2-yl)-1H-pyrazole-4-carboxamide,
5-Amino-1-(2-(5-chlorothiopheN-2-yl)phenyl)-N-(5-(trifluoromethyl)pyridin-2-yl)-1H-pyrazole-4-carboxamide,
5-Amino-N-(5-chloropyridin-2-yl)-1-(2-(pyrrolidin-1-ylsulfonyl)phenyl)-1H-pyrazole-4-carboxamide,
5-Amino-N-(5-chloropyridin-2-yl)-1-(2-(N-methyl-N-(pyridin-3-yl)sulfamoyl)phenyl)-1H-pyrazole-4-carboxamide,
5-Amino-1-(2-bromophenyl)-3-methyl-N-[5-trifluoromethyl-2-pyridyl]pyrazole-4-carboxamide,
5-Amino-N-(5-chloro-2-pyridyl)-1-(2-fluoro-6-methylphenyl)pyrazole-4-carboxamide,
5-Amino-N-(5-chloro-2-pyridyl)-1-(2-fluoro-6-methoxyphenyl)pyrazole-4-carboxamide,
5-Amino-1-(2-chlorophenyl)-N-(5-chloro-2-pyridyl)-3-methyl-pyrazole-4-carboxamide,
5-Amino-1-(2-chlorophenyl)-3-methyl-N-[5-trifluoromethyl-2-pyridyl]pyrazole-4-carboxamide,
5-Amino-3-methyl-1-(2-morphelinophenyl)-N-[5-trifluoromethyl-2-pyridyl]pyrazole-4-carboxamide,
5-Amino-1-(2-bromo-6-fluorophenyl)-N-(5-chloro-2-pyridyl)-3-methyl-pyrazole-4-carboxamide,
5-Amino-3-isopropyl-1-(o-tolyl)-N-[5-(trifluoromethyl)-2-pyridyl]pyrazole-4-carboxamide,
5-Amino-1-(2-fluoro-6-methylphenyl)-3-methyl-N-[5-trifluoromethyl-2-pyridyl]pyrazole-4-carboxamide,
5-Amino-1-(2-fluoro-6-methoxyphenyl)-N-[5-trifluoromethyl-2-pyridyl]pyrazole-4-carboxamide,
5-Amino-1-[2-(2-methoxyethoxy)phenyl]-3-methyl-N-[5-trifluoromethyl-2-pyridyl]pyrazole-4-carboxamide,
5-Amino-1-(3-fluoro-2-methoxyphenyl)-N-[5-trifluoromethyl-2-pyridyl]pyrazole-4-carboxamide,
5-Amino-N-(5-chloro-2-pyridyl)-1-(3-fluoro-2-methoxyphenyl)pyrazole-4-carboxamide,
5-Amino-1-(2,6-difluorophenyl)-N-[5-trifluoromethyl-2-pyridyl]pyrazole-4-carboxamide,
5-Amino-1-(2,6-dimethylphenyl)-N-[5-trifluoromethyl-2-pyridyl]pyrazole-4-carboxamide,
5-Amino-1-(2,6-difluorophenyl)-3-methyl-N-[5-trifluoromethyl-2-pyridyl]pyrazole-4-carboxamide,
5-Amino-1-(2,6-dimethylphenyl)-3-methyl-N-[5-trifluoromethyl-2-pyridyl]pyrazole-4-carboxamide,
5-Amino-1-(2-chloro-6-methylphenyl)-3-methyl-N-[5-trifluoromethyl-2-pyridyl]pyrazole-4-carboxamide,
5-Amino-1-(2,6-dichlorophenyl)-N-[5-trifluoromethyl-2-pyridyl]pyrazole-4-carboxamide,
5-Amino-1-(2-chloro-6-methylphenyl)-N-[5-trifluoromethyl-2-pyridyl]pyrazole-4-carboxamide,
5-Amino-1-(2,6-dichlorophenyl)-3-methyl-N-[5-trifluoromethyl-2-pyridyl]pyrazole-4-carboxamide,
5-Amino-1-(2-bromo-3-methylphen yl)-N-(5-chloropyridin-2-yl)-1H-pyrazole-4-carboxamide,
1-([1,1'-Biphenyl]-2-yl)-5-amino-N-(5-chloropyridin-2-yl)-1H-pyrazole-4-carboxamide,
5-Amino-1-(2-(2-methoxypyridin-4-yl)phenyl)-N-(5-(trifluoromethyl)pyridin-2-yl)-1H-pyrazole-4-carboxamide,
5-Amino-N-(5-chloropyridin-2-yl)-1-(2-(pyridin-3-yl)phenyl)-1H-pyrazole-4-carboxamide, 5-Amino-N-(5-chloropyridin-2-yl)-1-(2-(2-methoxypyridin-4-yl)phenyl)-1H-pyrazole-4-carboxamide,
5-Amino-N-(5-chloropyridin-2-yl)-1-(2-(1-methyl-1H-pyrazol-4-yl)phenyl)-1H-pyrazole-4-carboxamide,
5-Amino-3-methyl-1-(2-(pyridin-3-yl)phenyl)-N-(5-(trifluoromethyl)pyridin-2-yl)-1H-pyrazole-4-carboxamide,
5-Amino-1-(2-(2-methoxypyridin-4-yl)phenyl)-3-methyl-N-(5-(trifluoromethyl)pyridin-2-yl)-1H-pyrazole-4-carboxamide,
5-Amino-1-(2-(pyridin-3-yl)phenyl)-N-(5-(trifluoromethyl)pyridin-2-yl)-1H-pyrazole-4-carboxamide,
5-Amino-1-(2-(pyridin-4-yl)phenyl)-N-(5-(trifluoromethyl)pyridin-2-yl)-1H-pyrazole-4-carboxamide,
5-Amino-1-(2-(5-fluoropyridin-3-yl)phenyl)-N-(5-(trifluoromethyl)pyridin-2-yl)-1H-pyrazole-4-carboxamide,
5-Amino-N-(5-chloropyridin-2-yl)-1-(2-(6-methoxypyridin-3-yl)phenyl)-1H-pyrazole-4-carboxamide,
1-(2-(1-Pyrazol-4-yl)phenyl)-5-amino-N-(5-chloropyridin-2-yl)-1H-pyrazole-4-carboxamide,
5-Amino-N-(5-chloropyridin-2-yl)-1-(3-fluoro-2-(2-methoxypyridin-4-yl)phenyl)-1H-pyrazole-4-carboxamide,
5-Amino-N-(5-chloropyridin-2-yl)-1-(2-hydroxyphenyl)-1H-pyrazole-4-carboxamide,
5-Amino-1-(2-hydroxyphenyl)-N-(5-(trifluoromethyl)pyridin-2-yl)-1H-pyrazole-4-carboxamide,
5-Amino-N-(5-chloropyridin-2-yl)-1-(2-ethoxyphenyl)-1H-pyrazole-4-carboxamide,
5-Amino-N-(5-chloropyridin-2-yl)-1-(2-(2-(dimethylamino)ethoxy)phenyl)-1H-pyrazole-4-carboxamide,
(R)-5-Amino-N-(5-chloropyridin-2-yl)-1-(2-((tetrahydrofuraN-3-yl)oxy)phenyl)-1H-pyrazole-4-carboxamide,
5-Amino-N-(5-chloropyridin-2-yl)-1-(2-((1-methylpiperidiN-4-yl)oxy)phenyl)-1H-pyrazole-4-carboxamide,
5-Amino-1-(2-(benzyloxy)phenyl)-N-(5-chloropyridin-2-yl)-1H-pyrazole-4-carboxamide,
5-Amino-1-(2-isopropoxyphenyl)-N-(5-(trifluoromethyl)pyridin-2-yl)-1H-pyrazole-4-carboxamide,
5-Amino-N-(4-chloro-2-(2-(dimethylamino)ethoxy)phenyl)-1-(o-tolyl)-1H-pyrazole-4-carboxamide,
(R)-5-Amino-N-(4-chloro-2-((tetrahydrofuraN3-yl)oxy)phenyl)-1-(o-tolyl)-1H-pyrazole-4-carboxamide,
5-Amino-N-(4-chloro-2-ethoxyphenyl)-1-(o-tolyl)-1H-pyrazole-4-carboxamide,
5-Amino-N-(4-chloro-2-(2-methoxyethoxy)phenyl)-1-(o-tolyl)-1H-pyrazole-4-carboxamide,
5-Amino-N-(4-chloro-2-((1-methylpiperidiN-4-yl)oxy)phenyl)-1-(o-tolyl)-1H-pyrazole-4-carboxamide,
5-Amino-1-(2-((2-methoxyethyl)amino)phenyl)-N-(5-(trifluoromethyl)pyridin-2-yl)-1H-pyrazole-4-carboxamide,
5-Amino-1-(2-((2-methoxyethyl)(methyl)amino)phenyl)-N-(5-(trifluoromethyl)pyridin-2-yl)-1H-pyrazole-4-carboxamide,
5-Amino-1-(2-(3-methoxypyrrolidin-1-yl)phenyl)-N-(5-(trifluoromethyl)pyridin-2-yl)-1H-pyrazole-4-carboxamide,
5-Amino-1-(2-(4-methoxypiperidiN-1-yl)phenyl)-N-(5-(trifluoromethyl)pyridin-2-yl)-1H-pyrazole-4-carboxamide,
5-Amino-1-(2-((3-methyloxetan-3-yl)methoxy)phenyl)-N-(5-(trifluoromethyl)pyridin-2-yl)-1H-pyrazole-4-carboxamide,
1-(2-(2-(1H-Imidazol-1-yl)ethoxy)phenyl)-5-amino-N-(5-(trifluoromethyl)pyridin-2-yl)-1H-pyrazole-4-carboxamide,
5-Amino-1-(2-((tetrahydro-2H-pyraN-4-yl)oxy)phenyl)-N-(5-(trifluoromethyl)pyridin-2-yl)-1H-pyrazole-4-carboxamide,
5-Amino-1-(2-((tetrahydrofuraN-3-yl)oxy)phenyl)-N-(5-(trifluoromethyl)pyridin-2-yl)-1H-pyrazole-4-carboxamide,
5-Amino-1-(2-((4-methylmorpholin-2-yl)methoxy)phenyl)-N-(5-(trifluoromethyl)pyridin-2-yl)-1H-pyrazole-4-carboxamide,
1-(2-(2-(1H-Pyrazol-1-yl)ethoxy)phenyl)-5-amino-N-(5-(trifluoromethyl)pyridin-2-yl)-1H-pyrazole-4-carboxamide,
5-Amino-1-(2-((1-methylpiperidin-3-yl)methoxy)phenyl)-N-(5-(trifluoromethyl)pyridin-2-yl)-1H-pyrazole-4-carboxamide,
5-Amino-1-(2-(2-amino-2-oxoethoxy)phenyl)-N-(5-(trifluoromethyl)pyridin-2-yl)-1H-pyrazole-4-carboxamide,
5-Amino-1-(2-(2-amino-2-oxoethoxy)phenyl)-3-ethyl-N-(5-(trifluoromethyl)pyridin-2-yl)-1H-pyrazole-4-carboxamide,
5-Amino-1-(2-(2-amino-2-oxoethoxy)phenyl)-N-(5-(trifluoromethoxy)pyridin-2-yl)-1H-pyrazole-4-carboxamide,
5-Amino-1-(2-(2-amino-2-oxoethoxy)-3-fluorophenyl)-N-(5-(trifluoromethyl)pyridin-2-yl)-1H-pyrazole-4-carboxamide,
5-Amino-1-(2-(2-amino-2-oxoethoxy)phenyl)-N-(5-chloropyridin-2-yl)-3-ethyl-1H-pyrazole-4-carboxamide,
5-Amino-1-(2-(2-(methylamino)-2-oxoethoxy)phenyl)-N-(5-(trifluoromethyl)pyridin-2-yl)-1H-pyrazole-4-carboxamide,
5-Amino-1-(2-((2,2-dimethyl-1,3-dioxolaN-4-yl)methoxy)phenyl)-N-(5-(trifluoromethyl)pyridin-2-yl)-1H-pyrazole-4-carboxamide,
5-Amino-1-(2-(2-amino-1-fluoro-2-oxoethoxy)phenyl)-N-(5-(trifluoromethyl)pyridin-2-yl)-1H-pyrazole-4-carboxamide,
5-Amino-1-(2-(2-amino-2-oxoethoxy)phenyl)-3-methyl-N-(5-(trifluoromethyl)pyridin-2-yl)-1H-pyrazole-4-carboxamide,
5-Amino-1-(2-(2,2,3,3,3-pentafluoropropoxy)phenyl)-N-(5-(trifluoromethyl)pyridin-2-yl)-1H-pyrazole-4-carboxamide,
5-Amino-1-(2-(2,2,2-trifluoroethoxy)phenyl)-N-(5-(trifluoromethyl)pyridin-2-yl)-1H-pyrazole-4-carboxamide,
5-Amino-1-[2-(oxetaN-3-yloxy)phenyl]-N-[5-(trifluoromethyl)pyridin-2-yl]-1H-pyrazole-4-carboxamide,
5-Amino-1-[2-[(5-methylisoxazol-3-yl)methoxy]phenyl]-N-[5-(trifluoromethyl)pyridin-2-yl]-1H-pyrazole-4-carboxamide,
5-Amino-1-[2-(3-methoxypropoxy)phenyl]-N-[5-(trifluoromethyl)pyridin-2-yl]-1H-pyrazole-4-carboxamide,
5-Amino-1-(2-(2-hydroxyethoxy)phenyl)-N-(5-(trifluoromethyl)pyridin-2-yl)-1H-pyrazole-4-carboxamide,
5-Amino-1-(2-(2-hydroxyethoxy)phenyl)-3-methyl-N-(5-(trifluoromethyl)pyridin-2-yl)-1H-pyrazole-4-carboxamide,
5-Amino-N-(5-chloropyridin-2-yl)-3-ethyl-1-(2-(2-hydroxyethoxy)phenyl)-1H-pyrazole-4-carboxamide,
5-Amino-N-(5-chloropyridin-2-yl)-1-(2-(2-hydroxyethoxy)phenyl)-1H-pyrazole-4-carboxamide, 5-Amino-3-ethyl-1-(2-(2-hydroxyethoxy)phenyl)-N-(5-(trifluoromethyl)pyridin-2-yl)-1H-pyrazole-4-carboxamide, 5-Amino-1-(2-(difluoromethoxy)phenyl)-N-(5-(trifluoromethyl)pyridin-2-yl)-1H-pyrazole-4-carboxamide, 5-Amino-1-(3-fluoro-2-methylphenyl)-N-(5-(trifluoromethyl)pyridin-2-yl)-1H-imidazole-4-carboxamide, 5-Amino-N-(5-chloropyridin-2-yl)-1-(3-fluoro-2-methylphenyl)-1H-imidazole-4-carboxamide, 5-Amino-N-(4-bromophenyl)-1-(2-methoxyphenyl)-1H-imidazole-4-carboxamide, 5-Amino-N-(4-chlorophenyl)-1-(2-methoxyphenyl)-1H-imidazole-4-carboxamide, 5-Amino-1-(2-methoxyphenyl)-N-(4-(trifluoromethyl)phenyl)-1H-imidazole-4-carboxamide, 5-Amino-1-(2-(6-aminopyridin-3-yl)phenyl)-N-(5-chloropyridin-2-yl)-1H-pyrazole-4-carboxamide, 5-Amino-1-(2-(6-aminopyridin-3-yl)phenyl)-N-(5-(trifluoromethyl)pyridin-2-yl)-1H-pyrazole-4-carboxamide, 5-Amino-N-(5-chloropyridin-2-yl)-1-(2-(6-(dimethylamino)pyridin-3-yl)phenyl)-1H-pyrazole-4-carboxamide, 5-Amino-N-(5-chloropyridin-2-yl)-1-(2-(5-methoxypyridin-3-yl)phenyl)-1H-pyrazole-4-carboxamide, 5-Amino-1-(2-(2-(4-methylpiperaziN-1-yl)-2-oxoethoxy)phenyl)-N-(5-(trifluoromethyl)pyridin-2-yl)-1H-pyrazole-4-carboxamide, tert-Butyl 3-(2-(5-amino-4-((5-chloropyridin-2-yl)carbamoyl)-1H-pyrazol-1-yl)phenyl)-5,6-dihydropyridine-1(2H)-carboxylate, tert-Butyl 5-(2-(5-amino-4-((5-chloropyridin-2-yl)carbamoyl)-1H-pyrazol-1-yl)phenyl)-3,4-dihydropyridine-1(2H)-carboxylate, tert-Butyl 4-(2-(5-amino-4-((5-chloropyridin-2-yl)carbamoyl)-1H-pyrazol-1-yl)phenyl)-5,6-dihydropyridine-1(2H)-carboxylate, 5-Amino-1-(2-(2-oxo-2-(pyrrolidin-1-yl)ethoxy)phenyl)-N-(5-(trifluoromethyl)pyridin-2-yl)-1H-pyrazole-4-carboxamide, 5-amino-1-(2-(N-methyl-N-(pyridin-3-yl)sulfamoyl)phenyl)-N-(5-(trifluoromethyl)pyridin-2-yl)-1H-pyrazole-4-carboxamide, or a pharmaceutically acceptable salt, N-oxide, or isotopically-labeled derivative thereof.

16. A pharmaceutical composition comprising the compound according to claim 1 and a pharmaceutically acceptable diluent or carrier.

17. A combination product for simultaneous, separate, or sequential use in the treatment of the human or animal body comprising (i) the compound according to claim 1; and (ii) at least one additional compound chosen from:
(a) Opioid receptor agonists,
(b) Opioid receptor partial agonists,
(c) NSAIDS,
(d) COX-2 inhibitors,
(e) Ion channel modulators,
(f) Centrally acting agents,
(g) Agents for neuropathic pain,
(h) Agents for cancer pain,
(i) Anti-fibrotics,
(j) Prostacyclin analogues,
(k) Endothelin antagonists,
(l) Phosphodiesterase V inhibitors,
(m) Guanylate cyclase stimulators,
(n) Oral and inhaled corticosteroids,
(o) Phosphodiesterase IV,
(p) Beta2-adrenoceptor agonists,
(q) Muscarinic antagonists,
(r) Xantines,
(s) Mast cell stabilizers,
(t) Leukotriene modifiers,
(u) Th2 cytokine inhibitors,
(v) Thromboxane antagonists/thromboxane synthase inhibitors,
(w) Anti-IgE therapy compounds,
(x) Histamine antagonists,
(y) Antiinflammatory agents,
(z) JAK inhibitors,
(aa) Syk inhibitors,
(ab) Immunosupressants,
(ac) Antipruritic agents, and
(ad) Anti-tussive agents, Decongestants, Mucolytics, Expectorants, or Proton Pump Inhibitors.

18. A method for treating a subject afflicted with a pathological condition or a disease mediated by modulation of voltage-gated sodium channels in particular Nav1.7 comprising administering to the subject an effective amount of the compound according to claim 1.

19. The method according to claim 18, wherein the pathological condition or disease is chosen from pain, idiopathic couch, chronic cough, cough related to respiratory diseases, respiratory diseases, itch, dermatological diseases, epilepsy, schizophrenia and bipolar disorder.

20. The method according to claim 19, wherein the pain disease is chosen from acute pain, chronic pain, inflammatory pain, visceral pain, nociceptive pain, neurophatic pain, postherpetic pain, trigeminal neuralgia, diabetic neuropathy, chronic back pain, chronic pelvic pain, migraine and pain resulting from cancer and chemotherapy.

* * * * *

UNITED STATES PATENT AND TRADEMARK OFFICE
CERTIFICATE OF CORRECTION

PATENT NO. : 10,214,509 B2
APPLICATION NO. : 15/567668
DATED : February 26, 2019
INVENTOR(S) : James Duffy et al.

Page 1 of 1

It is certified that error appears in the above-identified patent and that said Letters Patent is hereby corrected as shown below:

In the Claims

Claim 1, Column 145, Line 64, "a linear or branched CIA alkyl group," should read -- a linear or branched $C_{1-4}$ alkyl group, --.

Claim 1, Column 146, Line 2, "a lineal linear or branched" should read -- a linear or branched --.

Claim 1, Column 146, Line 30, "a $C_{6-6}$ aryl group," should read -- a $C_{6-8}$ aryl group, --.

Claim 7, Column 147, Lines 58-59, "wherein $R_6$ is selected chosen from" should read -- wherein $R_6$ is chosen from --.

Claim 15, Column 149, Line 32, "methyl]phen y]-1-o-tolyl)" should read
-- methyl]phenyl]-1-o-tolyl) --.

Claim 15, Column 150, Line 33, "pyrazol e-4-carboxamide" should read -- pyrazole-4-carboxamide --.

Claim 15, Column 150, Line 46, "(2-methoxyphenyl)-H-" should read -- (2-methoxyphenyl)-*1H*- --.

Claim 15, Column 154, Line 27, "(2-morphelinophenyl)" should read -- (2-morpholinophenyl) --.

Claim 19, Column 158, Lines 40-41, "idiopathic couch" should read -- idiopathic cough --.

Signed and Sealed this
Fourteenth Day of May, 2019

Andrei Iancu
*Director of the United States Patent and Trademark Office*